US011655469B2

(12) United States Patent
Saleh et al.

(10) Patent No.: US 11,655,469 B2
(45) Date of Patent: May 23, 2023

(54) MICRORNAS AND METHODS OF THEIR USE

(71) Applicants: The United States of America, as represented by the Secretary, Dept. of Health and Human Services, Bethesda, MD (US); miRecule, Inc., Rockville, MD (US)

(72) Inventors: Anthony D. Saleh, Potomac, MD (US); Carter Van Waes, Brookeville, MD (US); Zhong Chen, Bethesda, MD (US); Hui Cheng, Falls Church, VA (US)

(73) Assignees: The United States of America, as represented by the Secretary, Department of Health and Human Services, Bethesda, MD (US); miRenlo, Inc., Rockville, MD (US)

( * ) Notice: Subject to any disclaimer, the term of this patent is extended or adjusted under 35 U.S.C. 154(b) by 794 days.

(21) Appl. No.: 16/082,852

(22) PCT Filed: Mar. 7, 2017

(86) PCT No.: PCT/US2017/021178
§ 371 (c)(1),
(2) Date: Sep. 6, 2018

(87) PCT Pub. No.: WO2017/156015
PCT Pub. Date: Sep. 14, 2017

(65) Prior Publication Data
US 2019/0284554 A1    Sep. 19, 2019

Related U.S. Application Data

(60) Provisional application No. 62/304,844, filed on Mar. 7, 2016.

(51) Int. Cl.
| | | |
|---|---|---|
| *C07H 21/04* | (2006.01) | |
| *C12N 15/113* | (2010.01) | |
| *A61K 47/69* | (2017.01) | |
| *A61K 47/68* | (2017.01) | |
| *A61P 35/00* | (2006.01) | |
| *A61K 31/7088* | (2006.01) | |
| *A61K 45/06* | (2006.01) | |
| *C12Q 1/6886* | (2018.01) | |

(52) U.S. Cl.
CPC ........ *C12N 15/113* (2013.01); *A61K 31/7088* (2013.01); *A61K 45/06* (2013.01); *A61K 47/6849* (2017.08); *A61K 47/6913* (2017.08); *A61P 35/00* (2018.01); *C12Q 1/6886* (2013.01); *C12N 2310/141* (2013.01); *C12N 2310/315* (2013.01); *C12N 2310/346* (2013.01); *C12N 2320/32* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 8,586,727 B2 | 11/2013 | Kelnar et al. | |
| 8,796,238 B2 | 8/2014 | Forbes | |
| 2007/0248659 A1 | 10/2007 | Shanahan et al. | |
| 2008/0306006 A1 | 12/2008 | Croce et al. | |
| 2009/0092974 A1 | 4/2009 | Davison et al. | |
| 2009/0148535 A1* | 6/2009 | Bamdad | C12N 15/113 424/499 |
| 2009/0203051 A1 | 8/2009 | Gray et al. | |
| 2011/0143950 A1 | 6/2011 | Zama et al. | |
| 2013/0115299 A1 | 5/2013 | Chiou et al. | |
| 2014/0011862 A1* | 1/2014 | Bradner | A61K 31/5517 435/6.12 |
| 2015/0313932 A1 | 11/2015 | Carrasco et al. | |

(Continued)

FOREIGN PATENT DOCUMENTS

| | | |
|---|---|---|
| JP | 2006-248978 | 9/2006 |
| JP | 2009-519339 | 5/2009 |
| JP | 2010-535246 | 11/2010 |

(Continued)

OTHER PUBLICATIONS

Final Office Action dated Feb. 28, 2022, issued for Japanese Application No. 2018-547943 (9 pages, including English translation of Final Office Action).
Shiah et al., "MIRNA-dependent regulation of DNA methyltransferose-3b in the retinoid acid metabolic genes during oral carcinogenesis," *Proceeding of Annual Meeting of the Japanese Cancer Association*, Abstract P-1125, vol. 73, 2014.
Syed et al., "miR-30 is downregulated in human squamous cell carcinoma and UVB exposed keratinocytes," *Journal of Investigative Dermatology*, Abstract 598, vol. 135, pp. S99-S105, 2015.

(Continued)

*Primary Examiner* — Kimberly Chong
(74) *Attorney, Agent, or Firm* — Klarquist Sparkman, LLP

(57) ABSTRACT

Disclosed herein are methods of treating a tumor in a subject, including administering to the subject one or more miRNA nucleic acids or variants (such as mimics or mimetics) thereof with altered expression in the tumor. Also disclosed herein are compositions including one or more miRNA nucleic acids. In some examples, the miRNA nucleic acids are modified miRNAs, for example, and miRNA nucleic acid including one or more modified nucleotides and/or a 5'-end and/or 3'-end modification. In particular examples, the modified miRNA nucleic acid is an miR-30a nucleic acid. Further disclosed herein are methods of diagnosing a subject as having a tumor with altered expression of one or more miRNA nucleic acids. In some embodiments, the methods include detecting expression of one or more miRNAs in a sample from the subject and comparing the expression in the sample from the subject to a control.

10 Claims, 38 Drawing Sheets
Specification includes a Sequence Listing.

(56) References Cited

U.S. PATENT DOCUMENTS

2017/0218372 A1* 8/2017 Milsom .............. C12N 15/1135

FOREIGN PATENT DOCUMENTS

| JP | 2012-529295 | 11/2012 |
|---|---|---|
| JP | 2014-506791 | 3/2014 |
| JP | 2014-530222 | 11/2014 |
| WO | WO 2003/093441 | 11/2003 |
| WO | WO 2005/017145 | 2/2005 |
| WO | WO 2006/099169 | 9/2006 |
| WO | WO 2006/133022 | 12/2006 |
| WO | WO 2007/033023 | 3/2007 |
| WO | WO 2007/070483 | 6/2007 |
| WO | WO 2007/149521 | 12/2007 |
| WO | WO 2008/069940 | 6/2008 |
| WO | WO 2008/088858 | 7/2008 |
| WO | WO 2009/018492 | 2/2009 |
| WO | WO 2010/065630 | 6/2010 |
| WO | WO 2010/144485 | 12/2010 |
| WO | WO 2012/106586 | 8/2012 |
| WO | WO 2012/106591 | 8/2012 |
| WO | WO 2013/052965 | 4/2013 |

OTHER PUBLICATIONS

"Squamous cell carcinoma—Wikipedia", XP055722287, Retrieved from the Internet: https://en.wikipedia.org/wiki/Squamous_cell_carcinoma, May 27, 2020 (retrieved on Aug. 13, 2020) (6 pages).

Chernolovskaya et al., "Chemical modification of siRNA," *Current Opinion in Molecular Therapeutics*, vol. 12, No. 2, pp. 158-167, 2010.

De Paula et al., "Hydrophobization and bioconjugation for enhanced siRNA delivery and targeting," *RNA*, vol. 13, No. 4, pp. 431-456, 2007.

Manoharan et al., "RNA interference and chemically modified small interfering RNAs," *Current Biology in Chemical Biology*, vol. 8, No. 6, pp. 570-579, 2004.

Baraniskin et al., "MiR-30s-5p suppresses tumor growth in colon carcinoma by targeting DTL," *Carcinogenesis*, vol. 33, No. 4, pp. 732-739, 2012.

Batchu et al., "Enhanced phosphorylation of p53 by micro-26a leading to growth inhibition of pancreatic cancer," *Surgery*, vol. 158, No. 4, pp. 981-987, 2015.

Fukumoto et al., "Tumor-suppressive microRNAs (*miR-26a/b, miR-29a/b/c* and *miR-218*) concertedly suppressed metastasis-promoting LOXL2 in head and neck squamous cell carcinoma," *Journal of Human Genetics*, vol. 61, No. 2, pp. 109-118, 2016.

Gao and Liu, "The role of miR-26 in tumors and normal tissues (Review)," *Oncology Letters*, vol. 2, pp. 1019-1023, 2011.

He et al., "MicroRNA-375 targets AEG-1 in hepatocellular carcinoma and suppresses liver cancer cell growth in vitro and in vivo," *Oncogene*, vol. 31, No. 28, pp. 3357-3369, 2012.

Hoadley et al., "Multiplatform Analysis of 12 Cancer Types Reveals Molecular Classification within and across Tissues of Origin," *Cell* vol. 15 8, pp. 929-944, 2014.

Hou et al., "MicroRNA as ideal biomarker for the diagnosis of various carcinomas," *Tumor Biology*, vol. 36, No. 4, pp. 2641-2649, 2015.

Kano et al., "*miR-145, miR-133a* and *miR-133b*: Tumor-suppressive miRNAs target FSCN1 in esophageal squamous cell carcinoma," *International Journal of Cancer*, vol. 127, No. 12, pp. 2804-2814, 2010.

Kao et al., "miR-30 as a tumor suppressor connects EGF/Src signal to ERG and EMT," *Oncogene*, vol. 33, No. 19, pp. 2495-2503, 2014.

Karatas et al., "Role of miR-145 in human laryngeal squamous cell carcinoma," *Head and Neck*, vol. 3 8, No. 2, pp. 260-266, 2016.

Kim et al., "Development of microRNA-145 for therapeutic application in breast cancer," *Journal of Controlled Release*, vol. 155, No. 3, pp. 427-434, 2011.

Kota et al., "Therapeutic microRNA Delivery Suppresses Tumorigenesis in a Murine Liver Cancer Model," *Cell*, vol. 137, No. 6, pp. 1005-1017, 2009.

Lindenbergh-van der Plas et al., "Identification of Lethal microRNAs Specific for Head and Neck Cancer," *Clinical Cancer Research*, vol. 19, No. 20, pp. 5647-5657, 2013.

Ling et al., "MicroRNA-30c serves as an independent biochemical recurrence predictor and potential tumor suppressor for prostate cancer," *Molecular Biology Reports*, vol. 41, No. 5, pp. 2779-2788, 2014.

Nohata et al., "Tumor suppressive *microRNA-375* regulates oncogene *AEG-1/MTDH* in head and neck squamous cell carcinoma (HNSCC)," *Journal of Human Genetics*, vol. 56, No. 8, pp. 595-601, 2011.

Saad et al., "Alcohol-dysregulated miR-30a and miR-934 in head and neck squamous cell carcinoma," *Molecular Cancer*, 14:181, 2015 (14 pages).

Stahlhut et al., "MicroRNAs and the cancer phenotype: profiling, signatures and clinical implications," *Genome Medicine*, 5:111, 2013 (12 pages).

Tusher et al., "Significance analysis of microarrays applied to the ionizing radiation response," *PNAS*, vol. 98, No. 9, pp. 5116-5121, 2001.

Yan et al., "The emerging role of miR-375 in cancer," *International Journal of Cancer*, vol. 135, No. 5, pp. 1011-1018, 2013.

Yang et al., "Inhibition of cancer stem cell-like properties and reduced chemoradioresistance of glioblastoma using microRNA145 with cationic polyurethane-short branch PEI," *Biomaterials*, vol. 33, No. 5, pp. 1462-1476, 2012.

Yu et al., "miR145 Targets the SOX9/ADAM17 Axis to Inhibit Tumor-Initiating Cells and IL-6-Mediated Paracrine Effects in Head and Neck Cancer," *Cancer Research*, vol. 73, No. 11, pp. 3425-3440, 2013.

Zhang et al., "MicroRNA-30a suppresses breast tumor growth and metastasis by targeting metadherin," *Oncogene*, vol. 33, No. 24, pp. 3119-3128, 2014.

Zhang et al., "Progress in microRNA delivery," *Journal of Controlled Release*, vol. 172, No. 3, pp. 962-974, 2013.

Zhang et al., "Role of MicroRNA 30a Targeting Insulin Receptor Substrate 2 in Colorectal Tumorigenesis," *Molecular and Cellular Biology*, vol. 35, No. 6, pp. 988-1000, 2015.

Zhang et al., "Role of microRNA-30c Targeting ADAM19 in Colorectal Cancer," *PLoS One*, vol. 10, No. 3, e0120698, 2015 (14 pages).

Zhao et al., "miR-30-5p Functions as a Tumor Suppressor and Novel Therapeutic Tool by Targeting the Oncogenic Wnt/β Catenin/BCL9 Pathway," *Cancer Research*, vol. 74, No. 6, pp. 1801-1813, 2014.

\* cited by examiner

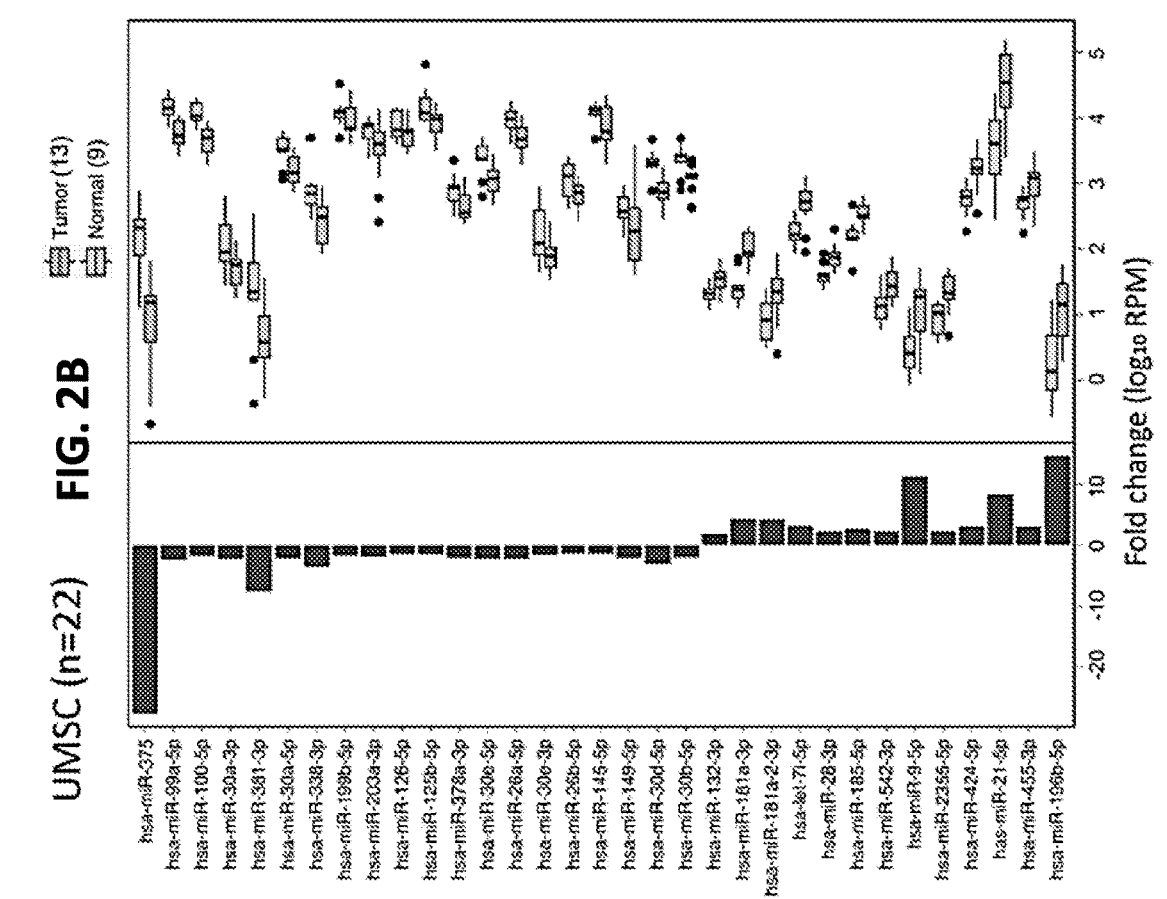
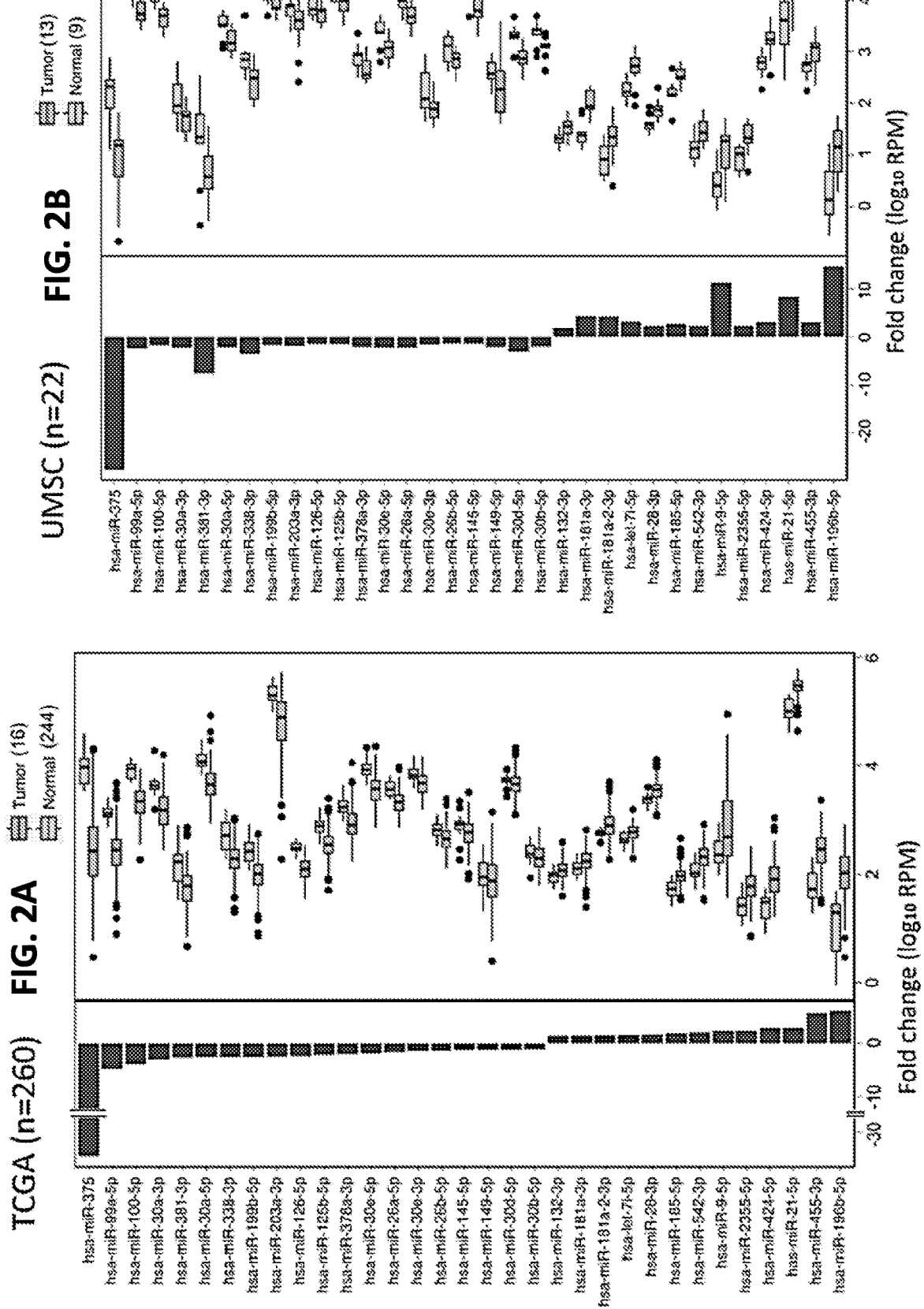
FIG. 2A
FIG. 2B

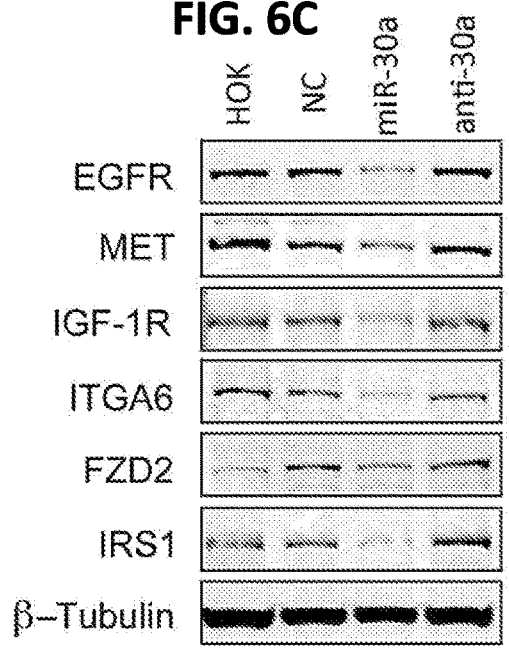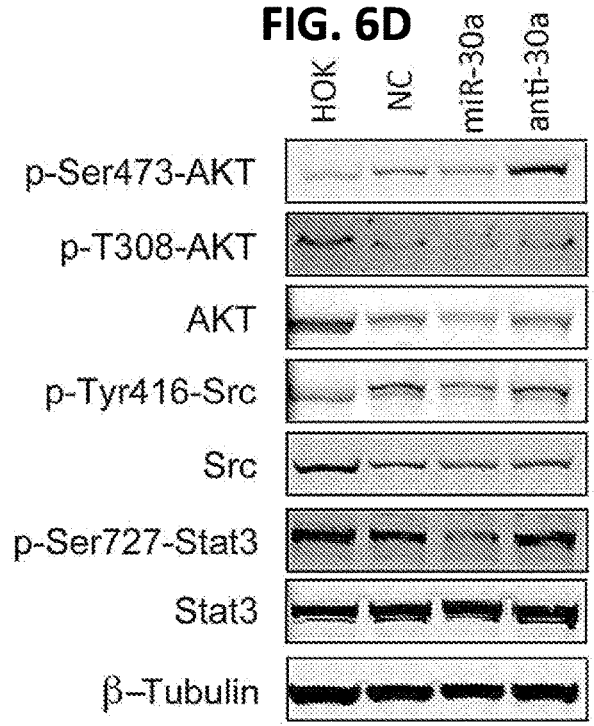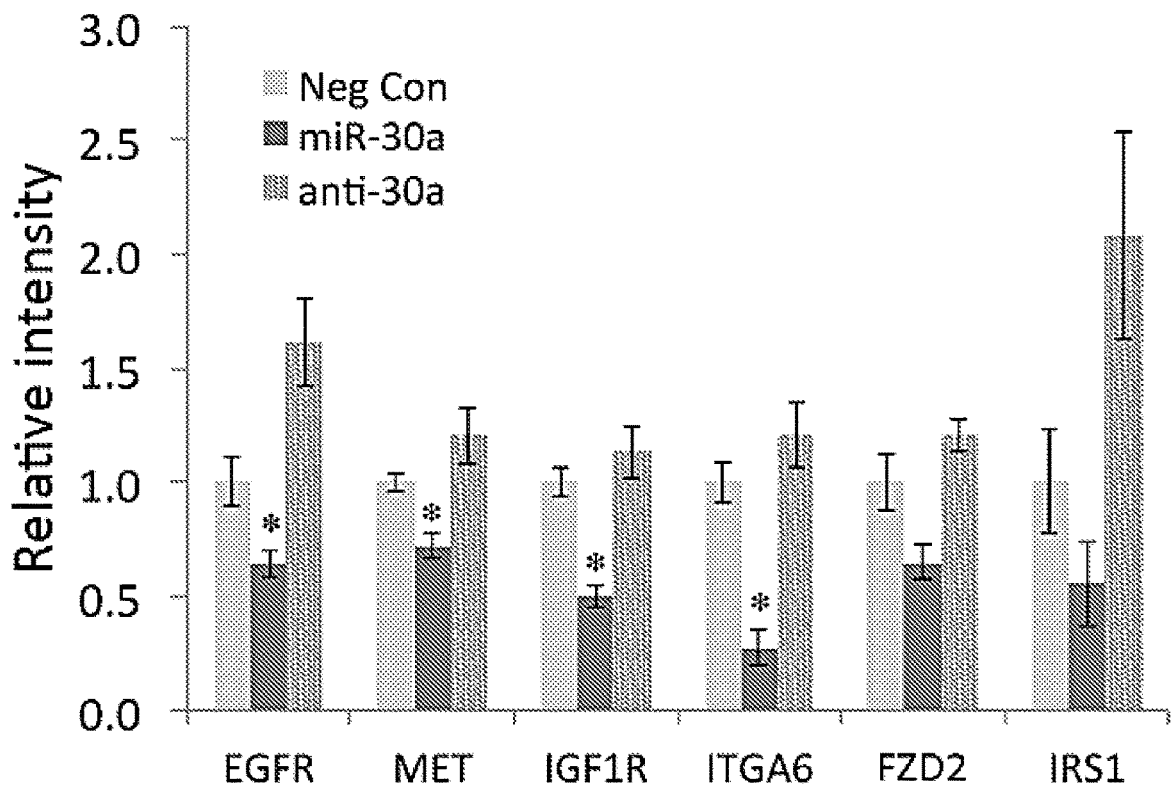

UM-SCC-1

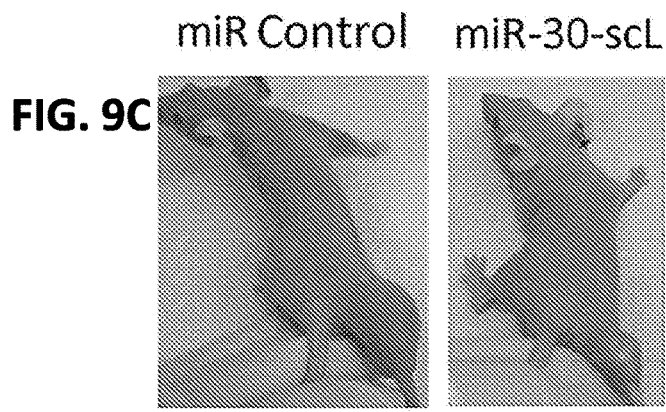
FIG. 9C
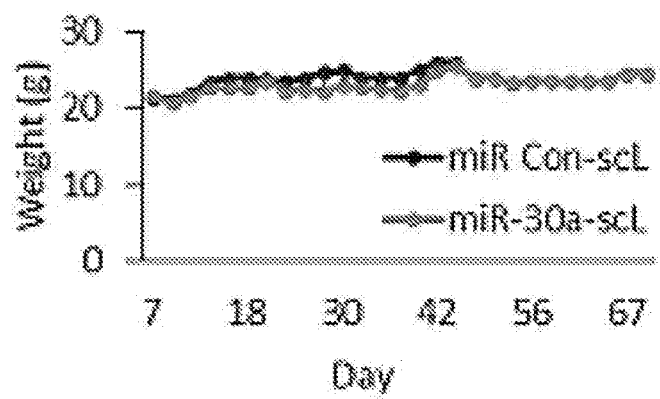
FIG. 9D
UM-SCC-46
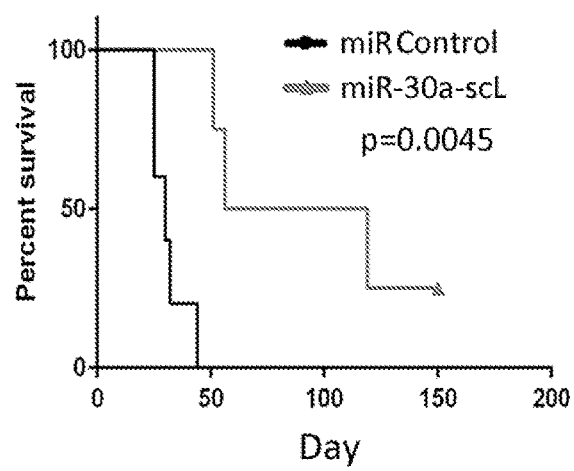
FIG. 9E
UM-SCC-47
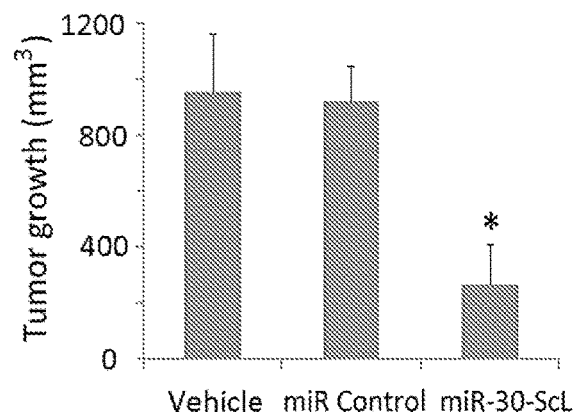

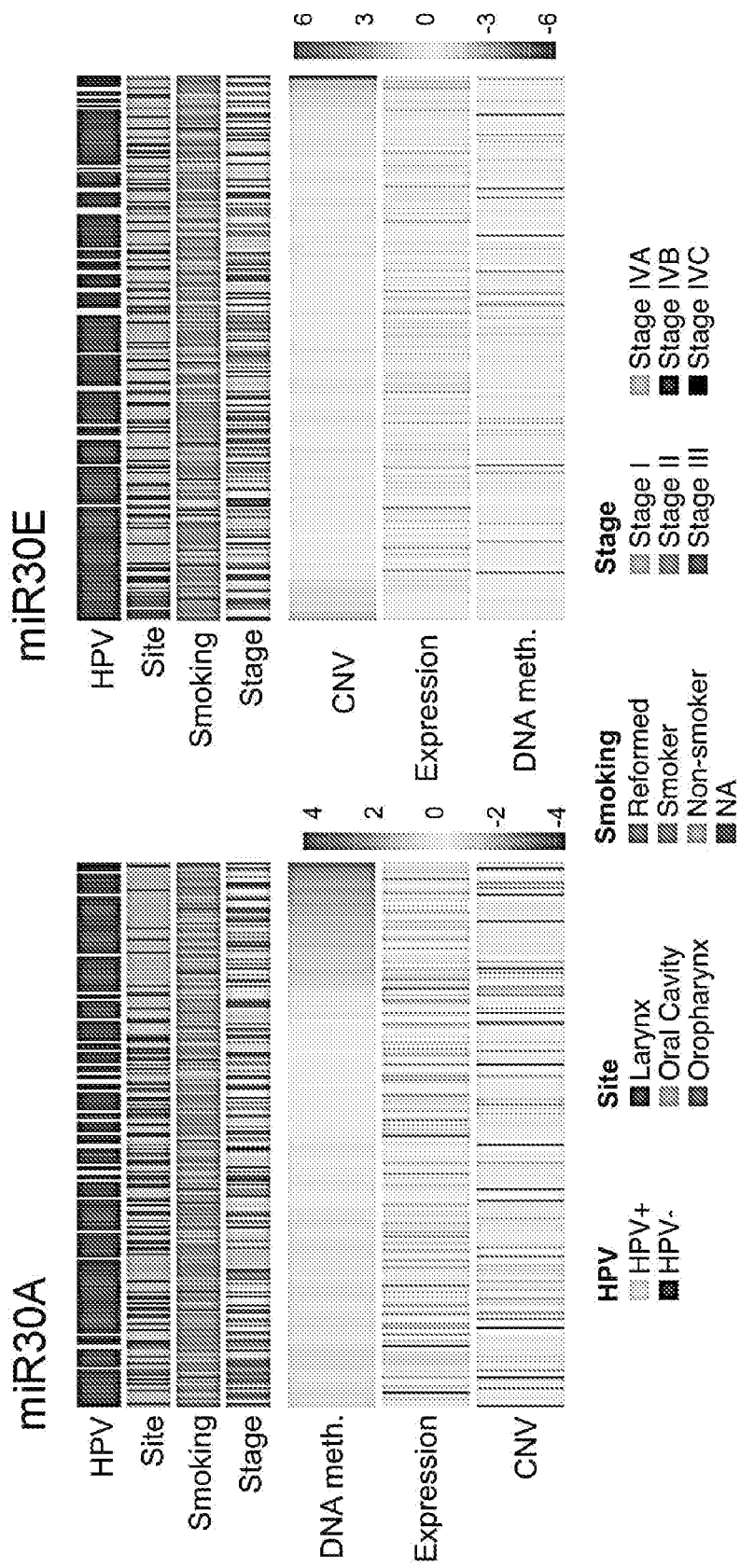

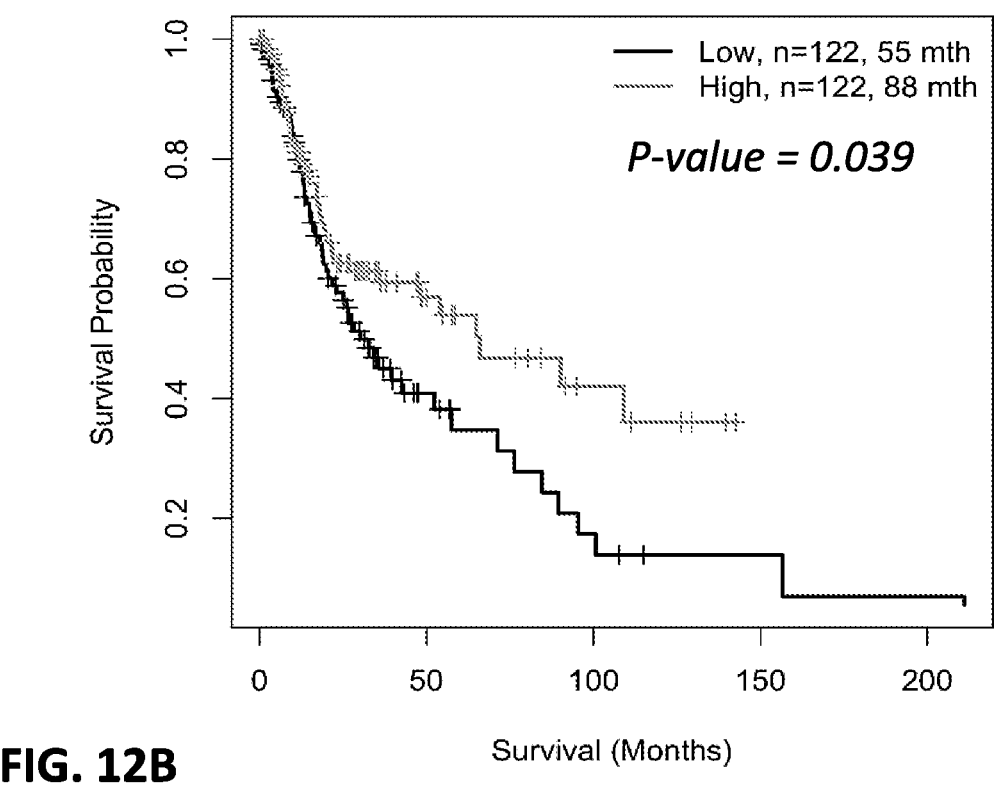
FIG. 12B
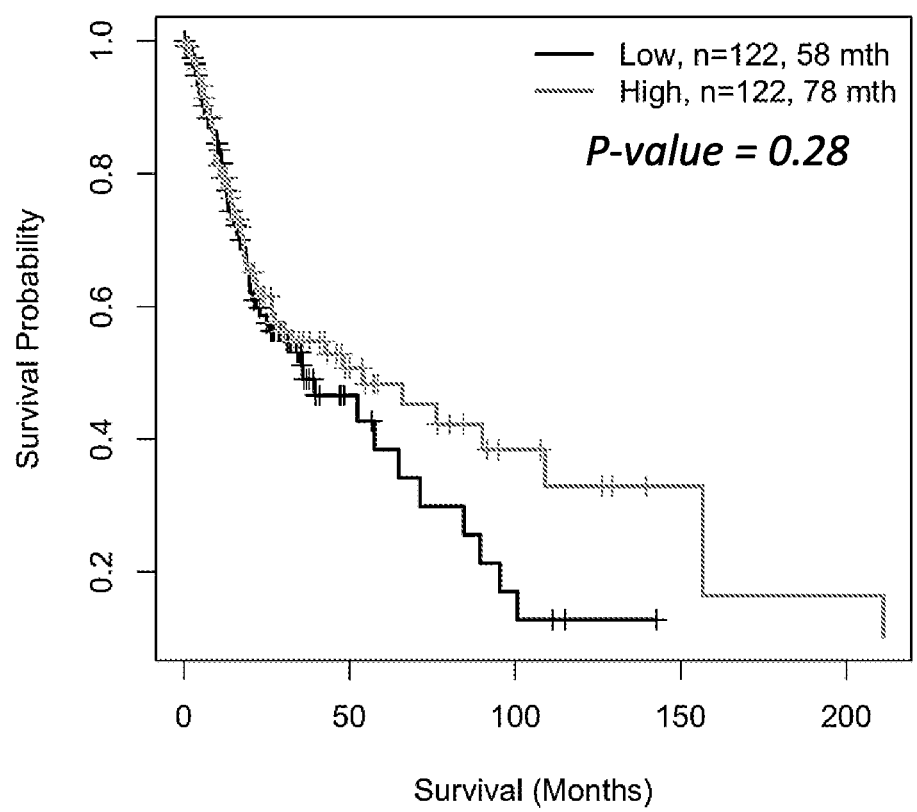

SEQUENCE LISTING

```
<160> NUMBER OF SEQ ID NOS: 158

<210> SEQ ID NO 1
<211> LENGTH: 22
<212> TYPE: RNA
<213> ORGANISM: Homo sapiens

<400> SEQUENCE: 1
uguaaacauc cucgacugga ag                                                22

<210> SEQ ID NO 2
<211> LENGTH: 22
<212> TYPE: RNA
<213> ORGANISM: Homo sapiens

<400> SEQUENCE: 2
uguaaacauc cuacacucag cu                                                22

<210> SEQ ID NO 3
<211> LENGTH: 23
<212> TYPE: RNA
<213> ORGANISM: Homo sapiens

<400> SEQUENCE: 3
uguaaacauc cuacacucuc agc                                               23

<210> SEQ ID NO 4
<211> LENGTH: 22
<212> TYPE: RNA
<213> ORGANISM: Homo sapiens

<400> SEQUENCE: 4
uguaaacauc cccgacugga ag                                                22

<210> SEQ ID NO 5
<211> LENGTH: 22
<212> TYPE: RNA
<213> ORGANISM: Homo sapiens

<400> SEQUENCE: 5
uguaaacauc cuugacugga ag                                                22
```

```
<210> SEQ ID NO 6
<211> LENGTH: 22
<212> TYPE: RNA
<213> ORGANISM: Homo sapiens

<400> SEQUENCE: 6
cuuucagucg gauguuugca gc                                            22

<210> SEQ ID NO 7
<211> LENGTH: 22
<212> TYPE: RNA
<213> ORGANISM: Homo sapiens

<400> SEQUENCE: 7
cugggaggug gauguuuacu uc                                            22

<210> SEQ ID NO 8
<211> LENGTH: 22
<212> TYPE: RNA
<213> ORGANISM: Homo sapiens

<400> SEQUENCE: 8
cugggagagg guuguuuacu cc                                            22

<210> SEQ ID NO 9
<211> LENGTH: 22
<212> TYPE: RNA
<213> ORGANISM: Homo sapiens

<400> SEQUENCE: 9
cugggagaag gcuguuuacu cu                                            22

<210> SEQ ID NO 10
<211> LENGTH: 22
<212> TYPE: RNA
<213> ORGANISM: Homo sapiens

<400> SEQUENCE: 10
cuuucaguca gauguuugcu gc                                            22

<210> SEQ ID NO 11
<211> LENGTH: 22
<212> TYPE: RNA
<213> ORGANISM: Homo sapiens

<400> SEQUENCE: 11
cuuucagucg gauguuuaca gc                                            22

<210> SEQ ID NO 12
<211> LENGTH: 22
<212> TYPE: RNA
<213> ORGANISM: Homo sapiens

<400> SEQUENCE: 12
uucaaguaau ccaggauagg cu                                            22

<210> SEQ ID NO 13
<211> LENGTH: 22
<212> TYPE: RNA
<213> ORGANISM: Homo sapiens

<400> SEQUENCE: 13
ccuauucuug guuacuugca cg                                            22
```

```
<210> SEQ ID NO 14
<211> LENGTH: 22
<212> TYPE: RNA
<213> ORGANISM: Homo sapiens

<400> SEQUENCE: 14
ccuauucuug auuacuuguu uc                                              22

<210> SEQ ID NO 15
<211> LENGTH: 21
<212> TYPE: RNA
<213> ORGANISM: Homo sapiens

<400> SEQUENCE: 15
uucaaguaau ucaggauagg u                                               21

<210> SEQ ID NO 16
<211> LENGTH: 22
<212> TYPE: RNA
<213> ORGANISM: Homo sapiens

<400> SEQUENCE: 16
ccuguucucc auuacuuggc uc                                              22

<210> SEQ ID NO 17
<211> LENGTH: 22
<212> TYPE: RNA
<213> ORGANISM: Homo sapiens

<400> SEQUENCE: 17
uuuguucguu cggcucgcgu ga                                              22

<210> SEQ ID NO 18
<211> LENGTH: 23
<212> TYPE: RNA
<213> ORGANISM: Homo sapiens

<400> SEQUENCE: 18
guccaguuuu cccaggaauc ccu                                             23

<210> SEQ ID NO 19
<211> LENGTH: 22
<212> TYPE: RNA
<213> ORGANISM: Homo sapiens

<400> SEQUENCE: 19 ggauccugg aaauacuguu cu                                               22

<210> SEQ ID NO 20
<211> LENGTH: 22
<212> TYPE: RNA
<213> ORGANISM: Homo sapiens

<400> SEQUENCE: 20
aacaauaucc uggugcugag ug                                              22

<210> SEQ ID NO 21
<211> LENGTH: 22
<212> TYPE: RNA
<213> ORGANISM: Homo sapiens

<400> SEQUENCE: 21
uccagcauca gugauuuugu ug                                              22
```

```
<210> SEQ ID NO 22
<211> LENGTH: 22
<212> TYPE: RNA
<213> ORGANISM: Homo sapiens

<400> SEQUENCE: 22
uccuucauuc caccggaguc ug                                              22

<210> SEQ ID NO 23
<211> LENGTH: 21
<212> TYPE: RNA
<213> ORGANISM: Homo sapiens

<400> SEQUENCE: 23
gauuucagug gagugaaguu c                                               21

<210> SEQ ID NO 24
<211> LENGTH: 22
<212> TYPE: RNA
<213> ORGANISM: Homo sapiens

<400> SEQUENCE: 24
uagcaccauc ugaaaucggu ua                                              22

<210> SEQ ID NO 25
<211> LENGTH: 23
<212> TYPE: RNA
<213> ORGANISM: Homo sapiens

<400> SEQUENCE: 25
uagcaccauu ugaaaucagu guu                                             23

<210> SEQ ID NO 26
<211> LENGTH: 22
<212> TYPE: RNA
<213> ORGANISM: Homo sapiens

<400> SEQUENCE: 26
uagcaccauu ugaaaucggu ua                                              22

<210> SEQ ID NO 27
<211> LENGTH: 22
<212> TYPE: RNA
<213> ORGANISM: Homo sapiens

<400> SEQUENCE: 27
acugauuucu uuugguguuc ag                                              22

<210> SEQ ID NO 28
<211> LENGTH: 24
<212> TYPE: RNA
<213> ORGANISM: Homo sapiens

<400> SEQUENCE: 28
gcugguuuca uauggugguu uaga                                            24

<210> SEQ ID NO 29
<211> LENGTH: 22
<212> TYPE: RNA
<213> ORGANISM: Homo sapiens

<400> SEQUENCE: 29
```

```
cugguuucac augguggcuu ag                                              22

<210> SEQ ID NO 30
<211> LENGTH: 22
<212> TYPE: RNA
<213> ORGANISM: Homo sapiens

<400> SEQUENCE: 30
ugaccgauuu cuccuggugu uc                                              22

<210> SEQ ID NO 31
<211> LENGTH: 22
<212> TYPE: RNA
<213> ORGANISM: Homo sapiens

<400> SEQUENCE: 31
agggcuuagc ugcuugugag ca                                              22

<210> SEQ ID NO 32
<211> LENGTH: 21
<212> TYPE: RNA
<213> ORGANISM: Homo sapiens

<400> SEQUENCE: 32
uucacagugg cuaaguuccg c                                               21

<210> SEQ ID NO 33
<211> LENGTH: 22
<212> TYPE: RNA
<213> ORGANISM: Homo sapiens

<400> SEQUENCE: 33
agagcuuagc ugauugguga ac                                              22

<210> SEQ ID NO 34
<211> LENGTH: 21
<212> TYPE: RNA
<213> ORGANISM: Homo sapiens

<400> SEQUENCE: 34
uucacagugg cuaaguucug c                                               21

<210> SEQ ID NO 35
<211> LENGTH: 22
<212> TYPE: RNA
<213> ORGANISM: Homo sapiens

<400> SEQUENCE: 35
caguuaucac agugcugaug cu                                              22

<210> SEQ ID NO 36
<211> LENGTH: 21
<212> TYPE: RNA
<213> ORGANISM: Homo sapiens

<400> SEQUENCE: 36
uacaguacug ugauaacuga a                                               21

<210> SEQ ID NO 37
<211> LENGTH: 24
<212> TYPE: RNA
<213> ORGANISM: Artificial Sequence
<220> FEATURE:
<223> OTHER INFORMATION: Modified miR-30 guide strand
```

```
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-O-,methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um

<400> SEQUENCE: 37
uguaaacauc cucgacugga agcu                                      24

<210> SEQ ID NO 38
<211> LENGTH: 24
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (8)..(8)
<223> OTHER INFORMATION: 2-O-methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm

<400> SEQUENCE: 38
uguaaacauc cucgacugga agcu                                      24

<210> SEQ ID NO 39
<211> LENGTH: 24
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
```

```
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm

<400> SEQUENCE: 39
uguaaacauc cucgacugga agcu                                          24

<210> SEQ ID NO 40
<211> LENGTH: 24
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um

<400> SEQUENCE: 40
uguaaacauc cucgacugga agcu                                          24

<210> SEQ ID NO 41
<211> LENGTH: 24
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
```

<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm

<400> SEQUENCE: 41
uguaaacauc cucgacugga agcu    24

<210> SEQ ID NO 42
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm

<400> SEQUENCE: 42
uguaaacauc cucgacugga ag    22

<210> SEQ ID NO 43
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:

```
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (21)..(22)
<223> OTHER INFORMATION: phosphorothioate linakge

<400> SEQUENCE: 43
uguaaacauc cucgacugga ag                                              22

<210> SEQ ID NO 44
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (20)..(22)
<223> OTHER INFORMATION: phosphorothioage linkage
```

<400> SEQUENCE: 44
uguaaacauc cucgacugga ag				22

<210> SEQ ID NO 45
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (21)..(21)
<223> OTHER INFORMATION: 2'-deoxyadenosine
<220> FEATURE:
<221> NAME/KEY: misc_feature
<222> LOCATION: (21)..(22)
<223> OTHER INFORMATION: methyl phosphonate linkage

<400> SEQUENCE: 45
uguaaacauc cucgacugga ag				22

<210> SEQ ID NO 46
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)

```
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(21)
<223> OTHER INFORMATION: 2'-deoxyadenosine
<220> FEATURE:
<221> NAME/KEY: modified_base
<222> LOCATION: (20)..(22)
<223> OTHER INFORMATION: methylphosphonate linkage

<400> SEQUENCE: 46
uguaaacauc cucgacugga ag                                              22

<210> SEQ ID NO 47
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(21)
<223> OTHER INFORMATION: 2'-O-methyladenosine
<220> FEATURE:
<221> NAME/KEY: modified_base
```

```
<222> LOCATION: (22)..(22)
<223> OTHER INFORMATION: gm

<400> SEQUENCE: 47
uguaaacauc cucgacugga ag                                              22

<210> SEQ ID NO 48
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(19)
<223> OTHER INFORMATION: gm
<220> FEATURE:
<221> NAME/KEY: modified_base
<222> LOCATION: (20)..(21)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (22)..(22)
<223> OTHER INFORMATION: gm

<400> SEQUENCE: 48
uguaaacauc cucgacugga ag                                              22

<210> SEQ ID NO 49
<211> LENGTH: 23
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
```

```
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm

<400> SEQUENCE: 49
uguaaacauc cuacacucuc agc                                          23

<210> SEQ ID NO 50
<211> LENGTH: 23
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm

<400> SEQUENCE: 50
uguaaacauc cuacacucuc agc                                          23
```

<210> SEQ ID NO 51
<211> LENGTH: 23
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: cm
<220> FEATURE:
<221> NAME/KEY: modified_base
<222> LOCATION: (23)..(23)
<223> OTHER INFORMATION: gm

<400> SEQUENCE: 51
uguaaacauc cuacacucuc agc                                              23

<210> SEQ ID NO 52
<211> LENGTH: 23
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)

```
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: misc_feature
<222> LOCATION: (21)..(23)
<223> OTHER INFORMATION: phosphorthioage linkage
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm

<400> SEQUENCE: 52
uguaaacauc cuacacucuc agc                                            23

<210> SEQ ID NO 53
<211> LENGTH: 23
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
```

```
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: misc_feature
<222> LOCATION: (21)..(23)
<223> OTHER INFORMATION: phosphorothioage linkage
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm

<400> SEQUENCE: 53
uguaaacauc cuacacucuc agc                                        23

<210> SEQ ID NO 54
<211> LENGTH: 24
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker

<400> SEQUENCE: 54
agcuuccagu cggauguuua cacg                                       24

<210> SEQ ID NO 55
<211> LENGTH: 24
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
```

```
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (24)..(24)
<223> OTHER INFORMATION: gm

<400> SEQUENCE: 55
agcuuccagu cggauguuua cacg                                          24

<210> SEQ ID NO 56
<211> LENGTH: 22
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: gm

<400> SEQUENCE: 56
cuuccagucg gauguuuaca cg                                            22

<210> SEQ ID NO 57
<211> LENGTH: 18
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
```

```
<220> FEATURE:
<221> NAME/KEY: modified_base
<222> LOCATION: (2)..(3)
<223> OTHER INFORMATION: cm
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 57
uccagucgga uguuuaca                                              18

<210> SEQ ID NO 58
<211> LENGTH: 18
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: cm
<220> FEATURE:
<221> NAME/KEY: modified_base
<222> LOCATION: (4)..(4)
<223> OTHER INFORMATION: 2'-fluoroadenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluorouridine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoroguanosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoroadeonsine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoroguanosine
<220> FEATURE:
<221> NAME/KEY: modified_base
<222> LOCATION: (13)..(13)
```

```
<223> OTHER INFORMATION: um
<220> FEATURE:
<221> NAME/KEY: modified_base
<222> LOCATION: (14)..(14)
<223> OTHER INFORMATION: 2'-fluorouridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoroadenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 58
uccagucgga uguuuaca                                              18

<210> SEQ ID NO 59
<211> LENGTH: 18
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: cm
<220> FEATURE:
<221> NAME/KEY: modified_base
<222> LOCATION: (4)..(4)
<223> OTHER INFORMATION: 2'-fluoroadenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluorouridine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoroguanosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-fluoroadenosine
<220> FEATURE:
<221> NAME/KEY: modified_base
<222> LOCATION: (11)..(11)
<223> OTHER INFORMATION: um
<220> FEATURE:
<221> NAME/KEY: modified_base
```

```
<222> LOCATION: (12)..(12)
<223> OTHER INFORMATION: 2'-fluoroguanosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluorouridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoroadenosine
<220> FEATURE:
<221> NAME/KEY: misc_feature
<222> LOCATION: (16)..(18)
<223> OTHER INFORMATION: phosphorothioate linkage
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 59
uccagucgga uguuuaca                                                 18

<210> SEQ ID NO 60
<211> LENGTH: 18
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: cm
<220> FEATURE:
<221> NAME/KEY: modified_base
<222> LOCATION: (4)..(4)
<223> OTHER INFORMATION: 2'-fluoroadenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluorouridine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoroguanosine
<220> FEATURE:
<221> NAME/KEY: modified_base
<222> LOCATION: (9)..(9)
<223> OTHER INFORMATION: gm
<220> FEATURE:
```

-continued

```
<221> NAME/KEY: modified_base
<222> LOCATION: (10)..(10)
<223> OTHER INFORMATION: 2'-fluoroadenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-fluoroguanosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluorouridine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-fluoroadenosine
<220> FEATURE:
<221> NAME/KEY: modified_base
<222> LOCATION: (17)..(17)
<223> OTHER INFORMATION: 2'-deoxycytidine
<220> FEATURE:
<221> NAME/KEY: misc_feature
<222> LOCATION: (17)..(18)
<223> OTHER INFORMATION: methylphosphonage linkage
<220> FEATURE:
<221> NAME/KEY: modified_base
<222> LOCATION: (18)..(18)
<223> OTHER INFORMATION: 2'-O-methyladenosine

<400> SEQUENCE: 60
uccagucgga uguuuaca                                                  18

<210> SEQ ID NO 61
<211> LENGTH: 19
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-O-methyladenosine
```

<400> SEQUENCE: 61
ugagaguagg auguuuaca                                                         19

<210> SEQ ID NO 62
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm

<400> SEQUENCE: 62
uuuguucguu cggcucgcgu ga                                                     22

<210> SEQ ID NO 63
<211> LENGTH: 20
<212> TYPE: RNA
<213> ORGANISM: Artificial Sequence
<220> FEATURE:
<223> OTHER INFORMATION: miR-375 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (18)..(20)
<223> OTHER INFORMATION: 2'-O-methyladenosine

<400> SEQUENCE: 63
acgcgagccg aacgaacaaa                                                        20

<210> SEQ ID NO 64
<211> LENGTH: 22
<212> TYPE: RNA
<213> ORGANISM: Artificial Sequence
<220> FEATURE:

<223> OTHER INFORMATION: miR-26a-5p modified guide strand
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm

<400> SEQUENCE: 64
uucaaguaau ccaggauagg cu                                              22

<210> SEQ ID NO 65
<211> LENGTH: 21
<212> TYPE: RNA
<213> ORGANISM: Artificial Sequence
<220> FEATURE:
<223> OTHER INFORMATION: miR-26a-5p modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(21)
<223> OTHER INFORMATION: 2'-O-methyladenosine

<400> SEQUENCE: 65
ccuaucccug gauuacuuga a                                               21

<210> SEQ ID NO 66
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base

```
<222> LOCATION: (15)..(15)
<223> OTHER INFORMATION: gm

<400> SEQUENCE: 66
guccaguuuu cccaggaauc ccu                                          23

<210> SEQ ID NO 67
<211> LENGTH: 21
<212> TYPE: RNA
<213> ORGANISM: Artificial Sequence
<220> FEATURE:
<223> OTHER INFORMATION: miR-145-5p modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: cm

<400> SEQUENCE: 67
ggauuccugg aaauacugga c                                            21

<210> SEQ ID NO 68
<211> LENGTH: 23
<212> TYPE: RNA
<213> ORGANISM: Homo sapiens

<400> SEQUENCE: 68
gacugguuuu gcaacguuua cac                                          23

<210> SEQ ID NO 69
<211> LENGTH: 22
<212> TYPE: RNA
<213> ORGANISM: Homo sapiens

<400> SEQUENCE: 69
uuuuuuagga caccuguuua cu                                           22

<210> SEQ ID NO 70
<211> LENGTH: 21
<212> TYPE: RNA
<213> ORGANISM: Homo sapiens

<400> SEQUENCE: 70 auuuuuaua aaauguuuau u                                             21

<210> SEQ ID NO 71
<211> LENGTH: 24
<212> TYPE: RNA
<213> ORGANISM: Homo sapiens
```

<400> SEQUENCE: 71
gcauccauuu caguuuguuu acuu                                          24

<210> SEQ ID NO 72
<211> LENGTH: 24
<212> TYPE: RNA
<213> ORGANISM: Homo sapiens

<400> SEQUENCE: 72
agcuuccagu cggauguuua cacg                                          24

<210> SEQ ID NO 73
<211> LENGTH: 23
<212> TYPE: RNA
<213> ORGANISM: Artificial Sequence
<220> FEATURE:
<223> OTHER INFORMATION: miR-30-5p modified guide strand
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base

```
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm

<400> SEQUENCE: 73
uguaaacauc cuacacucuc agc                                           23

<210> SEQ ID NO 74
<211> LENGTH: 23
<212> TYPE: RNA
<213> ORGANISM: Artificial Sequence
<220> FEATURE:
<223> OTHER INFORMATION: miR-30-5p modified guide strand
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
```

<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm

<400> SEQUENCE: 74
uguaaacauc cuacacucuc agc          23

<210> SEQ ID NO 75
<211> LENGTH: 22
<212> TYPE: RNA
<213> ORGANISM: Artificial Sequence
<220> FEATURE:
<223> OTHER INFORMATION: miR-30-5p modified passenger strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um

```
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 75
uguaaacauc cucgacugga ag                                        22

<210> SEQ ID NO 76
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
```

```
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: gm

<400> SEQUENCE: 76
uguaaacauc cucgacugga ag                                               22

<210> SEQ ID NO 77
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (6)..(6)
<223> OTHER INFORMATION: 2'-fluoroadenosine
<220> FEATURE:
<221> NAME/KEY: modified_base
```

```
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioage linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 77
uguaaacauc cucgacugga ag                                              22

<210> SEQ ID NO 78
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
```

```
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: 2'-fluorocytidine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorotihioate linkage
<220> FEATURE:
<221> NAME/KEY: modified_base
<222> LOCATION: (21)..(21)
<223> OTHER INFORMATION: 2'-fluoroadenosine
```

```
<220> FEATURE:
<221> NAME/KEY: modified_base
<222> LOCATION: (22)..(22)
<223> OTHER INFORMATION: gm

<400> SEQUENCE: 78
uguaaacauc cucgacugga ag                                            22

<210> SEQ ID NO 79
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: 2'-fluoroadenosine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
```

```
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioage linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 79
uguaaacauc cucgacugga ag                                              22

<210> SEQ ID NO 80
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: 2'-fluorocytidine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
```

```
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioage linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 80
uguaaacauc cucgacugga ag                                                  22

<210> SEQ ID NO 81
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidne
<220> FEATURE:
<221> NAME/KEY: modified_base
<222> LOCATION: (12)..(12)
<223> OTHER INFORMATION: um
<220> FEATURE:
```

```
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 81
uguaaacauc cucgacugga ag                                          22

<210> SEQ ID NO 82
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: 2'-O-methyladenosine
```

```
<220> FEATURE:
<221> NAME/KEY: modified_base
<222> LOCATION: (7)..(7)
<223> OTHER INFORMATION: 2'-fluorocytidine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(21)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (22)..(22)
<223> OTHER INFORMATION: gm

<400> SEQUENCE: 82
uguaaacauc cucgacugga ag                                              22

<210> SEQ ID NO 83
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
```

```
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methtyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methtyladenosine
<220> FEATURE:
<221> NAME/KEY: modified_base
<222> LOCATION: (22)..(22)
<223> OTHER INFORMATION: gm

<400> SEQUENCE: 83
uguaaacauc cucgacugga ag                                              22

<210> SEQ ID NO 84
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
```

```
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (20)..(22)
<223> OTHER INFORMATION: phosphorothioate
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 84
uguaaacauc cucgacugga ag                                        22

<210> SEQ ID NO 85
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
```

```
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-fluoroguanosine

<400> SEQUENCE: 85
uguaaacauc cucgacugga ag                                          22

<210> SEQ ID NO 86
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
```

```
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-fluoroguanosine

<400> SEQUENCE: 86
uguaaacauc cucgacugga ag                                            22

<210> SEQ ID NO 87
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
```

```
<223> OTHER INFORMATION: gm

<400> SEQUENCE: 87
uguaaacauc cucgacugga ag                                          22

<210> SEQ ID NO 88
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-fluoroguanosine

<400> SEQUENCE: 88
uguaaacauc cucgacugga ag                                          22

<210> SEQ ID NO 89
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
```

```
<222> LOCATION: (2)..(2)
<223> OTHER INFORMATION: gm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-fluorocytidine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-fluoroguanidine

<400> SEQUENCE: 89
uguaaacauc cucgacugga ag                                           22

<210> SEQ ID NO 90
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: cm
<220> FEATURE:
```

```
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-fluoroguanosine

<400> SEQUENCE: 90
uguaaacauc cucgacugga ag                                          22

<210> SEQ ID NO 91
<211> LENGTH: 22
<212> TYPE: RNA
<213> ORGANISM: Artificial Sequence
<220> FEATURE:
<223> OTHER INFORMATION: miR-30 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: gm
```

```
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluorouguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: gm

<400> SEQUENCE: 91
uguaaacauc cucgacugga ag                                              22

<210> SEQ ID NO 92
<211> LENGTH: 18
<212> TYPE: RNA
<213> ORGANISM: Artificial Sequence
<220> FEATURE:
<223> OTHER INFORMATION: miR-30 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: cm
<220> FEATURE:
<221> NAME/KEY: modified_base
<222> LOCATION: (4)..(4)
<223> OTHER INFORMATION: 2'-fluoroadeonosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluorouridine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
```

```
<223> OTHER INFORMATION: 2'-fluoroguanosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluorouridine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-fluorouridine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 92
uccagucgga uguuuaca                                                  18

<210> SEQ ID NO 93
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
```

```
<222> LOCATION: (16)..(16)
<223> OTHER INFORMATION: cm
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 93
uuuguucguu cggcucgcgu ga                                              22

<210> SEQ ID NO 94
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 94
uuuguucguu cggcucgcgu ga                                              22
```

```
<210> SEQ ID NO 95
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouiridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouiridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 95
uuuguucguu cggcucgcgu ga                                           22

<210> SEQ ID NO 96
<211> LENGTH: 22
<212> TYPE: RNA
<213> ORGANISM: Artificial Sequence
<220> FEATURE:
<223> OTHER INFORMATION: miR-375 modified guide strand
```

```
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorouridine
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 96
uuuguucguu cggcucgcgu ga                                              22

<210> SEQ ID NO 97
<211> LENGTH: 22
<212> TYPE: RNA
<213> ORGANISM: Artificial Sequence
<220> FEATURE:
```

```
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorouridine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 97
```
uuuguucguu cggcucgcgu ga          22

<210> SEQ ID NO 98
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorouridine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorocytidine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguanosine
<220> FEATURE:

```
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 98
uuuguucguu cggcucgcgu ga                                              22

<210> SEQ ID NO 99
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: um
```

```
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 99
uuuguucguu cggcucgcgu ga                                              22

<210> SEQ ID NO 100
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(3)
<223> OTHER INFORMATION: um
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguansine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguansine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguansine
<220> FEATURE:
<221> NAME/KEY: modified_base
<222> LOCATION: (22)..(22)
```

<223> OTHER INFORMATION: 2'-O-methyladenosine

<400> SEQUENCE: 100
uuuguucguu cggcucgcgu ga                                                    22

<210> SEQ ID NO 101
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(2)
<223> OTHER INFORMATION: um
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 101
uuuguucguu cggcucgcgu ga                                                    22

<210> SEQ ID NO 102
<211> LENGTH: 22
<212> TYPE: RNA
<213> ORGANISM: Artificial Sequence

```
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorouridine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorocytidine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoroguanosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-fluorouridine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluorouguanosine
<220> FEATURE:
```

<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 102
uuuguucguu cggcucgcgu ga                                              22

<210> SEQ ID NO 103
<211> LENGTH: 22
<212> TYPE: RNA
<213> ORGANISM: Artificial Sequence
<220> FEATURE:
<223> OTHER INFORMATION: miR-375 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoroguanosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: 2'-fluorouridine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluoroguanosine

```
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroguanosine
<220> FEATURE:
<221> NAME/KEY: modified_base
<222> LOCATION: (22)..(22)
<223> OTHER INFORMATION: 2'-O-methyladenosine

<400> SEQUENCE: 103
uuuguucguu cggcucgcgu ga                                              22

<210> SEQ ID NO 104
<211> LENGTH: 20
<212> TYPE: RNA
<213> ORGANISM: Artificial Sequence
<220> FEATURE:
<223> OTHER INFORMATION: miR-375 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-fluorocytidine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-fluoroadenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-fluorocytidine
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
```

```
<223> OTHER INFORMATION: 2'-fluoroadenosine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-fluorocytidine
<220> FEATURE:
<221> NAME/KEY: modified_base
<222> LOCATION: (18)..(20)
<223> OTHER INFORMATION: 2'-O-methyladenosine

<400> SEQUENCE: 104
acgcgagccg aacgaacaaa                                              20

<210> SEQ ID NO 105
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 105
uucaaguaau ccaggauagg cu                                           22
```

-continued

```
<210> SEQ ID NO 106
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: misc_feature
<222> LOCATION: (20)..(22)
<223> OTHER INFORMATION: phosphorothiate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 106
uucaaguaau ccaggauagg cu                                              22

<210> SEQ ID NO 107
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (8)..(9)
<223> OTHER INFORMATION: 2'-O-methyladenosine
<220> FEATURE:
```

```
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 107
uucaaguaau ccaggauagg cu                                           22

<210> SEQ ID NO 108
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouiridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (13)..(13)
<223> OTHER INFORMATION: 2'-O-methyladenosine
```

```
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 108
uucaaguaau ccaggauagg cu                                           22

<210> SEQ ID NO 109
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2;-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (19)..(19)
```

-continued

```
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 109
uucaaguaau ccaggauagg cu                                              22

<210> SEQ ID NO 110
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
```

-continued

```
<222> LOCATION: (19)..(19)
<223> OTHER INFORMATION: 2'-fluoroguannosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 110
uucaaguaau ccaggauagg cu                                               22

<210> SEQ ID NO 111
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
```

-continued

```
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 111
uucaaguaau ccaggauagg cu                                              22

<210> SEQ ID NO 112
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
```

```
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 112
uucaaguaau ccaggauagg cu                                              22

<210> SEQ ID NO 113
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(9)
```

```
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(12)
<223> OTHER INFORMATION: cm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (16)..(16)
<223> OTHER INFORMATION: 2'-fluoroadenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 113
uucaaguaau ccaggauagg cu                                           22

<210> SEQ ID NO 114
<211> LENGTH: 22
<212> TYPE: RNA
<213> ORGANISM: Artificial Sequence
<220> FEATURE:
<223> OTHER INFORMATION: miR-26 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
```

```
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-fluoroadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluoroadenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroguanosine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um

<400> SEQUENCE: 114
uucaaguaau ccaggauagg cu                                        22
```

```
<210> SEQ ID NO 115
<211> LENGTH: 21
<212> TYPE: RNA
<213> ORGANISM: Artificial Sequence
<220> FEATURE:
<223> OTHER INFORMATION: miR-26 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: misc_feature
<222> LOCATION: (1)..(2)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (4)..(4)
<223> OTHER INFORMATION: 2'-fluoroadenosine
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (6)..(6)
<223> OTHER INFORMATION: 2'-fluorocytidine
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: 2'-fluorocytidine
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (14)..(14)
<223> OTHER INFORMATION: 2'-fluorouridine
<220> FEATURE:
<221> NAME/KEY: misc_feature
<222> LOCATION: (15)..(15)
<223> OTHER INFORMATION: 2'-O-methyladenosine
<220> FEATURE:
<221> NAME/KEY: misc_feature
<222> LOCATION: (16)..(16)
<223> OTHER INFORMATION: 2'-fluorocytidine
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (18)..(18)
<223> OTHER INFORMATION: 2'-fluorouridine
<220> FEATURE:
<221> NAME/KEY: misc_feature
<222> LOCATION: (19)..(19)
<223> OTHER INFORMATION: gm
<220> FEATURE:
<221> NAME/KEY: misc_feature
<222> LOCATION: (20)..(21)
<223> OTHER INFORMATION: 2'-O-methyladenosine

<400> SEQUENCE: 115
ccuaucccug gauuacuuga a                                              21
```

<210> SEQ ID NO 116
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um

<400> SEQUENCE: 116
guccaguuuu cccaggaauc ccu                                              23

<210> SEQ ID NO 117
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)

-continued

```
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um

<400> SEQUENCE: 117
guccaguuuu cccaggaauc ccu                                              23

<210> SEQ ID NO 118
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
```

```
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um

<400> SEQUENCE: 118
guccaguuuu cccaggaauc ccu                                              23

<210> SEQ ID NO 119
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um
```

<400> SEQUENCE: 119
guccaguuuu cccaggaauc ccu                                              23

<210> SEQ ID NO 120
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um -continued

<400> SEQUENCE: 120
guccaguuuu cccaggaauc ccu                                           23

<210> SEQ ID NO 121
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)

```
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um

<400> SEQUENCE: 121
guccaguuuu cccaggaauc ccu                                             23

<210> SEQ ID NO 122
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(10)
<223> OTHER INFORMATION: um
<220> FEATURE:
<221> NAME/KEY: modified_base
<222> LOCATION: (11)..(13)
<223> OTHER INFORMATION: cm
<220> FEATURE:
<221> NAME/KEY: modified_base
<222> LOCATION: (14)..(14)
<223> OTHER INFORMATION: 2'-fluoroadenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-fluoroguanosine
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
```

```
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um

<400> SEQUENCE: 122
guccaguuuu cccaggaauc ccu                                              23

<210> SEQ ID NO 123
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluorocytidine
<220> FEATURE:
```

```
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(16)
<223> OTHER INFORMATION: 2'-fluoroguanosine
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-fluoroadenosine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um

<400> SEQUENCE: 123
guccaguuuu cccaggaauc ccu                                           23

<210> SEQ ID NO 124
<211> LENGTH: 23
<212> TYPE: RNA
<213> ORGANISM: Artificial Sequence
<220> FEATURE:
<223> OTHER INFORMATION: miR-145-5p modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-fluoroadenosine
```

```
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-fluorocytidine
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-fluoroguanosine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: 2'-fluoroadenosine
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-fluorocytidine
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: modified_base
<222> LOCATION: (22)..(22)
<223> OTHER INFORMATION: cm
<220> FEATURE:
<221> NAME/KEY: modified_base
<222> LOCATION: (23)..(23)
<223> OTHER INFORMATION: 2'-fluorouridine

<400> SEQUENCE: 124
```
guccaguuuu cccaggaauc ccu                                    23

<210> SEQ ID NO 125
<211> LENGTH: 21
<212> TYPE: RNA
<213> ORGANISM: Artificial Sequence
<220> FEATURE:
<223> OTHER INFORMATION: miR-145-5p modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-fluorouridine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluorocytidine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluorouridine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-fluorouridine
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-fluorocytidine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-fluoroguanosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: cm

<400> SEQUENCE: 125
ggauuccugg aaauacugga c                                              21

<210> SEQ ID NO 126
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-O-methyladenosine

<400> SEQUENCE: 126
uacaguacug ugauaacuga a                                              21

<210> SEQ ID NO 127
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:

```
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-fluoroadenosine
<220> FEATURE:
<221> NAME/KEY: modified_base
<222> LOCATION: (21)..(21)
<223> OTHER INFORMATION: 2'-O-methyladenosine

<400> SEQUENCE: 127
uacaguacug ugauaacuga a                                              21

<210> SEQ ID NO 128
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
```

```
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-fluoroadenosine
<220> FEATURE:
<221> NAME/KEY: modified_base
<222> LOCATION: (21)..(21)
<223> OTHER INFORMATION: 2'-O-methyladenosine

<400> SEQUENCE: 128
uacaguacug ugauaacuga a                                              21

<210> SEQ ID NO 129
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
```

```
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-fluoroadenosine
<220> FEATURE:
<221> NAME/KEY: modified_base
<222> LOCATION: (21)..(21)
<223> OTHER INFORMATION: 2'-O-methyladenosine

<400> SEQUENCE: 129
uacaguacug ugauaacuga a                                      21

<210> SEQ ID NO 130
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
```

```
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-fluoroadenosine
<220> FEATURE:
<221> NAME/KEY: modified_base
<222> LOCATION: (21)..(21)
<223> OTHER INFORMATION: 2'-O-methyladenosine

<400> SEQUENCE: 130
uacaguacug ugauaacuga a                                          21

<210> SEQ ID NO 131
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
```

```
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-fluoroadenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-fluoroadenosine
<220> FEATURE:
<221> NAME/KEY: modified_base
<222> LOCATION: (21)..(21)
<223> OTHER INFORMATION: 2'-O-methyladenosine

<400> SEQUENCE: 131
uacaguacug ugauaacuga a                                             21

<210> SEQ ID NO 132
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
```

```
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluoroadenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-fluoroadenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-fluoroadenosine
<220> FEATURE:
<221> NAME/KEY: modified_base
<222> LOCATION: (21)..(21)
<223> OTHER INFORMATION: 2'-O-methyladenosine

<400> SEQUENCE: 132
uacaguacug ugauaacuga a                                      21

<210> SEQ ID NO 133
```

-continued

```
<211> LENGTH: 21
<212> TYPE: RNA
<213> ORGANISM: Artificial Sequence
<220> FEATURE:
<223> OTHER INFORMATION: miR-101 modified guide strand
<220> FEATURE:
<221> NAME/KEY: modified_base
<222> LOCATION: (1)..(1)
<223> OTHER INFORMATION: 2'-fluorouridine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluoroadenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-fluorouridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoroadenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-fluorocytidine
<220> FEATURE:
<221> NAME/KEY: modified_base
<222> LOCATION: (18)..(18)
<223> OTHER INFORMATION: um
<220> FEATURE:
<221> NAME/KEY: modified_base
```

```
<222> LOCATION: (19)..(19)
<223> OTHER INFORMATION: 2'-fluoroguanosine
<220> FEATURE:
<221> NAME/KEY: misc_feature
<222> LOCATION: (19)..(21)
<223> OTHER INFORMATION: phosphorothioate linkage
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: 2'-fluoroadenosine

<400> SEQUENCE: 133
uacaguacug ugauaacuga a                                              21

<210> SEQ ID NO 134
<211> LENGTH: 19
<212> TYPE: RNA
<213> ORGANISM: Artificial Sequence
<220> FEATURE:
<223> OTHER INFORMATION: miR-101 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-O-methyladenosine

<400> SEQUENCE: 134
caguuaucac aguacugua                                                 19

<210> SEQ ID NO 135
<211> LENGTH: 19
<212> TYPE: RNA
<213> ORGANISM: Artificial Sequence
<220> FEATURE:
<223> OTHER INFORMATION: miR-101 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: 2'-O-methyladenosine
<220> FEATURE:
```

<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-fluorouridine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-fluoroadenosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-fluorocytidine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-fluoroadenosine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-fluorouridine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-O-methyladenosine

<400> SEQUENCE: 135
caguuaucac aguacugua                                                    19

<210> SEQ ID NO 136
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine

```
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm

<400> SEQUENCE: 136
gcugguuuca uauggugguu uaga                                              24

<210> SEQ ID NO 137
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 137
```
gcugguuuca uaugggugguu uaga                                              24

<210> SEQ ID NO 138
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 138
gcugguuuca uaugggugguu uaga                                              24

<210> SEQ ID NO 139
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base

```
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 139
gcugguuuca uauggugguu uaga                                                24

<210> SEQ ID NO 140
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
```

```
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 140
gcugguuuca uauggugguu uaga                                            24

<210> SEQ ID NO 141
<211> LENGTH: 24
<212> TYPE: RNA
<213> ORGANISM: Artificial Sequence
<220> FEATURE:
<223> OTHER INFORMATION: miR-29 modified guide strand
```

-continued

```
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
```

<223> OTHER INFORMATION: 2'-O-methyladenosine

<400> SEQUENCE: 141
gcugguuuca uaugguggu uaga                                                    24

<210> SEQ ID NO 142
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluorouridine
<220> FEATURE:
<221> NAME/KEY: modified_base

```
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 142
gcugguuuca uauggugguu uaga                                              24

<210> SEQ ID NO 143
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
```

<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 143
gcugguuuca uauggugguu uaga                                              24

<210> SEQ ID NO 144
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoroguanosine

```
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 144
```
gcugguuuca uauggugguu uaga            24

```
<210> SEQ ID NO 145
<211> LENGTH: 24
<212> TYPE: RNA
<213> ORGANISM: Artificial Sequence
<220> FEATURE:
<223> OTHER INFORMATION: miR-29 modified guide strand
<220> FEATURE:
<221> NAME/KEY: modified_base
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-fluorouridine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluoroguanosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-fluorocytidine
<220> FEATURE:
<221> NAME/KEY: modified_base
<222> LOCATION: (10)..(10)
<223> OTHER INFORMATION: 2'-fluoroadenosine
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: 2'-fluorouridine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroguanosine
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: gm
<220> FEATURE:
<221> NAME/KEY: modified_base
```

```
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: 2'-fluorouridine
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: modified_base
<222> LOCATION: (23)..(23)
<223> OTHER INFORMATION: 2'-fluoroguanosine
<220> FEATURE:
<221> NAME/KEY: modified_base
<222> LOCATION: (24)..(24)
<223> OTHER INFORMATION: 2'-O-methyladenosine

<400> SEQUENCE: 145
gcugguuuca uauggugguu uaga                                          24

<210> SEQ ID NO 146
<211> LENGTH: 22
<212> TYPE: RNA
<213> ORGANISM: Artificial Sequence
<220> FEATURE:
<223> OTHER INFORMATION: miR-29 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm

<400> SEQUENCE: 146
uaaaccacca uaugaaacca gc                                            22

<210> SEQ ID NO 147
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (8)..(8)
<223> OTHER INFORMATION: 2'-O-methyladenosine
<220> FEATURE:
```

```
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um

<400> SEQUENCE: 147
agagcuuagc ugauuggnga ac                                              22

<210> SEQ ID NO 148
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
```

```
<220> FEATURE:
<221> NAME/KEY: modified_base
<222> LOCATION: (22)..(22)
<223> OTHER INFORMATION: cm

<400> SEQUENCE: 148
agagcuuagc ugauuggugra ac                                                 22

<210> SEQ ID NO 149
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: cm

<400> SEQUENCE: 149
agagcuuagc ugauuggugra ac                                                 22

<210> SEQ ID NO 150
```

```
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: cm

<400> SEQUENCE: 150
agagcuuagc ugauuggugc ac                                              22

<210> SEQ ID NO 151
<211> LENGTH: 22
<212> TYPE: RNA
<213> ORGANISM: Artificial Sequence
```

```
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorocytidine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: cm

<400> SEQUENCE: 151
agagcuuagc ugauugguga ac                                              22

<210> SEQ ID NO 152
<211> LENGTH: 22
<212> TYPE: RNA
```

```
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorocytidine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: cm
```

<400> SEQUENCE: 152
agagcuuagc ugauuggugaac 22

<210> SEQ ID NO 153
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorocytidine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)

```
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: cm

<400> SEQUENCE: 153
agagcuuagc ugauuggugc ac                                              22

<210> SEQ ID NO 154
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorocytidine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
```

```
<222> LOCATION: (13)..(13)
<223> OTHER INFORMATION: 2'-O-methyladenosine
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (16)..(16)
<223> OTHER INFORMATION: 2'-fluoroguanosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-fluorouridine
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: cm

<400> SEQUENCE: 154
agagcuuagc ugauuggguga ac                                              22

<210> SEQ ID NO 155
<211> LENGTH: 22
<212> TYPE: RNA
<213> ORGANISM: Artificial Sequence
<220> FEATURE:
<223> OTHER INFORMATION: miR-27 modified guide strand
<220> FEATURE:
<221> NAME/KEY: modified_base
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-fluorocytidine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-fluorouridine
<220> FEATURE:
```

<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-fluoroguanosine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(11)
<223> OTHER INFORMATION: 2'-fluorouridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-fluoroadenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-fluorouridine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: 2'-fluoroguanosine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-fluoroguanosine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: modified_base
<222> LOCATION: (21)..(21)
<223> OTHER INFORMATION: 2'-fluoroadenosine
<220> FEATURE:
<221> NAME/KEY: modified_base
<222> LOCATION: (22)..(22)
<223> OTHER INFORMATION: 2'-fluorocytidine

<400> SEQUENCE: 155
agagcuuagc ugauuggguga ac                                    22

<210> SEQ ID NO 156
<211> LENGTH: 22
<212> TYPE: RNA
<213> ORGANISM: Artificial Sequence
<220> FEATURE:
<223> OTHER INFORMATION: miR-27 modified passenger strand
<220> FEATURE:
<221> NAME/KEY: misc_feature
<222> LOCATION: (1)..(1)
<223> OTHER INFORMATION: amino C6 linker

```
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: um

<400> SEQUENCE: 156
guucaccaau cagcuaagcu cu                                                  22

<210> SEQ ID NO 157
<211> LENGTH: 22
<212> TYPE: RNA
<213> ORGANISM: Artificial Sequence
<220> FEATURE:
<223> OTHER INFORMATION: miR-27 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: 2'-fluorocytidine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-fluorocytidine
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: 2'-fluoroadenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (13)..(13)
<223> OTHER INFORMATION: 2'-fluoroguanosine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
```

```
<223> OTHER INFORMATION: 2'-fluorouridine
<220> FEATURE:
<221> NAME/KEY: modified_base
<222> LOCATION: (16)..(16)
<223> OTHER INFORMATION: 2'--O-methyladenosine
<220> FEATURE:
<221> NAME/KEY: modified_base
<222> LOCATION: (17)..(17)
<223> OTHER INFORMATION: 2'-fluoroadenosine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-fluorocytidine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: um

<400> SEQUENCE: 157
guucaccaau cagcuaagcu cu                                              22

<210> SEQ ID NO 158
<211> LENGTH: 22
<212> TYPE: RNA
<213> ORGANISM: Artificial Sequence
<220> FEATURE:
<223> OTHER INFORMATION: miR-27 modified passenger strand
<220> FEATURE:
<221> NAME/KEY: misc_feature
<222> LOCATION: (1)..(1)
<223> OTHER INFORMATION: amino C6 linker
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-fluoroadenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: 2'-fluorocytidine
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-fluorocytidine
<220> FEATURE:
<221> NAME/KEY: modified_base
<222> LOCATION: (9)..(9)
<223> OTHER INFORMATION: cm
<220> FEATURE:
<221> NAME/KEY: modified_base
```

```
<222> LOCATION: (13)..(13)
<223> OTHER INFORMATION: 2'-fluorouridine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-fluoroadenosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-fluorocytidine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm

<400> SEQUENCE: 158
uaaaccacca uaugaaacca gc                                              22
```

MICRORNAS AND METHODS OF THEIR USE

CROSS REFERENCE TO RELATED APPLICATION

This claims the benefit of U.S. Provisional Application No. 62/304,844, filed Mar. 7, 2016, which is incorporated herein by reference in its entirety.

FIELD

This disclosure relates to treatment and/or diagnosis of cancer, particularly methods utilizing microRNAs.

BACKGROUND

Deregulation of microRNA (miR) expression has emerged as a potentially important contributory driver of aberrantly expressed mRNAs that mediate the complex malignant phenotypes of cancers (Stahlhut and Slack, *Genome Med.* 5:111, 2013). It is less clear which miRs co-regulate critical mRNA targets within diverse pathways and gene programs that coordinate the malignant phenotype. Since a single miR may simultaneously target multiple mRNAs, miR-based therapeutics may help mitigate intrinsic or acquired resistance observed using more selective small molecule or biologic therapies targeting a single oncogene or pathway in cancer.

SUMMARY

Disclosed herein are miRNAs that have increased or decreased expression in cancers. The disclosed miRNAs or mimics and/or mimetics thereof can be utilized in methods of treating and/or diagnosing a subject with cancer (such as a malignant tumor).

Disclosed herein are methods of treating a subject with cancer. The methods include administering to a subject one or more miRNA nucleic acids (or mimics or mimetics thereof) with altered expression in a tumor. In some examples, the methods include administering to a subject with cancer an effective amount of an miR-30 nucleic acid, an miR-26a-5p nucleic acid, an miR-26b-5p nucleic acid, an miR-145-5p nucleic acid, an miR-338-3p nucleic acid, an miR-375 nucleic acid, an miR-29 nucleic acid, an miR-27 nucleic acid, an miR-101 nucleic acid, a mimic or mimetic thereof, an miR complementary to any one of miR-30, miR-26a-5p, miR-26b-5p, miR145-5p, miR-338-3p, miR-375, or a combination of any two or more thereof. In particular examples, the subject has a squamous cell carcinoma, such as head and neck squamous cell carcinoma (HNSCC). In additional examples, the methods include administering to the subject an effective amount of at least one of the miRNA nucleic acids listed in any one of Table 1, Table 3, Table 4, Table 5, Table 18, Table 20, Table 21, and Table 23, a mimic or mimetic thereof, a complementary oligonucleotide, or a combination of any two or more thereof. In some examples, the miRNA nucleic acids are administered as duplex miRNA nucleic acids and/or are included in a vector. In some examples, the miRNA nucleic acid and/or mimic or mimetic thereof decreases expression of one or more mRNAs listed in Tables 6 to 14.

Also disclosed herein are compositions including one or more miRNA nucleic acids, such as at least one of the miRNAs listed in any one of Table 1, Table 3, Table 4, Table 5, Table 18, Table 20, Table 21, and Table 23. In some examples, the miRNA nucleic acids are modified miRNAs, for example, an miRNA nucleic acid including one or more sequence modifications, modified nucleotides, and/or a 5'-end and/or 3'-end modification. In particular examples, the modified miRNA nucleic acid is an miR-30a nucleic acid, including, but not limited to the modified miRNAs provided herein as SEQ ID NOs: 37-61. In other examples, the modified miRNA nucleic acid includes the miRNA nucleic acids provided herein as SEQ ID NOs: 62-67. In still further examples, the modified miRNA nucleic acid includes the miRNA nucleic acids provided herein as SEQ ID NOs: 73-158. In some examples, the miRNA nucleic acids include duplex miRNA nucleic acids and/or are included in a vector.

Further disclosed herein are methods of diagnosing a subject as having a tumor with altered expression of one or more miRNA nucleic acids. In some embodiments, the methods include detecting expression of one or more miR-NAs listed in any one of Tables 1, 3, 4, 5, 18, and 20 in a sample from the subject and comparing the expression in the sample from the subject to a control. In some examples, an altered amount of miRNA expression compared to the control indicates that the subject has a tumor. In some examples, the methods include detecting expression of one or more of an miR-30 nucleic acid, an miR-26a-5p nucleic acid, an miR-26b-5p nucleic acid, an miR-145-5p nucleic acid, an miR-338-3p nucleic acid, or an miR-375 nucleic acid and determining that the subject has a tumor (including, but not limited to, a squamous cell carcinoma tumor) if expression of one or more of the miRNAs is decreased compared to the control. In some embodiments, the methods further include administering one or more miRNA nucleic acids to the subject, such as one or more of an miR-30 nucleic acid, an miR-26a-5p nucleic acid, an miR-26b-5p nucleic acid, an miR-145-5p nucleic acid, an miR-338-3p nucleic acid, an miR-375 nucleic acid, or a mimic or mimetic thereof.

The foregoing and other features of the disclosure will become more apparent from the following detailed description, which proceeds with reference to the accompanying figures.

BRIEF DESCRIPTION OF THE DRAWINGS

FIGS. 2A and 2B are a pair of graphs showing 33 miRNAs that were identified as differentially expressed by SAMseq in both TCGA (FIG. 2A) and USMC (FIG. 2B) HNSCC tumor cohorts when compared with mucosa controls. For each, left: fold-change of median expression between tumor and mucosa, presented by linear scale. Right: box and whisker plot of median expression distribution of mucosa and tumor as log 10 RPM. Medians are represented by thick black lines in the middle, bars represent $25^{th}$ and $75^{th}$ percentile, and outliers are displayed as individual points. FDR≤0.05.

FIG. 3C is a graph showing anti-proliferative of miRNA mimics 96 hours after transfection in UM-SCC-1, presented as percentage of miRNA mimic control. FIG. 3D shows expression of hsa-miR-30-5p family members in mucosa and tumor specimens from the TCGA cohort. Bars represent SEM and * denotes (q<0.2 samseq tools). miR-30a-5p and miR-30e-5p are the highest expressed family members in mucosa specimens and display the greatest reduction in tumor specimens.

FIGS. 6A-6E are a series of panels showing validation of miR-30a predicted targets in HNSCC cell lines. FIG. 6A shows base pairing of miR-30a (SEQ ID NO: 1) with 3' UTR of target mRNAs EGFR (SEQ ID NO: 68), IGF1R (SEQ ID NO: 69), MET (SEQ ID NO: 70), and IRS-1 (SEQ ID NO: 71), predicted by Mfold (available on the World Wide Web at unafold.rna.albany.edu/?q=mfold). Bases in red depict binding of seed sequence. Underlined bases in mRNA were deleted in mutant 3' UTR control reporters. FIG. 6B shows relative luciferase activity measured 48 hours after co-transfection of UM-SCC-46 cells with miR30a or anti-30a and vector containing wild type 3' UTR (left) or mutant 3' UTR (right) cloned behind a Renilla luciferase gene. A positive control vector (Pos Con) containing 5×miR-30 binding sites and a negative GAPDH 3' UTR control are also displayed. All data represent the mean of three independent experiments and error bars represent SEM. (*) Denotes p-value <0.05 by student's T-test. FIGS. 6C and 6D are images of Western blots showing expression of miR-30 targets (FIG. 6C) and phosphorylation of downstream signaling molecules (FIG. 6D) using whole cell lysates from human oral keratinocytes (HOK) or UM-SCC-46 cells 72 hours after transfection with miR-30a, anti-30a, or negative control miR (NC) oligonucleotides. FIG. 6E is a graph showing protein levels of miR-30-5p targets analyzed from triplicate experiments.

FIG. 7A is a graph showing proliferation measured by XTT assay in 6 replicates at day 5 following transfection with control (NC) or miR-30a mimic across primary human oral keratinocytes (HOK) and ten HNSCC cell lines. FIG. 7B is a graph showing basal level of miR-30a expression measured by qRT-PCR in HOK cells and ten HNSCC cell line when in log growth phase. The relative miR-30a expression level was normalized to the mean expression of the cell lines.

FIG. 7C is a graph showing colony formation assay of UM-SCC-46 cells following 48 h transfection with miR-30a or anti-miR30a oligonucleotides. Colonies were counted in three wells and repeated in three independent experiments. FIG. 7D is a graph showing UM-SCC-46 cells transfected with miR-30a-5p mimic for 48 hrs, and treated with 2 µM cisplatin for 3 h and then washed. Cell density was measured by XTT assay 72 h after cisplatin treatment. The mean of at least three experiments±SEM, * denotes p<0.05 by a Student's t-test.

FIG. 7E is a graph of colony formation UM-SCC-46 cells following 48 hours transfection with miR30a and anti-miR-30a oligonucleotides. Colonies were counted in three wells and repeated in three independent experiments. FIG. 7F is a graph showing cell density of UM-SCC-46 cells transfected with miR-30a mimic for 48 hours and treated with 2 µM cisplatin for three hours and then washed away. Cell density was measured by XTT assay 72 hours after cisplatin treatment. All data represents the mean of at least three experiments and error bars represent SEM. FIG. 7G is a graph showing cell viability of UM-SCC-46 cells transfected with control (Neg con), miR-30a, or anti-miR-30a duplex. * p-value <0.05 by student's T-test.

FIG. 7H is a digital image showing representative images of colony formation assays with control, miR-30a-5p, or anti-30a transfections. FIG. 7I is a pair of graphs showing proliferation in UM-SCC-46 cells by an XTT assay in 6 replicates at days 0, 1, 3 and 5 following transfection with control, miR-30a-5p, or its anti-miR, or in combination with cisplatin treatment at the IC50 dose.

FIG. 8C is representative light microscopy images of invasion membranes (100×) for UM-SCC-1. FIG. 8D is a graph of relative quantitation of invading cells for UM-SCC-1 (left) and UM-SCC-46 (right). All data represents the mean of at least three experiments and error bars represent SEM. (*) Denotes p-value <0.05 by student's T-test.

FIGS. 9A-9E are a series of panels showing effect of miR-30a-5p mimic on in vivo HNSCC xenograft tumors. FIG. 9A is a series of images of tumors and organs from athymic nu/nu female mice intramuscularly injected with UM-SCC-46 cells. The tumors were grown to ~300 mm³, then the mice were injected intravenously (IV) with 100 µg (~5 mg/kg) of complexed FITC-labeled control oligonucleotide or control vehicle. 24 hours after injection, mice were sacrificed for tumor and organ harvest. FIG. 9B is a graph of tumor growth in mice bearing UM-SCC-46 xenograft tumors ~150 mm³ injected IV with nine doses of 60 µg (~3 mg/kg) of complexed miR-30a mimic packaged in nanoparticles (miR-30a-scL) or control on Monday, Wednesday, and Friday (MWF) for 3 weeks. The graph displays mean tumor volume for each group and error bars represent SEM. Representative images of tumor size at the end of treatment on day 24 are shown in FIG. 9C for a control and miR-30a-scL treated mouse (top) and mouse weight during treatment (bottom). FIG. 9D shows Kaplan-Meier survival analysis between mice treated with control or miR-30a-scL. FIG. 9E shows mean tumor volume in mice with HPV+UM-SCC-47 xenograft tumors grown to ~150 mm$^3$, and injected IV with four doses of 60 µg miR-30a-scL or control on MWF schedule. 24 hours after the last treatment, mice were sacrificed and tumor tissue collected for molecular analysis. Error bars represent SEM, and (*) Denotes p-value <0.05 by student's T-test.

FIGS. 11A-11F are a series of panels showing association of copy number variation (CNV), methylation, and expression of miR-30 family members with HNSCC clinical features. FIGS. 11A and 11B are Interactive Genome Viewer (IGV, Broad Institute) plots displaying frequency of homozygous and heterozygous deletions on chromosome locations that overlap with MIR30A/C2 (FIG. 11A) and MIR30E/C1 (FIG. 11B) genes. Blue represents reduced copy number and red represents increased copy number. Samples are ordered based on values for CNV. FIGS. 11C and 11D show HNSCC samples from TCGA (n=260) displayed in columns and sorted by DNA methylation of miR30A promoter (FIG. 11C) or CNV or miR30E (FIG. 11D). Clinical features (colored bars, top four rows) and genetic characteristics (heat maps, bottom three rows) are assorted accordingly. A significant correlation between CNV and expression of miR-30e-5p (FIG. 11E) and methylation and low expression of miR-30a-5p (FIG. 11F) was observed. Low expression of miR-30a-5p was significantly correlated with tumors occurring in the oral cavity, and low expression of miR-30e-5p was significantly correlated with HPV negative tumors occurring in the larynx.

FIGS. 12A and 12B are a series of Kaplan-Meier survival plots showing lower expression of miR-30e correlated with lower overall survival (FIG. 12 A, left), CNV loss of the MIR30E loci correlated with lower overall survival (FIG. 12A, middle), and survival analysis for tumors expressing low or high levels of miR-30e-5p occurring in oropharynx revealed a survival difference, whereby high expression of miR-30e-5p predicted better prognosis (FIG. 12A, right) and lower expression of miR-26a-5p (FIG. 12B, top) and miR-26b-5p (FIG. 12B, bottom) correlated with lower overall survival.

FIG. 14A shows tumor growth in control mice, mice treated with radiation therapy (RT), mice treated with miR-30a-scl, and mice treated with miR-30a-006-scl and radiation therapy (M006-scl+RT). FIG. 14B is a Kaplan-Meier survival plot in control, radiation treated (RT), M-miR-006 (M-006), M-006 plus radiation, and cisplatin treated mice.

SEQUENCE LISTING

Figure 1:
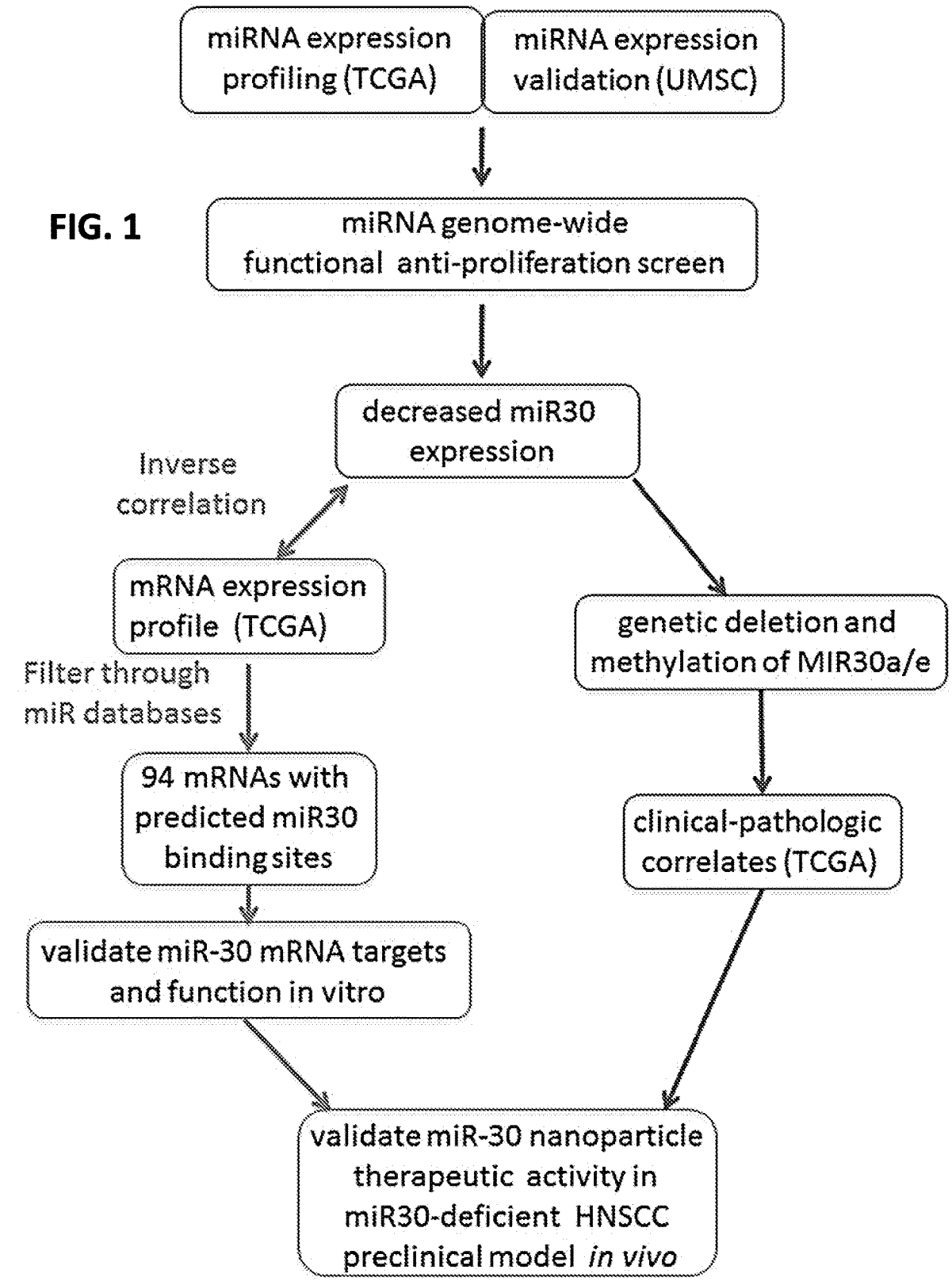
FIG. 1 is a diagram showing exemplary methods for screening and validation of miR-30 expression and function in HNSCC.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NOs: 1-36 are the nucleotide sequences of exemplary mature miRNAs.

SEQ ID NOs: 37-53 are modified miR-30a guide strand nucleotide sequences.

SEQ ID NOs: 54-61 are modified miR-30a passenger strand nucleotide sequences.

SEQ ID NOs: 62 and 63 are modified miR-375 guide and passenger strands, respectively.

SEQ ID NOs: 64 and 65 are modified miR-26a-5p guide and passenger strands, respectively.

SEQ ID NOs: 66 and 67 are modified miR-145-5p guide and passenger strands, respectively.

SEQ ID NO: 68 is an epidermal growth factor receptor (EGFR) 3' untranslated region (UTR) nucleotide sequence.

SEQ ID NO: 69 is an insulin growth factor-1 receptor (IGFR1) 3' UTR nucleotide sequence.

SEQ ID NO: 70 is a MET 3' UTR nucleotide sequence.

SEQ ID NO: 71 is an insulin receptor substrate 1 (IRS-1) 3' UTR nucleotide sequence.

SEQ ID NO: 72 is an exemplary miR-30a passenger strand nucleotide sequence.

SEQ ID NOs: 73-92 are additional exemplary modified miR-30a guide and passenger strands.

SEQ ID NOs: 93-104 are additional exemplary modified miR-375 guide and passenger strands.

SEQ ID NOs: 105-115 are additional exemplary modified miR-26 guide and passenger strands.

SEQ ID NOs: 116-125 are additional exemplary modified miR-145-5p guide and passenger strands.

SEQ ID NOs: 126-135 are additional exemplary modified miR-101 guide and passenger strands.

SEQ ID NOs: 136-146 are additional exemplary modified miR-29 guide and passenger strands.

SEQ ID NOs: 147-158 are additional exemplary modified miR-27 guide and passenger strands.

DETAILED DESCRIPTION

Genome-wide expression profiling studies have demonstrated broad deregulation and heterogeneity in mRNA and miR expression in primary tumors and cell lines. This underscores the complexity and challenge in identifying miRs and mRNAs of critical importance in the malignant phenotype and therapeutic resistance, from among hundreds of candidates. However, until the recent publication of the head and neck and pan-cancer analyses from The Cancer Genome Atlas (TCGA) (Cancer Genome Atlas Network Nature 517:576-582, 2015; Hoadley et al., Cell 158:929-944, 2014), comprehensive data from multiple platforms has not been available from such a large dataset to compare and identify the most significantly altered miRs, inversely expressed mRNAs, and contribution of genomic alterations driving their expression.

Alternatively, functional screens employing miR libraries have identified miRs contributing to different features of the malignant phenotype in HNSCC (Lindenbergh-van der Plas et al., Clin. Cancer Res. 19:5647-5657, 2013). However, prioritization has been difficult and many candidate miRs identified by expression profiling of tumors or in vitro screens often do not translate to therapeutic activity in vivo. Thus far, few tumor suppressive miRs driven by genetic and epigenetic alterations have been identified through integrated genomic and functional analyses. Even fewer miRs have been shown to regulate diverse mRNA programs, and implicated in the malignant phenotype, clinical features, or therapeutic resistance of HNSCC.

Disclosed herein are miRs that can be utilized to treat or inhibit cancer (for example, cancer where expression of one or more miRNAs is altered) and/or for diagnosis of cancer in a subject. To identify miRs of potential regulatory, biologic, and/or therapeutic importance in cancer, the inventors employed an integrated approach that combined structural and functional genomic analyses. The inventors compared analysis of expression of miRs and inversely correlated mRNAs from TCGA and a validation data set of HNSCC tumors, with functional screening for anti-proliferative miRs in vitro. Integration of data from TCGA from 279 HNSCC tumor specimens and the functional screen of a 781 miR library uncovered nine under-expressed and inhibitory miRs, of which four were members of the miR-30-5p family. In particular, the inventors determined that decreased miR-30a expression is inversely related to overexpression of a program of growth factor receptor, signaling and metastatic mRNAs implicated in the biology and clinical features of HNSCC. As disclosed herein, the role of miR-30-5p in tumor suppression was confirmed in regulation of several classical oncogenes centering on growth factor receptor tyrosine kinases, signaling, and metastasis. Finally, disclosed herein are synthetic miR-30a-5p mimic formulations which can delay tumor growth when delivered in xenograft tumor models of HNSCC.

I. Abbreviations

CNV copy number variation
HNSCC head and neck squamous cell carcinoma
miRNA or miR microRNA
RPM reads per million base pairs
RSEM RNA-Seq by Expectation Maximization
SCC squamous cell carcinoma
TCGA The Cancer Genome Atlas
XTT sodium 3'-[1-(phenylaminocarbonyl)-3,4-tetrazolium]-bis (4-methoxy-6-nitro) benzene sulfonic acid hydrate II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. The materials, methods and examples are illustrative only and not intended to be limiting.

In order to facilitate review of the various embodiments of this disclosure, the following explanations of specific terms are provided:

Altered expression: An alteration in expression of a miR nucleic acid refers to a change or difference, such as an increase or decrease, in the level of the miR nucleic acid that is detectable in a biological sample, for example relative to a control. An "alteration" in expression includes an increase in expression (up-regulation) or a decrease in expression (down-regulation). In some examples, the difference is relative to a control or reference value, such as an amount of microRNA expression in a sample from a healthy control subject or a population of healthy control subjects.

Cancer: A malignant neoplasm (e.g., a tumor) that has undergone characteristic anaplasia with loss of differentiation, increased rate of growth, invasion of surrounding tissue, and is capable of metastasis. Metastatic cancer is a cancer at one or more sites in the body other than the site of origin of the original (primary) cancer from which the metastatic cancer is derived. In some examples, cancer is a condition in which expression of one or more miRNAs is altered (for example, increased or decreased) in the neoplasm, compared to normal or healthy tissue of the same tissue type. Exemplary cancers include but are not limited to squamous cell carcinomas (such as HNSCC).

Control: A "control" refers to a sample or standard used for comparison with a test sample, such as a sample obtained from a healthy subject (or a population of healthy subjects). In some embodiments, the control is a sample obtained from a healthy subject (or a population of healthy subjects) or non-malignant tissue from the same subject and of the same histologic type as the cancer (also referred to herein as a "normal" control). In some embodiments, the control is a historical control or standard value (e.g., a previously tested control sample or group of samples that represent baseline or normal values, such as baseline or normal values in a healthy subject). In some examples the control is a standard value representing the average value (or average range of values) obtained from a plurality of samples (such as an average value or range of values of expression of one or more miR nucleic acids from normal subjects).

Effective amount: An amount of an agent (such as one or more miRNAs) that is sufficient to produce a desired response, such as reducing or inhibiting one or more signs or symptoms associated with a condition or disease. In some examples, an "effective amount" is an amount that treats or inhibits one or more signs or symptoms of a tumor. In some examples, an "effective amount" is a therapeutically effective amount in which the agent alone or with one or more additional therapies, induces the desired response, such as a decrease in size of a tumor in a subject, number of tumors in a subject, size or number of tumor metastases in a subject, and/or an increase in survival of a subject (such as disease-free survival, metastasis-free survival, or overall survival).

Isolated: An "isolated" biological component (such as a nucleic acid molecule, protein, or cell) has been substantially separated or purified away from other biological components (for example, in the cell or tissue of an organism, or the organism itself, in which the component naturally occurs, such as other chromosomal and extra-chromosomal DNA and RNA, proteins and cells). Nucleic acid molecules and proteins that have been "isolated" include those purified by standard purification methods. The term also embraces nucleic acid molecules (including microRNAs) and proteins prepared by recombinant expression in a host cell as well as chemically synthesized nucleic acid molecules and proteins.

microRNA (miRNA): Single-stranded, small non-coding RNA molecules that regulate gene expression. miRNAs are generally about 16-27 nucleotides in length. miRNAs typically modulate gene expression (e.g., increase or decrease translation) by promoting cleavage of target mRNAs or by blocking translation of the cellular transcript. miRNAs are processed from primary transcripts known as pri-miRNA to short stem-loop structures called precursor (pre)-miRNA and finally to functional, mature miRNA. Mature miRNA molecules are partially complementary to one or more messenger RNA molecules, and their primary function is to down-regulate gene expression. As utilized herein, "miR nucleic acid" or "miRNA nucleic acid" refers to any of a pri-miRNA, a pre-miRNA, an miRNA duplex, or a mature miRNA.

miRNA sequences are publicly available. For example, miRBase (mirbase.org) includes a searchable database of annotated miRNA sequences. miRNA sequences are also available through other databases known to one of ordinary skill in the art, including the National Center for Biotechnology Information (ncbi.nlm nih gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de). Based on miRNA sequences from one organism (such as mouse), one of ordinary skill in the art can utilize the available databases to determine a corresponding miRNA from another organism (such as human).

miRNA Mimic or Mimetic: An miRNA mimetic includes an miRNA has the same sequence as the native or wild type miRNA, but has a modified backbone, a modified base, and/or a 5' or 3' end modification. In some examples an miRNA mimetic is may less susceptible to degradation or nuclease activity. An miRNA mimic is an miRNA with at least one sequence modification and having 75% or higher sequence identity to a native or wild type miRNA and that also binds to the same mRNA(s) with similar affinity as the wild type or native miRNA. The disclosed miRNAs may also be both an miRNA mimetic and an miRNA mimic, for example, an miRNA with at least one sequence modification (e.g., 75% or higher sequence identity) to a wild type miRNA, and also having a modified backbone, base, and/or end modification.

Sample (or biological sample): A specimen containing DNA, RNA (including mRNA), protein, or combinations thereof, in some examples, obtained from a subject. Examples include, but are not limited to, peripheral blood, urine, saliva, tissue biopsy, fine needle aspirate, surgical specimen, and autopsy material. In some examples, a sample includes a tumor sample, such as a fresh, frozen, or fixed tumor sample.

Subject: Living multi-cellular vertebrate organisms, a category that includes human and non-human mammals (such as laboratory or veterinary subjects).

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and/or other genetic elements. An expression vector is a vector that contains the necessary regulatory sequences to allow transcription and translation of the inserted nucleic acid(s). In some embodiments herein, the vector is a plasmid vector. In other embodiments, the vector is a viral vector.

III. miRNAs

Disclosed herein are miRNAs that are differentially regulated in cancers, including but not limited to squamous cell tumors. These miRNAs can be utilized in methods for treating tumors, and may also be used in diagnostic methods. Also disclosed are modified miRNAs that can also be utilized in compositions and methods of treatment.

miRNAs are small non-coding RNA molecules that regulate gene expression. Mature miRNAs are generally about 17-25 nucleotides in length. miRNAs typically modulate gene expression (e.g., increase or decrease translation) by promoting cleavage of target mRNAs or by blocking translation of the cellular transcript. miRNAs are processed from primary transcripts known as "pri-miRNA" to short stem-loop structures called "precursor (pre)-miRNA." The pre-miRNA is processed to an miRNA duplex and finally to functional, mature single-stranded miRNA. During processing of the miRNA duplex, one strand (referred to as the "passenger" strand) is degraded, while the other strand (the "guide" strand) is the mature miRNA molecule. Mature miRNA molecules are partially complementary to one or more messenger RNA molecules, and their primary function is to down-regulate gene expression. As disclosed herein, an miRNA nucleic acid includes precursor miRNAs, as well as processed or mature miRNA nucleic acids. For example, an miRNA nucleic acid may be a pri-miRNA, a pre-miRNA, an miRNA duplex, or a mature miRNA nucleic acid.

miRNA sequences are publicly available. One of ordinary skill in the art can identify miRNA precursors, as well as processed or mature miRNAs, for example, utilizing publicly available databases. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de). Based on miRNA sequences from one organism (such as mouse), one of ordinary skill in the art can utilize the available databases to determine a corresponding miRNA from another organism (such as human).

In some examples, microRNA functions by activating cleavage or destabilization of a target mRNA or non-coding RNA, which can be detected by RT-PCR, is situ hybridization, FRET, northern blot, or sequencing. It may also function by inhibiting translation of a target mRNA into a protein, which may be detected by Western blot, immune blotting, florescence polarization assay, enzyme activity assay, FRET, immunofluorescence, immunohistochemistry, ELISA, or mass spectrometry. The resulting change in expression of targeted mRNAs or non-coding RNA may result in repression of a number of cancer relevant phenotypes including cell proliferation, resisting cell death, pro-inflammatory processes, increased migration and invasion, angiogenesis, evasion of immune destruction, replicative immortality, decreased genome stability, deregulated cellular energetics, and/or deregulation of epigenetic processes which effect tumor growth and progression.

In some examples, the miRNA nucleic acids of use in the compositions and methods disclosed herein include the mature miRNAs listed in Table 1. In other examples, the miRNA nucleic acids include those with at least 75% sequence identity to those listed in Table 1 (e.g., miRNA mimics), as long as such modified miRNAs retain one or more functions of the unmodified miRNA. For example, the miRNA nucleic acid includes or consists of a nucleic acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% 99%, or 100% identical to the nucleic acid sequence of one of the miRNAs listed in Table 1. Additional miRNA nucleic acids of use in the disclosed compositions and methods include the modified miRNAs (including guide and/or passenger strands) shown in Tables 18, 20, 21, and 23, or miRNAs with at least 75% sequence identity (for example, at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to those shown in Tables 18, 20, 21, and 23 (e.g., miRNA mimetics and/or mimics), as long as such modified miRNAs retain one or more functions of the unmodified miRNA. In some examples, the miRNAs with at least 75% sequence identity to those shown in Table 1, Table 18, Table 20, Table 21, or Table 23 include at least one (such as 1, 2, 3, 4, 5, 6, 7, 8, 9, 10, or more) non-naturally occurring nucleotide.

TABLE 1

Exemplary mature human miRNAs differentially expressed in tumors

| Human miRNA | Sequence | SEQ ID NO: |
|---|---|---|
| hsa-miR-30a-5p | UGUAAACAUCCUCGACUGGAAG | 1 |
| hsa-miR-30b-5p | UGUAAACAUCCUACACUCAGCU | 2 |
| hsa-miR-30c-5p | UGUAAACAUCCUACACUCUCAGC | 3 |
| hsa-miR-30d-5p | UGUAAACAUCCCCGACUGGAAG | 4 |
| hsa-miR-30e-5p | UGUAAACAUCCUUGACUGGAAG | 5 |
| hsa-miR-30a-3p | CUUUCAGUCGGAUGUUUGCAGC | 6 |
| hsa-miR-30b-3p | CUGGGAGGUGGAUGUUUACUUC | 7 |
| hsa-miR-30c-1-3p | CUGGGAGAGGGUUGUUUACUCC | 8 |
| hsa-miR-30c-2-3p | CUGGGAGAAGGCUGUUUACUCU | 9 |
| hsa-miR-30d-3p | CUUUCAGUCAGAUGUUUGCUGC | 10 |
| hsa-miR-30e-3p | CUUUCAGUCGGAUGUUUACAGC | 11 |
| hsa-miR-26a-5p | UUCAAGUAAUCCAGGAUAGGCU | 12 |
| hsa-miR-26a-1-3p | CCUAUUCUUGGUUACUUGCACG | 13 |
| hsa-miR-26a-2-3p | CCUAUUCUUGAUUACUUGUUUC | 14 |
| hsa-miR-26b-5p | UUCAAGUAAUUCAGGAUAGGU | 15 |
| hsa-miR-26b-3p | CCUGUUCUCCAUUACUUGGCUC | 16 |
| hsa-miR-375 | UUUGUUCGUUCGGCUCGCGUGA | 17 |
| hsa-miR-145-5p | GUCCAGUUUUCCCAGGAAUCCCU | 18 |
| hsa-miR-145-3p | GGAUUCCUGGAAAUACUGUUCU | 19 |
| hsa-miR-338-5p | AACAAUAUCCUGGUGCUGAGUG | 20 |
| hsa-miR-338-3p | UCCAGCAUCAGUGAUUUUGUUG | 21 |
| hsa-miR-205-5p | UCCUUCAUUCCACCGGAGUCUG | 22 |
| hsa-miR-205-3p | GAUUUCAGUGGAGUGAAGUUC | 23 |
| hsa-miR-29a-3p | UAGCACCAUCUGAAAUCGGUUA | 24 |
| hsa-miR-29b-3p | UAGCACCAUUUGAAAUCAGUGUU | 25 |

TABLE 1-continued

Exemplary mature human miRNAs differentially expressed in tumors

| Human miRNA | Sequence | SEQ ID NO: |
|---|---|---|
| hsa-miR-29c-3p | UAGCACCAUUUGAAAUCGGUUA | 26 |
| hsa-miR-29a-5p | ACUGAUUUCUUUUGGUGUUCAG | 27 |
| hsa-miR-29b-1-5p | GCUGGUUUCAUAUGGUGGUUUAGA | 28 |
| hsa-miR-29b-2-5p | CUGGUUUCACAUGGUGGCUUAG | 29 |
| hsa-miR-29c-5p | UGACCGAUUUCUCCUGGUGUUC | 30 |
| hsa-miR-27a-5p | AGGGCUUAGCUGCUUGUGAGCA | 31 |
| hsa-miR-27a-3p | UUCACAGUGGCUAAGUUCCGC | 32 |
| hsa-miR-27b-5p | AGAGCUUAGCUGAUUGGUGAAC | 33 |
| hsa-miR-27b-3p | UUCACAGUGGCUAAGUUCUGC | 34 |
| hsa-miR-101-5p | CAGUUAUCACAGUGCUGAUGCU | 35 |
| hsa-miR-101-3p | UACAGUACUGUGAUAACUGAA | 36 |

In additional examples, an miRNA nucleic acid includes an miRNA nucleic acid that is slightly longer or shorter than the nucleotide sequence of any one of the miRNA nucleic acids disclosed herein (such as SEQ ID NOs: 1-67 or 72 or 73-158), as long as the miRNA nucleic acid retains a function of the particular miRNA, such as hybridization to an miRNA target sequence or formation of an miRNA duplex. For example, an miRNA nucleic acid can include a few nucleotide deletions or additions at the 5'- or 3'-end of the nucleotide sequence of an miRNA described herein, such as addition or deletion of 1, 2, 3, 4, or more nucleotides from the 5'- or 3'-end, or combinations thereof (such as a deletion from one end and an addition to the other end). In particular examples, modified miRNAs described herein include addition of one or more nucleotides at the 3' end, such as addition of one or more nucleotides (for example, 1, 2, 3, or more nucleotides) at the 3' end of an miRNA passenger strand.

Also provided by the present disclosure are miRNAs that include variations to the miRNA sequence (such as a variation of the sequence shown in any of SEQ ID NOs: 1-67 or 72 or 73-158), as long as such modified miRNAs retain one or more functions of the unmodified miRNA. In some examples, the modifications provide increased stability of a guide strand-passenger strand duplex. In some examples, the modifications include substitutions at one or more nucleotides (such as 1, 2, 3, 4, 5, or more nucleotides) in an miRNA. In particular examples, the modifications include substitution of one or more of positions 1, 6, and 20 of an miR-30 passenger strand (such as miR-30a-5p).

Also provided are miRNA mimetics, such as miRNA nucleic acids that include one or more modified nucleotides or nucleic acid analogs. In some embodiments, the isolated miRNA includes at least one nucleobase modification, for example to increase nuclease resistance, enhance half-life and/or improve efficacy. Nucleobase modifications suitable for application to microRNAs are well known in the art (see, for example, U.S. Patent Application Publication Nos. 2010/0298407; 2007/0213292; 2006/0287260; 2006/0035254; 2006/0008822; and 2005/0288244).

In some examples (for example, to increase nuclease resistance and/or binding affinity to a target nucleic acid molecule), an miRNA of the disclosure includes 2'-O-methyl, 2'-fluorine, 2'-O-methoxyethyl, 2'-O-aminopropyl, 2'-amino sugar modifications and/or phosphorothioate linkages. Inclusion of locked nucleic acids (LNA), ethylene nucleic acids (ENA) (e.g., 2'-4'-ethylene-bridged nucleic acids) and certain nucleobase modifications can also increase binding affinity to the target. The inclusion of pyranose sugars in the oligonucleotide backbone can also decrease endonucleolytic cleavage. Additional modifications include morpholinos, peptide nucleic acids (PNA), unlocked nucleic acids (UNA), α-L-LNA, 4'-C-hydroxymethyl-DNA, 2'-N-adamantylmethylcarbonyl-2'-amino-LNA, 2'-N-pyren-1-ylmethyl-T-amino-LNA, ET-aminoethyl, T-guanidinoethyl, T-cyanoethyl, T-aminopropyl, oxetane-LNA, T,4'-carbocyclic-LNA-locked nucleic acid, T,4'-carbocyclic-ENA-locked nucleic acid, T-deoxy-T-N,4'-C-ethylene-LNA, altritol nucleic acid, hexitol nucleic acid, T-aminoethoxymethyl, and T-aminopropoxymethyl.

Additional miRNA mimetics include miRNAs with modified backbones or non-natural internucleoside linkages. Oligomers having modified backbones include those that retain a phosphorus atom in the backbone and those that do not have a phosphorus atom in the backbone. Modified oligonucleotides that do not have a phosphorus atom in their internucleoside backbone are generally referred to in the art as nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriesters, and boranophosphates. Various salts, mixed salts and free acid forms are also included.

miRNAs having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other examples, the modified miRNAs (e.g., miRNA mimetics) include one or more substituted sugar moieties. Such modifications include 2'-O-methyl, 2'-methoxyethoxy, 2'-dimethylaminooxyethoxy, 2'-aminopropoxy, and 2'-fluoro modifications. Modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar.

In further examples, a modified miRNA (e.g., an miRNA mimetic) includes a modification at the 5' or 3' end. Such modifications include a primary amino group (for example, with a carbon spacer, such as amino-C3, amino-C6, or amino-C12) at the 5' end of the miRNA. Additional end modifications include UNAs, methylphosphonate, phosphithorate, an inverted base, or an N-methyl-G cap.

In other embodiments, the miRNA includes two or more modifications, such as two or more modifications selected from a base substitution, a modification at an internucleoside linkage, a modified sugar, or a modification at the 5' and/or 3' end. For duplex miRNA molecules, the modification(s) may be present on the guide strand, the passenger strand, or both.

In some examples, the modified (e.g., mimic or mimetic) miRNA nucleic acids disclosed herein include a 5' end amino modification, such as a 5'-amino C6 modification (such as a 5'-amino C6 modified passenger strand). In other examples, the modified (e.g., mimic or mimetic) miRNA nucleic acid includes one or more nucleotides (such as 1, 2, 3, 4, 5, 6, 7, 8, or more nucleotides) with a 2' modification (such as 2'-O-Me). The 2' modified nucleotides may be internal to the miRNA (none of the modifications are on the 5' or 3' end nucleotide) or may include the 5' and/or 3' end nucleotides. In some examples, an miRNA guide strand includes one or more nucleotides (such as 3-10, 4-9, or 5-8 nucleotides) having a 2' modification. In specific examples, a guide strand includes 2' modifications on one or more internal nucleotides, and in some examples, not on a 5' or 3' end nucleotide. In other examples, an miRNA passenger stand includes one or more nucleotides (such as 3-10, 4-8, or 5-7 nucleotides) having a 2' modification. In specific examples, a passenger strand includes 2' modifications on a 5' or 3' end nucleotide, but may also include 2' modification of one or more internal nucleotides. In particular, non-limiting examples, modified miRNAs include those shown in Tables 18, 20, 21, and 23, below.

In some embodiments, the disclosed miRNA nucleic acids or modified (e.g., mimetic or mimic) miRNA nucleic acids are associated with a detectable label. In some examples, the miRNA nucleic acid is conjugated to a fluorescent label (such as fluorescein isothiocyanate, coumarin, Cy3, Cy5, Cy7, or Alexa Fluor® dyes), a hapten (such as digoxigenin or Myc), or a radioactive label. In other embodiments, the miRNA nucleic acid is associated with a peptide or protein (for example, to facilitate targeted delivery), such as tat, MACV GP1, folate receptor, or penetratin. One of skill in the art can select additional detectable labels or peptides depending on the particular circumstances.

IV. Methods and Compositions for Treating or Inhibiting Cancer

Disclosed herein are miRNAs that are differentially expressed in tumors. These miRNAs can be utilized in methods to treat or inhibit cancer in a subject. Thus, disclosed herein are methods of treating or inhibiting cancer in a subject that include administering to the subject an effective amount of one or more miRNAs. In particular examples, the methods include administering to a subject with cancer one or more miRNAs that are down-regulated in a tumor to a subject with a tumor (such as a squamous cell carcinoma).

In some embodiments, the methods include administering to a subject with a tumor an effective amount of at least one isolated miR-30 nucleic acid (such as a miR-30a-5p, miR-30b-5p, miR-30c-5p, miR-30d-5p, or miR-30e-5p nucleic acid) or a mimic or mimetic thereof, or a vector encoding the miR-30 nucleic acid or a mimic or mimetic thereof. Specific non-limiting examples of miR-30 nucleic acids includes SEQ ID NOs: 1-11 and 66 disclosed herein. In additional examples, the methods include administering to a subject with a tumor an effective amount of a variant or modified (e.g., a mimic or mimetic) miR-30 nucleic acid. The modified miR-30 nucleic acid may be administered as an miR-30 duplex including a guide strand and a passenger strand, for example selected from SEQ ID NOs: 37-61 and 73-92. In particular non-limiting examples, a modified miR-30 nucleic acid includes an miR-30 duplex including SEQ ID NOs: 41 and 55, an miR-30 duplex including SEQ ID NOs: 42 and 56, an miR-30 duplex including SEQ ID NOs: 42 and 57, an miR-30 duplex including SEQ ID NOs: 50 and 61, an miR-30 duplex including SEQ ID NOs: 73 and 61, or an miRNA duplex including SEQ ID NOs: 74 and 61. Additional examples of modified miR-30 duplexes include those in Tables 19 and 22, below.

In further embodiments, the methods include administering to a subject with a tumor an effective amount of one or more of an isolated miR-30 (such as a miR-30a-5p, miR-30b-5p, miR-30c-5p, miR-30d-5p, and/or miR-30e-5p), miR-26a-5p, miR-26b-5p, miR-375, miR-145-5p, miR-338-3p, miR-27, miR-29, or miR-101 nucleic acid, a mimic or mimetic of any thereof, or a combination of any two or more thereof, including one or more duplex miR nucleic acids or vectors encoding the miR nucleic acid(s). The modified miR nucleic acid may be administered as an miR duplex including a guide strand and a passenger strand, for example selected from SEQ ID NOs: 62-67 and 93-158.

In particular examples, the methods include administering to a subject with a tumor an effective amount of a combination of miR-30, miR-145, miR-26a, and miR-375 nucleic acids. In a specific non-limiting example, the methods include administering to the subject a combination of miR-30a-014 (SEQ ID NOs: 41 and 55), miR-145, miR-26a, and miR-375. In further examples, the methods include administering at least 2 (for example, at least 2, at least 3, at least 4, at least 5, at least 6, at least 7, at least 8, at least 9, at least 10, or more) miRNAs from any one of Tables 1, 3, 4, 5, 18, 20, 21, and 23 (such as 2-10, 4-20, 6-30, 10-50, or more). The miRNAs may be administered as single-stranded miR nucleic acids, duplex miR nucleic acids (such as a duplex of a guide strand and a passenger strand), or vectors including miR nucleic acids.

In other examples, the methods include administering to a subject with a tumor an effective amount of two or more miR-30, miR-145, miR-375, and miR-26a nucleic acids. In some examples, the methods include administering to the subject an miR-30 nucleic acid (such as an miR-30a-5p nucleic acid or a modified miR-30a nucleic acid, such as those in Tables 18, 19, and 21) and an miR-145 nucleic acid. In other examples, the methods include administering to the subject an miR-145 nucleic acid and an miR-375 nucleic acid. In further examples, the methods include administering to the subject an miR-30 nucleic acid (such as an miR-30a-5p nucleic acid or a modified miR-30a nucleic acid, such as those in Tables 18 and 19) and an miR-375 nucleic acid. In some examples, the methods include administering to the subject an miR-145 nucleic acid and an miR-26a nucleic acid. In additional examples, the methods include administering to the subject an miR-26a nucleic acid and an miR-375 nucleic acid. In other examples, the methods include administering to the subject an miR-30 nucleic acid (such as an miR-30a-5p nucleic acid or a modified miR-30a nucleic acid, such as those in Tables 18 and 19) and an miR-26a nucleic acid.

The disclosed methods can be used to treat or inhibit a cancer in a subject. Exemplary cancers include Acute Lymphoblastic Leukemia (ALL), Acute Myeloid Leukemia (AML), Cancer in Adrenocortical carcinoma, AIDS-Related Cancers (e.g., Kaposi Sarcoma, AIDS-Related Lymphoma, Primary CNS Lymphoma), Anal Cancer, Appendix Cancer, Astrocytomas, Atypical Teratoid/Rhabdoid Tumor, Basal Cell Carcinoma, Bile Duct Cancer, Bladder Cancer, Bone Cancer (e.g., Ewing Sarcoma Family of Tumors, Osteosarcoma and Malignant Fibrous Histiocytoma), Brain Tumor (e.g., Astrocytomas, Brain Stem. Glioma, Central Nervous System Atypical Teratoid/Rhabdoid Tumor, Central Nervous System Embryonal Tumors, Central Nervous System Germ Cell Tumors, Craniopharyngioma, Ependymoma), Breast Cancer, Bronchial Tumors, Burkitt Lymphoma, Carcinoid Tumor, Cardiac (Heart) Tumors, Central Nervous System (e.g., Atypical Teratoid; Rhabdoid Tumor, Embryonal Tumors, Germ Cell Tumor, Lymphoma, Primary), Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Cutaneous T-Cell Lymphoma, Ductal Carcinoma In Situ (DCIS), Endometrial Cancer, Ependymoma, Esophageal Cancer, Esthesioneuroblastoma, Ewing Sarcoma, Extracranial. Germ Cell Tumor, Extragonadal Germ Cell Tumor, Eye Cancer (e.g., Intraocular Melanoma, Retinoblastoma), Fallopian Tube Cancer, Gallbladder Cancer, Gastric Cancer, Gastrointestinal Carcinoid Tumor, Gastrointestinal Stromal Tumors (GIST), Germ Cell Tumor (e.g., Extracranial, Extragonadal, Ovarian, Testicular), Gestational Trophoblastic Disease, Glioma, Hairy Cell Leukemia, Head and Neck Cancer, Heart Cancer, Hepatocellular Cancer, Hodgkin Lymphoma, Hypopharyngeal Cancer, Islet Cell Tumors, Pancreatic Neuroendocrine Tumors, Kaposi Sarcoma, Kidney (e.g., Renal Cell, Wilms Tumor), Langerhans Cell Histiocytosis, Laryngeal Cancer, Hairy Cell Leukemia, Lip and Oral Cavity Cancer, Liver Cancer, Lung Cancer (e.g., Non-Small Cell, Small Cell), Lymphoma (e.g., AIDS-Related, Burkitt, Cutaneous T-Cell, Hodgkin, Non-Hodgkin, Primary Central Nervous System), Waldenstrom Macroglohulinemia, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Multiple Myeloma, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oropharyngeal Cancer, Ovarian Cancer (e.g., Epithelial, Germ Cell Tumor, Low Malignant Potential Tumor), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasnalultiple Myeloma, Pleuropulmonary Blastoma, Primary Central Nervous System (CNS) Lymphoma, Primary Peritoneal Cancer, Prostate Cancer, Rectal Cancer, Retinoblastoma, Rhabdomyosarcoma, Salivary Gland Cancer, Sarcomas (e.g., Ewing Sarcoma, Kaposi, Osteosarcoma, Rhabdomyosarcoma, Soft Tissue Sarcoma, Uterine Sarcoma, Vascular Tumors), Sezary Syndrome, Skin Cancer (e.g., Melanoma, Merkel Cell. Carcinoma, Nonmelanoma), Small Intestine Cancer, Squamous Cell Carcinoma, Stomach Cancer, T-Cell Lymphoma, Cutaneous, Testicular Cancer, Throat Cancer, Thymoma and Thymic Carcinoma, Thyroid Cancer, Unknown Primary Carcinoma, Unusual Cancers of Childhood, Urethral Cancer, Uterine Cancer, Uterine Sarcoma, Vaginal Cancer, Vascular Tumors, Vulvar Cancer, or Wilms Tumor.

In some non-limiting embodiments, the methods include treating or inhibiting a squamous cell carcinoma (SCC), such as head and neck squamous cell carcinoma, lung squamous cell carcinoma, or cervical squamous cell carcinoma. SCC is a cancer of the carcinoma type that may occur in many different organs, including the skin, lips, mouth, esophagus, urinary bladder, prostate, lungs, vagina, and cervix. It is a malignant tumor of squamous epithelium (epithelium that shows squamous cell differentiation). In some examples, the tumor is a HNSCC, for example, oral squamous carcinoma (such as tumors of the lip, tongue, hard palate, floor of mouth, or buccal mucosa), oropharyngeal squamous carcinoma (such as tumors of the soft palate, base of the tongue, or tonsillar region), hypopharyngeal squamous carcinoma (such as tumors of the pyriform sinus, posterior pharyngeal wall, or postcricoid region), nasopharyngeal squamous carcinoma (such as tumors of the maxillary antrum), or laryngeal squamous carcinoma. In other examples, the tumor is a lung SCC or cervical SCC. In further examples, the tumor is a squamous cell carcinoma of the thyroid, esophageal SCC, squamous cell carcinoma of the skin, squamous cell carcinoma of the breast, or squamous cell carcinoma of the urinary bladder.

In further non-limiting embodiments, the methods include treating or inhibiting cervical adenocarcinoma, colorectal carcinoma, prostate carcinoma, breast adenocarcinoma, or pancreatic carcinoma.

In some embodiments, a subject is administered an effective amount of a composition including one or more miRNAs or modified miRNAs disclosed herein. Pharmaceutical compositions that include one or more of the miRNAs disclosed herein (such as 2, 3, 4, 5, or more miRNAs) can be formulated with an appropriate solid or liquid carrier, depending upon the particular mode of administration chosen. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

One skilled in the art can readily determine an effective amount of a disclosed miR nucleic acid (or combination of miR nucleic acids) to be administered to a subject, for example, taking into account factors such as the type of tumor being treated, the extent of disease progression, the age, health and sex of the subject, the size (e.g., weight and/or height) of the subject, and the route of administration. For example, the effective amount can be based on the approximate body weight of a subject to be treated. Such effective amounts can be administered by any suitable route. In some examples, an effective amount of an miR nucleic acid (or combination of miR nucleic acids) administered to a subject ranges from about 5 µg/kg to about 100 mg/kg of body weight, such as about 100 µg/kg to about 10 mg/kg, about 1 mg/kg to about 25 mg/kg, about 20 mg/kg to about 40 mg/kg, about 30 mg/kg to about 50 mg/kg, or about 40 mg/kg to about 100 mg/kg. In one non-limiting example, the amount administered is about 5 mg/kg of an miR nucleic acid (or a combination of miR nucleic acids).

In some embodiments, the compositions are administered in unit dosage form, for example, suitable for individual administration of particular doses. In some examples, a unit dosage contains from about 1 mg to about 5 g of one or more miR nucleic acid molecules (such as about 5 mg to about 50 mg, about 10 mg to about 200 mg, about 100 mg to about 2.5 g, about 250 mg to about 1 g, or about 500 mg to about 5 g). In some examples, a unit dosage contains about 1 mg, 5 mg, 10 mg, 25 mg, 50 mg, 100 mg, 250 mg, 500 mg, 750 mg, 1 g, 1.5 g, 2 g, 2.5 g, 3 g, 4 g, or 5 g of one or more miR nucleic acids.

One skilled in the art can also readily determine an appropriate dosage regimen for the administration of a disclosed miR nucleic acid (or combination of miR nucleic acids) to a subject. For example, the miR nucleic acid(s) can be administered to the subject once (e.g., as a single injection or deposition) or in repeated doses. In some examples, the miR nucleic acid (or combination of miR nucleic acids) is administered once or twice daily, twice per week, three times per week, weekly, biweekly, or monthly for an extended period of time as needed to achieve a desired therapeutic outcome (such as a decrease in one or more signs or symptoms of a tumor). In other examples, the miR nucleic acid(s) are administered in a continuous manner (for example using a pump, implant, or continuous release formulation).

Therapeutic agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral, or by gene gun. Intranasal administration refers to delivery of the compositions into the nose and nasal passages through one or both of the nares and can comprise delivery by a spraying mechanism or droplet mechanism, or through aerosolization of the nucleic acid. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local. In particular, non-limiting examples, administration is intravenous. In other examples, administration is subcutaneous, intramuscular, or intraperitoneal. One of skill in the art can select an appropriate route of administration, depending on the therapeutic agent(s), the condition being treated, the health and treatment history of the subject, and other relevant clinical factors.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some embodiments, liposomes are used to deliver a disclosed miR nucleic acid or combination of miR nucleic acids to a subject. Liposomes can also increase the blood half-life of the gene products. Suitable liposomes for use in the compositions and methods disclosed herein can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. In a particular example, liposomes are formed with one or more disclosed miR nucleic acids and cationic lipids, such as dioleoyltrimethylammonium phosphate (DOTAP) and dioleoylphosphatidylethanolamine (DOPE).

A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a miR nucleic acid to a subject. Cationic lipids and polymers that can be used to deliver therapeutic RNA molecules have been described (see, for example, Zhang et al., *J Control Release.* 123(1): 1-10, 2007; Vorhies et al., *Methods Mol. Biol.* 480:11-29, 2009; and U.S. Patent Application Publication No. 2009/0306194). In some examples, the liposome further includes a molecule that increases targeting of the complex to a tumor, for example a molecule that binds to the transferrin receptor (such as an anti-transferrin receptor antibody or a fragment thereof). In one example, the liposome includes an anti-transferrin receptor single chain antibody fragment (see for example, Pirollo et al., *Hum. Gene Ther.* 17:117-124, 2006; Pirollo et al., *Cancer Res.* 67:2938-2943, 2007). Additional targeting molecules include folate receptor, EGFR, MET, ROR1, GLUT1, Cadherin, CD44, PSMA, and MAGE. Polypeptide carriers can also be used to administer an miR nucleic acid to a subject (see, for example, Rahbek et al., *J. Gene Med.* 10:81-93, 2008). One of skill in the art can identify additional targeting molecules or polypeptide carriers.

In some embodiments, the method includes administering a vector encoding one or more of the disclosed miRNA nucleic acids or a mimic or mimetic thereof (such as any of SEQ ID NOs: 1-67 and 72, 73-158, or a mimic and/or mimetic thereof). Vectors for use in the disclosed methods can be of non-viral (for example, plasmids) or viral (for example, adenovirus, adeno-associated virus, retrovirus, herpes virus, vaccinia virus) origin. Suitable vectors, such as gene therapy vectors, are well known in the art.

In some examples, the miRNA nucleic acid is expressed from recombinant circular or linear DNA plasmids using any suitable promoter. Suitable promoters for expressing RNA from a plasmid include, for example, the U6 or H1 RNA pol III promoter sequences, a cytomegalovirus promoter, an SV40 promoter or metallothionein promoter. Selection of other suitable promoters is within the skill in the art. The recombinant plasmids can also comprise inducible or regulatable promoters for expression of the miR gene products.

In one non-limiting embodiment, the miRNA nucleic acid is expressed as an RNA precursor molecule from a plasmid, and the precursor molecule is processed into a functional or mature miRNA within the target cell. Selection of plasmids suitable for expressing the miRNAs, methods for inserting nucleic acid sequences into the plasmid to express the gene products, and methods of delivering the recombinant plasmid to the cells of interest are within the skill in the art (see, for example, Zeng et al., *Mol. Cell* 9:1327-1333, 2002; Tuschl, *Nat. Biotechnol.*, 20:446-448, 2002; Brummelkarnp et al., *Science* 296:550-553, 2002; Miyagishi et al., *Nat. Biotechnol.* 20:497-500, 2002; Paddison et al., *Genes Dev.* 16:948-958, 2002; Lee et al., *Nat. Biotechnol.* 20:500-505, 2002; and Paul et al., *Nat. Biotechnol.* 20:505-508, 2002). The present disclosure also includes methods of treating a subject with combinations of one or more of the miRNA nucleic acids in combination with one or more other agents useful in the treatment of a cancer. For example, the compounds of this disclosure can be administered in combination with effective doses of one or more tumor therapies, including but not limited to, surgery, chemotherapeutic agent(s), radiation, gene therapy, hormone therapy, immunotherapy, and antisense oligonucleotide therapy. A skilled clinician can select an appropriate combination of therapies based on the type of tumor being treated, the subject's clinical history, overall condition, and other factors. The term "administration in combination" or "co-administration" refers to both concurrent and sequential administration of the active agents or therapies.

Chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and thioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

In a particular example, if the subject has HNSCC, the chemotherapeutic agent includes cisplatin, carboplatin, cetuximab, bevacizumab, erlotinib, bleomycin, paclitaxel/carboplatin or a combination of two or more thereof. In another example, if the subject has lung SCC, the chemotherapeutic agent includes cisplatin or carboplatin, alone or in combination with etoposide, gemcitabine, paclitaxel, vinorelbine, topotecan, or irinotecan. One of skill in the art can select appropriate additional treatments (such as chemotherapy) based on factors such as the type of cancer, the stage of cancer, molecular profile of the cancer, and the health and treatment history of the subject.

V. Methods of Diagnosing Tumors

Disclosed herein are methods of diagnosing a tumor in a subject. In some examples, the methods include identifying a tumor in a subject by detecting a change in amount of one or more miRNAs (such as an increase or decrease) in a sample from the subject, for example compared to a control. In some examples, the methods further include administering a treatment to a subject diagnosed as having a tumor. In one example, the subject is diagnosed as having a tumor that expresses a decreased amount of one or more miRNAs (for example as compared to a control) and a composition including an effective amount of the one or more miRNAs with decreased expression is administered to the subject.

Samples used in the methods described herein, such as a tissue or other biological sample, can be prepared using any method known in the art. Samples include any solid or fluid sample obtained from, excreted by or secreted by a subject. For example, a sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A sample can also be a sample obtained from any organ or tissue (including a biopsy or autopsy specimen, such as a tumor biopsy) or can include a cell (whether a primary cell or cultured cell) or medium conditioned by any cell, tissue or organ. In particular embodiments, the sample includes a tumor sample or a blood sample. The samples can be obtained from subjects for routine screening or from subjects that are suspected of having a disorder, such as a tumor.

In some embodiments, the methods include detecting an amount of one or more of miR-30 (such as miR-30a-5p, miR-30b-5p, miR-30c-5p, miR-30d-5p, or miR-30e-5p), miR-26a-5p, miR-26b-5p, miR-145-5p, miR-338-3p, miR-375, miR-27, miR-29, or miR-101 in a sample from a subject (such as a tumor sample from the subject). In other embodiments, the methods include detecting an amount of one or more miRNAs listed in Tables 1, 3, 4, 5, 18, and 20, below. In particular examples, the methods include detecting expression of either a mature form of the miR or a precursor form (e.g., a pri-miRNA or pre-miRNA) of the miR. Typically, miR detection methods involve sequence specific detection, such as by RT-PCR or microarray analysis. miR-specific primers and probes can be designed using the precursor and mature miR nucleic acid sequences that are known in the art (e.g., available on the World Wide Web at mirbase.org).

In some embodiments of the methods, the change in expression (e.g., a statistically significant increase or decrease in expression) of one or more miR nucleic acids is at least 2-fold, such as at least 3-fold, at least 4-fold, at least 5-fold, at least 10-fold, including about 3-fold, about 4-fold, about 5-fold, about 6-fold, about 7-fold, about 8-fold, about 9-fold, about 10-fold, about 30-fold, and about 100-fold in a sample from the subject. In some examples, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include a sample obtained from a healthy subject (or a population of healthy subjects) or a historical control or standard value (e.g., a previously tested control sample or group of samples that represent baseline or normal values, such as baseline or normal values in a healthy subject). In some examples the control is a standard value representing the average value (or average range of values) obtained from a plurality of samples (such as an average value or range of values of expression of one or more miR nucleic acids from normal subjects).

In some embodiments, the methods further include providing an appropriate therapy for the subject diagnosed with a tumor. In some examples, the therapy includes administering an agent that inhibits expression of one or more miRNA nucleic acids, such as an agent that inhibits a miR nucleic acid identified as up-regulated in a sample from a subject relative to a control. In other examples, the therapy includes administering an agent that includes administering one or more miR nucleic acids, such one or more miR nucleic acids that are been identified as down-regulated in a sample from a subject relative to a control (for example, as described in Section IV).

The following examples are provided to illustrate certain particular features and/or embodiments. These examples should not be construed to limit the disclosure to the particular features or embodiments described.

Example 1

Materials and Methods

HNSCC Patient Samples:

Fresh frozen HNSCC tissue and mucosa samples were collected from University of Michigan Medical Center as part of an IRB approved protocol. The clinical characterization of the HNSCC patients is summarized in Table 2. The collected tissues were snap frozen and mounted in OCT freezing media (Fisher), cut in 7 micrometer sections, and stained by H&E standard methods. The stained slides were scanned using a SCANSCOPE image capture device (Aperio), and examined with IMAGESCOPE software (Aperio) to ensure the presence of tumor or mucosa squamous epithelium. The stained slides were used to macrodissect tissue blocks to attain a minimum of 70% desired squamous tumor or epithelium cells in each sample.

TABLE 2

Tumor, treatment, and outcome characteristics of human HNSCC specimens

| Specimen | Gender | Age | Primary Sites | Stage/TNM | Differentiation | Tobacco/pack | Alcohol/Quit |
|---|---|---|---|---|---|---|---|
| 2900 | M | 57 | Lateral tongue | T2N0M0 | Moderate | NA | NA |
| 3100 | M | 75 | Anterior tongue | T1N0M0 | Poor | MD | MD |
| 3300 | F | 60 | Lateral tongue | T3N1M0 | Moderate | NA | NA |
| 4300 | F | 47 | Lateral tongue | T3N0M0 | Well | Y/14 | NA |
| 4500 | F | 25 | Anterior tongue | T4N2cM0 | Moderate | NA | NA |
| 8200 | M | 72 | Tonsil | T4N0M0 | Well | Y/150 | Y |
| 8400 | M | 44 | Lateral tongue | T2N0M0 | Well | Y/20 | Y/Y |
| 8500 | F | 40 | Lateral tongue | T2N0M0 | Well | NA | NA |
| 8800 | M | 47 | Floor of mouth | T4N2bM0 | Moderate | Y/45 | Y |
| 4400 | F | 41 | Floor of mouth | T1N0M0 | Well | Y/60 | Y/Y |
| 7300 | M | 55 | Floor of mouth | T4N2cM0 | Well | Y/30 | Y |
| 7500 | F | 71 | Hard palate | T4N0M0 | Moderate | NA | NA |
| 7800 | M | 55 | Lateral tongue | T4N2bM0 | Poor | Y/60 | Y/Y |
| 8300 | F | 50 | Lateral tongue | T2N0M0 | Well | Y/28 | NA |

HNSCC tumor specimens from oral cavity were obtained from University of Michigan and designated as UMSC.
Primary sites, the origin of the primary tumor; TNM, tumor-node-metastasis (staging system).
Y: Yes; NA: not available.

microRNA Isolation, Library Preparation and Sequencing from HNSCC Samples:

Large and small RNA was purified using mirVana™ miRNA isolation Kit (Life Technologies) following a modified manufacturer's protocol. Fifteen-twenty mg of frozen tissue was homogenized in 1 mL of TRIZOL (Invitrogen) using a TissueLyser II tissue disrupter (Qiagen). Following homogenization, extraction was performed using a standard phenol-chloroform method. To the extracted aqueous phase, 10% additive (v/v) was added and then the standard manufacturer's protocol for fractionating large and small RNA was performed. RNA concentration was determined using a NANODROP spectrometer (Thermo Scientific), and total RNA integrity was verified on a Bioanalyzer 2100 instrument using an RNA 6000 Nano kit (Agilent Technologies). Sufficient presence of microRNA in small RNA enriched samples was verified by Bioanalyzer using the small RNA kit (Agilent Technologies).

Small RNA sequencing libraries were constructed using the SOLiD™ Total RNA-Seq Kit (Life Technologies) by manufacturer's protocol. Briefly, 1 µg of enriched small RNA (<200 bases) was used for ligation into sequencing adaptors. cDNA libraries were reverse transcribed and then size selected by separation on denaturing urea 10% PAGE. Bands were excised that correspond to an insert size of 18-38 nucleotides. The library was then amplified and barcoded by in-gel PCR. Library size was verified using the DNA 1000 kit on the Bioanalyzer 2100 (Agilent Technologies). cDNA library concentration was determined by RT-PCR by the SOLiD™ library TAQMAN quantification kit. Equal parts of eight cDNA libraries were multiplexed together and 0.6 pmol of multiplexed pool was used for emulsion PCR using the SOLiD™ EZ Bead™ system with E20 reagents. Emulsification, amplification, and bead enrichment were carried out according to the manufacturer's protocols. Enriched beads for each pool were 3' labeled using the SOLiD™ pre-deposition plus kit according to the manufacturer's protocol. $4 \times 10^8$ beads were deposited per lane of a 6-lane flow chip, and sequencing of the flow chip was then performed on the SOLiD™ 5500 system next generation sequencer with SOLiD™ Small RNA SP Kit (Life Technologies).

microRNA Mapping, Expression Profiling Quantification, and Differential Abundance Analysis:

The sequencing reads were mapped to human reference genome Hg19 using miRNA module in LifeScope™ 2 (Life Technologies). The downstream steps were mainly performed using miRDeep2 software package (Friedlander et al., *Nature Biotechnology* 26:407-415, 2008). Briefly, the mapping results in sam format were converted to the arf format used in miRDeep2 and in turn the miRDeep2.pl script was used to identify all the known and novel miRNAs in the sequencing results using default settings. Finally all the identified miRNAs were quantified based on the reads numbers assigned to them and normalized using the total counts per million in that sample.

SAMseq's (samr v2.0, R 3.0.2) two-class unpaired analyses with a read count input matrix and an FDR threshold of 0.05 was used to identify miRNAs that were differentially expressed. Each run generated a pair of files: genes "up" and "down," then ranked the filtered results by a median-based fold change.

miRNA Hierarchical Cluster Analysis:

Hierarchical cluster analysis of microRNA expression was performed using Partek Genomics Suite 6.6 from notebook. RPM (reads per million)-normalized microRNA expression was ranked by variance across both normal and tumor samples and the top 50% most variant microRNAs were selected to remove low expressers. Differentially expressed microRNA between tumor and mucosa specimens were compared and filtered by p-value <0.05 following a two-tailed student's T test. Expression data were scaled to the mean expression, and then hierarchical clustering was performed using Pearson's dissimilarity algorithm with complete linkage.

Integrative Analysis to Identify miRNA-mRNA Pairs in HNSCC TCGA Data:

miRNA and mRNA abundance for 279 tumor specimens were extracted from Level 3 data (available on the World Wide Web at tcga-data.nci.nih.gov/docs/publications/hnsc_2014). miRNA read counts for 5p and 3p strands were normalized to RPM aligned to miRBase annotated miRNAs. miRNAs were ranked by RPM variance across the samples, and the most variable 50% with a minimum expression of at least 50 RPM were used for integrated analysis. Gene expression was calculated from RNA-Seq data with RSEM v1.1.132 and zeros replaced with the minimum non-zero RSEM values (0.0033). The most-variant 50% of genes were used for integrated analysis. Both miRNA and mRNA expression data were $\log_2$ transformed.

A multi-step approach was applied to identify miRNA-mRNA target relationship. Linear regression was used to identify pair-wise negative correlation of miRNA and mRNA expression, in conjunction with available prediction tools from miRNA target databases. A high confidence dataset of global miRNA-mRNA interactions was generated.

Copy Number Variation (CNV) Data Analysis:

Copy number data for 279 tumor specimens were extracted from Level 3 data. The CNV number associated with each gene was defined as the segmented GISTICS value at the corresponding genomic location. The Integrative Genomics Viewer (IGV) was used to visualize copy number data. Linear regression was applied to assess the correlation between miRNA expression and CNV.

TCGA DNA Methylation Data Analysis:

For DNA methylation data analysis, we used Level 3 DNA methylation data for 279 tumor specimens from TCGA (The Cancer Genome Atlas, *Nature* 517:576-582, 2015). The data were represented as beta values ($\beta$) from Illumina Human Methylation 450 k array. CpG probes in promoter regions of miRNAs from miR-30 family were found using coordinates of transcription start sites (TSS) from PROmiRNA (available on the World Wide Web at promirna.molgen.mpg.de; Marsico et al., *Genome Biol.* 14:R84, 2013). The promoter region was specified as +/−1500 bp from TSS. For every CpG probe, we estimated the difference of miRNA abundance between unmethylated ($\beta<0.1$) and methylated ($\beta>0.3$) samples using t-test. BH corrected P-values (FDR) from t-test were used to find CpG probes that significantly differentially expressed between unmethylated and methylated groups using 0.05 as a threshold. Then, methylation beta values were averaged across significant probes per miR and correlated with the corresponding miR expression using Spearman's correlation test.

Survival Analysis:

The R survival statistical package, version 2.37-2 (available on the World Wide Web at CRAN.R-project.org/package=survival) was used to analyze overall survival times, produce Kaplan-Meier plots, and compute log-rank test p-values. Subjects were dichotomized as low miRNA expression (<median) and high miRNA expression (≥median), using the median expression of each miRNA as a cutoff. To compare overall survival time by CNV, subjects were categorized as having MIR30E/A deletion if their GISTIC copy number value was less than −0.1, otherwise they were considered to have no deletion.

Associations of miR-30 Genetic Alterations and Expression with Stage, Site, Smoking and HPV Status of HNSCC from TCGA Datasets:

Fisher's exact tests were used to assess associations between miR-30a expression/methylation and clinical characteristics, or between miR-30e expression/copy number loss and clinical characteristics. Statistical analyses were performed using R version 3.2.2. Significance was defined as p<0.05. Tumor site was classified as oral cavity if the tumor samples came from any of the following anatomic subdivisions: buccal mucosa, floor of mouth, hard palate, lip, oral cavity, oral tongue, and alveolar ridge; tumor site was classified as oropharynx if the tumor samples came from tonsil, base of tongue or oropharynx.

Inverse Correlation of miR-30a Expression with Putative Target Genes:

Linear regression analysis was performed as described previously (Cancer Genome Atlas, Nature 517:576-582, 2015) to assess inverse relationship between expressions of miR-30a-5p and its putative target genes using HNSCC TCGA datasets. P-values from linear regression measure the statistical significance of inverse relationship.

HNSCC Cell Lines:

A panel of 10 HNSCC cell lines was obtained from the University of Michigan squamous cell carcinoma (UM-SCC) series (Brenner et al., Head Neck 32:417-426, 2010). The origin of these UM-SCC cell lines was authenticated by genotyping with 9 markers as described in Brenner et al. Preserved frozen stocks of lines were used within three months of culture. UM-SCC cell lines were cultured in minimal essential medium supplemented with 10% fetal calf serum, penicillin and streptomycin (100 µg/mL), MEM Non-Essential Amino Acids, and Sodium Pyruvate (1 mM). Human primary oral keratinocytes (HOK) from oral gingival mucosa were purchased from Lonza, and used as a control cell line. The cells were cultured in serum free Oral Keratinocyte Medium with supplements (Science Cell) for less than five passages.

In Vitro microRNA Mimic Viability Screen:

Cells were maintained in MEM containing 10% heat inactivated fetal bovine serum (FBS) supplemented with non-essential amino acids and sodium pyruvate. Transfections were performed in 384 well plates (Corning 3570). Cell viability was measured using CELLTITER-GLO luminescent cell viability assay (Promega). For transfections, 20 µL of serum free media containing LIPOFECTAMINE RNAiMax reagent (0.1 µL) was added to wells containing miRNA mimic (0.8 pmol). Lipid and miRNA mimic were allowed to complex for 45 min at ambient temperature before addition of 1500 cells in MEM, 20% FBS to yield final transfection mixtures containing 20 nM miRNA mimic in MEM, 10% FBS.

The screening campaign was conducted a miRNA mimic library (Qiagen) based on Sanger miRBase 13.0 and consisting of ~800 mimics Viability (CellTiter Glo, Promega) was assayed 72 h post-transfection on a PerkinElmer Envision 2104 Multilabel plate reader. Ambion SILENCER Select Negative Control #2 was incorporated on all screening plates for normalization (16 wells per plate; the median negative control value on each plate was used to normalize sample wells). Qiagen's AllStars Cell Death control was incorporated as a positive transfection control (16 wells per plate). All screen plates exhibited assay z'-factors greater than 0.6. Negative control normalized viability data was converted into robust z-scores using the median absolute deviation (MAD) (Chung et al., J. Biomol. Screen 13:149-158, 2008).

RT-PCR Validation of mRNA Targets:

$2 \times 10^5$ UM-SCC-46 cells were plated in each well of a 6-well plate. 15 nM of mirVana microRNA mimic or inhibitor (Life Technologies) was reverse transfected using 3.75 µL of LIPOFECTAMINE RNAiMAX (Life Technologies) by standard manufacturer's protocol for 48-72 hr. Then cells were washed with normal media and PBS, and collected into 0.5 mL TRIZOL reagent. Total RNA was purified using mirVana miRNA isolation Kit (Ambion). Two µg of total RNA was reverse transcribed using high capacity cDNA reverse transcription kit (Applied Biosystems) following manufacturer's instructions. mRNA expression levels were assessed by real time-PCR using TAQMAN gene expression assays (Applied Biosystems), and 40 ng of cDNA was used in each reaction. Reactions were run on an ABI 7900HT real-time PCR machine. Expression levels were normalized to 18S RNA as an endogenous loading control.

Western Blotting:

UM-SCC-46 cells were transfected as described above and then lysed into 100 µL of SDS lysis buffer (1% SDS, 50 mM Tris pH 8.0, 10 mM EDTA, Protease inhibiter (Roche), and Halt Phosphatase Inhibitor (Thermo Scientific)). Samples were sonicated using a probe sonicator four times for 5 sec each on ice. Lysates were cleared by centrifugation at 14,000×g for 10 min at 4° C. Protein concentration was determined using the BCA Protein Assay (Thermo Scientific). 25 µg of total protein was subjected to SDS-PAGE on a 4-12% gradient Bis-Tris gel (Invitrogen). Protein was transferred to a 0.45-µm PVDF IMMOBILON-FL membrane (Millipore) using the XCELL transfer system (Invitrogen). Primary antibodies used for probing are listed below. Appropriate IRDye fluorescently labeled secondary antibodies were used for detection at a dilution of 1:5000 on an ODYSSEY® Quantitative Florescent imager using standard manufacturer's protocol (LI-COR). Bands were quantitated using Odyssey imaging software version 3.0.30.

Primary Antibodies:

EGFR 1:1000 dilution (Cell Signaling Technology, #4405), FRZD2 1:500 dilution (Abcam, #52565), IRS1 1:1000 dilution (Cell Signaling Technology, #3407), ITGA6 1:1000 dilution (Cell Signaling Technology, #3750), IGF1R 1:1000 dilution (Cell Signaling Technology, #3018), MET 1:1000 dilution (Cell Signaling Technology, #8198), Pan-AKT 1:1000 dilution (Cell Signaling Technology, #2920), pi-AKT Ser473 1:1000 dilution (Cell Signaling Technology, #4060) Src 1:1000 dilution (Cell Signaling Technology, #2110), pi-Src Tyr416 1:1000 dilution (Cell Signaling Technology, #2101), Stat3 1:1000 dilution (Cell Signaling Technology, #9139), pi-Stat3 Ser727 1:1000 dilution (Cell Signaling Technology, #9134).

Luciferase Reporter Assays:

Vectors encoding the wild-type or mutant 3' UTR of EGFR, IGF1R, MET, and IRS1 cloned behind Renilla luciferase were purchased from Switchgear Genomics. Cells were seeded at $1 \times 10^4$ per well in white bottom 96-well plates. The next day, 100 ng of vector and 15 nM of microRNA mimics were co-transfected using 0.2 µL of DharmaFECT™ Duo transfection reagent (Thermo Scientific). Cells were incubated for 48 hr. For normalization of cell number, 100 µL of CELLTITER-FLUOR cell viability assay reagent (Promega) was added to each well, and cells were incubated for 30 min at 37° C. Florescence was read at 505 nm for assessing cell viability. Luciferase activity was detected using the Renilla-Glo® Luciferase Assay System (Promega) following manufacturer's instructions. Relative luciferase activity was normalized to florescence viability readings for each well. All measurements represent the mean of 6 replicates in each experimental condition.

XTT Proliferation Assay:

Cells were seeded at $2 \times 10^3$ cells/well in 96-well plates and reverse transfected with 15 nM oligonucleotide for 48 hours with 0.15 µL of RNAiMAX as described above. Following transfection, 200 µL of control or media containing 2 µM cisplatin was placed on cells for 3 hr. Cells were washed with warm media, and then fresh media was added. Cell proliferation was assayed on the indicated days with sodium 3'-[1-(phenylaminocarbonyl)-3,4-tetrazolium]-bis (4-methoxy-6-nitro) benzene sulfonic acid hydrate (XTT) Cell Proliferation Kit (Roche Diagnostics), following manufacturer's instructions. XTT assay reagent was added for 4 hours prior to assay. At each time point, absorbance was read at 450 nM and 655 nm, and A absorbance was calculated. All time points represent the mean of 6 replicates in each experimental condition.

Migration Assay:

Cells were seeded at $4 \times 10^5$ cells/well in 6-well plates and reverse transfected with 15 µM oligonucleotide for 48 hours as described above. After transfection, the media was replaced and a scratch devoid of cells was created in each well laterally and longitudinally with a p1000 pipet tip. Four marked locations in each scratch were imaged a various time points at 100× magnification. The area of the scratch was determined using ImageJ software (Schneider et al., *Nat. Methods* 9:971-675, 2012), and the percent of migration into the empty area over time was calculated.

MATRIGEL Invasion Assay:

Cells were seeded in 6-well plates and reverse transfected with 15 nM oligonucleotide for 48 hours with RNAiMAX as described above. Following transfection, cells were trypsinized and suspended in DMEM without additives. BioCoat™ Growth Factor Reduced Invasion Chambers were prepared as per manufacturer's instructions (BD Biosciences). $5 \times 10^4$ cells were placed in the top of each chamber. The bottom sides of chambers were placed in wells containing 100 ng/mL rEGF (Millipore) as a chemoattractant in DMEM. Chambers were incubated for 24 hours at 37° C. Non-invading cells were removed by scrubbing the top of invasion membranes, and invading cells were stained with 0.05% crystal violet solution in methanol for 1 min (Sigma). Invasion membranes were mounted on glass slides and invading cells counted at 100× magnification.

Colony Formation Assay:

Cells were seeded in 6-well plates and reverse transfected with 15 nM oligonucleotide for 48 hours with RNAiMAX as described above. Following transfection, cells were trypsinized and re-plated in 6-well plates at varying densities. Cells were incubated for 11 days and then stained with 0.1% crystal violet/methanol solution. Colonies with >50 cells were counted in three replicate wells, and the fraction of surviving cells was calculated.

Development of miR30a Nanoparticles Bearing Anti-transferrin Receptor Single-chain Antibody Fragment: Fluorescent siRNA to test nanoparticle in vivo delivery was synthesized by Trilink Biotechnologies, and the formulation of the oligonucleotides into liposomes was performed as previously described (Pirollo et al., Hum. Gene Ther. 17:117-124, 2006; Pirollo et al., Cancer Res. 67:2938-2943, 2007; Yu et al., Nucleic Acids Res. 32:e48, 2004). Briefly, 1:1 molar ratios of each single-stranded antisense and cognate sense oligonucleotide were annealed. Cationic liposome (dioleoyltrimethylammonium phosphate (DOTAP) and dioleoylphosphatidylethanolamine (DOPE), Avanti Polar Lipids, Alabaster, Ala.) was prepared at a 1:1 molar ratio by ethanol injection (Xu et al., Nol. Med. 7:723-734, 2001). The anti-transferrin receptor single-chain antibody fragment (TfRscFv) was mixed with the liposome at the previously established ratio of 1:30 (w/w) (Yu et al., Nucleic Acids Res. 32:e48, 2004). The miRNA molecules were subsequently added to the admixture at a ratio of 1 µg siRNA to 7 nmol liposome, followed by sizing and confirmation of nanosize particle distributions of the final immunoliposome formulations by dynamic light scattering with a Malvern Zetasizer 3000 HS (Malvern, Worcestershire, UK). miR-30a mimic oligonucleotide with a guide strand sequence 5' UGUAAACAUCCUCGACUGGAAG-3' (SEQ ID NO: 1) and a passenger strand sequence of 5'-AGCUUCCAGUCG-GAUGUUUACACG-3' (SEQ ID NO: 72) were synthesized by Trilink Biotechnologies. Following annealing the mimic was formulated as described above. Complexed miR30a mimic is referred to as miR-30a-scL.

In Vivo Tumor Targeting and Growth Assays:

All animal experiments were carried out under protocols approved by the Animal Care and Use Committee of the NIDCD, and were in compliance with the Guide for the Care and Use of Laboratory Animal Resource, (1996) National Research Council. Six to eight week old athymic nu/nu female mice (obtained from Frederick Cancer Research and Development Center, NCI) were injected subcutaneously (s.c.) with $2 \times 10^6$ UM-SCC-46 cells in 100 µL of 30% Type 3 BME Cultrex (Trevigen)/MEM media on the right leg. Once tumors reached ~100 mm³ (approximately 1 week after injection), mice were randomized into four groups for treatment (n=4-5 mice each); Control and miR-30a-scL. Nine doses of 3 mg/kg miR-30a-scL was administered via tail vain injection on Monday, Wednesday, and Friday (MWF) over three weeks for a total of nine dosages. Tumor size was measured on MWF with external calipers and volume calculated with the formula $V=\frac{1}{2} L^*W^2$. Tumor growth is reported as mean volume with standard error of the mean. Kaplan-Meier survival analysis was performed in GraphPad PRISM software (v6.05). Survival statistics were performed using the Log-rank (Mantel-Cox) test, and Hazard ratio calculated via Log-rank test.

Immunofluorescence:

Fresh tumors were embedded in OCT and then frozen immediately on dry ice. Tumor tissues were sectioned into 5 µm sections. Sections were fixed for 7 minutes at −20° C. with ice-cold methanol (EMD Millipore Corporation, Billerica, Mass.). Samples were then washed three times with PBS. Sections were blocked by incubation in a humidifying chamber at RT for one hour with blocking solution 1 (3% BSA+0.05% Tween 20 in 1×PBS) followed by a one-hour incubation with blocking solution 2 (10% NGS in 1×PBS). Sections were then incubated with primary antibody diluted in dilution solution (1% BSA+0.1% Tween 20 in 1×PBS) overnight at 4° C. in a humidifying chamber. After washing the cells five times with 1×PBS, the slides were mounted with Vectashield mounting medium with DAPI (Vector Laboratories Inc, Burlingame, Calif.) in the dark. Samples were analyzed on a LSM 780 confocal microscope (Carl Zeiss Microimaging, Thornwood, N.Y.). Confocal data was analyzed using Zen 2012 SP1 (black edition) software and the degree of color intensity was ascertained using Zen 2012 (blue edition) software.

Example 2

Decreased Expression of miR-30 Family Members in HNSCC Tissue

Figure 2D:
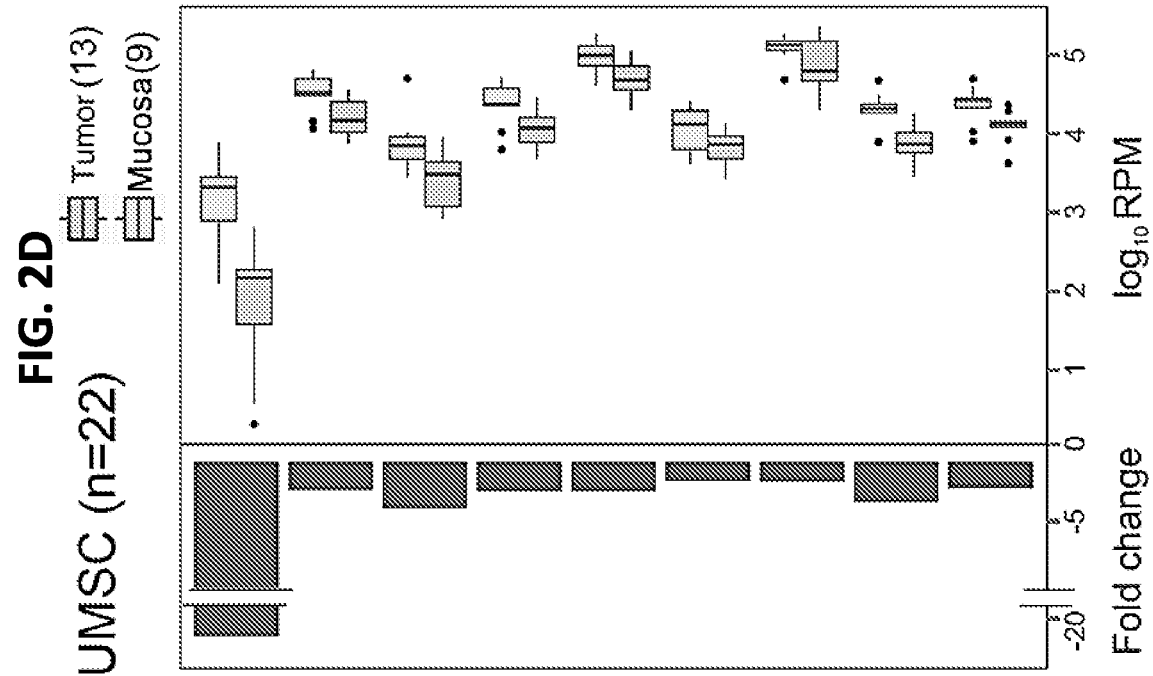
FIGS. 2C and 2D are a pair of graphs showing decreased expression of nine miRNAs in TCGA (FIG. 2C) and UMSC (FIG. 2D) HNSCC cohorts. Fold-change of median expression between tumor and mucosa controls is displayed on the left of each graph. Box and whisker plots of median expression distribution of mucosa and tumor are presented on the right of each graph as $\log_{10}$ RPM (reads per million base pairs). Medians are represented by the thick black lines in the middle, bars represent $25^{th}$ and $75^{th}$ percentile, outliers are displayed as individual points.
Figure 2C:
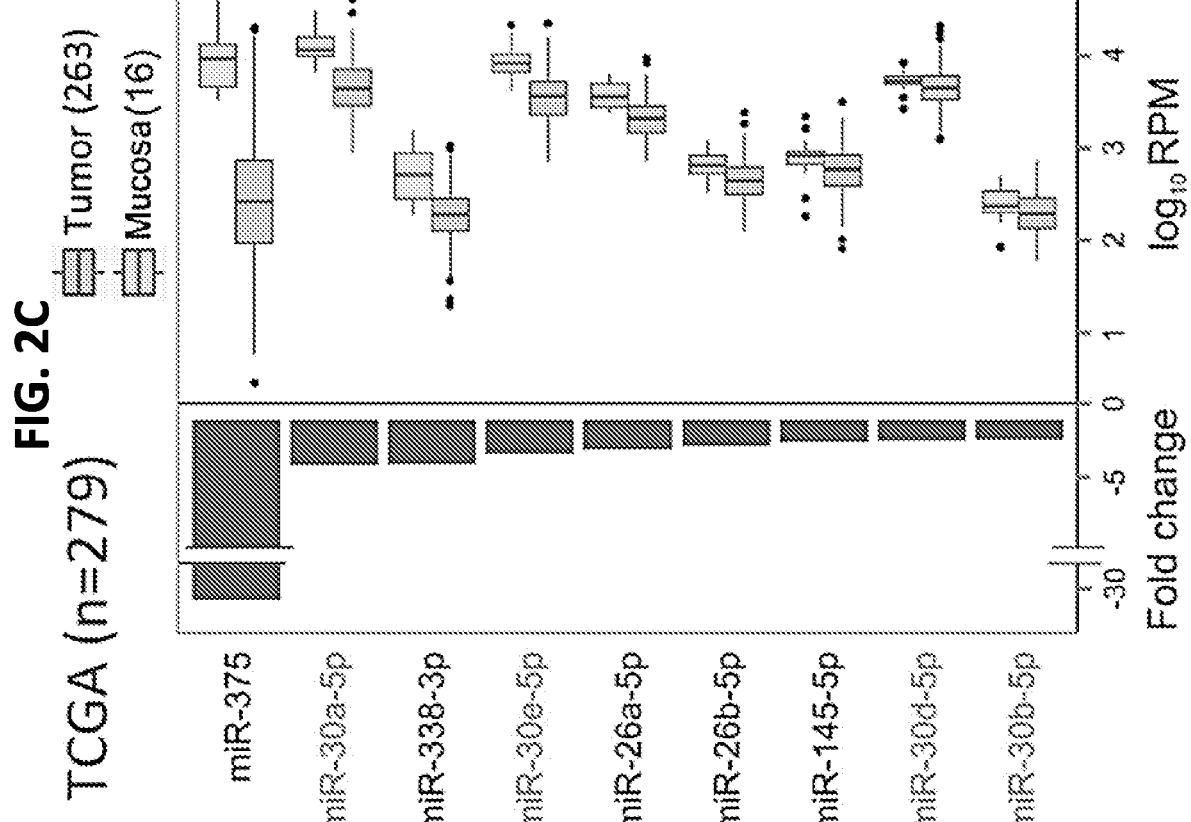

To examine miRNA (miRs) differentially expressed in HNSCC tissues, miR sequencing data of 279 HNSCC with 16 squamous mucosa control specimens published by TCGA (Cancer Genome Atlas 2015) were analyzed. Through differential expression analysis between tumor and mucosa specimens, 129 miRs, including 77 increased and 53 decreased miRs (FDR<0.2; Table 3, FIG. 1; FIGS. 2A and 2B) were identified. These observations were validated by miR sequencing and expression analysis of an independent panel of 13 HNSCC specimens from oral cavity and 9 matched mucosa samples from the University of Michigan (Table 4). Pair-wise comparison of significantly altered and validated miRs in both data sets uncovered decreased expression of several members of the miR-30 family, and several miRs identified in prior studies (FIGS. 2C and 2D; Tables 3 and 4). Notably, miR-30-5p family members exhibited at least 2-fold decreased expression spanning >70% of specimens in both cohorts.

TABLE 3

Differentially expressed miRNAs in HNSCC (TCGA set)

| miRNA | MIMAT ID | Geneind | Score | FoldChange | qval |
|---|---|---|---|---|---|
| Increased expression | | | | | |
| hsa-miR-21-5p | MIMAT0000076 | 12 | 1799.9 | 2.848 | 0 |
| hsa-miR-196b-5p | MIMAT0001080 | 101 | 1719.9 | 6.054 | 0 |
| hsa-miR-455-3p | MIMAT0004784 | 126 | 1714.45 | 5.598 | 0 |
| hsa-miR-106b-3p | MIMAT0004672 | 150 | 1699.15 | 2.131 | 0 |
| hsa-let-7d-3p | MIMAT0004484 | 142 | 1658.35 | 1.833 | 0 |
| hsa-miR-151a-5p | MIMAT0004697 | 123 | 1634.75 | 2.301 | 0 |
| hsa-miR-423-5p | MIMAT0004748 | 124 | 1620.05 | 2.205 | 0 |
| hsa-miR-424-5p | MIMAT0001341 | 103 | 1554.25 | 2.837 | 0 |
| hsa-miR-181b-5p | MIMAT0000257 | 43 | 1513.55 | 1.724 | 0 |
| hsa-miR-1307-3p | MIMAT0005951 | 132 | 1488.5 | 1.985 | 0 |
| hsa-miR-320a | MIMAT0000510 | 83 | 1418.85 | 1.965 | 0 |
| hsa-miR-185-5p | MIMAT0000455 | 79 | 1402.75 | 1.853 | 0 |
| hsa-let-7d-5p | MIMAT0000065 | 4 | 1402.05 | 1.483 | 0 |
| hsa-miR-2355-5p | MIMAT0016895 | 133 | 1388.9 | 2.368 | 0 |
| hsa-miR-193b-3p | MIMAT0002819 | 110 | 1374.6 | 3.458 | 0 |
| hsa-miR-183-5p | MIMAT0000261 | 45 | 1361.35 | 2.469 | 0 |
| hsa-miR-25-3p | MIMAT0000081 | 16 | 1347.85 | 1.547 | 0 |
| hsa-miR-99b-3p | MIMAT0004678 | 151 | 1333.4 | 1.798 | 0 |
| hsa-miR-181a-5p | MIMAT0000256 | 42 | 1325.4 | 1.582 | 0 |
| hsa-miR-182-5p | MIMAT0000259 | 44 | 1308.85 | 2.178 | 0 |
| hsa-miR-93-5p | MIMAT0000093 | 24 | 1282.15 | 2.317 | 0 |
| hsa-miR-589-5p | MIMAT0004799 | 128 | 1276.8 | 1.686 | 0 |
| hsa-miR-28-3p | MIMAT0004502 | 117 | 1236.75 | 1.574 | 0 |
| hsa-miR-103a-3p | MIMAT0000101 | 30 | 1230.4 | 1.437 | 0 |
| hsa-miR-92b-3p | MIMAT0003218 | 112 | 1223.3 | 2.018 | 0 |
| hsa-miR-146b-5p | MIMAT0002809 | 109 | 1221.2 | 1.906 | 0 |
| hsa-miR-944 | MIMAT0004987 | 131 | 1211.9 | 1.928 | 0 |
| hsa-miR-197-3p | MIMAT0000227 | 33 | 1171.35 | 1.551 | 0 |
| hsa-miR-542-3p | MIMAT0003389 | 115 | 1155.65 | 1.97 | 0 |
| hsa-miR-92a-3p | MIMAT0000092 | 23 | 1132.25 | 1.612 | 0 |
| hsa-miR-423-3p | MIMAT0001340 | 102 | 1129.25 | 1.848 | 0 |
| hsa-miR-708-5p | MIMAT0004926 | 130 | 1119.8 | 1.866 | 0 |
| hsa-miR-15b-5p | MIMAT0000417 | 57 | 1097.6 | 1.473 | 0 |
| hsa-miR-148b-3p | MIMAT0000759 | 99 | 1097.4 | 1.442 | 0 |
| hsa-miR-484 | MIMAT0002174 | 107 | 1084.6 | 1.556 | 0 |
| hsa-miR-342-3p | MIMAT0000753 | 97 | 1063.8 | 1.875 | 0 |
| hsa-let-7i-5p | MIMAT0000415 | 56 | 1049.75 | 1.504 | 0 |
| hsa-miR-224-5p | MIMAT0000281 | 53 | 1038 | 2.3 | 0 |
| hsa-miR-16-5p | MIMAT0000069 | 8 | 1025.6 | 1.404 | 0 |
| hsa-miR-210-3p | MIMAT0000267 | 49 | 1022.25 | 2.406 | 0 |
| hsa-miR-222-3p | MIMAT0000279 | 51 | 1021.1 | 1.716 | 0 |
| hsa-miR-151a-3p | MIMAT0000757 | 98 | 1020.25 | 1.43 | 0 |
| hsa-miR-181a-2-3p | MIMAT0004558 | 145 | 1015.45 | 1.452 | 0 |
| hsa-miR-106b-5p | MIMAT0000680 | 86 | 993 | 1.334 | 0 |
| hsa-miR-17-5p | MIMAT0000070 | 9 | 991.5 | 1.816 | 0 |
| hsa-let-7e-5p | MIMAT0000066 | 5 | 983.4 | 1.6 | 0 |
| hsa-miR-193a-5p | MIMAT0004614 | 121 | 929.5 | 1.591 | 0 |
| hsa-miR-15a-5p | MIMAT0000068 | 7 | 929 | 1.501 | 0 |
| hsa-miR-708-3p | MIMAT0004927 | 154 | 915.35 | 1.55 | 0 |
| hsa-miR-132-3p | MIMAT0000426 | 63 | 898.15 | 1.336 | 0 |
| hsa-miR-181a-3p | MIMAT0000270 | 136 | 878.8 | 1.372 | 0 |
| hsa-miR-191-5p | MIMAT0000440 | 70 | 859.15 | 1.539 | 0 |
| hsa-miR-9-5p | MIMAT0000441 | 71 | 810.95 | 2.349 | 0 |
| hsa-miR-99b-5p | MIMAT0000689 | 89 | 778.8 | 1.323 | 0 |
| hsa-miR-574-3p | MIMAT0003239 | 113 | 738.3 | 1.38 | 0 |
| hsa-miR-205-5p | MIMAT0000266 | 48 | 721.95 | 1.562 | 0 |
| hsa-let-7i-3p | MIMAT0004585 | 146 | 708.95 | 1.506 | 0.113 |
| hsa-miR-365a-3p | MIMAT0000710 | 92 | 695.85 | 1.406 | 0.212 |
| hsa-miR-223-3p | MIMAT0000280 | 52 | 690 | 1.721 | 0.212 |
| hsa-miR-20a-5p | MIMAT0000075 | 11 | 687.7 | 1.623 | 0.212 |
| hsa-miR-425-5p | MIMAT0003393 | 116 | 678.25 | 1.683 | 0.212 |
| hsa-miR-200c-3p | MIMAT0000617 | 84 | 667.55 | 1.401 | 0.212 |
| hsa-miR-625-3p | MIMAT0004808 | 153 | 655.6 | 1.371 | 0.212 |
| hsa-miR-155-5p | MIMAT0000646 | 85 | 631.85 | 1.358 | 0.311 |
| hsa-miR-192-5p | MIMAT0000222 | 32 | 629.6 | 1.233 | 0.311 |
| hsa-miR-21-3p | MIMAT0004494 | 143 | 615.1 | 1.748 | 0.406 |
| hsa-miR-186-5p | MIMAT0000456 | 80 | 613.95 | 1.177 | 0.406 |
| hsa-miR-23a-3p | MIMAT0000078 | 14 | 578.15 | 1.224 | 0.602 |
| hsa-miR-200c-5p | MIMAT0004657 | 149 | 536.1 | 1.448 | 0.787 |
| hsa-miR-98-5p | MIMAT0000096 | 25 | 525.65 | 1.1 | 0.787 |
| hsa-miR-629-5p | MIMAT0004810 | 129 | 505.75 | 1.178 | 0.974 |
| hsa-miR-24-3p | MIMAT0000080 | 15 | 482.85 | 1.075 | 1.311 |
| hsa-miR-146a-5p | MIMAT0000449 | 76 | 477.95 | 1.237 | 1.311 |
| hsa-miR-221-3p | MIMAT0000278 | 50 | 477 | 1.227 | 1.311 |

TABLE 3-continued

Differentially expressed miRNAs in HNSCC (TCGA set)

| miRNA | MIMAT ID | Geneind | Score | FoldChange | qval |
|---|---|---|---|---|---|
| hsa-miR-142-3p | MIMAT0000434 | 66 | 430.8 | 1.419 | 1.838 |
| hsa-miR-28-5p | MIMAT0000085 | 20 | 402.7 | 1.09 | 2.323 |
| hsa-miR-22-3p | MIMAT0000077 | 13 | 391.85 | 1.163 | 2.479 |
| Decreased expression | | | | | |
| hsa-miR-101-3p | MIMAT0000099 | 28 | −1893.1 | 0.269 | 0 |
| hsa-miR-100-5p | MIMAT0000098 | 27 | −1867.35 | 0.259 | 0 |
| hsa-miR-126-5p | MIMAT0000444 | 137 | −1849.95 | 0.417 | 0 |
| hsa-miR-375 | MIMAT0000728 | 93 | −1819.6 | 0.029 | 0 |
| hsa-miR-99a-5p | MIMAT0000097 | 26 | −1811.3 | 0.207 | 0 |
| hsa-let-7c-5p | MIMAT0000064 | 3 | −1629.3 | 0.286 | 0 |
| hsa-miR-30a-5p | MIMAT0000087 | 22 | −1600.15 | 0.391 | 0 |
| hsa-miR-30e-5p | MIMAT0000692 | 90 | −1598 | 0.522 | 0 |
| hsa-miR-27b-3p | MIMAT0000419 | 59 | −1545.15 | 0.414 | 0 |
| hsa-miR-199b-5p | MIMAT0000263 | 46 | −1544.4 | 0.398 | 0 |
| hsa-miR-378a-5p | MIMAT0000731 | 139 | −1537.6 | 0.396 | 0 |
| hsa-miR-125b-5p | MIMAT0000423 | 61 | −1530.95 | 0.467 | 0 |
| hsa-miR-338-3p | MIMAT0000763 | 100 | −1482.1 | 0.397 | 0 |
| hsa-miR-29a-3p | MIMAT0000086 | 21 | −1469.7 | 0.474 | 0 |
| hsa-miR-29c-3p | MIMAT0000681 | 87 | −1439.25 | 0.286 | 0 |
| hsa-miR-30a-3p | MIMAT0000088 | 135 | −1417.6 | 0.332 | 0 |
| hsa-miR-26a-5p | MIMAT0000082 | 17 | −1361.5 | 0.595 | 0 |
| hsa-miR-140-3p | MIMAT0004597 | 119 | −1347.05 | 0.579 | 0 |
| hsa-miR-378a-3p | MIMAT0000732 | 94 | −1330.5 | 0.489 | 0 |
| hsa-miR-10b-5p | MIMAT0000254 | 40 | −1282 | 0.485 | 0 |
| hsa-miR-23b-3p | MIMAT0000418 | 58 | −1268.4 | 0.656 | 0 |
| hsa-miR-203a-3p | MIMAT0000264 | 47 | −1176.7 | 0.409 | 0 |
| hsa-miR-381-3p | MIMAT0000736 | 96 | −1054.75 | 0.376 | 0 |
| hsa-miR-486-5p | MIMAT0002177 | 108 | −983.9 | 0.474 | 0 |
| hsa-miR-379-5p | MIMAT0000733 | 95 | −980.65 | 0.527 | 0 |
| hsa-miR-30e-3p | MIMAT0000693 | 138 | −881.8 | 0.687 | 0 |
| hsa-miR-26b-5p | MIMAT0000083 | 18 | −879.55 | 0.691 | 0 |
| hsa-miR-199a-3p | MIMAT0000232 | 35 | −874.45 | 0.712 | 0 |
| hsa-miR-199b-3p | MIMAT0004563 | 118 | −869.1 | 0.71 | 0 |
| hsa-miR-582-3p | MIMAT0004797 | 127 | −720.2 | 0.693 | 0.964 |
| hsa-miR-451a | MIMAT0001631 | 105 | −692.2 | 0.458 | 1.299 |
| hsa-miR-126-3p | MIMAT0000445 | 73 | −639.75 | 0.709 | 2.003 |
| hsa-miR-143-3p | MIMAT0000435 | 67 | −633.15 | 0.651 | 2.003 |
| hsa-miR-199a-5p | MIMAT0000231 | 34 | −611.7 | 0.695 | 2.633 |
| hsa-miR-29b-3p | MIMAT0000100 | 29 | −580.2 | 0.837 | 2.633 |
| hsa-miR-10a-5p | MIMAT0000253 | 39 | −569.5 | 0.596 | 2.758 |
| hsa-miR-206 | MIMAT0000462 | 82 | −535.9 | 0.05 | 2.88 |
| hsa-miR-145-5p | MIMAT0000437 | 68 | −535.8 | 0.793 | 2.88 |
| hsa-miR-34a-5p | MIMAT0000255 | 41 | −508.05 | 0.787 | 3.023 |
| hsa-miR-127-5p | MIMAT0004604 | 120 | −497.3 | 0.875 | 3.023 |
| hsa-miR-127-3p | MIMAT0000446 | 74 | −483.45 | 0.779 | 3.137 |
| hsa-miR-30d-5p | MIMAT0000245 | 38 | −475.45 | 0.846 | 3.274 |
| hsa-miR-148a-3p | MIMAT0000243 | 36 | −466.6 | 0.899 | 3.274 |
| hsa-miR-144-5p | MIMAT0004600 | 148 | −412.75 | 0.565 | 3.864 |
| hsa-miR-30b-5p | MIMAT0000420 | 60 | −404.5 | 0.895 | 3.992 |
| hsa-miR-200b-3p | MIMAT0000318 | 54 | −390.75 | 0.933 | 4.118 |
| hsa-miR-17-3p | MIMAT0000071 | 134 | −349.75 | 0.852 | 4.713 |
| hsa-miR-374a-3p | MIMAT0004688 | 152 | −314.95 | 0.808 | 5.143 |
| hsa-miR-532-5p | MIMAT0002888 | 111 | −276.15 | 0.894 | 5.982 |
| hsa-miR-149-5p | MIMAT0000450 | 77 | −271.75 | 0.823 | 5.982 |
| hsa-miR-150-5p | MIMAT0000451 | 78 | −195 | 0.779 | 7.762 |
| hsa-let-7b-5p | MIMAT0000063 | 2 | −184.35 | 0.97 | 8.004 |
| hsa-let-7a-5p | MIMAT0000062 | 1 | −174.75 | 0.898 | 8.242 |

TABLE 4

Validation of differentially expressed miRNAs in HNSCC (UMSC set)

| miRNA | MIMAT ID | Geneind | Score | FoldChange | qval |
|---|---|---|---|---|---|
| Increased expression | | | | | |
| hsa-miR-517a-3p | MIMAT0002852 | 1414 | 54.65 | 3.3E+09 | 0 |
| hsa-miR-517c-3p | MIMAT0002866 | 1416 | 54.55 | 1.5E+09 | 0 |
| hsa-miR-517b-3p | MIMAT0002857 | 1415 | 52.95 | 3.3E+09 | 0 |
| hsa-miR-132-5p | MIMAT0004594 | 167 | 49.8 | 3.551 | 0 |
| hsa-miR-542-5p | MIMAT0003340 | 1467 | 46.5 | 4.807 | 0 |
| hsa-miR-223-5p | MIMAT0004570 | 365 | 45.5 | 10.963 | 0 |

TABLE 4-continued

Validation of differentially expressed miRNAs in HNSCC (UMSC set)

| miRNA | MIMAT ID | Geneind | Score | FoldChange | qval |
|---|---|---|---|---|---|
| hsa-miR-29b-1-5p | MIMAT0004514 | 415 | 45.35 | 4.115 | 0 |
| hsa-miR-2355-5p | MIMAT0016895 | 373 | 42.1 | 2.314 | 4.332 |
| hsa-miR-196a-5p | MIMAT0000226 | 292 | 41.3 | 11.348 | 4.332 |
| hsa-miR-196b-5p | MIMAT0001080 | 294 | 41.15 | 14.732 | 4.332 |
| hsa-miR-181a-3p | MIMAT0000270 | 241 | 40.4 | 4.319 | 5.56 |
| hsa-miR-181a-2-3p | MIMAT0004558 | 242 | 39.3 | 4.229 | 5.56 |
| hsa-miR-941 | MIMAT0004984 | 1722 | 39.15 | 4.512 | 5.56 |
| hsa-miR-503-5p | MIMAT0002874 | 1382 | 39.05 | 18.902 | 5.56 |
| hsa-miR-132-3p | MIMAT0000426 | 166 | 38.4 | 1.889 | 6.749 |
| hsa-miR-520f-3p | MIMAT0002830 | 1445 | 36.75 | 2.5E+08 | 6.749 |
| hsa-miR-9-5p | MIMAT0000441 | 1701 | 36.5 | 11.27 | 6.749 |
| hsa-miR-519d-3p | MIMAT0002853 | 1434 | 35.95 | 3.7E+08 | 7.95 |
| hsa-miR-515-3p | MIMAT0002827 | 1407 | 35.8 | 2.6E+08 | 7.95 |
| hsa-miR-519e-3p | MIMAT0002829 | 1435 | 35.15 | 1.5E+08 | 7.95 |
| hsa-miR-520g-3p | MIMAT0002858 | 1446 | 35.1 | 3.1E+08 | 7.95 |
| hsa-miR-520h | MIMAT0002867 | 1447 | 35 | 4.2E+08 | 7.95 |
| hsa-miR-301b-3p | MIMAT0004958 | 421 | 34.95 | 2.786 | 7.95 |
| hsa-miR-424-5p | MIMAT0001341 | 825 | 34.75 | 3.119 | 7.95 |
| hsa-miR-21-5p | MIMAT0000076 | 332 | 34.55 | 8.413 | 7.95 |
| hsa-miR-455-5p | MIMAT0003150 | 1068 | 34.5 | 2.6 | 7.95 |
| hsa-miR-542-3p | MIMAT0003389 | 1466 | 34.15 | 2.303 | 8.87 |
| hsa-miR-185-5p | MIMAT0000455 | 254 | 33.75 | 2.669 | 9.747 |
| hsa-miR-187-3p | MIMAT0000262 | 258 | 33.05 | 4.158 | 11.136 |
| hsa-miR-28-3p | MIMAT0004502 | 400 | 32.15 | 2.285 | 11.764 |
| hsa-miR-450b-5p | MIMAT0004909 | 1024 | 32.05 | 2E+08 | 11.764 |
| hsa-let-7i-5p | MIMAT0000415 | 16 | 32 | 3.185 | 11.764 |
| hsa-miR-455-3p | MIMAT0004784 | 1067 | 31.45 | 3.077 | 13.442 |
| hsa-miR-1256 | MIMAT0005907 | 92 | 31.1 | 2.352 | 15.247 |
| hsa-miR-518d-5p | MIMAT0005456 | 1423 | 29.65 | 1.3E+08 | 20.059 |
| hsa-miR-34c-5p | MIMAT0000686 | 614 | 29.6 | 2.194 | 20.059 |
| hsa-miR-146a-3p | MIMAT0004608 | 203 | 29.3 | 3.4E+08 | 20.059 |
| hsa-miR-214-5p | MIMAT0004564 | 347 | 29.15 | 2.011 | 20.059 |
| hsa-miR-29a-5p | MIMAT0004503 | 413 | 29.15 | 1.772 | 20.059 |
| Decreased Expression | | | | | |
| hsa-miR-100-5p | MIMAT0000098 | 19 | −53.5 | 0.548 | 0 |
| hsa-miR-99a-5p | MIMAT0000097 | 1730 | −52.65 | 0.408 | 0 |
| hsa-miR-375 | MIMAT0000728 | 741 | −51.5 | 0.036 | 0 |
| hsa-miR-204-5p | MIMAT0000265 | 319 | −50.5 | 0.103 | 0 |
| hsa-miR-92b-3p | MIMAT0003218 | 1710 | −48.4 | 0.352 | 0 |
| hsa-miR-423-5p | MIMAT0004748 | 824 | −47.25 | 0.553 | 0 |
| hsa-miR-1247-5p | MIMAT0005899 | 82 | −46.75 | 0.092 | 0 |
| hsa-miR-139-5p | MIMAT0000250 | 187 | −46.15 | 0.344 | 0 |
| hsa-miR-99a-3p | MIMAT0004511 | 1731 | −45.75 | 0.267 | 0 |
| hsa-miR-125b-2-3p | MIMAT0004603 | 99 | −45.65 | 0.302 | 0 |
| hsa-miR-30d-5p | MIMAT0000245 | 445 | −44.15 | 0.318 | 0 |
| hsa-miR-193a-3p | MIMAT0000459 | 284 | −42.75 | 0.321 | 0 |
| hsa-miR-365a-3p | MIMAT0000710 | 657 | −42.4 | 0.393 | 0 |
| hsa-miR-378b | MIMAT0014999 | 750 | −40.9 | 0.307 | 0 |
| hsa-miR-328-3p | MIMAT0000752 | 585 | −40.35 | 0.42 | 0 |
| hsa-miR-338-3p | MIMAT0000763 | 595 | −40.1 | 0.276 | 0 |
| hsa-miR-497-5p | MIMAT0002820 | 1368 | −39.95 | 0.319 | 0 |
| hsa-miR-92a-3p | MIMAT0000092 | 1707 | −39.8 | 0.639 | 0 |
| hsa-miR-378e | MIMAT0018927 | 753 | −39.65 | 0.347 | 0 |
| hsa-miR-30a-5p | MIMAT0000087 | 438 | −39.4 | 0.452 | 0 |
| hsa-miR-26a-5p | MIMAT0000082 | 391 | −38.85 | 0.435 | 0 |
| hsa-miR-195-5p | MIMAT0000461 | 290 | −38.7 | 0.429 | 0 |
| hsa-miR-30c-5p | MIMAT0000244 | 442 | −37.9 | 0.386 | 0 |
| hsa-miR-210-3p | MIMAT0000267 | 334 | −37.3 | 0.477 | 2.822 |
| hsa-miR-30e-5p | MIMAT0000692 | 447 | −37.15 | 0.434 | 2.822 |
| hsa-miR-423-3p | MIMAT0001340 | 823 | −37.05 | 0.513 | 2.822 |
| hsa-miR-30b-5p | MIMAT0000420 | 440 | −36.8 | 0.488 | 2.822 |
| hsa-miR-136-3p | MIMAT0004606 | 181 | −35.4 | 0.319 | 2.822 |
| hsa-miR-200b-5p | MIMAT0004571 | 313 | −35.4 | 0.548 | 2.822 |
| hsa-miR-24-1-5p | MIMAT0000079 | 381 | −35.4 | 0.641 | 2.822 |
| hsa-miR-378d | MIMAT0018926 | 752 | −35.1 | 0.365 | 2.822 |
| hsa-miR-378g | MIMAT0018937 | 755 | −34.95 | 0.364 | 2.822 |
| hsa-miR-887-3p | MIMAT0004951 | 1692 | −34.85 | 0.249 | 2.822 |
| hsa-miR-205-5p | MIMAT0000266 | 320 | −34.5 | 0.405 | 2.822 |
| hsa-miR-885-5p | MIMAT0004947 | 1691 | −34.4 | 0 | 2.822 |
| hsa-miR-211-5p | MIMAT0000268 | 335 | −34 | 0.074 | 2.822 |
| hsa-miR-378f | MIMAT0018932 | 754 | −33.95 | 0.361 | 2.822 |
| hsa-miR-222-3p | MIMAT0000279 | 362 | −33.8 | 0.596 | 2.822 |
| hsa-miR-23c | MIMAT0018000 | 379 | −33.65 | 0.598 | 2.822 |
| hsa-miR-378c | MIMAT0016847 | 751 | −33.45 | 0.516 | 2.822 |
| hsa-miR-376a-3p | MIMAT0000729 | 742 | −32.85 | 0.483 | 4.58 |

TABLE 4-continued

Validation of differentially expressed miRNAs in HNSCC (UMSC set)

| miRNA | MIMAT ID | Geneind | Score | FoldChange | qval |
|---|---|---|---|---|---|
| hsa-miR-335-5p | MIMAT0000765 | 591 | −32.75 | 0.218 | 4.58 |
| hsa-miR-378i | MIMAT0019074 | 757 | −32.5 | 0.558 | 4.58 |
| hsa-miR-378a-3p | MIMAT0000732 | 748 | −32.45 | 0.477 | 4.58 |
| hsa-miR-378h | MIMAT0018984 | 756 | −32.45 | 0.296 | 4.58 |
| hsa-miR-125b-5p | MIMAT0000423 | 97 | −32.4 | 0.624 | 4.58 |
| hsa-miR-381-3p | MIMAT0000736 | 762 | −32.35 | 0.129 | 4.58 |
| hsa-miR-24-3p | MIMAT0000080 | 380 | −32.3 | 0.856 | 4.58 |
| hsa-miR-486-3p | MIMAT0004762 | 1351 | −32.1 | 0.172 | 4.58 |
| hsa-miR-664a-3p | MIMAT0005949 | 1647 | −32.1 | 0.34 | 4.58 |
| hsa-miR-532-3p | MIMAT0004780 | 1461 | −32 | 0.37 | 4.58 |
| hsa-miR-30a-3p | MIMAT0000088 | 439 | −31.65 | 0.429 | 4.58 |
| hsa-miR-95-3p | MIMAT0000094 | 1726 | −31.5 | 0.444 | 5.174 |
| hsa-miR-337-5p | MIMAT0004695 | 594 | −30.9 | 0.251 | 5.478 |
| hsa-miR-361-5p | MIMAT0000703 | 627 | −29.85 | 0.601 | 7.87 |
| hsa-miR-874-3p | MIMAT0004911 | 1683 | −29.85 | 0.397 | 7.87 |
| hsa-miR-200a-3p | MIMAT0000682 | 310 | −29.55 | 0.326 | 8.977 |
| hsa-miR-145-5p | MIMAT0000437 | 198 | −29.25 | 0.65 | 9.861 |
| hsa-miR-4284 | MIMAT0016915 | 862 | −28.7 | 0.281 | 10.464 |
| hsa-miR-377-5p | MIMAT0004689 | 747 | −28.65 | 0.133 | 10.464 |
| hsa-miR-30e-3p | MIMAT0000693 | 448 | −28.55 | 0.585 | 10.464 |
| hsa-miR-33b-5p | MIMAT0003301 | 601 | −28.2 | 0.313 | 10.746 |
| hsa-miR-744-5p | MIMAT0004945 | 1666 | −28.2 | 0.396 | 10.746 |
| hsa-miR-186-5p | MIMAT0000456 | 256 | −27.35 | 0.516 | 13.582 |
| hsa-miR-499a-5p | MIMAT0002870 | 1372 | −27 | 0 | 14.255 |
| hsa-miR-141-3p | MIMAT0000432 | 190 | −26.75 | 0.471 | 14.255 |
| hsa-miR-26b-5p | MIMAT0000083 | 394 | −26.7 | 0.667 | 14.255 |
| hsa-miR-181c-5p | MIMAT0000258 | 244 | −26.45 | 0.399 | 14.255 |
| hsa-miR-133b | MIMAT0000770 | 173 | −26.35 | 0.106 | 14.255 |
| hsa-miR-203a-3p | MIMAT0000264 | 318 | −26.3 | 0.51 | 14.255 |
| hsa-miR-136-5p | MIMAT0000448 | 180 | −26.25 | 0.628 | 14.968 |
| hsa-miR-376c-3p | MIMAT0000720 | 745 | −25.95 | 0.294 | 14.968 |
| hsa-miR-3622a-5p | MIMAT0018003 | 647 | −25.9 | 0 | 14.968 |
| hsa-miR-154-5p | MIMAT0000452 | 226 | −25.85 | 0.397 | 14.968 |
| hsa-miR-133a-3p | MIMAT0000427 | 172 | −25.75 | 0.099 | 14.968 |
| hsa-miR-574-3p | MIMAT0003239 | 1543 | −25.7 | 0.434 | 14.968 |
| hsa-mir-1280 | MIMAT0005946 | 132 | −25.65 | 0.425 | 14.968 |
| hsa-miR-149-5p | MIMAT0000450 | 214 | −25.65 | 0.473 | 14.968 |
| hsa-miR-214-3p | MIMAT0000271 | 346 | −25.6 | 0.492 | 14.968 |
| hsa-miR-1291 | MIMAT0005881 | 146 | −25.3 | 0 | 16.057 |
| hsa-miR-126-5p | MIMAT0000444 | 101 | −25.2 | 0.627 | 16.057 |
| hsa-miR-484 | MIMAT0002174 | 1348 | −25.15 | 0.525 | 16.057 |
| hsa-miR-23a-3p | MIMAT0000078 | 375 | −24.9 | 0.79 | 16.057 |
| hsa-miR-99b-5p | MIMAT0000689 | 1732 | −24.9 | 0.676 | 16.057 |
| hsa-miR-199b-5p | MIMAT0000263 | 304 | −24.7 | 0.562 | 16.435 |
| hsa-miR-1271-5p | MIMAT0005796 | 118 | −24.45 | 0.624 | 16.686 |
| hsa-miR-1268a | MIMAT0005922 | 111 | −24.3 | 0 | 16.933 |
| hsa-miR-186-3p | MIMAT0004612 | 257 | −24.1 | 0.396 | 17.415 |
| hsa-miR-3615 | MIMAT0017994 | 635 | −24.1 | 0.37 | 17.415 |
| hsa-miR-422a | MIMAT0001339 | 822 | −23.7 | 0 | 18.026 |
| hsa-miR-1249-3p | MIMAT0005901 | 84 | −23.4 | 0.287 | 18.627 |

Example 3 miR-30 Family Members Inhibit HNSCC Proliferation

Figure 3A:
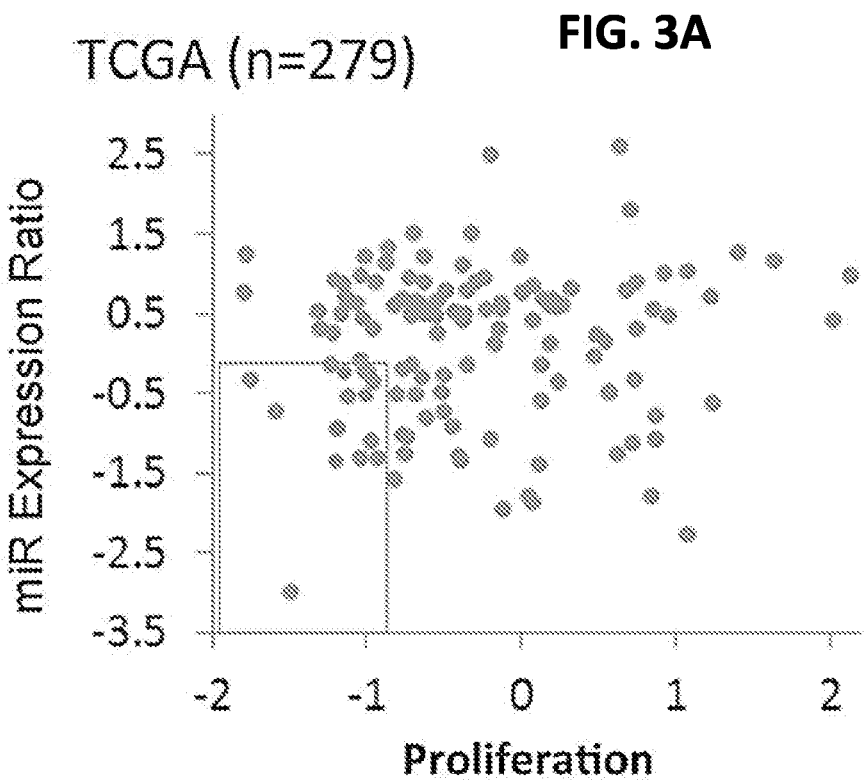
FIGS. 3A-3D are a series of graphs showing the effect of miRNAs with decreased expression on HNSCC proliferation. MicroRNAs displayed anti-proliferative activity in an in vitro genome wide RNAi screening in the HNSCC cell line UM-SCC-1. Scatter plots display differentially expressed microRNAs ($\log_2$ tumor vs. mucosa in y axis) vs. statistical distribution for proliferation score (Median Absolute Deviation (MAD)) using TCGA (FIG. 3A) and UMSC (FIG. 3B) expression data. The box in the lower left portion of the plot denotes microRNA expression ratios (y axis) that are repressed with anti-proliferative activity in RNAi screening (x axis). miR-30-5p family members are marked in red.
Figure 3B:
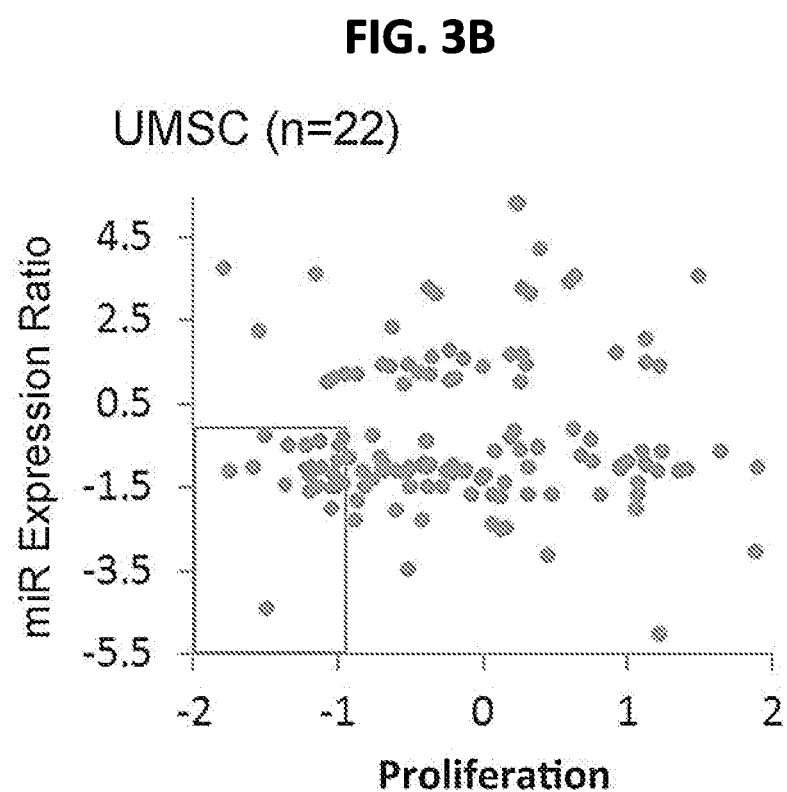
Figure 3C:
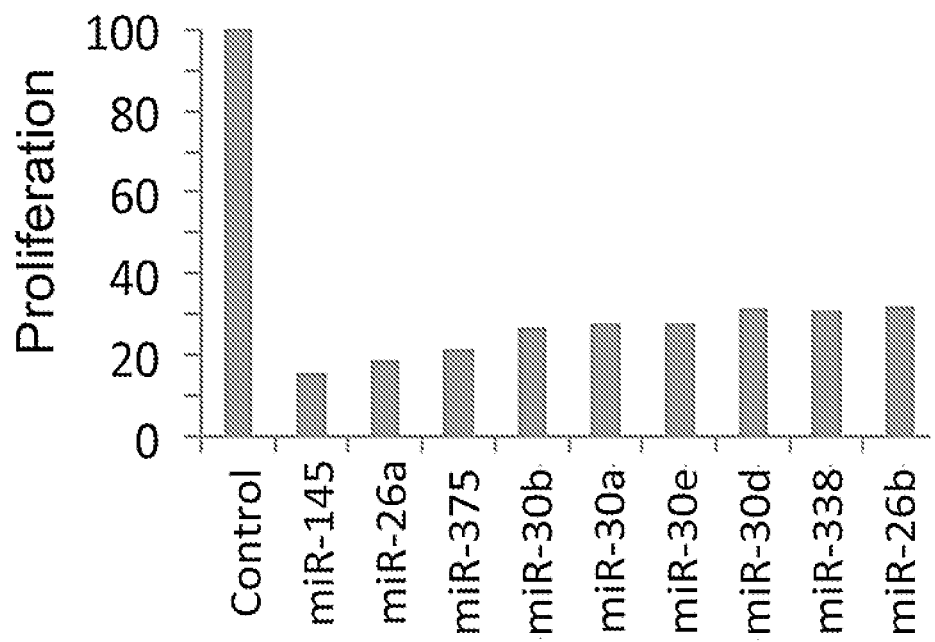
Figure 3D:
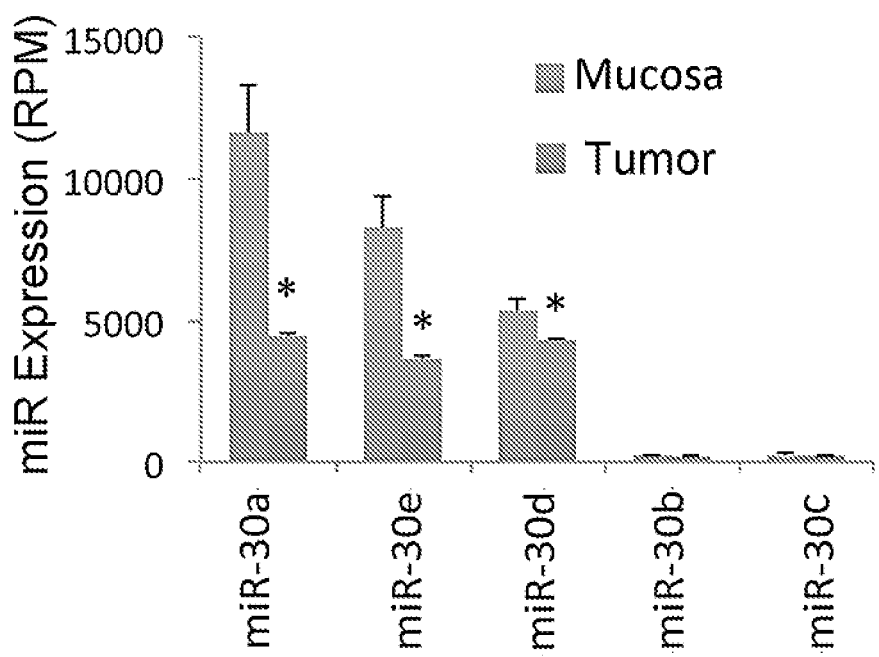

An independent functional genomics screen was performed after transfecting a library of 781 miRs into the human HNSCC line UM-SCC-1 to identify candidate miRs that inhibited proliferation (Table 5). To enrich screening hits for miRs with relevance to disease biology, miRs that displayed high anti-proliferative activity (MAD score <−1) were filtered against miRs that also displayed reduced expression by sequence profiling in both TCGA and UMSC validation datasets (FIGS. 3A and 3B). Nine miRs with decreased expression in tumor specimens were identified that displayed significant inhibitory activity when re-expressed during the functional genomic screen (FIG. 3C). Strikingly, several members of the miR-30-5p family were again present among this highly selected class of miRs, supporting the biologic and functional importance of miR-30-5p family members in HNSCC. Among these, miR-30a-5p and miR-30e-5p were the most highly expressed in mucosa samples and decreased across the tumor specimens (FIG. 3D).

TABLE 5

Candidate miRNAs that inhibit HNSCC proliferation

| Gene | Signal | MAD Score | MIMAT ID |
|---|---|---|---|
| hsa-miR-29b-1-5p | 4.187766 | −2.2489101 | MIMAT0004514 |
| hsa-miR-593-5p | 8.12201 | −2.0705311 | MIMAT0003261 |
| hsa-miR-603 | 9.64568 | −2.0014477 | MIMAT0003271 |
| hsa-miR-137 | 10.4889 | −1.9632159 | MIMAT0000429 |
| hsa-miR-217 | 10.51062 | −1.9622312 | MIMAT0000274 |
| hsa-miR-570-3p | 10.55155 | −1.9603754 | MIMAT0003235 |
| hsa-miR-27b-5p | 13.10053 | −1.8448044 | MIMAT0004588 |
| hsa-miR-216b-5p | 13.18732 | −1.8448692 | MIMAT0004959 |
| hsa-miR-589-5p | 14.47781 | −1.7823586 | MIMAT0004799 |

TABLE 5-continued

Candidate miRNAs that inhibit HNSCC proliferation

| Gene | Signal | MAD Score | MIMAT ID |
| --- | --- | --- | --- |
| hsa-miR-9-5p | 14.53328 | -1.7798433 | MIMAT0000441 |
| hsa-miR-145-5p | 15.30917 | -1.7446645 | MIMAT0000437 |
| hsa-miR-96-5p | 15.68504 | -1.7276227 | MIMAT0000095 |
| hsa-miR-657 | 15.87208 | -1.7191421 | MIMAT0003335 |
| hsa-miR-608 | 17.80167 | -1.6316544 | MIMAT0003276 |
| hsa-miR-619-3p | 18.3711 | -1.6058364 | MIMAT0003288 |
| hsa-miR-548o-3p | 18.76871 | -1.5878087 | MIMAT0005919 |
| hsa-miR-26a-5p | 18.84667 | -1.584274 | MIMAT0000082 |
| hsa-miR-633 | 19.39796 | -1.5592783 | MIMAT0003303 |
| hsa-miR-542-5p | 19.68481 | -1.5462724 | MIMAT0003340 |
| hsa-miR-330-3p | 20.29708 | -1.5185119 | MIMAT0000751 |
| hsa-miR-1272 | 20.4797 | -1.5102322 | MIMAT0005925 |
| hsa-miR-136-5p | 20.69347 | -1.5005399 | MIMAT0000448 |
| hsa-miR-1236-3p | 20.87731 | -1.4922045 | MIMAT0005591 |
| hsa-miR-375 | 21.15436 | -1.4796432 | MIMAT0000728 |
| hsa-miR-875-5p | 21.1604 | -1.4793693 | MIMAT0004922 |
| hsa-miR-802 | 21.51106 | -1.4634702 | MIMAT0004185 |
| hsa-miR-1270 | 21.73955 | -1.4531104 | MIMAT0005924 |
| hsa-miR-491-5p | 21.80712 | -1.4500466 | MIMAT0002807 |
| hsa-miR-548d-3p | 21.98693 | -1.441894 | MIMAT0003323 |
| hsa-miR-1201 | 22.4862 | -1.4192573 | dead |
| hsa-miR-1826 | 22.56671 | -1.4156069 | dead |
| hsa-miR-888-5p | 22.91194 | -1.3999539 | MIMAT0004916 |
| hsa-miR-513a-3p | 23.13434 | -1.3898705 | MIMAT0004777 |
| hsa-miR-612 | 23.63225 | -1.367295 | MIMAT0003280 |
| hsa-miR-30c-5p | 23.73198 | -1.3627735 | MIMAT0000244 |
| hsa-miR-1299 | 23.87786 | -1.356159 | MIMAT0005887 |
| hsa-miR-1975 | 24.18666 | -1.3421584 | dead |
| hsa-miR-24-1-5p | 24.37669 | -1.3335424 | MIMAT0000079 |
| hsa-miR-340-5p | 24.59735 | -1.3235374 | MIMAT0004692 |
| hsa-miR-138-2-3p | 24.66306 | -1.320558 | MIMAT0004596 |
| hsa-miR-541-5p | 24.8673 | -1.3112979 | MIMAT0004919 |
| hsa-miR-142-3p | 25.09606 | -1.300926 | MIMAT0000434 |
| hsa-miR-544a | 25.14354 | -1.2987732 | MIMAT0003164 |
| hsa-miR-567 | 25.30231 | -1.2915744 | MIMAT0003231 |
| hsa-miR-146a-5p | 25.30952 | -1.2912476 | MIMAT0000449 |
| hsa-miR-630 | 25.58343 | -1.2788285 | MIMAT0003299 |
| hsa-miR-18a-5p | 25.87251 | -1.2657217 | MIMAT0000072 |
| hsa-miR-616-3p | 25.9572 | -1.2618816 | MIMAT0004805 |
| hsa-miR-215-5p | 26.08764 | -1.2559675 | MIMAT0000272 |
| hsa-miR-578 | 26.42948 | -1.2404685 | MIMAT0003243 |
| hsa-miR-30b-5p | 26.86759 | -1.2206044 | MIMAT0000420 |
| hsa-miR-186-5p | 27.10501 | -1.2098401 | MIMAT0000456 |
| hsa-miR-590-5p | 27.12312 | -1.2090186 | MIMAT0003258 |
| hsa-miR-518c-5p | 27.12724 | -1.2088321 | MIMAT0002847 |
| hsa-miR-7-5p | 27.31268 | -1.200424 | MIMAT0000252 |
| hsa-miR-342-3p | 27.32802 | -1.1997288 | MIMAT0000753 |
| hsa-miR-30a-5p | 27.47793 | -1.1929316 | MIMAT0000087 |
| hsa-miR-30e-5p | 27.52222 | -1.1909236 | MIMAT0000692 |
| hsa-miR-153-3p | 27.61561 | -1.1866895 | MIMAT0000439 |
| hsa-miR-139-5p | 27.66021 | -1.1846672 | MIMAT0000250 |
| hsa-miR-421 | 27.67275 | -1.1840984 | MIMAT0003339 |
| hsa-miR-522-3p | 27.88499 | -1.1744755 | MIMAT0002868 |
| hsa-miR-580-3p | 27.89437 | -1.1740503 | MIMAT0003245 |
| hsa-miR-642a-5p | 28.16026 | -1.1619948 | MIMAT0003312 |
| hsa-miR-200c-3p | 28.36733 | -1.152606 | MIMAT0000617 |
| hsa-miR-503-5p | 28.56057 | -1.1438447 | MIMAT0002874 |
| hsa-miR-17-5p | 28.65503 | -1.139562 | MIMAT0000070 |
| hsa-miR-125b-2-3p | 28.79045 | -1.1334221 | MIMAT0004603 |
| hsa-miR-20a-5p | 28.9898 | -1.1243834 | MIMAT0000075 |
| hsa-miR-205-5p | 29.07725 | -1.1204183 | MIMAT0000266 |
| hsa-miR-618 | 29.10751 | -1.1190463 | MIMAT0003287 |
| hsa-miR-30e-3p | 29.33285 | -1.1088292 | MIMAT0000692 |
| hsa-miR-124-5p | 29.93332 | -1.0816041 | MIMAT0004591 |
| hsa-miR-29a-5p | 30.21309 | -1.0689194 | MIMAT0004503 |
| hsa-miR-129-2-3p | 30.31542 | -1.0642796 | MIMAT0004605 |
| hsa-miR-599 | 30.36961 | -1.0618225 | MIMAT0003267 |
| hsa-miR-191-5p | 30.40741 | -1.0601087 | MIMAT0000440 |
| hsa-miR-548b-5p | 30.48026 | -1.0568057 | MIMAT0004798 |
| hsa-miR-1244 | 30.49915 | -1.0559492 | MIMAT0005896 |
| hsa-miR-452-5p | 30.56421 | -1.0529995 | MIMAT0001635 |
| hsa-miR-664a-3p | 30.57374 | -1.0525673 | MIMAT0005949 |
| hsa-miR-1184 | 30.70965 | -1.0464051 | MIMAT0005829 |
| hsa-miR-586 | 30.75168 | -1.0444994 | MIMAT0003252 |
| hsa-miR-573 | 30.87112 | -1.0390839 | MIMAT0003238 |
| hsa-miR-885-5p | 30.99188 | -1.0336087 | MIMAT0004947 |
| hsa-miR-548h-5p | 31.03215 | -1.031783 | MIMAT0005928 |
| hsa-miR-542-3p | 31.06854 | -1.0301329 | MIMAT0003389 |
| hsa-miR-338-3p | 31.07923 | -1.0296484 | MIMAT0000763 |
| hsa-miR-200b-3p | 31.15171 | -1.0263622 | MIMAT0000318 |
| hsa-miR-651-5p | 31.20514 | -1.0239397 | MIMAT0003321 |
| hsa-miR-155-5p | 31.22419 | -1.0230761 | MIMAT0000646 |
| hsa-miR-526b-5p | 31.3515 | -1.0173037 | MIMAT0002835 |
| hsa-miR-1178-3p | 31.37379 | -1.0162931 | MIMAT0005823 |
| hsa-miR-449b-5p | 31.38433 | -1.015815 | MIMAT0003327 |
| hsa-miR-216a-5p | 31.44441 | -1.0130911 | MIMAT0000273 |
| hsa-miR-224-5p | 31.57519 | -1.0071617 | MIMAT0000281 |
| hsa-miR-19b-3p | 31.59959 | -1.0060554 | MIMAT0000074 |
| hsa-miR-506-3p | 31.61057 | -1.0055571 | MIMAT0002878 |
| hsa-miR-30d-5p | 31.62978 | -1.0046861 | MIMAT0000245 |
| hsa-miR-26b-5p | 31.69762 | -1.0016106 | MIMAT0000083 |

Example 4

Correlation of Inversely Expressed Targets of miRNAs and Pro-Growth Signaling and Metastasis mRNAs To identify the network of target mRNAs regulated by several miRNAs in HNSCC and underlying their potential function, the reduced expression of miR-30a-5p, miR-30b-5p, miR-30d-5p, miR-30e-5p, miR-26a-5p, miR-26b-5p, miR-145-5p, miR-205-5p, and miR-375 were each analyzed for inverse correlation with mRNAs of potentially biologic importance in cancer. Linear regression analysis was performed between each miRNA and genome-wide mRNA expression levels obtained from RNA-seq performed on 279 HNSCC tumor specimens in the TCGA dataset. The results are shown in Tables 6-14.

Figure 4:
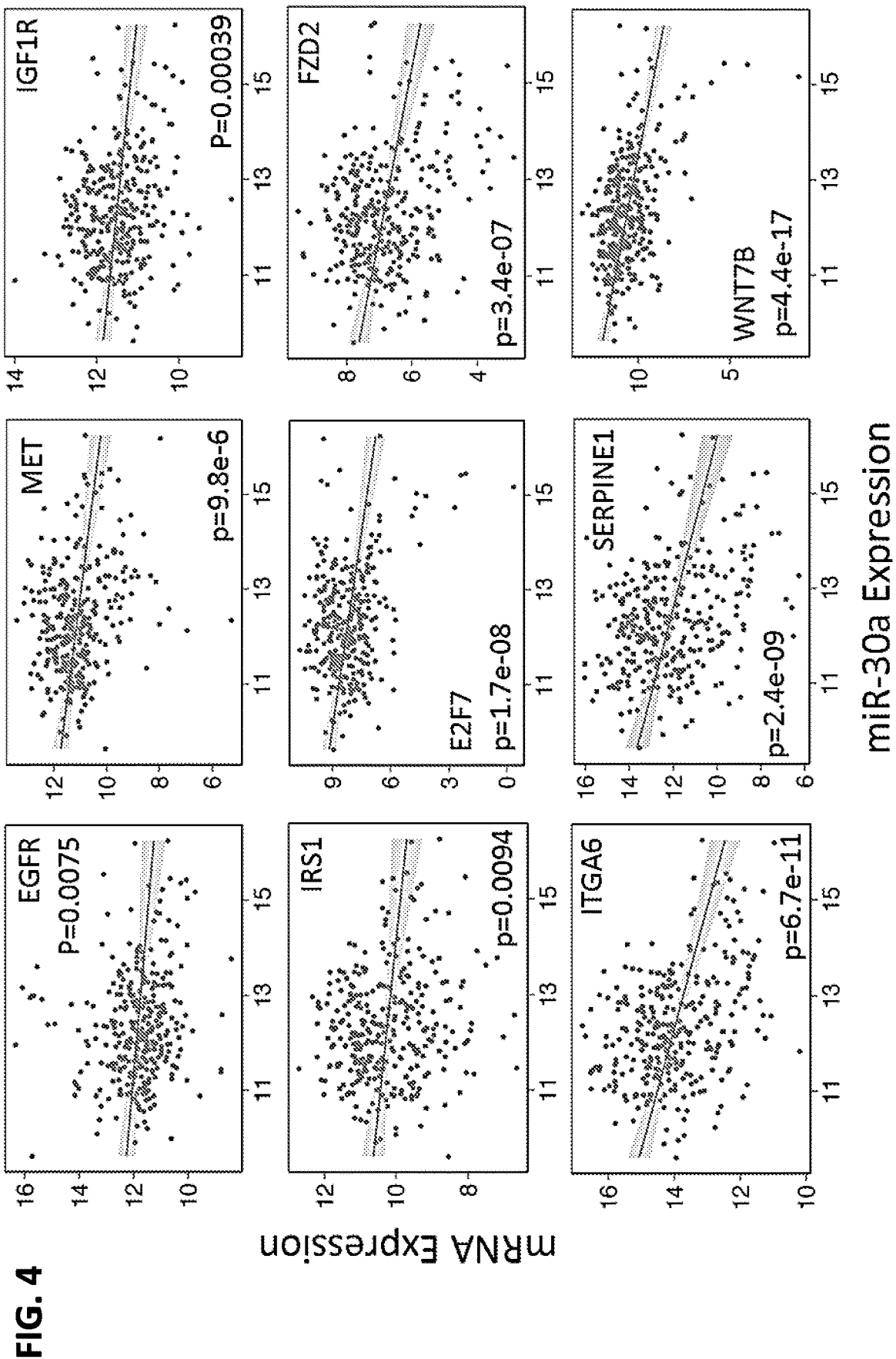
FIG. 4 is a series of panels showing expression of miR-30a-5p ($\log_{10}$ RPM, x axis) vs. mRNA expression ($\log_{10}$RSEM (RNA-Seq by Expectation Maximization), y axis) from the HNSCC TCGA dataset, and filtered for mRNAs containing predicted miR-30 binding sites. Linear regression scatterplots are presented for the indicated mRNAs with p values.

As an example, 91 mRNAs were detected as inversely expressed to miR-30a using an FDR ≤0.05, and also contained predicted or verified binding sites for miR-30a-5p in the 3' UTR based on the Ingenuity Pathway Analysis (IPA) microRNA target filter (Table 6). The significant anti-correlation of miR-30a-5p with several representative target genes is presented in FIG. 4. miR-30a-5p expression displayed an inverse relationship to several oncogenes previously shown to be overexpressed in HNSCC, including EGFR, MET, ITGA6 and SERPINE1 (FIG. 4) (Van Waes et al., *Cancer Res.* 55:5434-5444, 1995; Van Waes et al., *Int. J. Radiat. Oncol. Biol. Phys.* 77:447-454, 2010; Freudlsperger et al., *Expert Opin. Ther. Targets* 15:63-74, 2011).

TABLE 6 mRNAs inversely expressed and containing predicted or validated binding sites to miR-30a-5p

| Source | Confidence | Symbol | t.stat | p-value | q-value |
|---|---|---|---|---|---|
| TarBase,TargetScan Human | Experimentally Observed, High (predicted) | NT5E | −2.67544 | 0.00785943 | 0.042443335 |
| TarBase,TargetScan Human | Experimentally Observed, High (predicted) | SLC7A11 | −7.34317 | 1.8519E−12 | 2.47526E−10 |
| TarBase | Experimentally Observed | WNT5A | −3.21244 | 0.00145446 | 0.011477956 |
| TarBase | Experimentally Observed | MET | −4.49672 | 9.7643E−06 | 0.000186635 |
| miRecords | Experimentally Observed | STX1A | −5.73134 | 2.3616E−08 | 1.04475E−06 |
| TargetScan Human | High (predicted) | ADAM12 | −5.8907 | 1.0009E−08 | 4.93575E−07 |
| TargetScan Human | High (predicted) | ADAMTS14 | −4.448 | 1.2095E−05 | 0.000223621 |
| TargetScan Human | High (predicted) | ADAMTS6 | −3.11958 | 0.00198133 | 0.014647111 |
| TargetScan Human | High (predicted) | AFAP1L2 | −3.57478 | 0.00040639 | 0.004129055 |
| TargetScan Human | High (predicted) | BCL11B | −7.45518 | 9.0434E−13 | 1.30665E−10 |
| TargetScan Human | High (predicted) | BNC1 | −10.1613 | 3.9863E−21 | 3.3215E−18 |
| TargetScan Human | High (predicted) | CALB2 | −2.60695 | 0.00957701 | 0.049262735 |
| TargetScan Human | High (predicted) | CAMK2N2 | −4.33529 | 1.9703E−05 | 0.000337565 |
| TargetScan Human | High (predicted) | CBX2 | −7.41229 | 1.1909E−12 | 1.66992E−10 |
| TargetScan Human | Moderate (predicted) | CCNA1 | −3.39196 | 0.00078393 | 0.007013279 |
| TargetScan Human | High (predicted) | CCNE2 | −3.58521 | 0.00039112 | 0.004002625 |
| TargetScan Human | Moderate (predicted) | CD80 | −3.23442 | 0.00135044 | 0.010822133 |
| TargetScan Human | High (predicted) | CDCA7 | −2.94594 | 0.00346369 | 0.022650361 |
| TargetScan Human | Moderate (predicted) | CDHR1 | −3.55523 | 0.00043656 | 0.004375406 |
| TargetScan Human | High (predicted) | CELSR3 | −4.19807 | 3.5211E−05 | 0.000549357 |
| TargetScan Human | Moderate (predicted) | CERS3 | −6.93548 | 2.3632E−11 | 2.38628E−09 |
| TargetScan Human | High (predicted) | CHST1 | −3.42212 | 0.00070477 | 0.006439431 |
| TargetScan Human | High (predicted) | CHST2 | −6.88903 | 3.1387E−11 | 3.07078E−09 |
| TargetScan Human | High (predicted) | CNGB3 | −4.62375 | 5.5397E−06 | 0.000115408 |
| TargetScan Human | High (predicted) | COL13A1 | −6.52577 | 2.7564E−10 | 2.0983E−08 |
| TargetScan Human | High (predicted) | CTHRC1 | −3.81302 | 0.00016563 | 0.001984823 |
| TargetScan Human | High (predicted) | DDIT4 | −3.52927 | 0.00047985 | 0.004724036 |
| TargetScan Human | Moderate (predicted) | DSP | −5.75525 | 2.0785E−08 | 9.34316E−07 |
| TargetScan Human | High (predicted) | E2F7 | −5.78932 | 1.7316E−08 | 7.96717E−07 |
| TargetScan Human | High (predicted) | EFNA3 | −4.17635 | 3.8546E−05 | 0.000592557 |
| TargetScan Human | Moderate (predicted) | EGFR | −2.69295 | 0.00746753 | 0.040839291 |
| TargetScan Human | High (predicted) | EPB41L4B | −3.15221 | 0.00177887 | 0.013456245 |
| TargetScan Human | High (predicted) | FAM43A | −4.71164 | 3.7153E−06 | 8.21663E−05 |
| TargetScan Human | High (predicted) | FAP | −4.57488 | 6.8998E−06 | 0.000139116 |
| TargetScan Human | High (predicted) | FOXD1 | −5.39201 | 1.3836E−07 | 4.85439E−06 |
| TargetScan Human | High (predicted) | FZD2 | −5.21242 | 3.41E−07 | 1.05844E−05 |
| TargetScan Human | High (predicted) | GJA1 | −6.45364 | 4.2012E−10 | 3.04202E−08 |

TABLE 6-continued mRNAs inversely expressed and containing predicted or validated binding sites to miR-30a-5p

| Source | Confidence | Symbol | t.stat | p-value | q-value |
|---|---|---|---|---|---|
| TargetScan Human | High (predicted) | GLDC | −2.71789 | 0.00693956 | 0.038631316 |
| TargetScan Human | Moderate (predicted) | GNRHR | −4.11924 | 4.8817E−05 | 0.000721673 |
| TargetScan Human | High (predicted) | GRHL1 | −2.67624 | 0.00784124 | 0.042369061 |
| TargetScan Human | High (predicted) | HEPHL1 | −5.0097 | 9.1733E−07 | 2.48043E−05 |
| TargetScan Human | High (predicted) | HOXA11 | −5.77494 | 1.8706E−08 | 8.52358E−07 |
| TargetScan Human | High (predicted) | HTRA3 | −2.92943 | 0.00364778 | 0.023577439 |
| TargetScan Human | High (predicted) | IGF1R | −3.52927 | 0.00021693 | 0.000384284 |
| TargetScan Human | High (predicted) | IL1A | −6.20891 | 1.7114E−09 | 1.04732E−07 |
| TargetScan Human | High (predicted) | IL28RA | −4.58937 | 6.4663E−06 | 0.000131627 |
| TargetScan Human | High (predicted) | IRS1 | −2.61196 | 0.00944086 | 0.048733913 |
| TargetScan Human | High (predicted) | IRX4 | −4.38851 | 1.5668E−05 | 0.000278244 |
| TargetScan Human | High (predicted) | ITGA5 | −5.94408 | 7.4786E−09 | 3.82354E−07 |
| TargetScan Human | High (predicted) | ITGA6 | −6.76279 | 6.7415E−11 | 6.04954E−09 |
| TargetScan Human | High (predicted) | KIAA1804 | −3.06917 | 0.00233624 | 0.016671132 |
| TargetScan Human | High (predicted) | KIF3C | −4.79377 | 2.5442E−06 | 5.94757E−05 |
| TargetScan Human | High (predicted) | LHX1 | −7.00892 | 1.5048E−11 | 1.59942E−09 |
| TargetScan Human | High (predicted) | LOX | −3.09258 | 0.00216471 | 0.015701083 |
| TargetScan Human | High (predicted) | LRRC3 | −4.33577 | 1.9662E−05 | 0.000336972 |
| TargetScan Human | High (predicted) | MAF | −3.14025 | 0.00185073 | 0.013882679 |
| TargetScan Human | High (predicted) | MFHAS1 | −4.75352 | 3.065E−06 | 6.97331E−05 |
| TargetScan Human | High (predicted) | MYBL2 | −7.83707 | 7.4462E−14 | 1.39556E−11 |
| TargetScan Human | High (predicted) | MYH10 | −3.74269 | 0.00021693 | 0.002477083 |
| TargetScan Human | Moderate (predicted) | MYO1H | −2.68 | 0.00775571 | 0.042020701 |
| TargetScan Human | High (predicted) | NEFL | −5.76182 | 2.0067E−08 | 9.0609E−07 |
| TargetScan Human | High (predicted) | NID1 | −4.56143 | 7.3271E−06 | 0.000146362 |
| TargetScan Human | High (predicted) | NOD2 | −5.23065 | 3.115E−07 | 9.79208E−06 |
| TargetScan Human | High (predicted) | NREP | −3.09434 | 0.00215234 | 0.015631917 |
| TargetScan Human | High (predicted) | NTM | −3.79283 | 0.00017904 | 0.002115612 |
| TargetScan Human | High (predicted) | ONECUT2 | −2.66567 | 0.0080862 | 0.043367382 |
| TargetScan Human | High (predicted) | OVOL1 | −3.56263 | 0.0004249 | 0.00428063 |
| TargetScan Human | High (predicted) | PAG1 | −3.29063 | 0.00111491 | 0.009292512 |
| TargetScan Human | High (predicted) | PCDH17 | −2.62238 | 0.00916308 | 0.047653736 |
| TargetScan Human | High (predicted) | PDGFRB | −3.1546 | 0.00176483 | 0.013372471 |
| TargetScan Human | Moderate (predicted) | PHLDB2 | −7.25139 | 3.3136E−12 | 4.15821E−10 |
| TargetScan Human | Moderate (predicted) | PNPLA1 | −6.83038 | 4.4825E−11 | 4.20919E−09 |
| TargetScan Human | High (predicted) | PPFIA1 | −3.44793 | 0.000643 | 0.005981654 |
| TargetScan Human | High (predicted) | PPP1R14C | −5.52887 | 6.8493E−08 | 2.63407E−06 |
| TargetScan Human | High (predicted) | PPP4R4 | −2.9497 | 0.00342301 | 0.022444469 |

TABLE 6-continued mRNAs inversely expressed and containing predicted or validated binding sites to miR-30a-5p

| Source | Confidence | Symbol | t.stat | p-value | q-value |
|---|---|---|---|---|---|
| TargetScan Human | High (predicted) | RAB38 | −5.19914 | 3.6418E−07 | 1.11991E−05 |
| TargetScan Human | High (predicted) | RHEBL1 | −2.87936 | 0.00426207 | 0.026591947 |
| TargetScan Human | High (predicted) | RTN4R | −5.76779 | 1.9436E−08 | 8.81367E−07 |
| TargetScan Human | High (predicted) | SCN8A | −3.00949 | 0.00283162 | 0.019369396 |
| TargetScan Human | High (predicted) | SERPINE1 | −6.14674 | 2.4297E−09 | 1.4251E−07 |
| TargetScan Human | High (predicted) | SLC44A5 | −4.0284 | 7.0695E−05 | 0.000981803 |
| TargetScan Human | Moderate (predicted) | SLCO6A1 | −4.63823 | 5.189E−06 | 0.000109185 |
| TargetScan Human | High (predicted) | SNX10 | −6.11018 | 2.9822E−09 | 1.70412E−07 |
| TargetScan Human | High (predicted) | SOCS1 | −2.84294 | 0.00476672 | 0.028990247 |
| TargetScan Human | Moderate (predicted) | STAT1 | −2.94123 | 0.0035153 | 0.022913435 |
| TargetScan Human | High (predicted) | THBS2 | −3.48948 | 0.00055409 | 0.00530563 |
| TargetScan Human | High (predicted) | TMC7 | −4.4635 | 1.1301E−05 | 0.000211182 |
| TargetScan Human | Moderate (predicted) | TNFSF9 | −4.07698 | 5.8042E−05 | 0.000833474 |
| TargetScan Human | High (predicted) | TRIM9 | −2.6338 | 0.00886708 | 0.046491218 |
| TargetScan Human | High (predicted) | TRPA1 | −5.02466 | 8.5363E−07 | 2.33216E−05 |
| TargetScan Human | High (predicted) | WNT7B | −8.91065 | 4.4225E−17 | 1.68683E−14 |

TABLE 7 mRNAs inversely expressed and containing predicted or validated binding sites to miR-30b-5p (MIMAT0000420)

| Gene | beta | t.stat | p.value | FDR |
|---|---|---|---|---|
| ABCA12 | −0.003 | −3.7 | 0.00024 | 0.0029 |
| ABCA6 | −0.0024 | −3.2 | 0.0014 | 0.012 |
| ADAM12 | −0.0041 | −4.6 | 7.70E−06 | 0.00019 |
| ADAM19 | −0.0016 | −2.6 | 0.0095 | 0.048 |
| ADAMTS14 | −0.0026 | −4 | 6.90E−05 | 0.0011 |
| ADAMTS3 | −0.0034 | −4.1 | 4.80E−05 | 0.00083 |
| ADAMTS5 | −0.003 | −4.3 | 2.50E−05 | 0.00049 |
| ADAMTS9 | −0.0018 | −2.8 | 0.0058 | 0.033 |
| ADRA2A | −0.0031 | −2.7 | 0.0079 | 0.042 |
| AFAP1L2 | −0.0018 | −3.6 | 0.00039 | 0.0043 |
| AGAP2 | −0.0014 | −2.8 | 0.0049 | 0.03 |
| AJAP1 | −0.0042 | −3.3 | 0.0012 | 0.01 |
| ANGPT2 | −0.0022 | −4.1 | 5.70E−05 | 0.00094 |
| ANTXR1 | −0.0018 | −3.7 | 0.00028 | 0.0033 |
| APOL6 | −0.0018 | −3.3 | 0.0011 | 0.0095 |
| ARHGAP29 | −0.0016 | −2.9 | 0.004 | 0.026 |
| ARHGAP42 | −0.0017 | −3.2 | 0.0014 | 0.011 |
| ARNTL2 | −0.0018 | −4.4 | 1.30E−05 | 0.00029 |
| ARRDC4 | −0.002 | −3.9 | 0.00012 | 0.0017 |
| ARSE | −0.0043 | −4 | 8.30E−05 | 0.0013 |
| ATP8B2 | −0.0016 | −3.2 | 0.0018 | 0.014 |
| BCHE | −0.0039 | −2.9 | 0.0047 | 0.029 |
| BDKRB2 | −0.0022 | −4.8 | 3.40E−06 | 9.80E−05 |
| BICD1 | −0.0018 | −4 | 8.10E−05 | 0.0012 |
| BMP2 | −0.0021 | −3.2 | 0.0014 | 0.012 |
| BNC1 | −0.0021 | −4.1 | 4.80E−05 | 0.00083 |
| BNC2 | −0.0022 | −2.9 | 0.0041 | 0.026 |
| BST1 | −0.0014 | −2.6 | 0.0092 | 0.047 |
| CACNA1C | −0.003 | −4.8 | 2.40E−06 | 7.50E−05 |
| CALB2 | −0.0049 | −4.6 | 7.90E−06 | 0.00019 |
| CALCR | −0.0042 | −2.6 | 0.0098 | 0.049 |
| CALD1 | −0.0026 | −5.6 | 5.10E−08 | 3.10E−06 |
| CAMK2N1 | −0.0019 | −3.1 | 0.0023 | 0.017 |

TABLE 7-continued mRNAs inversely expressed and containing predicted or validated binding sites to miR-30b-5p (MIMAT0000420)

| Gene | beta | t.stat | p.value | FDR |
|---|---|---|---|---|
| CCNA1 | −0.0048 | −3.1 | 0.0021 | 0.016 |
| CCRN4L | −0.0023 | −4.9 | 1.90E−06 | 6.00E−05 |
| CD248 | −0.0018 | −2.7 | 0.0078 | 0.042 |
| CD84 | −0.0023 | −2.7 | 0.0083 | 0.044 |
| CDH11 | −0.0033 | −3.9 | 0.00014 | 0.0019 |
| CDH13 | −0.0021 | −3.5 | 0.00046 | 0.0049 |
| CDK6 | −0.0021 | −4.5 | 1.10E−05 | 0.00026 |
| CHN1 | −0.0023 | −4.2 | 4.50E−05 | 0.00078 |
| CHST2 | −0.0026 | −3.4 | 0.00078 | 0.0073 |
| CLCA2 | −0.0034 | −4.9 | 2.00E−06 | 6.50E−05 |
| CLEC5A | −0.0019 | −3.5 | 5.00E−04 | 0.0052 |
| CLSTN2 | −0.0041 | −3.9 | 0.00011 | 0.0016 |
| CNRIP1 | −0.0019 | −3.8 | 0.00022 | 0.0027 |
| CNTN1 | −0.0035 | −2.9 | 0.0038 | 0.024 |
| COL12A1 | −0.004 | −5.3 | 2.70E−07 | 1.30E−05 |
| COL13A1 | −0.002 | −3.6 | 0.00042 | 0.0045 |
| COL14A1 | −0.0021 | −3 | 0.0033 | 0.022 |
| COL5A2 | −0.0043 | −5.2 | 3.40E−07 | 1.50E−05 |
| COL8A1 | −0.0039 | −3.9 | 0.00014 | 0.0019 |
| CPN2 | −0.0088 | −4.8 | 3.00E−06 | 8.80E−05 |
| CSGALNACT1 | −0.0021 | −4.4 | 1.70E−05 | 0.00035 |
| CTGF | −0.0022 | −3.4 | 0.00093 | 0.0084 |
| CTHRC1 | −0.0029 | −3.4 | 0.00087 | 0.0079 |
| CTSK | −0.0037 | −5.1 | 5.40E−07 | 2.20E−05 |
| CYP8B1 | −0.0044 | −2.9 | 0.0046 | 0.028 |
| DACT1 | −0.003 | −3.4 | 0.00092 | 0.0083 |
| DAPP1 | −0.0014 | −2.7 | 0.0067 | 0.037 |
| DCBLD1 | −0.0025 | −5 | 9.60E−07 | 3.50E−05 |
| DDX60 | −0.0028 | −4.3 | 2.90E−05 | 0.00056 |
| DENND2A | −0.0016 | −2.9 | 0.0047 | 0.029 |
| DENND2C | −0.0015 | −2.9 | 0.0036 | 0.023 |
| DGKI | −0.0032 | −3.2 | 0.0016 | 0.013 |
| DIO2 | −0.0023 | −3 | 0.0027 | 0.019 |
| DLEU7 | −0.0027 | −3 | 0.0026 | 0.018 |
| DLX1 | −0.004 | −3.2 | 0.0016 | 0.013 |
| DNASE2B | −0.0065 | −3 | 0.0034 | 0.023 |
| DOCK10 | −0.0016 | −2.7 | 0.0077 | 0.041 |
| DSC1 | −0.0088 | −5.7 | 2.50E−08 | 1.70E−06 |
| DSC3 | −0.0011 | −2.7 | 0.0067 | 0.037 |
| DSEL | −0.003 | −4.7 | 5.00E−06 | 0.00013 |
| DSP | −0.0015 | −2.7 | 0.0073 | 0.04 |
| ECM2 | −0.0025 | −4.1 | 4.90E−05 | 0.00084 |
| EDIL3 | −0.0042 | −5.1 | 7.80E−07 | 3.00E−05 |
| EDNRA | −0.0032 | −5.6 | 4.70E−08 | 2.90E−06 |
| EDNRB | −0.0017 | −2.9 | 0.0036 | 0.024 |
| EFCAB4B | −0.0019 | −2.9 | 0.0036 | 0.023 |
| ELFN2 | −0.0038 | −2.8 | 0.0047 | 0.029 |
| EML1 | −0.0026 | −4.6 | 8.10E−06 | 2.00E−04 |
| EML5 | −0.0018 | −2.7 | 0.0079 | 0.042 |
| ENPEP | −0.0019 | −3 | 0.0031 | 0.021 |
| ENPP1 | −0.0021 | −2.8 | 0.0058 | 0.034 |
| EPHA3 | −0.0028 | −3.2 | 0.0016 | 0.013 |
| FAM124A | −0.0016 | −2.8 | 0.0058 | 0.034 |
| FAM155A | −0.0026 | −3 | 0.0031 | 0.021 |
| FAM20A | −0.0019 | −2.8 | 0.0054 | 0.032 |
| FAM26E | −0.0036 | −5.5 | 7.80E−08 | 4.40E−06 |
| FAM43A | −0.002 | −4.1 | 5.50E−05 | 0.00092 |
| FAP | −0.0042 | −4.9 | 1.60E−06 | 5.30E−05 |
| FBLN7 | −0.0019 | −3.3 | 0.0011 | 0.0096 |
| FBXO39 | −0.0023 | −3.1 | 0.0025 | 0.018 |
| FGD5 | −0.0015 | −2.9 | 0.0043 | 0.027 |
| FGF5 | −0.0064 | −3.4 | 0.00072 | 0.0069 |
| FIGN | −0.0033 | −3.2 | 0.0014 | 0.011 |
| FLVCR2 | −0.0027 | −5 | 9.70E−07 | 3.50E−05 |
| FMN1 | −0.0026 | −3.3 | 0.0012 | 0.01 |
| FRMD5 | −0.0038 | −3 | 0.0031 | 0.021 |
| GALNT13 | −0.0038 | −2.7 | 0.0074 | 0.04 |
| GALNT6 | −0.0042 | −5.6 | 5.60E−08 | 3.40E−06 |
| GBP1 | −0.0024 | −3.2 | 0.0014 | 0.011 |
| GCOM1 | −0.0029 | −3 | 0.0025 | 0.018 |
| GFPT2 | −0.0022 | −3.2 | 0.0017 | 0.013 |
| GJA1 | −0.0032 | −5.3 | 2.20E−07 | 1.10E−05 |
| GOLGA6L1 | −0.0061 | −3 | 0.0031 | 0.021 |
| GOLGA7B | −0.0037 | −3.9 | 0.00011 | 0.0016 |
| GPM6B | −0.0017 | −3.3 | 0.00093 | 0.0084 |

TABLE 7-continued mRNAs inversely expressed and containing predicted or validated binding sites to miR-30b-5p (MIMAT0000420)

| Gene | beta | t.stat | p.value | FDR |
|---|---|---|---|---|
| GPR124 | −0.0021 | −3.7 | 0.00023 | 0.0029 |
| GPR157 | −0.0017 | −3.2 | 0.0017 | 0.013 |
| GPRIN3 | −0.0021 | −3.1 | 0.0019 | 0.015 |
| GUCY1A2 | −0.0029 | −4 | 7.10E−05 | 0.0011 |
| GUCY1A3 | −0.0024 | −3.7 | 0.00031 | 0.0036 |
| GXYLT2 | −0.002 | −2.6 | 0.0091 | 0.047 |
| HAPLN1 | −0.0032 | −3.1 | 0.0024 | 0.017 |
| HAS2 | −0.0035 | −4.3 | 2.70E−05 | 0.00053 |
| HECW1 | −0.0034 | −3.5 | 0.00046 | 0.0049 |
| HEPHL1 | −0.0063 | −4.5 | 1.00E−05 | 0.00024 |
| HGF | −0.0043 | −4 | 7.30E−05 | 0.0012 |
| HHIPL1 | −0.003 | −4.6 | 6.70E−06 | 0.00017 |
| HMCN1 | −0.0043 | −5.2 | 4.90E−07 | 2.00E−05 |
| HOXA1 | −0.0023 | −3.4 | 9.00E−04 | 0.0082 |
| HS3ST3A1 | −0.0026 | −3.5 | 0.00056 | 0.0057 |
| HS3ST3B1 | −0.0021 | −3 | 0.0034 | 0.022 |
| HTRA3 | −0.0031 | −3.8 | 0.00017 | 0.0022 |
| IFIT1 | −0.0036 | −3.9 | 0.00014 | 0.002 |
| IL1A | −0.0032 | −3.2 | 0.0017 | 0.013 |
| INHBA | −0.0041 | −3.9 | 0.00013 | 0.0019 |
| IRS1 | −0.0021 | −4 | 7.20E−05 | 0.0011 |
| ITGA1 | −0.0025 | −4.2 | 3.60E−05 | 0.00065 |
| ITGA5 | −0.0024 | −3.8 | 0.00018 | 0.0023 |
| ITGA6 | −0.0021 | −3.7 | 0.00028 | 0.0033 |
| ITGA8 | −0.0038 | −3.6 | 0.00041 | 0.0045 |
| ITGA9 | −0.0018 | −2.7 | 0.0066 | 0.037 |
| JAM2 | −0.0022 | −3.5 | 0.00063 | 0.0063 |
| KCND2 | −0.003 | −3 | 0.0034 | 0.023 |
| KCNJ15 | −0.0028 | −4.3 | 2.10E−05 | 0.00042 |
| KIAA1024 | −0.0015 | −2.8 | 0.0055 | 0.032 |
| KIAA1644 | −0.0034 | −4 | 9.80E−05 | 0.0015 |
| KLF7 | −0.0027 | −5.6 | 5.70E−08 | 3.40E−06 |
| KLHL4 | −0.0036 | −2.6 | 0.0087 | 0.045 |
| KRT82 | −0.0051 | −2.7 | 0.0068 | 0.038 |
| KRTAP1-5 | −0.0054 | −2.8 | 0.0057 | 0.033 |
| LAMA1 | −0.0042 | −3.4 | 0.00078 | 0.0073 |
| LAMA4 | −0.003 | −5.1 | 7.00E−07 | 2.70E−05 |
| LAMC3 | −0.0038 | −4.9 | 1.80E−06 | 6.00E−05 |
| LHX1 | −0.0095 | −4.1 | 5.50E−05 | 0.00092 |
| LHX8 | −0.0041 | −2.9 | 0.0045 | 0.028 |
| LHX9 | −0.0059 | −2.8 | 0.0057 | 0.033 |
| LILRB2 | −0.0022 | −3 | 0.0032 | 0.021 |
| LIPC | −0.0028 | −3.1 | 0.0019 | 0.015 |
| LOX | −0.0023 | −3.5 | 0.00055 | 0.0056 |
| LPAR3 | −0.002 | −3.3 | 0.00096 | 0.0086 |
| LPPR4 | −0.0018 | −2.9 | 0.0043 | 0.027 |
| LPPR5 | −0.0078 | −4 | 8.30E−05 | 0.0013 |
| LRCH2 | −0.0026 | −3.4 | 0.00078 | 0.0073 |
| LRRC15 | −0.006 | −5.2 | 4.50E−07 | 1.90E−05 |
| LRRC17 | −0.0033 | −3.1 | 0.0022 | 0.016 |
| LSAMP | −0.0028 | −2.9 | 0.004 | 0.026 |
| LTBP2 | −0.0021 | −3.8 | 0.00019 | 0.0024 |
| MAF | −0.0014 | −2.8 | 0.0048 | 0.029 |
| MAN1A1 | −0.0019 | −3.5 | 5.00E−04 | 0.0052 |
| MAP2 | −0.004 | −4.8 | 2.70E−06 | 8.00E−05 |
| ME1 | −0.0017 | −2.7 | 0.0073 | 0.04 |
| MFAP3L | −0.0024 | −3.5 | 0.00047 | 0.005 |
| MICAL2 | −0.0022 | −3.9 | 1.00E−04 | 0.0015 |
| MME | −0.0045 | −5.2 | 4.90E−07 | 2.00E−05 |
| MMP16 | −0.0055 | −5.2 | 3.40E−07 | 1.50E−05 |
| MOCS1 | −0.0015 | −3 | 0.0029 | 0.02 |
| MPZL3 | −0.0025 | −4.8 | 2.30E−06 | 7.30E−05 |
| MS4A7 | −0.0024 | −3.6 | 0.00044 | 0.0047 |
| MXRA5 | −0.0033 | −4.6 | 6.20E−06 | 0.00016 |
| MYH10 | −0.0025 | −4.7 | 4.20E−06 | 0.00012 |
| NAV3 | −0.0042 | −5.3 | 2.10E−07 | 1.00E−05 |
| NEGR1 | −0.0036 | −3.8 | 2.00E−04 | 0.0026 |
| NFASC | −0.0017 | −3.1 | 0.0025 | 0.018 |
| NHSL2 | −0.0024 | −2.7 | 0.0082 | 0.043 |
| NID1 | −0.0032 | −4.9 | 1.70E−06 | 5.50E−05 |
| NID2 | −0.0033 | −4.5 | 9.40E−06 | 0.00022 |
| NIPAL1 | −0.0025 | −4.1 | 6.30E−05 | 0.001 |
| NIPAL4 | −0.0044 | −4.3 | 2.10E−05 | 0.00043 |
| NLRP3 | −0.0017 | −2.7 | 0.0083 | 0.044 |
| NOD2 | −0.0027 | −5.2 | 4.40E−07 | 1.80E−05 |

TABLE 7-continued mRNAs inversely expressed and containing predicted or validated binding sites to miR-30b-5p (MIMAT0000420)

| Gene | beta | t.stat | p.value | FDR |
|---|---|---|---|---|
| NRG1 | −0.0025 | −3.2 | 0.0014 | 0.011 |
| NT5E | −0.0033 | −4.1 | 5.80E−05 | 0.00096 |
| NTM | −0.0034 | −4.9 | 2.10E−06 | 6.70E−05 |
| NTNG1 | −0.0051 | −2.9 | 0.0039 | 0.025 |
| OLFML2A | −0.0015 | −2.9 | 0.004 | 0.026 |
| PAG1 | −0.0021 | −4 | 8.40E−05 | 0.0013 |
| PAQR5 | −0.0036 | −4.4 | 1.60E−05 | 0.00034 |
| PCDH10 | −0.0071 | −3.9 | 0.00013 | 0.0018 |
| PCDH17 | −0.0025 | −3.7 | 0.00023 | 0.0028 |
| PDE3A | −0.0035 | −4.5 | 1.10E−05 | 0.00025 |
| PDE7B | −0.0022 | −4 | 7.50E−05 | 0.0012 |
| PDGFC | −0.0025 | −4.5 | 9.10E−06 | 0.00022 |
| PDGFRB | −0.0028 | −4.2 | 3.60E−05 | 0.00065 |
| PHLDB2 | −0.0018 | −3.2 | 0.0016 | 0.013 |
| PI15 | −0.0023 | −2.9 | 0.0043 | 0.027 |
| PLA2G4D | −0.0034 | −2.7 | 0.0072 | 0.04 |
| PLXDC1 | −0.0018 | −3.2 | 0.0015 | 0.012 |
| PLXDC2 | −0.0025 | −4.5 | 1.20E−05 | 0.00027 |
| PLXNC1 | −0.0028 | −3.7 | 0.00024 | 0.003 |
| PNPLA1 | −0.0065 | −5.5 | 8.70E−08 | 4.90E−06 |
| PPFIA2 | −0.0049 | −3.4 | 0.00076 | 0.0072 |
| PPP1R14C | −0.0014 | −2.9 | 0.0035 | 0.023 |
| PRDM1 | −0.0021 | −4.9 | 2.00E−06 | 6.40E−05 |
| PRDM5 | −0.0023 | −4 | 9.20E−05 | 0.0014 |
| PREX2 | −0.0022 | −2.6 | 0.0098 | 0.049 |
| PRICKLE1 | −0.0027 | −4.4 | 1.30E−05 | 3.00E−04 |
| PRRG1 | −0.0018 | −3.8 | 0.00019 | 0.0024 |
| PRRX1 | −0.002 | −2.9 | 0.0037 | 0.024 |
| PTGDR | −0.0031 | −4.1 | 6.30E−05 | 0.001 |
| PTGER2 | −0.0021 | −2.9 | 0.0044 | 0.027 |
| PTGER3 | −0.0038 | −4.4 | 1.40E−05 | 0.00031 |
| PTGS1 | −0.0021 | −2.9 | 0.0043 | 0.027 |
| PTPRB | −0.0016 | −3.2 | 0.0014 | 0.012 |
| PTPRD | −0.0058 | −5.3 | 3.20E−07 | 1.40E−05 |
| RAB27B | −0.0019 | −3.5 | 5.00E−04 | 0.0052 |
| RAB38 | −0.0027 | −4 | 9.40E−05 | 0.0014 |
| RAB3B | −0.0057 | −4.1 | 4.80E−05 | 0.00083 |
| RAI14 | −0.0013 | −2.7 | 0.0076 | 0.041 |
| RASGRF2 | −0.0027 | −4.1 | 6.00E−05 | 0.00099 |
| RECK | −0.0022 | −3.9 | 0.00014 | 0.0019 |
| RFTN2 | −0.0016 | −2.9 | 0.0046 | 0.028 |
| RSAD2 | −0.0035 | −3.8 | 0.00019 | 0.0024 |
| RUNX1T1 | −0.0036 | −3.6 | 0.00044 | 0.0047 |
| S100A7A | −0.0065 | −3.6 | 0.00032 | 0.0037 |
| SAMHD1 | −0.0022 | −3.8 | 0.00019 | 0.0024 |
| SDC2 | −0.0023 | −3.5 | 0.00062 | 0.0062 |
| SDK2 | −0.0026 | −2.9 | 0.0038 | 0.024 |
| SEC14L2 | −0.0021 | −3.6 | 0.00039 | 0.0043 |
| SERPINE1 | −0.0032 | −3.7 | 0.00032 | 0.0037 |
| SERPING1 | −0.0024 | −4.1 | 6.20E−05 | 0.001 |
| SGIP1 | −0.0033 | −4.7 | 5.30E−06 | 0.00014 |
| SH3TC2 | −0.002 | −2.8 | 0.0052 | 0.031 |
| SHROOM4 | −0.0017 | −3 | 0.0034 | 0.022 |
| SLC10A6 | −0.0034 | −3.9 | 0.00012 | 0.0017 |
| SLC16A10 | −0.0018 | −2.8 | 0.0054 | 0.032 |
| SLC22A15 | −0.0014 | −2.8 | 0.0048 | 0.029 |
| SLC24A2 | −0.008 | −4.7 | 4.60E−06 | 0.00013 |
| SLC28A3 | −0.0043 | −5 | 8.70E−07 | 3.20E−05 |
| SLC2A9 | −0.0022 | −4.7 | 4.30E−06 | 0.00012 |
| SLC38A4 | −0.0031 | −3.9 | 0.00012 | 0.0017 |
| SLC39A8 | −0.0016 | −3.6 | 0.00043 | 0.0046 |
| SLC41A2 | −0.003 | −5.3 | 2.30E−07 | 1.10E−05 |
| SLC44A5 | −0.0026 | −2.6 | 0.0097 | 0.049 |
| SLC7A11 | −0.0027 | −2.9 | 0.0044 | 0.027 |
| SNAI1 | −0.0014 | −2.8 | 0.0058 | 0.034 |
| SNX10 | −0.0021 | −3.9 | 0.00011 | 0.0015 |
| SPTLC3 | −0.0061 | −6.1 | 3.40E−09 | 3.30E−07 |
| STC1 | −0.002 | −3 | 0.0025 | 0.018 |
| SULF2 | −0.0026 | −4.4 | 1.40E−05 | 0.00031 |
| TCHHL1 | −0.0077 | −3.4 | 0.00082 | 0.0076 |
| TGFA | −0.0023 | −5.2 | 4.30E−07 | 1.80E−05 |
| TGM5 | −0.0047 | −4.3 | 2.50E−05 | 0.00049 |
| THBS2 | −0.0041 | −5.2 | 4.10E−07 | 1.80E−05 |
| TIMP2 | −0.0035 | −6 | 8.00E−09 | 6.70E−07 |
| TIMP3 | −0.0029 | −4 | 7.80E−05 | 0.0012 |

TABLE 7-continued mRNAs inversely expressed and containing predicted or validated binding sites to miR-30b-5p (MIMAT0000420)

| Gene | beta | t.stat | p.value | FDR |
|---|---|---|---|---|
| TLL1 | −0.0027 | −2.8 | 0.0058 | 0.034 |
| TLN2 | −0.0015 | −2.8 | 0.0051 | 0.03 |
| TLR8 | −0.0031 | −3.6 | 0.00035 | 0.004 |
| TM4SF18 | −0.0019 | −3.9 | 0.00014 | 0.0019 |
| TM6SF2 | −0.004 | −3.2 | 0.0017 | 0.014 |
| TMEM154 | −0.0023 | −4.2 | 4.50E−05 | 0.00079 |
| TMEM26 | −0.0025 | −3.7 | 0.00028 | 0.0033 |
| TMEM79 | −0.0021 | −3.4 | 7.00E−04 | 0.0067 |
| TMEM86A | −0.0031 | −5.5 | 9.80E−08 | 5.40E−06 |
| TNFSF13B | −0.0019 | −2.7 | 0.0073 | 0.04 |
| TREML2 | −0.0038 | −4.3 | 2.80E−05 | 0.00053 |
| TRPA1 | −0.0047 | −4.4 | 1.40E−05 | 0.00032 |
| TRPC6 | −0.0019 | −3.5 | 0.00059 | 0.0059 |
| TRPS1 | −0.0024 | −4.8 | 3.40E−06 | 9.80E−05 |
| TSHZ2 | −0.0018 | −2.8 | 0.0048 | 0.029 |
| TSPAN11 | −0.003 | −4.1 | 5.90E−05 | 0.00097 |
| TSPAN2 | −0.0034 | −4.1 | 5.80E−05 | 0.00095 |
| UNC5C | −0.0041 | −3.1 | 0.0022 | 0.016 |
| UNC80 | −0.0048 | −2.8 | 0.005 | 0.03 |
| USP2 | −0.0025 | −2.8 | 0.0047 | 0.029 |
| VCAN | −0.0038 | −4.4 | 1.90E−05 | 4.00E−04 |
| VGLL3 | −0.0036 | −4.9 | 1.40E−06 | 4.80E−05 |
| VIM | −0.0018 | −3.7 | 0.00031 | 0.0036 |
| WIPF1 | −0.0014 | −2.6 | 0.0092 | 0.047 |
| WISP1 | −0.0032 | −3.8 | 2.00E−04 | 0.0026 |
| WNT5A | −0.0034 | −5.6 | 4.40E−08 | 2.80E−06 |
| XYLT1 | −0.0018 | −2.7 | 0.0071 | 0.039 |
| ZCCHC24 | −0.0017 | −3.7 | 0.00023 | 0.0028 |
| ZDHHC21 | −0.0015 | −2.7 | 0.0076 | 0.041 |
| ZNF208 | −0.0035 | −2.7 | 0.0084 | 0.044 |
| ZNF365 | −0.0052 | −6.1 | 3.00E−09 | 3.00E−07 |
| ZNF521 | −0.0028 | −4.2 | 4.30E−05 | 0.00076 |
| ZNF681 | −0.003 | −2.9 | 0.0039 | 0.025 |

TABLE 8 mRNAs inversely expressed to and containing predicted or validated binding sites miR-30d-5p (MIMAT0000245)

| Gene | beta | t.stat | p.value | FDR |
|---|---|---|---|---|
| ABCC2 | −0.00014 | −3.3 | 0.0011 | 0.0095 |
| ACTBL2 | −0.00024 | −2.9 | 0.0043 | 0.027 |
| ADAM12 | −0.00015 | −3.2 | 0.0014 | 0.012 |
| ADAMTS14 | −0.00014 | −4.2 | 4.10E−05 | 0.00073 |
| AFAP1L2 | −0.00012 | −4.6 | 7.00E−06 | 0.00018 |
| AJAP1 | −0.00017 | −2.8 | 0.005 | 0.03 |
| ARNTL2 | −8.20E−05 | −4 | 9.00E−05 | 0.0014 |
| ARRDC4 | −7.50E−05 | −2.7 | 0.0067 | 0.037 |
| BDKRB2 | −0.00011 | −4.5 | 9.50E−06 | 0.00023 |
| BNC1 | −0.00014 | −5.2 | 4.60E−06 | 1.90E−05 |
| C6orf141 | −0.00023 | −5 | 1.20E−06 | 4.20E−05 |
| CALD1 | −1.00E−04 | −4.2 | 3.10E−05 | 0.00059 |
| CAMK2A | −0.00028 | −4.6 | 5.30E−06 | 0.00014 |
| CAMK2N1 | −0.00011 | −3.6 | 0.00044 | 0.0047 |
| CCNA1 | −0.00033 | −4.2 | 3.30E−05 | 0.00062 |
| CCRN4L | −0.00011 | −4.5 | 8.60E−06 | 0.00021 |
| CDH13 | −0.00011 | −3.7 | 0.00023 | 0.0029 |
| CDK6 | −0.00011 | −4.6 | 6.60E−06 | 0.00017 |
| CHST2 | −0.00013 | −3.2 | 0.0014 | 0.012 |
| CLCA2 | −0.00015 | −4.1 | 5.50E−05 | 0.00092 |
| CLCF1 | −8.70E−05 | −2.9 | 0.0039 | 0.025 |
| COL12A1 | −0.00017 | −4.2 | 3.30E−05 | 0.00062 |
| COL13A1 | −8.80E−05 | −3 | 0.0032 | 0.022 |
| COL5A2 | −0.00017 | −4 | 9.80E−05 | 0.0015 |
| CTHRC1 | −0.00013 | −2.8 | 0.0051 | 0.031 |
| DACT1 | −0.00013 | −2.8 | 0.0063 | 0.035 |
| DCBLD1 | −0.00016 | −6.5 | 3.80E−10 | 5.20E−08 |
| DDX60 | −0.00012 | −3.3 | 0.001 | 0.0089 |
| DLX1 | −0.00021 | −3.3 | 0.001 | 0.0092 |
| DNAH17 | −2.00E−04 | −3.4 | 0.00081 | 0.0075 |
| DNMT3B | −1.00E−04 | −3.7 | 0.00025 | 0.003 |
| DSC1 | −0.00029 | −3.5 | 0.00049 | 0.0052 |
| EDNRA | −9.10E−05 | −3 | 0.0031 | 0.021 |
| EML1 | −8.60E−05 | −2.9 | 0.0042 | 0.026 |
| EPHB2 | −1.00E−04 | −2.6 | 0.0088 | 0.046 |
| F3 | −0.00012 | −2.8 | 0.006 | 0.034 |
| FAM26E | −0.00011 | −3 | 0.0026 | 0.018 |
| FAP | −0.00019 | −4.2 | 4.00E−05 | 0.00072 |
| FOXD1 | −1.00E−04 | −2.9 | 0.004 | 0.025 |
| FOXL2 | −0.00021 | −2.9 | 0.0035 | 0.023 |
| FZD2 | −7.90E−05 | −3 | 0.0026 | 0.018 |
| GALNT6 | −0.00023 | −5.8 | 2.20E−08 | 1.60E−06 |
| GBP1 | −0.00013 | −3.4 | 0.00073 | 0.007 |
| GJA1 | −0.00016 | −5.1 | 6.20E−07 | 2.50E−05 |
| GOLGA7B | −0.00024 | −4.9 | 1.60E−06 | 5.40E−05 |
| GPR39 | −0.00015 | −3 | 0.003 | 0.021 |
| HAS2 | −0.00013 | −3.1 | 0.002 | 0.015 |
| HECW1 | −0.00013 | −2.7 | 0.0082 | 0.043 |
| HEPHL1 | −0.00026 | −3.6 | 0.00042 | 0.0046 |
| HOXA1 | −0.00014 | −3.9 | 0.00011 | 0.0015 |
| HSPB3 | −3.00E−04 | −3.2 | 0.0017 | 0.013 |
| HTRA3 | −0.00016 | −3.8 | 0.00018 | 0.0024 |
| IFFO2 | −7.80E−05 | −2.7 | 0.0082 | 0.043 |
| IFIT1 | −0.00018 | −3.7 | 3.00E−04 | 0.0035 |
| IL1A | −0.00019 | −3.7 | 0.00024 | 0.003 |
| INHBA | −0.00023 | −4.2 | 4.00E−05 | 0.00071 |
| IRS1 | −9.10E−05 | −3.3 | 0.00094 | 0.0084 |
| ITGA5 | −0.00016 | −5 | 8.60E−07 | 3.20E−05 |
| ITGA6 | −1.00E−04 | −3.5 | 0.00056 | 0.0057 |
| KCNJ15 | −0.00012 | −3.5 | 0.00057 | 0.0057 |

TABLE 8-continued mRNAs inversely expressed to and containing predicted or validated binding sites miR-30d-5p (MIMAT0000245)

| Gene | beta | t.stat | p.value | FDR |
|---|---|---|---|---|
| KIAA1644 | −0.00015 | −3.4 | 0.00066 | 0.0064 |
| KLF7 | −0.00011 | −4.3 | 2.20E−05 | 0.00045 |
| KRT82 | −0.00034 | −3.5 | 0.00048 | 0.0051 |
| LAMA1 | −0.00019 | −3 | 0.0032 | 0.022 |
| LETM2 | −1.00E−04 | −3.4 | 0.00089 | 0.0081 |
| LHX1 | −0.00061 | −5.2 | 4.70E−07 | 2.00E−05 |
| LPCAT1 | −9.50E−05 | −4 | 6.80E−05 | 0.0011 |
| LRRC17 | −0.00015 | −2.7 | 0.008 | 0.042 |
| MAF | −8.20E−05 | −3.2 | 0.0016 | 0.013 |
| MELK | −6.40E−05 | −2.9 | 0.0036 | 0.024 |
| MICAL2 | −1.00E−04 | −3.6 | 0.00037 | 0.0041 |
| MME | −0.00015 | −3.3 | 0.0011 | 0.0097 |
| MYH10 | −1.00E−04 | −3.7 | 0.00025 | 0.003 |
| NAV3 | −2.00E−04 | −4.7 | 4.00E−06 | 0.00011 |
| NEXN | −0.00015 | −3.7 | 0.00029 | 0.0034 |
| NIPAL4 | −2.00E−04 | −3.7 | 0.00023 | 0.0029 |
| NNMT | −0.00012 | −3.4 | 0.00088 | 0.008 |
| NOD2 | −1.00E−04 | −3.7 | 0.00027 | 0.0032 |
| NRG1 | −0.00015 | −3.8 | 2.00E−04 | 0.0026 |
| NT5E | −0.00017 | −4 | 8.60E−05 | 0.0013 |
| PAQR5 | −0.00015 | −3.5 | 5.00E−04 | 0.0052 |
| PDGFC | −0.00013 | −4.4 | 1.40E−05 | 0.00031 |
| PHLDB2 | −1.00E−04 | −3.6 | 0.00033 | 0.0037 |
| PNPLA1 | −2.00E−04 | −3.2 | 0.0017 | 0.013 |
| PPP1R14C | −0.00014 | −6.3 | 1.50E−09 | 1.60E−07 |
| PSMB9 | −8.70E−05 | −2.8 | 0.0056 | 0.032 |
| PTGS1 | −0.00011 | −3 | 0.0028 | 0.02 |
| PTPRD | −0.00019 | −3.3 | 0.001 | 0.0091 |
| RAB38 | −0.00016 | −4.6 | 7.60E−06 | 0.00019 |
| RSAD2 | −0.00014 | −2.8 | 0.0051 | 0.03 |
| S100A7A | −0.00026 | −2.8 | 0.0057 | 0.033 |
| SEC14L2 | −0.00013 | −4.4 | 1.60E−05 | 0.00035 |
| SERPINA3 | −0.00024 | −3.8 | 0.00018 | 0.0023 |
| SERPINE1 | −0.00021 | −4.7 | 5.00E−06 | 0.00014 |
| SERPING1 | −9.30E−05 | −3 | 0.0034 | 0.023 |
| SLC24A2 | −0.00034 | −3.7 | 0.00022 | 0.0027 |
| SLC2A9 | −8.60E−05 | −3.4 | 0.00077 | 0.0072 |
| SLC7A5 | −8.00E−05 | −2.8 | 0.0056 | 0.033 |
| SNX10 | −1.00E−04 | −3.6 | 0.00039 | 0.0043 |
| SPTLC3 | −0.00017 | −3.2 | 0.0018 | 0.014 |
| SULF2 | −0.00013 | −4.3 | 2.50E−05 | 0.00049 |
| SYNC | −0.00011 | −3.2 | 0.0014 | 0.011 |
| TGFA | −1.00E−04 | −4.3 | 2.60E−05 | 0.00051 |
| THBS2 | −0.00013 | −3 | 0.0028 | 0.019 |
| TIMP3 | −0.00012 | −3.1 | 0.0021 | 0.016 |
| TLL1 | −0.00013 | −2.7 | 0.0081 | 0.043 |
| TLN2 | −7.40E−05 | −2.8 | 0.0061 | 0.035 |
| TMEM86A | −8.60E−05 | −2.9 | 0.0045 | 0.028 |
| TNFSF9 | −0.00012 | −4 | 8.30E−05 | 0.0013 |
| TRPA1 | −0.00015 | −2.7 | 0.0082 | 0.043 |
| USP2 | −0.00013 | −2.8 | 0.0048 | 0.029 |
| ZNF365 | −0.00015 | −3.2 | 0.0017 | 0.013 |

TABLE 9 mRNAs inversely expressed and containing predicted or validated binding sites to miR-30e-5p (MIMAT0000692)

| Gene | beta | t.stat | p.value | FDR |
|---|---|---|---|---|
| 42433 | −2.00E−04 | −3.8 | 0.00017 | 0.0022 |
| ABCA12 | −0.00011 | −3.3 | 0.0011 | 0.0093 |
| ABCC11 | −0.00013 | −4.5 | 9.80E−06 | 0.00023 |
| ABCC2 | −0.00011 | −3.4 | 0.00086 | 0.0079 |
| ACTBL2 | −0.00018 | −2.8 | 0.0056 | 0.033 |
| ACTC1 | −0.00032 | −3 | 0.0029 | 0.02 |
| ADAM12 | −0.00023 | −6.4 | 5.60E−10 | 7.20E−08 |
| ADAMTS14 | −0.00014 | −5.4 | 1.80E−07 | 9.00E−06 |
| ADAMTS5 | −8.70E−05 | −3 | 0.0033 | 0.022 |
| ADRA1D | −0.00011 | −2.8 | 0.0055 | 0.032 |
| ANGPT2 | −0.00012 | −5.8 | 1.80E−08 | 1.30E−06 |
| ANTXR2 | −6.60E−05 | −2.7 | 0.0078 | 0.042 |
| ARRDC4 | −7.10E−05 | −3.2 | 0.0013 | 0.011 |
| BAG2 | −9.10E−05 | −3.8 | 0.00015 | 0.002 |
| BICD1 | −9.00E−05 | −4.8 | 2.90E−06 | 8.50E−05 |
| BMP2 | −9.50E−05 | −3.6 | 0.00045 | 0.0048 |
| BNC1 | −9.70E−05 | −4.6 | 8.20E−06 | 2.00E−04 |
| BVES | −0.00012 | −3.9 | 0.00014 | 0.002 |
| C1QL1 | −0.00015 | −4 | 7.60E−05 | 0.0012 |
| C3orf72 | −0.00036 | −5 | 1.20E−06 | 4.20E−05 |
| C6orf141 | −0.00013 | −3.3 | 0.0011 | 0.0093 |
| CALD1 | −0.00012 | −6.4 | 9.60E−10 | 1.10E−07 |
| CAMK2A | −0.00017 | −3.5 | 0.00064 | 0.0063 |
| CCNA1 | −0.00029 | −4.7 | 4.30E−06 | 0.00012 |
| CCRN4L | −9.40E−05 | −4.9 | 1.90E−06 | 6.20E−05 |
| CD248 | −0.00012 | −4.7 | 4.60E−06 | 0.00013 |
| CDH11 | −0.00014 | −3.9 | 0.00011 | 0.0016 |
| CDH13 | −1.00E−04 | −4.3 | 2.50E−05 | 0.00049 |
| CDK6 | −9.20E−05 | −4.6 | 5.40E−06 | 0.00014 |
| CHN1 | −6.50E−05 | −2.8 | 0.0056 | 0.033 |
| CHST2 | −0.00017 | −5.5 | 1.00E−07 | 5.60E−06 |
| CLCF1 | −6.40E−05 | −2.7 | 0.0081 | 0.043 |
| CLSTN2 | −0.00012 | −2.8 | 0.0058 | 0.033 |
| COL12A1 | −0.00022 | −7.4 | 2.00E−12 | 5.90E−10 |
| COL13A1 | −0.00013 | −5.9 | 1.20E−08 | 9.10E−07 |
| COL5A2 | −0.00022 | −6.6 | 1.90E−10 | 2.80E−08 |
| COL8A1 | −0.00016 | −3.9 | 0.00011 | 0.0015 |
| CSMD3 | −0.00031 | −3.2 | 0.0016 | 0.013 |
| CTHRC1 | −0.00018 | −5.1 | 6.60E−07 | 2.60E−05 |
| CTSK | −9.10E−05 | −3 | 0.003 | 0.021 |
| DACT1 | −0.00017 | −4.7 | 3.80E−06 | 0.00011 |
| DCBLD1 | −0.00013 | −6.8 | 9.60E−11 | 1.60E−08 |
| DCLK3 | −8.70E−05 | −3.2 | 0.0017 | 0.013 |
| DDIT4 | −8.20E−05 | −3.6 | 0.00043 | 0.0046 |
| DDX60 | −8.70E−05 | −3.1 | 0.002 | 0.015 |
| DLX1 | −0.00035 | −7.3 | 4.80E−12 | 1.20E−09 |
| DNAH17 | −0.00014 | −3 | 0.0032 | 0.022 |
| DNMT3B | −0.00011 | −4.8 | 2.30E−06 | 7.10E−05 |
| DSC1 | −0.00022 | −3.3 | 0.0011 | 0.0098 |
| DSG2 | −5.90E−05 | −3 | 0.0031 | 0.021 |
| EBF2 | −0.00014 | −2.7 | 0.0081 | 0.043 |
| EDIL3 | −0.00011 | −3.1 | 0.002 | 0.015 |
| EDNRA | −9.80E−05 | −4 | 7.20E−05 | 0.0011 |
| EGFR | −6.10E−05 | −2.6 | 0.0088 | 0.045 |
| EIF5A2 | −7.80E−05 | −3.7 | 0.00024 | 0.0029 |
| ELAVL2 | −0.00015 | −2.6 | 0.0092 | 0.047 |
| EML1 | −9.70E−05 | −4.1 | 4.90E−05 | 0.00084 |
| ENPEP | −0.00015 | −6 | 7.40E−09 | 6.30E−07 |
| EPB41L4B | −7.00E−05 | −3.4 | 0.00093 | 0.0084 |
| EPHB2 | −0.00011 | −3.6 | 0.00038 | 0.0042 |
| FADS1 | −8.30E−05 | −3.3 | 0.0011 | 0.0094 |
| FAM26E | −0.00014 | −5 | 8.50E−07 | 3.20E−05 |
| FAP | −0.00023 | −6.9 | 3.80E−11 | 7.20E−09 |
| FGF5 | −0.00044 | −5.9 | 1.40E−08 | 1.10E−06 |
| FOXD1 | −1.00E−04 | −3.6 | 0.00036 | 0.004 |
| FOXL2 | −0.00028 | −5.1 | 6.30E−07 | 2.50E−05 |
| FSD1L | −5.50E−05 | −2.9 | 0.0036 | 0.023 |
| FST | −0.00017 | −5.8 | 1.60E−08 | 1.20E−06 |
| FZD2 | −0.00012 | −6.3 | 1.00E−09 | 1.20E−07 |
| GALNT6 | −0.00018 | −5.9 | 1.30E−08 | 1.00E−06 |
| GFPT2 | −8.80E−05 | −3.1 | 0.0025 | 0.018 |
| GJA1 | −0.00015 | −6.2 | 2.70E−09 | 2.70E−07 |
| GOLGA7B | −0.00021 | −5.4 | 1.20E−07 | 6.40E−06 |
| GUCY1A2 | −0.00014 | −4.8 | 2.90E−06 | 8.80E−05 |
| GXYLT2 | −9.00E−05 | −2.8 | 0.0059 | 0.034 |
| HAPLN1 | −0.00024 | −5.6 | 4.80E−08 | 3.00E−06 |
| HAS2 | −0.00011 | −3.1 | 0.0022 | 0.016 |
| HDAC9 | −7.50E−05 | −2.7 | 0.0079 | 0.042 |
| HECW1 | −2.00E−04 | −5 | 9.50E−07 | 3.50E−05 |
| HEPHL1 | −0.00016 | −2.6 | 0.0097 | 0.049 |
| HEYL | −0.00012 | −5.1 | 6.80E−07 | 2.70E−05 |
| HHIPL1 | −9.10E−05 | −3.3 | 0.001 | 0.009 |
| HOXA1 | −0.00011 | −3.8 | 0.00021 | 0.0027 |
| HOXA11 | −0.00017 | −2.7 | 0.0066 | 0.037 |

TABLE 9-continued mRNAs inversely expressed and containing predicted or validated binding sites to miR-30e-5p (MIMAT0000692)

| Gene | beta | t.stat | p.value | FDR |
|---|---|---|---|---|
| HOXD11 | −0.00035 | −6.5 | 5.30E-10 | 6.80E-08 |
| HOXD8 | −9.50E-05 | −4.8 | 2.20E-06 | 6.80E-05 |
| HSPB3 | −0.00039 | −5.5 | 1.20E-07 | 6.20E-06 |
| HTRA3 | −2.00E-04 | −6.2 | 2.80E-09 | 2.80E-07 |
| IFIT1 | −0.00013 | −3.3 | 0.00099 | 0.0088 |
| IFIT1B | −0.00025 | −3.1 | 0.0018 | 0.014 |
| IL1A | −0.00012 | −2.9 | 0.0044 | 0.027 |
| INHBA | −0.00034 | −8.5 | 2.10E-15 | 1.50E-12 |
| IRS1 | −7.50E-05 | −3.5 | 0.00061 | 0.0061 |
| IRX4 | −0.00017 | −3.4 | 0.00088 | 0.008 |
| ITGA1 | −1.00E-04 | −4.1 | 6.50E-05 | 0.001 |
| ITGA5 | −2.00E-04 | −8.5 | 1.70E-15 | 1.30E-12 |
| ITGA6 | −0.00011 | −5 | 8.50E-07 | 3.20E-05 |
| KCND2 | −0.00016 | −3.7 | 0.00026 | 0.0032 |
| KCNJ15 | −9.80E-05 | −3.6 | 0.00046 | 0.0048 |
| KIAA1644 | −0.00013 | −3.7 | 0.00026 | 0.0031 |
| KIF3C | −0.00012 | −6.4 | 8.20E-10 | 1.00E-07 |
| KLF14 | −0.00016 | −2.7 | 0.0083 | 0.044 |
| KLF7 | −0.00011 | −5.6 | 5.70E-08 | 3.40E-06 |
| KRT82 | −0.00022 | −2.8 | 0.0054 | 0.032 |
| LAMA1 | −0.00027 | −5.4 | 1.30E-07 | 6.60E-06 |
| LAMA4 | −0.00011 | −4.5 | 9.20E-06 | 0.00022 |
| LAMC3 | −9.70E-05 | −2.9 | 0.0036 | 0.024 |
| LETM2 | −6.40E-05 | −2.6 | 0.0095 | 0.048 |
| LHX1 | −0.00045 | −4.7 | 4.40E-06 | 0.00012 |
| LHX5 | −0.00032 | −4 | 7.10E-05 | 0.0011 |
| LOX | −8.40E-05 | −3 | 0.0028 | 0.019 |
| LPAR3 | −7.70E-05 | −3.1 | 0.0021 | 0.016 |
| LPCAT1 | −9.00E-05 | −4.9 | 1.90E-06 | 6.10E-05 |
| LPPR5 | −0.00025 | −3.1 | 0.0025 | 0.018 |
| LRRC15 | −0.00017 | −3.4 | 0.00067 | 0.0065 |
| LRRC17 | −0.00014 | −3.2 | 0.0016 | 0.013 |
| LRRC3 | −6.40E-05 | −2.8 | 0.005 | 0.03 |
| LTBP2 | −8.90E-05 | −3.9 | 0.00011 | 0.0016 |
| MAP2 | −0.00011 | −3 | 0.0027 | 0.019 |
| MFAP3L | −7.80E-05 | −2.7 | 0.0067 | 0.037 |
| MICAL2 | −0.00013 | −6 | 7.90E-09 | 6.70E-07 |
| MME | −0.00019 | −5.2 | 3.50E-07 | 1.50E-05 |
| MMP16 | −0.00025 | −5.7 | 2.80E-08 | 1.90E-06 |
| MURC | −0.00017 | −3.6 | 0.00034 | 0.0039 |
| MXRA5 | −9.70E-05 | −3.3 | 0.0013 | 0.011 |
| MYH10 | −0.00013 | −6 | 6.50E-09 | 5.60E-07 |
| NAV3 | −0.00017 | −5 | 8.40E-07 | 3.10E-05 |
| NCAM1 | −0.00014 | −2.9 | 0.0035 | 0.023 |
| NEXN | −0.00014 | −4.4 | 1.70E-05 | 0.00037 |
| NID1 | −0.00017 | −6.6 | 2.80E-10 | 4.00E-08 |
| NID2 | −0.00016 | −5.4 | 1.40E-07 | 7.30E-06 |
| NIPAL4 | −0.00014 | −3.3 | 0.00096 | 0.0086 |
| NNMT | −9.60E-05 | −3.5 | 0.00057 | 0.0058 |
| NRG1 | −0.00012 | −3.8 | 0.00021 | 0.0027 |
| NT5E | −0.00018 | −5.4 | 1.40E-07 | 7.10E-06 |
| NTM | −0.00016 | −5.7 | 4.00E-08 | 2.50E-06 |
| NUAK1 | −9.60E-05 | −4.1 | 6.50E-05 | 0.0011 |
| OLFML2A | −6.00E-05 | −2.8 | 0.0052 | 0.031 |
| PAQR5 | −0.00011 | −3.2 | 0.0016 | 0.013 |
| PARVB | −7.80E-05 | −4.1 | 5.20E-05 | 0.00088 |
| PCDH17 | −8.90E-05 | −3.1 | 0.0018 | 0.014 |
| PDE3A | −8.90E-05 | −2.7 | 0.008 | 0.042 |
| PDGFC | −1.00E-04 | −4.3 | 2.60E-05 | 5.00E-04 |
| PDGFRB | −0.00012 | −4.4 | 1.60E-05 | 0.00035 |
| PDZK1 | −0.00011 | −2.7 | 0.0084 | 0.044 |
| PFN2 | −9.10E-05 | −3 | 0.0029 | 0.02 |
| PHLDB2 | −0.00015 | −7.1 | 1.30E-11 | 3.00E-09 |
| PI15 | −0.00013 | −4.2 | 3.30E-05 | 0.00062 |
| PLEKHG4B | −0.00011 | −2.7 | 0.0082 | 0.043 |
| PNPLA1 | −2.00E-04 | −4.1 | 5.40E-05 | 9.00E-04 |
| PPP1R14C | −1.00E-04 | −5.4 | 1.30E-07 | 6.80E-06 |
| PRICKLE1 | −7.20E-05 | −2.8 | 0.0054 | 0.032 |
| PRRG1 | −5.30E-05 | −2.7 | 0.0085 | 0.045 |
| PTPRD | −0.00013 | −2.8 | 0.0051 | 0.031 |
| RAB38 | −8.80E-05 | −3.1 | 0.0022 | 0.016 |
| RAB3B | −0.00016 | −2.7 | 0.0065 | 0.036 |
| RAI14 | −6.40E-05 | −3.1 | 0.0018 | 0.014 |
| RASD2 | −0.00011 | −3.1 | 0.0022 | 0.016 |

TABLE 9-continued mRNAs inversely expressed and containing predicted or validated binding sites to miR-30e-5p (MIMAT0000692)

| Gene | beta | t.stat | p.value | FDR |
|---|---|---|---|---|
| RASL11B | −9.70E-05 | −3 | 0.003 | 0.02 |
| RHOBTB1 | −8.30E-05 | −3.9 | 1.00E-04 | 0.0015 |
| RSAD2 | −0.00013 | −3.2 | 0.0013 | 0.011 |
| RTN4R | −6.80E-05 | −3.5 | 0.00053 | 0.0054 |
| S100A7A | −2.00E-04 | −2.7 | 0.0066 | 0.037 |
| SAMD4A | −6.90E-05 | −3.2 | 0.0015 | 0.012 |
| SDC2 | −9.50E-05 | −3.5 | 0.00065 | 0.0064 |
| SDK2 | −0.00012 | −3.3 | 0.0012 | 0.01 |
| SEC14L2 | −9.90E-05 | −4.1 | 5.00E-05 | 0.00085 |
| SERPINE1 | −0.00027 | −8.4 | 3.40E-15 | 2.30E-12 |
| SGCD | −0.00013 | −3.2 | 0.0017 | 0.013 |
| SGIP1 | −0.00014 | −4.9 | 1.60E-06 | 5.30E-05 |
| SLC16A10 | −8.70E-05 | −3.4 | 0.00087 | 0.008 |
| SLC24A2 | −0.00049 | −7.3 | 2.90E-12 | 8.10E-10 |
| SLC2A9 | −7.30E-05 | −3.6 | 0.00037 | 0.0041 |
| SLC35F3 | −0.00017 | −3.3 | 0.0011 | 0.0097 |
| SLC38A4 | −9.30E-05 | −2.8 | 0.0062 | 0.035 |
| SLC7A5 | −9.40E-05 | −4.2 | 4.20E-05 | 0.00074 |
| SNAI1 | −6.10E-05 | −2.8 | 0.0048 | 0.029 |
| SNX10 | −9.60E-05 | −4.4 | 1.90E-05 | 4.00E-04 |
| SOX11 | −0.00036 | −6.4 | 7.50E-10 | 9.30E-08 |
| SPSB4 | −0.00014 | −2.9 | 0.0039 | 0.025 |
| STAC | −0.00014 | −3.6 | 0.00036 | 0.004 |
| STC1 | −0.00011 | −4.2 | 3.30E-05 | 0.00061 |
| SULF2 | −1.00E-04 | −4.2 | 3.50E-05 | 0.00064 |
| SYNC | −0.00011 | −4.1 | 6.10E-05 | 0.001 |
| TCHHL1 | −0.00028 | −3 | 0.0031 | 0.021 |
| TGFA | −7.10E-05 | −3.8 | 0.00018 | 0.0023 |
| THBS2 | −2.00E-04 | −6.4 | 9.00E-10 | 1.10E-07 |
| TIMP2 | −8.20E-05 | −3.3 | 0.0013 | 0.011 |
| TIMP3 | −0.00013 | −4.4 | 1.30E-05 | 3.00E-04 |
| TLL1 | −0.00012 | −3 | 0.0017 | 0.023 |
| TLN2 | −8.30E-05 | −3.9 | 0.00011 | 0.0016 |
| TM6SF2 | −0.00026 | −5 | 9.00E-07 | 3.30E-05 |
| TMC7 | −8.40E-05 | −3.8 | 2.00E-04 | 0.0025 |
| TMEM26 | −8.00E-05 | −2.8 | 0.0056 | 0.033 |
| TMEM86A | −7.90E-05 | −3.3 | 0.0011 | 0.0095 |
| TNFSF9 | −7.90E-05 | −3.2 | 0.0017 | 0.013 |
| TRIB3 | −1.00E-04 | −5.4 | 1.20E-07 | 6.50E-06 |
| TRIM9 | −0.00013 | −3.7 | 0.00031 | 0.0036 |
| USP2 | −0.00012 | −3.5 | 6.00E-04 | 0.006 |
| VCAN | −0.00016 | −4.5 | 1.10E-05 | 0.00026 |
| WISP1 | −0.00011 | −3.2 | 0.0017 | 0.013 |
| WNT7B | −6.10E-05 | −3.3 | 0.0011 | 0.0096 |

TABLE 10 mRNAs inversely expressed and containing predicted or validated binding sites to miR-26a-5p (MIMAT0000082)

| Gene | beta | t.stat | p.value | FDR |
|---|---|---|---|---|
| ABCC11 | −0.00033 | −4.4 | 1.50E-05 | 0.00033 |
| ABCC2 | −0.00028 | −3.3 | 0.00098 | 0.0088 |
| ACVR1C | −0.00023 | −4 | 8.10E-05 | 0.0012 |
| ADAM12 | −0.00034 | −3.5 | 0.00051 | 0.0053 |
| ADM | −3.00E-04 | −5.3 | 3.10E-07 | 1.40E-05 |
| ANO1 | −0.00035 | −3.7 | 0.00023 | 0.0028 |
| ARRDC4 | −0.00022 | −3.9 | 0.00013 | 0.0018 |
| ARSJ | −0.00018 | −3 | 0.0026 | 0.018 |
| BEND6 | −2.00E-04 | −3.1 | 0.0021 | 0.015 |
| BICD1 | −0.00017 | −3.5 | 0.00057 | 0.0058 |
| C19orf77 | −0.00043 | −2.9 | 0.0035 | 0.023 |
| C3orf72 | −0.00079 | −4.2 | 3.00E-05 | 0.00057 |
| CCRN4L | −0.00021 | −4.3 | 2.60E-05 | 0.00051 |
| CDK6 | −0.00021 | −4.1 | 6.40E-05 | 0.001 |
| CHST2 | −0.00034 | −4.2 | 3.90E-05 | 0.00069 |
| COL11A1 | −0.00057 | −3.3 | 0.00094 | 0.0085 |
| COL12A1 | −0.00035 | −4.3 | 2.60E-05 | 0.00051 |
| COL4A2 | −0.00024 | −3.7 | 0.00028 | 0.0033 |

TABLE 10-continued mRNAs inversely expressed and containing predicted or validated binding sites to miR-26a-5p (MIMAT0000082)

| Gene | beta | t.stat | p.value | FDR |
| --- | --- | --- | --- | --- |
| COL5A1 | −0.00032 | −3.6 | 4.00E−04 | 0.0043 |
| CT62 | −0.00065 | −3 | 0.0031 | 0.021 |
| CYP27B1 | −0.00022 | −2.7 | 0.0066 | 0.037 |
| DCBLD1 | −0.00022 | −4.1 | 6.00E−05 | 0.00099 |
| DDIT4 | −3.00E−04 | −5.1 | 5.30E−07 | 2.20E−05 |
| DNAH17 | −0.00037 | −3 | 0.003 | 0.021 |
| DNAJB5 | −2.00E−04 | −3.8 | 0.00015 | 0.002 |
| DNMT3B | −0.00027 | −4.7 | 4.10E−06 | 0.00012 |
| DSC3 | −0.00015 | −3.4 | 0.00093 | 0.0084 |
| DSG2 | −0.00017 | −3.3 | 0.0012 | 0.01 |
| EIF5A2 | −0.00015 | −2.7 | 0.0078 | 0.042 |
| ENPEP | −0.00021 | −3.2 | 0.0015 | 0.012 |
| EREG | −4.00E−04 | −2.6 | 0.0093 | 0.048 |
| F2RL1 | −0.00023 | −3.3 | 0.0012 | 0.0099 |
| FADS1 | −0.00017 | −2.6 | 0.0098 | 0.049 |
| FAM83B | −0.00014 | −2.7 | 0.008 | 0.042 |
| FAM89A | −0.00025 | −4.9 | 1.50E−06 | 4.90E−05 |
| FAT1 | −0.00019 | −3.1 | 0.0019 | 0.015 |
| FERMT1 | −2.00E−04 | −4 | 8.10E−05 | 0.0012 |
| FHL2 | −0.00015 | −2.8 | 0.0049 | 0.03 |
| FN1 | −3.00E−04 | −2.8 | 0.0061 | 0.035 |
| FOXD1 | −0.00023 | −3.1 | 0.0022 | 0.016 |
| GOLGA7B | −3.00E−04 | −2.9 | 0.0038 | 0.024 |
| GPSM1 | −0.00019 | −3.6 | 4.00E−04 | 0.0044 |
| HAPLN1 | −0.00032 | −2.9 | 0.0043 | 0.027 |
| HAS3 | −0.00019 | −2.6 | 0.0088 | 0.045 |
| HES2 | −0.00022 | −4.8 | 2.90E−06 | 8.60E−05 |
| HHLA1 | −0.00058 | −2.9 | 0.0037 | 0.024 |
| HIST1H3H | −0.00019 | −2.9 | 0.0043 | 0.027 |
| HMGA2 | −0.00055 | −4.6 | 5.60E−06 | 0.00015 |
| HNF4A | −0.00065 | −3 | 0.0026 | 0.018 |
| HOXC9 | −0.00043 | −3.2 | 0.0014 | 0.011 |
| HOXD13 | −0.00057 | −2.6 | 0.0095 | 0.048 |
| HOXD8 | −0.00018 | −3.6 | 0.00034 | 0.0039 |
| HOXD9 | −0.00017 | −3.4 | 0.00079 | 0.0074 |
| HSD17B6 | −0.00021 | −4.3 | 2.20E−05 | 0.00045 |
| HSPA12A | −0.00021 | −2.9 | 0.0039 | 0.025 |
| HTR2C | −0.0011 | −3.9 | 0.00014 | 0.002 |
| HTR7 | −0.00038 | −3.8 | 0.00015 | 0.002 |
| INHBA | −0.00056 | −5.1 | 8.20E−07 | 3.10E−05 |
| ITGA3 | −0.00021 | −3.2 | 0.0015 | 0.012 |
| ITGA5 | −0.00033 | −5.2 | 4.50E−07 | 1.90E−05 |
| ITGA6 | −0.00027 | −4.5 | 8.70E−06 | 0.00021 |
| KANK4 | −0.00053 | −3.9 | 0.00012 | 0.0017 |
| KCNJ15 | −0.00025 | −3.6 | 0.00046 | 0.0048 |
| KIF26B | −0.00023 | −3.1 | 0.002 | 0.015 |
| KIF3C | −0.00024 | −4.6 | 7.10E−06 | 0.00018 |
| KIRREL | −0.00018 | −2.8 | 0.0052 | 0.031 |
| KLF7 | −0.00027 | −5.1 | 5.50E−07 | 2.20E−05 |
| LAMA1 | −0.00058 | −4.5 | 1.20E−05 | 0.00028 |
| LHFPL5 | −0.00052 | −2.7 | 0.0073 | 0.04 |
| LHX1 | −7.00E−04 | −2.8 | 0.0061 | 0.035 |
| LHX9 | −0.00085 | −3.8 | 0.00016 | 0.0022 |
| LMX1B | −0.00046 | −3 | 0.0034 | 0.022 |
| LOXL2 | −0.00035 | −4.6 | 6.70E−06 | 0.00017 |
| LPAR3 | −2.00E−04 | −3.2 | 0.0017 | 0.013 |
| LRP12 | −0.00015 | −2.9 | 0.0041 | 0.026 |
| MAGEA9B | −0.00089 | −2.8 | 0.0058 | 0.034 |
| MEIS3 | −0.00021 | −2.9 | 0.0036 | 0.024 |
| MET | −0.00019 | −4 | 9.80E−05 | 0.0015 |
| MFSD2A | −0.00016 | −3.4 | 0.00088 | 0.0081 |
| MME | −0.00029 | −3 | 0.0033 | 0.022 |
| MSX2 | −0.00032 | −4.1 | 4.80E−05 | 0.00082 |
| MYH10 | −0.00024 | −4.2 | 3.80E−05 | 0.00068 |
| NAGS | −0.00017 | −3.3 | 0.0011 | 0.0095 |
| NDRG1 | −3.00E−04 | −5.2 | 5.10E−07 | 2.10E−05 |
| NID1 | −0.00022 | −3 | 0.0029 | 0.02 |
| NKPD1 | −0.00026 | −3.1 | 0.0019 | 0.014 |
| NOX5 | −0.00036 | −3.2 | 0.0013 | 0.011 |
| OTUB2 | −0.00017 | −3.2 | 0.0018 | 0.014 |
| PCSK9 | −0.00031 | −3.6 | 0.00042 | 0.0046 |
| PHLDA1 | −0.00014 | −2.7 | 0.0079 | 0.042 |
| PHLDB2 | −0.00035 | −6.3 | 1.40E−09 | 1.60E−07 |
| PNPLA3 | −0.00037 | −3.8 | 0.00019 | 0.0025 |
| POPDC3 | −0.00044 | −3 | 0.0031 | 0.021 |
| PTPRH | −0.00036 | −3.8 | 0.00017 | 0.0023 |
| PYGL | −0.00034 | −5.6 | 7.10E−08 | 4.10E−06 |
| RBM44 | −0.00032 | −3.5 | 0.00049 | 0.0051 |
| RGS20 | −3.00E−04 | −3.4 | 7.00E−04 | 0.0068 |
| RNASE7 | −0.00034 | −2.6 | 0.0094 | 0.048 |
| SERPINA10 | −0.00058 | −3 | 0.0054 | 0.032 |
| SH2D5 | −0.00048 | −4.3 | 2.50E−05 | 0.00049 |
| SHANK2 | −0.00033 | −2.8 | 0.0049 | 0.03 |
| SLC22A1 | −0.00032 | −2.7 | 0.0071 | 0.039 |
| SLC2A9 | −0.00022 | −4.3 | 2.60E−05 | 0.00051 |
| SLC6A7 | −0.00048 | −2.9 | 0.0044 | 0.027 |
| SOX11 | −0.00072 | −4.8 | 2.50E−06 | 7.60E−05 |
| STON2 | −0.00023 | −5.1 | 7.50E−07 | 2.90E−05 |
| TFAP2E | −0.00029 | −3.9 | 0.00014 | 0.002 |
| TMC7 | −0.00024 | −4.3 | 2.40E−05 | 0.00048 |
| TNS4 | −0.00026 | −4 | 9.40E−05 | 0.0014 |
| TRIP13 | −0.00012 | −2.7 | 0.0077 | 0.041 |
| TRPC4 | −0.00024 | −2.7 | 0.0078 | 0.042 |
| TRPV3 | −0.00041 | −4.1 | 4.80E−05 | 0.00082 |
| ZIC5 | −0.00057 | −3.2 | 0.0017 | 0.013 |

TABLE 11 mRNAs inversely expressed and containing predicted or validated binding sites to miR-26b-5p (MIMAT0000083)

| Gene | beta | t.stat | p.value | FDR |
| --- | --- | --- | --- | --- |
| ADAM12 | −0.0015 | −3.7 | 0.00023 | 0.0028 |
| ADAMTS5 | −0.00088 | −2.8 | 0.0048 | 0.029 |
| ALX4 | −0.0025 | −3 | 0.0031 | 0.021 |
| APCDD1 | −0.00068 | −2.7 | 0.0069 | 0.038 |
| ARSJ | −0.00072 | −3 | 0.0028 | 0.019 |
| ASPN | −0.0012 | −2.7 | 0.0076 | 0.041 |
| AVPR1A | −0.00094 | −2.7 | 0.0068 | 0.038 |
| BCAT1 | −0.00093 | −2.7 | 0.0067 | 0.037 |
| BEND6 | −0.00069 | −2.6 | 0.0091 | 0.047 |
| BICD1 | −0.00057 | −2.8 | 0.0051 | 0.031 |
| C14orf37 | −0.00072 | −2.7 | 0.0074 | 0.04 |
| C3orf72 | −0.0021 | −2.7 | 0.0076 | 0.041 |
| CACNA1C | −0.00081 | −2.9 | 0.0036 | 0.024 |
| CALCRL | −0.00058 | −2.7 | 0.0084 | 0.044 |
| CCRN4L | −0.00057 | −2.8 | 0.0062 | 0.035 |
| CDH11 | −0.001 | −2.7 | 0.0066 | 0.037 |
| CLSTN2 | −0.0016 | −3.6 | 0.00034 | 0.0039 |
| CNTNAP2 | −0.0025 | −3.8 | 0.00018 | 0.0023 |
| COL10A1 | −0.0019 | −3.1 | 0.0022 | 0.016 |
| COL11A1 | −0.0024 | −3.5 | 0.00055 | 0.0056 |
| COL12A1 | −0.0012 | −3.7 | 0.00026 | 0.0031 |
| COL1A2 | −0.0013 | −3.3 | 0.0011 | 0.0092 |
| COL5A1 | −0.0012 | −3.1 | 0.002 | 0.015 |
| CRISPLD2 | −0.00084 | −3.2 | 0.0014 | 0.011 |
| DCBLD1 | −0.00064 | −2.9 | 0.0044 | 0.027 |
| DCLK1 | −0.0012 | −2.6 | 0.0089 | 0.046 |
| DNAH17 | −0.0013 | −2.6 | 0.009 | 0.046 |
| EFCAB4B | −0.00086 | −3.2 | 0.0017 | 0.013 |
| EML5 | −0.00084 | −3 | 0.0032 | 0.022 |
| ENPEP | −0.00084 | −3.1 | 0.002 | 0.015 |
| ENTPD3 | −0.00081 | −2.9 | 0.0037 | 0.024 |
| F2RL1 | −0.00082 | −2.9 | 0.0047 | 0.029 |
| FAM169A | −0.00068 | −3 | 0.0032 | 0.021 |
| FAM198B | −0.00083 | −3 | 0.0028 | 0.019 |
| FAM26E | −0.001 | −3.4 | 0.00076 | 0.0072 |
| FMN1 | −0.00092 | −2.7 | 0.0079 | 0.042 |
| FN1 | −0.0013 | −3.1 | 0.0023 | 0.017 |
| FNDC1 | −0.0014 | −3.1 | 0.0025 | 0.018 |
| FOXD1 | −0.00099 | −3.3 | 0.0011 | 0.0093 |
| GPC4 | −0.001 | −2.7 | 0.0079 | 0.042 |
| GPC6 | −0.0012 | −2.8 | 0.0049 | 0.03 |

TABLE 11-continued mRNAs inversely expressed and containing predicted or validated binding sites to miR-26b-5p (MIMAT0000083)

| Gene | beta | t.stat | p.value | FDR |
|---|---|---|---|---|
| GPX8 | −0.00068 | −3.3 | 0.0012 | 0.01 |
| GREB1 | −0.00076 | −2.9 | 0.0043 | 0.027 |
| GUCY1A2 | −0.00085 | −2.7 | 0.0067 | 0.037 |
| HOXA13 | −0.0036 | −4.3 | 2.80E−05 | 0.00054 |
| HOXD8 | −0.00069 | −3.3 | 0.00099 | 0.0088 |
| HS3ST3A1 | −0.00085 | −2.7 | 0.0084 | 0.044 |
| HSD17B6 | −0.00064 | −3.2 | 0.0016 | 0.012 |
| HTR7 | −0.0011 | −2.8 | 0.0053 | 0.031 |
| INPP4B | −0.00094 | −3.3 | 0.00097 | 0.0087 |
| ITGA5 | −0.00079 | −2.9 | 0.0037 | 0.024 |
| ITGA6 | −0.00064 | −2.6 | 0.0087 | 0.045 |
| KCND2 | −0.0014 | −3.2 | 0.0013 | 0.011 |
| KCNJ15 | −0.00093 | −3.2 | 0.0013 | 0.011 |
| KIF26B | −0.0012 | −3.9 | 0.00011 | 0.0016 |
| KIRREL | −0.00072 | −2.8 | 0.0061 | 0.035 |
| KLK2 | −0.0026 | −2.7 | 0.0068 | 0.038 |
| LAMA1 | −0.0017 | −3.1 | 0.0019 | 0.014 |
| LHX9 | −0.0024 | −2.6 | 0.0094 | 0.048 |
| LINGO1 | −0.00075 | −2.7 | 0.0074 | 0.04 |
| LMX1B | −0.0019 | −3 | 0.0033 | 0.022 |
| LOX | −0.00093 | −3.2 | 0.0014 | 0.012 |
| LOXL2 | −0.00094 | −3 | 0.0033 | 0.022 |
| LPAR3 | −0.00074 | −2.9 | 0.0046 | 0.028 |
| LRP12 | −0.00056 | −2.6 | 0.0086 | 0.045 |
| LUM | −0.00089 | −2.6 | 0.0087 | 0.045 |
| MFAP3L | −9.00E−04 | −3.1 | 0.0024 | 0.018 |
| MFAP5 | −0.0017 | −3.5 | 0.00047 | 0.005 |
| MME | −0.0016 | −4 | 7.30E−05 | 0.0011 |
| MMP16 | −0.0018 | −3.9 | 0.00012 | 0.0017 |
| MSX2 | −0.0011 | −3.5 | 0.00059 | 0.0059 |
| MYH10 | −0.00086 | −3.7 | 0.00026 | 0.0032 |
| NDRG1 | −0.00069 | −2.8 | 0.0056 | 0.033 |
| NID1 | −0.0013 | −4.6 | 5.30E−06 | 0.00014 |
| OTUB2 | −0.00063 | −2.9 | 0.0041 | 0.026 |
| PCDHB16 | −0.001 | −3.5 | 0.00049 | 0.0051 |
| PDE3A | −0.001 | −2.9 | 0.0036 | 0.023 |
| PGM2L1 | −0.00068 | −2.8 | 0.0062 | 0.035 |
| PHLDB2 | −0.00075 | −3.1 | 0.0018 | 0.014 |
| PLOD2 | −0.00075 | −3.5 | 0.00052 | 0.0054 |
| PRDM5 | −0.00069 | −2.7 | 0.0076 | 0.041 |
| PRKG1 | −0.00099 | −3 | 0.0026 | 0.019 |
| PRSS35 | −0.0019 | −2.8 | 0.0056 | 0.033 |
| PTPRD | −0.0017 | −3.5 | 0.00046 | 0.0049 |
| RBMS3 | −0.00088 | −3 | 0.0029 | 0.02 |
| RNF128 | −0.0012 | −2.7 | 0.0078 | 0.042 |
| RNF152 | −0.00066 | −2.8 | 0.0062 | 0.035 |
| SALL1 | −0.0017 | −2.6 | 0.0097 | 0.049 |
| SEMA6D | −0.0011 | −2.9 | 0.0037 | 0.024 |
| SESN3 | −0.001 | −4 | 8.90E−05 | 0.0014 |
| SFRP4 | −0.0017 | −2.7 | 0.0075 | 0.04 |
| SHANK2 | −0.0016 | −3.4 | 0.00068 | 0.0066 |
| SLC2A9 | −0.00062 | −2.9 | 0.0035 | 0.023 |
| SNX10 | −0.00066 | −2.8 | 0.0052 | 0.031 |
| SOX11 | −0.0017 | −2.7 | 0.0081 | 0.043 |
| SPOCK1 | −0.0013 | −3.1 | 0.0021 | 0.015 |
| ST6GALNAC5 | −0.0013 | −3.4 | 0.00078 | 0.0073 |
| STON2 | −0.00052 | −2.8 | 0.0059 | 0.034 |
| SULF1 | −0.001 | −2.9 | 0.0047 | 0.029 |
| SYT13 | −0.0033 | −3.8 | 2.00E−04 | 0.0026 |
| SYT14 | −0.0025 | −3.2 | 0.0016 | 0.013 |
| TET1 | −0.00077 | −2.7 | 0.0084 | 0.044 |
| TRPC4 | −0.0011 | −2.9 | 0.0046 | 0.028 |
| TRPS1 | −0.00063 | −2.8 | 0.0055 | 0.032 |
| VCAN | −0.0011 | −3 | 0.0031 | 0.021 |
| VEPH1 | −0.0021 | −3.9 | 0.00013 | 0.0018 |
| VGLL3 | −9.00E−04 | −2.8 | 0.0062 | 0.035 |
| WNT2 | −0.0015 | −2.8 | 0.0056 | 0.033 |
| WNT5A | −0.00078 | −2.9 | 0.0042 | 0.026 |
| WT1 | −0.0029 | −3 | 0.003 | 0.02 |
| ZFHX4 | −0.0014 | −4 | 9.50E−05 | 0.0014 |
| ZNF469 | −0.0011 | −3 | 0.0032 | 0.021 |
| ZNF704 | −0.00093 | −2.9 | 0.0035 | 0.023 |

TABLE 12 mRNAs inversely expressed and containing predicted or validated binding sites to miR-145-5p (MIMAT0000437)

| Gene | beta | t.stat | p.value | FDR |
|---|---|---|---|---|
| APOL1 | −0.00077 | −3.3 | 0.001 | 0.0091 |
| CCNA2 | −0.00037 | −3.2 | 0.0013 | 0.011 |
| CMPK2 | −0.00078 | −3.2 | 0.0018 | 0.014 |
| DDX60 | −0.00066 | −3 | 0.0031 | 0.021 |
| DEPDC1B | −0.00039 | −3 | 0.0027 | 0.019 |
| ELOVL7 | −7.00E−04 | −4 | 9.20E−05 | 0.0014 |
| EPHA4 | −0.00049 | −2.7 | 0.007 | 0.039 |
| ESCO2 | −0.00036 | −2.6 | 0.0088 | 0.046 |
| FAM169A | −0.00046 | −2.6 | 0.0089 | 0.046 |
| GCNT4 | −0.00054 | −2.9 | 0.004 | 0.026 |
| GPR150 | −0.0017 | −2.8 | 0.0048 | 0.029 |
| HOXA1 | −0.00064 | −2.8 | 0.0057 | 0.033 |
| HS6ST2 | −0.0012 | −3 | 0.0033 | 0.022 |
| IFI44L | −0.00094 | −3 | 0.0029 | 0.02 |
| KIAA0895 | −0.00043 | −2.7 | 0.0065 | 0.037 |
| PBK | −0.00036 | −2.7 | 0.0083 | 0.044 |
| PHEX | −7.00E−04 | −2.9 | 0.0042 | 0.027 |
| PRF1 | −0.00066 | −2.7 | 0.007 | 0.038 |
| RAB27B | −5.00E−04 | −2.8 | 0.0057 | 0.033 |
| SGPP2 | −0.00058 | −2.8 | 0.0059 | 0.034 |
| SH2D4A | −0.00043 | −2.6 | 0.0091 | 0.047 |
| SPC24 | −4.00E−04 | −2.6 | 0.0087 | 0.045 |
| TLX2 | −0.0019 | −2.8 | 0.005 | 0.03 |
| ZIC2 | −0.0013 | −4 | 8.70E−05 | 0.0013 |
| ZIC5 | −0.0018 | −3.3 | 0.001 | 0.0089 |
| PLEKHH1 | −0.00085 | −5.2 | 4.40E−07 | 1.90E−05 |
| GDPD4 | −0.0027 | −4.6 | 8.10E−06 | 2.00E−04 |
| CAGE1 | −0.0013 | −4 | 7.40E−05 | 0.0012 |
| C14orf73 | −0.0016 | −4 | 8.50E−05 | 0.0013 |
| C9orf84 | −0.00078 | −3.8 | 0.00017 | 0.0023 |
| C15orf42 | −0.00054 | −3.7 | 0.00023 | 0.0029 |
| SEC16B | −0.00074 | −3.6 | 0.00034 | 0.0039 |
| SATL1 | −0.00061 | −3.6 | 0.00036 | 0.004 |
| WARS | −0.00081 | −3.6 | 4.00E−04 | 0.0044 |
| POLQ | −0.00049 | −3.6 | 0.00041 | 0.0044 |
| CSAG3 | −0.0027 | −3.6 | 4.00E−04 | 0.0044 |
| OR2A1 | −0.001 | −3.6 | 0.00044 | 0.0047 |
| ZBP1 | −0.0012 | −3.5 | 0.00051 | 0.0053 |
| KIAA0101 | −0.00045 | −3.5 | 0.00051 | 0.0053 |
| NCRNA00114 | −0.0017 | −3.5 | 0.00057 | 0.0058 |
| NEIL3 | −0.00054 | −3.5 | 0.00059 | 0.0059 |
| CDCA2 | −0.00045 | −3.5 | 0.00064 | 0.0063 |
| HIST1H2AJ | −0.0016 | −3.4 | 0.00069 | 0.0066 |
| C16orf75 | −5.00E−04 | −3.4 | 0.00072 | 0.0069 |
| SLC44A5 | −0.0011 | −3.4 | 0.00092 | 0.0083 |
| CASP5 | −0.0013 | −3.3 | 0.00097 | 0.0087 |
| HERC5 | −0.00073 | −3.3 | 0.001 | 0.0089 |
| ACE2 | −0.00087 | −3.3 | 0.001 | 0.0091 |
| TTK | −0.00036 | −3.3 | 0.0011 | 0.0093 |
| RRM2 | −0.00039 | −3.3 | 0.0011 | 0.0098 |

TABLE 13 mRNAs inversely expressed and containing predicted or validated binding sites to miR-205-5p (MIMAT0000266)

| Gene | beta | t.stat | p.value | FDR |
|---|---|---|---|---|
| BAI3 | −9.90E−05 | −4 | 8.20E−05 | 0.0013 |
| 42430 | −5.30E−05 | −6.1 | 4.10E−09 | 3.80E−07 |
| A2M | −6.90E−05 | −9.2 | 1.10E−17 | 1.50E−14 |
| AASS | −2.40E−05 | −3 | 0.0027 | 0.019 |
| ABCA6 | −9.40E−05 | −8.8 | 1.90E−16 | 1.90E−13 |
| ABCC12 | −0.00012 | −3.8 | 0.00016 | 0.0021 |
| ABCD2 | −9.50E−05 | −5.3 | 2.30E−07 | 1.10E−05 |
| ACACB | −5.40E−05 | −5.8 | 2.30E−08 | 1.60E−06 |
| ACSL5 | −4.60E−05 | −4.5 | 1.00E−05 | 0.00024 |
| ACTC1 | −0.00012 | −2.9 | 0.0041 | 0.026 |
| ADAM28 | −5.20E−05 | −3.7 | 0.00022 | 0.0028 |
| ADAMTS16 | −0.00012 | −4.8 | 3.30E−06 | 9.70E−05 |

TABLE 13-continued mRNAs inversely expressed and containing predicted or validated binding sites to miR-205-5p (MIMAT0000266)

| Gene | beta | t.stat | p.value | FDR |
|---|---|---|---|---|
| ADAMTS18 | −0.00014 | −6.4 | 8.40E-10 | 1.00E-07 |
| ADAMTS4 | −4.80E-05 | −4.8 | 3.10E-06 | 9.20E-05 |
| ADAMTS5 | −8.20E-05 | −7.9 | 7.20E-14 | 3.30E-11 |
| ADAMTS9 | −7.20E-05 | −7.8 | 1.30E-13 | 5.70E-11 |
| ADAMTSL1 | −0.00011 | −8.8 | 2.30E-16 | 2.20E-13 |
| ADAMTSL2 | −2.60E-05 | −3.2 | 0.0013 | 0.011 |
| ADCY2 | −0.00011 | −5.4 | 1.50E-07 | 7.50E-06 |
| ADCYAP1 | −9.20E-05 | −4.7 | 3.50E-06 | 1.00E-04 |
| ADCYAP1R1 | −0.00011 | −3.6 | 0.00046 | 0.0048 |
| ADD2 | −0.00011 | −4.5 | 1.10E-05 | 0.00025 |
| ADH1B | −0.00018 | −4.8 | 2.30E-06 | 7.20E-05 |
| ADORA3 | −6.40E-05 | −6.1 | 3.90E-09 | 3.70E-07 |
| ADRA1B | −6.40E-05 | −3.1 | 0.0019 | 0.014 |
| AFF3 | −8.80E-05 | −5.5 | 1.00E-07 | 5.60E-06 |
| AGTR1 | −0.00019 | −7.9 | 8.50E-14 | 3.80E-11 |
| AKAP2 | −7.00E-05 | −6.8 | 9.10E-11 | 1.50E-08 |
| AKAP7 | −4.40E-05 | −5.8 | 1.90E-08 | 1.40E-06 |
| AKT3 | −4.10E-05 | −4.9 | 1.70E-06 | 5.70E-05 |
| ALCAM | −2.70E-05 | −2.7 | 0.0065 | 0.036 |
| ALDH3B1 | −4.50E-05 | −6 | 5.20E-09 | 4.70E-07 |
| ALPK3 | −6.60E-05 | −6.2 | 2.10E-09 | 2.20E-07 |
| ALX4 | −8.70E-05 | −2.8 | 0.006 | 0.034 |
| AMOT | −7.60E-05 | −4.8 | 2.70E-06 | 8.20E-05 |
| ANGPTL7 | −0.00017 | −5 | 1.30E-06 | 4.40E-05 |
| ANK2 | −0.00011 | −8.7 | 3.60E-16 | 3.30E-13 |
| ANTXR1 | −4.00E-05 | −5.2 | 3.40E-07 | 1.50E-05 |
| APBA1 | −2.50E-05 | −3.2 | 0.0015 | 0.012 |
| APLNR | −7.80E-05 | −7.2 | 8.00E-12 | 1.90E-09 |
| APOC4 | −8.90E-05 | −3 | 0.003 | 0.02 |
| APOL6 | −4.60E-05 | −5.6 | 5.10E-08 | 3.10E-06 |
| AQP1 | −5.70E-05 | −7.7 | 3.00E-13 | 1.10E-10 |
| AQP9 | −6.20E-05 | −4 | 8.50E-05 | 0.0013 |
| AR | −0.00012 | −5.9 | 1.40E-08 | 1.10E-06 |
| ARHGAP15 | −5.50E-05 | −5.7 | 2.90E-08 | 2.00E-06 |
| ARHGAP24 | −3.80E-05 | −4.2 | 3.90E-05 | 7.00E-04 |
| ARHGAP26 | −2.70E-05 | −3.2 | 0.0018 | 0.014 |
| ARHGAP31 | −4.90E-05 | −6.5 | 3.20E-10 | 4.50E-08 |
| ARHGAP42 | −3.30E-05 | −3.9 | 0.00012 | 0.0017 |
| ASPA | −0.00012 | −5 | 1.00E-06 | 3.60E-05 |
| ASTN1 | −8.80E-05 | −2.8 | 0.0053 | 0.031 |
| ATP10A | −8.80E-05 | −9.6 | 6.90E-19 | 1.30E-15 |
| ATP6V0A4 | −0.00011 | −4.3 | 2.00E-05 | 0.00042 |
| ATP8A1 | −6.00E-05 | −5.7 | 3.30E-08 | 2.20E-06 |
| ATRNL1 | −7.90E-05 | −3.2 | 0.0014 | 0.011 |
| AVPR1A | −5.00E-05 | −4 | 7.50E-05 | 0.0012 |
| AXIN2 | −5.90E-05 | −6.7 | 1.20E-10 | 1.90E-08 |
| B3GALT5 | −0.00012 | −3.2 | 0.0014 | 0.011 |
| B4GALT6 | −3.70E-05 | −4.1 | 6.00E-05 | 0.00099 |
| BACH2 | −3.60E-05 | −3.6 | 0.00039 | 0.0043 |
| BCAS1 | −4.30E-05 | −2.6 | 0.0097 | 0.049 |
| BCL2 | −4.50E-05 | −4.5 | 8.60E-06 | 0.00021 |
| BEND4 | −0.00013 | −4 | 9.20E-05 | 0.0014 |
| BEST3 | −9.70E-05 | −2.9 | 0.0038 | 0.025 |
| BHLHE41 | −3.50E-05 | −3.3 | 0.00098 | 0.0088 |
| BICC1 | −8.80E-05 | −6.9 | 3.80E-11 | 7.40E-09 |
| BICD1 | −2.10E-05 | −2.8 | 0.0053 | 0.031 |
| BMF | −2.10E-05 | −2.7 | 0.0073 | 0.04 |
| BMP3 | −0.00011 | −2.9 | 0.0041 | 0.026 |
| BMP6 | −5.50E-05 | −6.3 | 1.50E-09 | 1.60E-07 |
| BMP8A | −3.10E-05 | −2.7 | 0.0064 | 0.036 |
| BMPER | −5.50E-05 | −3.4 | 0.00073 | 0.007 |
| BNC2 | −9.10E-05 | −8.2 | 8.90E-15 | 5.30E-12 |
| BPI | −0.00012 | −3.8 | 2.00E-04 | 0.0025 |
| BST1 | −7.00E-05 | −9.2 | 1.60E-17 | 2.10E-14 |
| BTLA | −7.20E-05 | −4.5 | 9.00E-06 | 0.00022 |
| BTN3A2 | −3.00E-05 | −3.5 | 0.00047 | 0.0049 |
| C10orf10 | −3.50E-05 | −3.8 | 0.00017 | 0.0022 |
| C10orf128 | −8.30E-05 | −6.1 | 4.90E-09 | 4.50E-07 |
| C10orf131 | −7.40E-05 | −2.6 | 0.0089 | 0.046 |
| C10orf71 | −0.00015 | −3.3 | 0.0013 | 0.011 |
| C11orf21 | −7.70E-05 | −4.1 | 5.40E-05 | 9.00E-04 |
| C12orf68 | −4.30E-05 | −4 | 8.00E-05 | 0.0012 |
| C15orf52 | −2.90E-05 | −2.9 | 0.0044 | 0.027 |
| C17orf72 | −4.10E-05 | −4.7 | 4.60E-06 | 0.00013 |
| C17orf82 | −6.20E-05 | −3.3 | 0.0011 | 0.0093 |
| C1QTNF3 | −4.20E-05 | −2.9 | 0.0035 | 0.023 |
| C22orf34 | −0.00012 | −3.9 | 0.00013 | 0.0018 |
| C3orf36 | −4.70E-05 | −3.9 | 0.00015 | 0.002 |
| C4orf40 | −9.20E-05 | −3.3 | 0.001 | 0.0089 |
| C6 | −0.00022 | −6.2 | 2.70E-09 | 2.70E-07 |
| C7 | −0.00016 | −5.4 | 1.50E-07 | 7.60E-06 |
| CA13 | −3.50E-05 | −3.5 | 0.00061 | 0.0061 |
| CA3 | −0.00012 | −4.3 | 2.70E-05 | 0.00052 |
| CA8 | −0.00013 | −5.4 | 1.40E-07 | 7.10E-06 |
| CABP4 | −7.10E-05 | −3.8 | 0.00019 | 0.0024 |
| CACNA2D2 | −4.40E-05 | −4.4 | 1.90E-05 | 0.00039 |
| CADM1 | −6.80E-05 | −6.1 | 3.30E-09 | 3.20E-07 |
| CADPS2 | −6.50E-05 | −7.3 | 4.40E-12 | 1.20E-09 |
| CALCRL | −4.70E-05 | −6.2 | 2.50E-09 | 2.50E-07 |
| CALN1 | −1.00E-04 | −3.1 | 0.0024 | 0.017 |
| CAMK2A | −7.90E-05 | −4.3 | 2.70E-05 | 0.00052 |
| CAMK4 | −6.00E-05 | −4.4 | 1.50E-05 | 0.00032 |
| CCDC141 | −9.40E-05 | −6.1 | 4.10E-09 | 3.90E-07 |
| CCDC144A | −6.20E-05 | −2.7 | 0.0085 | 0.045 |
| CCDC152 | −5.50E-05 | −4.5 | 1.20E-05 | 0.00028 |
| CCDC68 | −7.20E-05 | −3.9 | 1.00E-04 | 0.0015 |
| CCDC80 | −7.00E-05 | −7.4 | 1.60E-12 | 4.90E-10 |
| CCDC85A | −9.80E-05 | −6.9 | 5.10E-11 | 9.40E-09 |
| CCL13 | −7.20E-05 | −5 | 8.40E-07 | 3.20E-05 |
| CCL21 | −6.20E-05 | −3.3 | 0.00098 | 0.0087 |
| CCL22 | −2.90E-05 | −2.7 | 0.0076 | 0.041 |
| CCR5 | −6.40E-05 | −5.4 | 1.20E-07 | 6.50E-06 |
| CCR7 | −4.30E-05 | −3.3 | 0.0011 | 0.0098 |
| CCR8 | −4.60E-05 | −2.7 | 0.0085 | 0.044 |
| CD163L1 | −6.30E-05 | −5.9 | 1.30E-08 | 1.00E-06 |
| CD180 | −6.50E-05 | −5.6 | 4.60E-08 | 2.90E-06 |
| CD1D | −5.30E-05 | −5.6 | 5.40E-08 | 3.30E-06 |
| CD226 | −6.90E-05 | −4.7 | 4.90E-06 | 0.00013 |
| CD28 | −6.60E-05 | −5.1 | 5.20E-07 | 2.10E-05 |
| CD300E | −8.30E-05 | −3.1 | 0.0025 | 0.018 |
| CD4 | −5.90E-05 | −6.3 | 1.50E-09 | 1.70E-07 |
| CD84 | −8.70E-05 | −6.8 | 8.00E-11 | 1.40E-08 |
| CD93 | −5.90E-05 | −7.9 | 6.20E-14 | 2.90E-11 |
| CDH11 | −7.90E-05 | −6 | 5.60E-09 | 5.00E-07 |
| CDK14 | −3.70E-05 | −3.4 | 0.00077 | 0.0072 |
| CECR1 | −6.80E-05 | −6.1 | 4.10E-09 | 3.80E-07 |
| CERKL | −6.50E-05 | −6.3 | 1.50E-09 | 1.70E-07 |
| CES1 | −9.70E-05 | −3.9 | 0.00012 | 0.0017 |
| CFL2 | −3.20E-05 | −4.6 | 5.80E-06 | 0.00015 |
| CHN1 | −4.70E-05 | −5.4 | 1.30E-07 | 6.70E-06 |
| CHRDL1 | −0.00017 | −6.2 | 2.00E-09 | 2.10E-07 |
| CHRFAM7A | −4.30E-05 | −3.3 | 0.00099 | 0.0088 |
| CHRNA7 | −8.00E-05 | −3.6 | 0.00039 | 0.0043 |
| CHRNB2 | −6.10E-05 | −2.8 | 0.005 | 0.03 |
| CHST11 | −2.60E-05 | −2.8 | 0.0051 | 0.03 |
| CHST6 | −6.40E-05 | −4.8 | 2.60E-06 | 7.90E-05 |
| CIITA | −5.40E-05 | −4.5 | 9.50E-06 | 0.00023 |
| CLDN11 | −8.70E-05 | −7.7 | 3.10E-13 | 1.20E-10 |
| CLEC10A | −6.90E-05 | −5.1 | 7.80E-07 | 3.00E-05 |
| CLIC5 | −9.30E-05 | −7 | 1.70E-11 | 3.60E-09 |
| CMKLR1 | −7.80E-05 | −7.7 | 3.60E-13 | 1.30E-10 |
| CMTM7 | −4.10E-05 | −4.8 | 2.30E-06 | 7.10E-05 |
| CMYA5 | −8.20E-05 | −4.3 | 2.50E-05 | 0.00049 |
| CNR1 | −0.00011 | −4.8 | 2.40E-06 | 7.40E-05 |
| CNTNAP2 | −8.70E-05 | −3.6 | 0.00036 | 0.0041 |
| COL14A1 | −8.50E-05 | −8.3 | 5.20E-15 | 3.40E-12 |
| COL1A1 | −7.20E-05 | −4.7 | 4.40E-06 | 0.00012 |
| CPE | −2.80E-05 | −2.8 | 0.0055 | 0.032 |
| CPEB1 | −9.80E-05 | −4.8 | 2.50E-06 | 7.70E-05 |
| CREB5 | −3.20E-05 | −3.1 | 0.0022 | 0.016 |
| CRISPLD2 | −5.20E-05 | −5.7 | 4.00E-08 | 2.60E-06 |
| CRMP1 | −3.80E-05 | −3.5 | 0.00064 | 0.0063 |
| CSF1 | −3.80E-05 | −5 | 1.30E-06 | 4.40E-05 |
| CSMD2 | −6.30E-05 | −3.9 | 0.00011 | 0.0016 |
| CTLA4 | −3.60E-05 | −2.6 | 0.0087 | 0.045 |
| CTSO | −4.90E-05 | −6.8 | 5.70E-11 | 1.00E-08 |
| CXCL11 | −8.90E-05 | −4 | 9.90E-05 | 0.0015 |
| CXCR5 | −5.80E-05 | −3.2 | 0.0018 | 0.014 |

TABLE 13-continued mRNAs inversely expressed and containing predicted or validated binding sites to miR-205-5p (MIMAT0000266)

| Gene | beta | t.stat | p.value | FDR |
|---|---|---|---|---|
| CXorf21 | −6.60E−05 | −5.5 | 8.40E−08 | 4.80E−06 |
| CXXC4 | −9.50E−05 | −3.2 | 0.0015 | 0.012 |
| CYBB | −8.00E−05 | −7 | 2.40E−11 | 4.90E−09 |
| CYP19A1 | −7.10E−05 | −5.4 | 1.30E−07 | 6.70E−06 |
| CYP21A2 | −5.50E−05 | −2.9 | 0.0046 | 0.028 |
| CYP2A7 | −8.30E−05 | −2.9 | 0.0047 | 0.029 |
| CYP4V2 | −4.60E−05 | −5.7 | 3.20E−08 | 2.10E−06 |
| CYSLTR2 | −9.20E−05 | −6.1 | 5.00E−09 | 4.50E−07 |
| CYTH4 | −4.90E−05 | −5.2 | 4.30E−07 | 1.80E−05 |
| DAAM2 | −7.20E−05 | −7.4 | 1.50E−12 | 4.60E−10 |
| DAB1 | −0.00012 | −4.2 | 3.60E−05 | 0.00065 |
| DACH1 | −8.90E−05 | −6.7 | 1.20E−10 | 1.90E−08 |
| DAGLA | −3.90E−05 | −4.2 | 3.50E−05 | 0.00064 |
| DBX2 | −0.00014 | −3.8 | 0.00019 | 0.0024 |
| DCHS1 | −5.60E−05 | −5.9 | 1.10E−08 | 8.90E−07 |
| DCHS2 | −6.70E−05 | −3.6 | 0.00036 | 0.004 |
| DCLK3 | −3.00E−05 | −2.8 | 0.0048 | 0.029 |
| DCN | −7.80E−05 | −7.9 | 8.70E−14 | 3.90E−11 |
| DDAH1 | −5.10E−05 | −5.6 | 5.10E−08 | 3.10E−06 |
| DDN | −4.50E−05 | −2.7 | 0.0067 | 0.037 |
| DDR2 | −8.20E−05 | −7.1 | 1.30E−11 | 2.80E−09 |
| DGKG | −5.20E−05 | −3.8 | 0.00017 | 0.0023 |
| DGKI | −8.30E−05 | −5.5 | 1.10E−07 | 6.00E−06 |
| DIO2 | −7.10E−05 | −6.2 | 1.80E−09 | 1.90E−07 |
| DLC1 | −4.60E−05 | −5.5 | 8.30E−08 | 4.70E−06 |
| DLG2 | −7.70E−05 | −3.4 | 0.00092 | 0.0083 |
| DMD | −3.80E−05 | −3.4 | 0.00081 | 0.0075 |
| DNAH9 | −5.70E−05 | −3.1 | 0.002 | 0.015 |
| DNM3 | −4.10E−05 | −4.6 | 6.30E−06 | 0.00016 |
| DOCK3 | −4.10E−05 | −3.8 | 0.00016 | 0.0022 |
| DOK6 | −7.10E−05 | −5.6 | 4.70E−08 | 2.90E−06 |
| DPP4 | −3.40E−05 | −2.8 | 0.0057 | 0.033 |
| DPYSL3 | −7.00E−05 | −7 | 2.60E−11 | 5.30E−09 |
| DUSP27 | −0.00014 | −3.3 | 0.0011 | 0.0093 |
| DUSP4 | −3.70E−05 | −4 | 9.30E−05 | 0.0014 |
| EBF1 | −6.20E−05 | −7.4 | 1.50E−12 | 4.70E−10 |
| ECM2 | −7.00E−05 | −7.8 | 1.80E−13 | 7.20E−11 |
| EDA2R | −0.00011 | −11 | 8.70E−24 | 4.10E−20 |
| EDIL3 | −7.50E−05 | −5.8 | 1.60E−08 | 1.20E−06 |
| EDN3 | −0.00019 | −5.2 | 3.80E−07 | 1.70E−05 |
| ELAVL4 | −7.70E−05 | −3.2 | 0.0014 | 0.011 |
| ELFN2 | −5.80E−05 | −2.7 | 0.0079 | 0.042 |
| ELOVL6 | −3.30E−05 | −3.7 | 3.00E−04 | 0.0035 |
| ELTD1 | −5.90E−05 | −8.9 | 1.10E−16 | 1.10E−13 |
| EMR2 | −3.10E−05 | −3.6 | 0.00035 | 0.004 |
| EMX2 | −6.20E−05 | −3.3 | 0.0012 | 0.01 |
| ENPP4 | −9.40E−05 | −8.2 | 9.20E−15 | 5.50E−12 |
| ENPP5 | −9.20E−05 | −4 | 8.40E−05 | 0.0013 |
| EPHA3 | −8.70E−05 | −6.5 | 3.90E−10 | 5.30E−08 |
| EPHA7 | −0.00014 | −4.5 | 1.20E−05 | 0.00027 |
| EPHX4 | −7.50E−05 | −4.4 | 1.50E−05 | 0.00032 |
| EPS8 | −6.90E−05 | −6.8 | 6.00E−11 | 1.10E−08 |
| ERBB4 | −0.00016 | −4.8 | 3.10E−06 | 9.20E−05 |
| ERC2 | −5.00E−05 | −3.4 | 0.00071 | 0.0068 |
| ERMN | −7.10E−05 | −5 | 1.00E−06 | 3.70E−05 |
| ESRRG | −0.00012 | −4.2 | 4.40E−05 | 0.00077 |
| ETV1 | −6.50E−05 | −6.2 | 2.80E−09 | 2.80E−07 |
| ETV5 | −4.30E−05 | −4.9 | 1.50E−06 | 5.20E−05 |
| ETV7 | −2.80E−05 | −2.7 | 0.0083 | 0.044 |
| F2RL2 | −6.40E−05 | −4.6 | 6.10E−06 | 0.00016 |
| FABP4 | −9.80E−05 | −3.9 | 0.00014 | 0.0019 |
| FAM124A | −6.00E−05 | −6.9 | 3.50E−11 | 6.80E−09 |
| FAM124B | −7.60E−05 | −7.5 | 1.00E−12 | 3.20E−10 |
| FAM131B | −5.10E−05 | −5.6 | 4.80E−08 | 3.00E−06 |
| FAM134B | −5.60E−05 | −5.3 | 2.80E−07 | 1.30E−05 |
| FAM155A | −9.20E−05 | −7 | 1.90E−11 | 4.10E−09 |
| FAM169A | −2.60E−05 | −3.1 | 0.0021 | 0.016 |
| FAM174B | −4.80E−05 | −6.5 | 3.80E−10 | 5.20E−08 |
| FAM179A | −3.80E−05 | −3.3 | 0.0012 | 0.01 |
| FAM180A | −5.10E−05 | −3.7 | 0.00029 | 0.0034 |
| FAM19A5 | −6.40E−05 | −5 | 8.40E−07 | 3.10E−05 |
| FAM26E | −6.80E−05 | −6.6 | 1.80E−10 | 2.80E−08 |
| FAM49A | −5.60E−05 | −7 | 1.70E−11 | 3.70E−09 |
| FAM78A | −4.90E−05 | −6 | 5.40E−09 | 4.90E−07 |
| FAR2 | −4.40E−05 | −5.6 | 4.80E−08 | 3.00E−06 |
| FBN1 | −8.50E−05 | −7.1 | 1.50E−11 | 3.30E−09 |
| FERMT2 | −7.20E−05 | −8.6 | 9.80E−16 | 7.80E−13 |
| FETUB | −9.80E−05 | −2.7 | 0.0067 | 0.037 |
| FGF1 | −4.50E−05 | −4.4 | 1.30E−05 | 3.00E−04 |
| FGF10 | −0.00016 | −5.2 | 4.90E−07 | 2.00E−05 |
| FGF14 | −0.00012 | −8.4 | 3.90E−15 | 2.60E−12 |
| FGF2 | −6.70E−05 | −5.7 | 2.90E−08 | 2.00E−06 |
| FGF7 | −9.30E−05 | −8.7 | 4.20E−16 | 3.80E−13 |
| FGFR1 | −6.00E−05 | −6.7 | 1.20E−10 | 2.00E−08 |
| FHL5 | −8.70E−05 | −5.4 | 1.30E−07 | 6.80E−06 |
| FMN1 | −4.80E−05 | −3.9 | 0.00014 | 0.002 |
| FMO2 | −9.40E−05 | −4.6 | 6.80E−06 | 0.00017 |
| FNDC5 | −5.30E−05 | −3.4 | 0.00092 | 0.0083 |
| FOXF1 | −5.60E−05 | −5.9 | 1.20E−08 | 9.40E−07 |
| FOXI2 | −9.30E−05 | −2.8 | 0.0052 | 0.031 |
| FPR1 | −6.20E−05 | −6.2 | 1.90E−09 | 2.00E−07 |
| FREM2 | −1.00E−04 | −3 | 0.0032 | 0.022 |
| FRY | −7.00E−05 | −6.9 | 3.20E−11 | 6.30E−09 |
| FSD2 | −0.00012 | −3.5 | 0.00048 | 0.005 |
| FSTL1 | −6.20E−05 | −7.1 | 1.00E−11 | 2.40E−09 |
| FXYD2 | −7.60E−05 | −4.7 | 4.80E−06 | 0.00013 |
| FXYD6 | −8.00E−05 | −6.7 | 1.00E−10 | 1.70E−08 |
| FZD3 | −4.90E−05 | −5.5 | 1.10E−07 | 5.90E−06 |
| FZD8 | −2.50E−05 | −2.7 | 0.0077 | 0.041 |
| GAB3 | −4.90E−05 | −5.6 | 5.00E−08 | 3.10E−06 |
| GABRA4 | −1.00E−04 | −2.9 | 0.0035 | 0.023 |
| GADD45G | −3.30E−05 | −3.7 | 0.00025 | 0.003 |
| GALNT13 | −6.30E−05 | −2.8 | 0.0048 | 0.029 |
| GALNT5 | −5.20E−05 | −3.4 | 9.00E−04 | 0.0082 |
| GCNT4 | −3.90E−05 | −4.4 | 1.70E−05 | 0.00036 |
| GDF10 | −0.00017 | −7.3 | 4.80E−12 | 1.20E−09 |
| GDPD1 | −2.20E−05 | −2.6 | 0.0095 | 0.048 |
| GDPD5 | −2.40E−05 | −3 | 0.0033 | 0.022 |
| GFRA1 | −7.80E−05 | −5 | 1.00E−06 | 3.70E−05 |
| GFRA2 | −6.30E−05 | −5.6 | 6.40E−08 | 3.80E−06 |
| GJA5 | −6.00E−05 | −6.2 | 2.20E−09 | 2.30E−07 |
| GLDN | −5.10E−05 | −4.8 | 2.30E−06 | 7.20E−05 |
| GLIS3 | −6.20E−05 | −6 | 7.40E−09 | 6.30E−07 |
| GLRB | −8.60E−05 | −5 | 9.90E−07 | 3.60E−05 |
| GNE | −2.30E−05 | −2.8 | 0.0054 | 0.032 |
| GNG2 | −3.90E−05 | −4.7 | 3.70E−06 | 0.00011 |
| GNG7 | −3.50E−05 | −3.6 | 0.00032 | 0.0037 |
| GOLM1 | −4.80E−05 | −6.2 | 2.00E−09 | 2.10E−07 |
| GPC6 | −0.00011 | −7.6 | 5.40E−13 | 1.90E−10 |
| GPM6A | −8.30E−05 | −3 | 0.0034 | 0.022 |
| GPR183 | −5.70E−05 | −6.2 | 2.60E−09 | 2.60E−07 |
| GPR31 | −9.40E−05 | −3 | 0.0033 | 0.022 |
| GPR4 | −3.40E−05 | −4.7 | 4.70E−06 | 0.00013 |
| GPR88 | −0.00015 | −5.1 | 6.20E−07 | 2.50E−05 |
| GPX8 | −3.60E−05 | −4.8 | 2.90E−06 | 8.60E−05 |
| GRAMD1B | −4.30E−05 | −3.8 | 0.00019 | 0.0025 |
| GRAP2 | −5.10E−05 | −4.4 | 1.40E−05 | 0.00031 |
| GRB14 | −6.60E−05 | −3.2 | 0.0017 | 0.013 |
| GREB1 | −3.50E−05 | −3.6 | 0.00037 | 0.0041 |
| GREM2 | −0.00012 | −5.6 | 4.50E−08 | 2.80E−06 |
| GRIA1 | −0.00012 | −3.7 | 3.00E−04 | 0.0035 |
| GRID1 | −4.60E−05 | −4.5 | 8.80E−06 | 0.00021 |
| GSG1L | −9.10E−05 | −3 | 0.0031 | 0.021 |
| GSR | −2.60E−05 | −2.9 | 0.004 | 0.026 |
| GUCA1A | −6.50E−05 | −3.5 | 0.00055 | 0.0056 |
| GUCY1A2 | −4.80E−05 | −4.3 | 2.60E−05 | 0.00051 |
| HCN1 | −9.90E−05 | −3.2 | 0.0013 | 0.011 |
| HDX | −8.00E−05 | −6.3 | 1.30E−09 | 1.50E−07 |
| HEYL | −4.10E−05 | −4.4 | 1.80E−05 | 0.00038 |
| HFE2 | −0.00017 | −3.6 | 4.00E−04 | 0.0043 |
| HHIPL1 | −5.30E−05 | −5.2 | 4.30E−07 | 1.80E−05 |
| HIST2H2BE | −2.20E−05 | −2.6 | 0.0095 | 0.048 |
| HLA-DPB1 | −6.10E−05 | −6.3 | 1.60E−09 | 1.80E−07 |
| HLA-DQB1 | −6.00E−05 | −5.1 | 8.20E−07 | 3.10E−05 |
| HS6ST3 | −9.80E−05 | −3 | 0.0032 | 0.021 |
| HSD11B1 | −9.10E−05 | −6.5 | 3.70E−10 | 5.00E−08 |
| HSPA12B | −6.10E−05 | −8.4 | 2.70E−15 | 1.90E−12 |
| HTR1F | −9.90E−05 | −4.1 | 5.30E−05 | 9.00E−04 |

TABLE 13-continued mRNAs inversely expressed and containing
predicted or validated binding sites to miR-205-5p
(MIMAT0000266)

| Gene | beta | t.stat | p.value | FDR |
|---|---|---|---|---|
| HUNK | −3.30E−05 | −2.8 | 0.0051 | 0.031 |
| ICA1L | −3.60E−05 | −4.6 | 6.20E−06 | 0.00016 |
| ICAM2 | −3.90E−05 | −5.4 | 1.90E−07 | 9.40E−06 |
| IFI44L | −4.70E−05 | −3.1 | 0.0021 | 0.016 |
| IGFBPL1 | −9.00E−05 | −2.7 | 0.0071 | 0.039 |
| IGLON5 | −3.50E−05 | −3.2 | 0.0017 | 0.013 |
| IKZF1 | −5.70E−05 | −5 | 1.10E−06 | 3.90E−05 |
| IKZF3 | −6.70E−05 | −3.5 | 0.00049 | 0.0051 |
| IL15 | −2.60E−05 | −3.1 | 0.0025 | 0.018 |
| IL16 | −4.40E−05 | −5.1 | 5.40E−07 | 2.20E−05 |
| IL17D | −6.70E−05 | −3.8 | 0.00018 | 0.0023 |
| IL18BP | −2.70E−05 | −3.2 | 0.0016 | 0.013 |
| IL21R | −4.70E−05 | −4 | 8.00E−05 | 0.0012 |
| IL5RA | −1.00E−04 | −3.2 | 0.0016 | 0.013 |
| IL6ST | −3.40E−05 | −4.3 | 2.90E−05 | 0.00055 |
| IMPG2 | −4.50E−05 | −2.7 | 0.0069 | 0.038 |
| IPCEF1 | −4.40E−05 | −4.2 | 3.40E−05 | 0.00063 |
| IRAK3 | −3.60E−05 | −3.6 | 0.00036 | 0.0041 |
| IRF1 | −2.40E−05 | −3 | 0.0033 | 0.022 |
| ITGA11 | −8.60E−05 | −5.8 | 2.00E−08 | 1.50E−06 |
| ITGA8 | −7.80E−05 | −4.7 | 5.20E−06 | 0.00014 |
| ITGB1BP2 | −5.90E−05 | −4.1 | 6.20E−05 | 0.001 |
| ITGB3 | −6.20E−05 | −5.8 | 1.50E−08 | 1.20E−06 |
| JPH4 | −7.10E−05 | −6.8 | 6.50E−11 | 1.20E−08 |
| KAL1 | −4.30E−05 | −3.7 | 0.00026 | 0.0031 |
| KAT2B | −3.00E−05 | −4 | 9.10E−05 | 0.0014 |
| KBTBD11 | −3.80E−05 | −3.9 | 0.00015 | 0.002 |
| KCNAB1 | −2.40E−05 | −3.3 | 0.0011 | 0.0094 |
| KCNB1 | −0.00018 | −6.1 | 4.90E−09 | 4.40E−07 |
| KCNC1 | −8.70E−05 | −3.3 | 0.0011 | 0.0095 |
| KCND1 | −2.70E−05 | −3 | 0.0031 | 0.021 |
| KCND2 | −0.00011 | −7.5 | 9.00E−13 | 2.90E−10 |
| KCNE4 | −5.60E−05 | −5.3 | 2.20E−07 | 1.00E−05 |
| KCNH1 | −6.50E−05 | −3.1 | 0.0019 | 0.014 |
| KCNJ16 | −0.00013 | −3.5 | 0.00047 | 0.0049 |
| KCNJ5 | −3.40E−05 | −2.7 | 0.0079 | 0.042 |
| KCNJ6 | −9.20E−05 | −3.2 | 0.0016 | 0.013 |
| KCNJ8 | −5.50E−05 | −5.9 | 1.00E−08 | 8.40E−07 |
| KCNK3 | −9.70E−05 | −5.6 | 5.20E−08 | 3.20E−06 |
| KCNMB1 | −3.70E−05 | −5.1 | 5.70E−07 | 2.30E−05 |
| KCNMB4 | −4.20E−05 | −3.5 | 0.00046 | 0.0049 |
| KCNN3 | −4.50E−05 | −4.3 | 2.40E−05 | 0.00048 |
| KCNQ1 | −3.10E−05 | −3.8 | 0.00016 | 0.0021 |
| KCNQ3 | −7.10E−05 | −3.9 | 1.00E−04 | 0.0015 |
| KCNT1 | −0.00013 | −4.1 | 6.10E−05 | 0.001 |
| KCNT2 | −0.00013 | −7.8 | 1.60E−13 | 6.70E−11 |
| KDELR3 | −2.80E−05 | −3.2 | 0.0016 | 0.012 |
| KDR | −4.70E−05 | −5.9 | 1.20E−08 | 9.50E−07 |
| KIAA1024 | −3.30E−05 | −3.8 | 0.00021 | 0.0026 |
| KIAA1199 | −4.70E−05 | −4.7 | 5.20E−06 | 0.00014 |
| KIAA1324L | −5.00E−05 | −5.5 | 1.10E−07 | 6.10E−06 |
| KIAA1462 | −6.50E−05 | −7.5 | 8.80E−13 | 2.90E−10 |
| KIF26B | −3.80E−05 | −3.5 | 0.00058 | 0.0058 |
| KIF5C | −5.30E−05 | −5.5 | 1.10E−07 | 5.90E−06 |
| KIF6 | −7.10E−05 | −3.6 | 0.00044 | 0.0047 |
| KIT | −7.30E−05 | −6.6 | 2.20E−10 | 3.20E−08 |
| KLF12 | −2.80E−05 | −3.2 | 0.0015 | 0.012 |
| KLF2 | −3.20E−05 | −4.2 | 4.10E−05 | 0.00072 |
| KLF9 | −4.20E−05 | −6.1 | 4.30E−09 | 4.00E−07 |
| KLHDC8A | −9.40E−05 | −6 | 5.90E−09 | 5.20E−07 |
| KLHL14 | −1.00E−04 | −3.9 | 0.00014 | 0.0019 |
| KLHL6 | −4.30E−05 | −4.4 | 1.60E−05 | 0.00035 |
| KLRB1 | −5.70E−05 | −4 | 8.80E−05 | 0.0013 |
| KLRG1 | −7.30E−05 | −6.3 | 1.40E−09 | 1.60E−07 |
| KLRK1 | −7.40E−05 | −5.3 | 2.50E−07 | 1.20E−05 |
| KMO | −3.60E−05 | −3.4 | 0.00089 | 0.0081 |
| KRBA2 | −3.00E−05 | −2.9 | 0.0035 | 0.023 |
| KSR2 | −8.30E−05 | −3.7 | 0.00022 | 0.0027 |
| LAMA4 | −5.80E−05 | −6.3 | 1.40E−09 | 1.60E−07 |
| LARGE | −2.50E−05 | −2.9 | 0.0037 | 0.024 |
| LAYN | −3.10E−05 | −3.3 | 0.001 | 0.0091 |
| LCA5 | −2.00E−05 | −2.8 | 0.0064 | 0.036 |
| LCN6 | −0.00014 | −4.5 | 1.20E−05 | 0.00027 |
| LCP2 | −5.10E−05 | −5.7 | 3.00E−08 | 2.00E−06 |
| LEF1 | −5.10E−05 | −5.8 | 2.30E−08 | 1.60E−06 |
| LGI2 | −5.80E−05 | −4.2 | 3.70E−05 | 0.00068 |
| LIFR | −3.20E−05 | −2.8 | 0.005 | 0.03 |
| LILRA1 | −9.30E−05 | −4.1 | 4.90E−05 | 0.00084 |
| LILRB1 | −6.30E−05 | −5.7 | 2.90E−08 | 2.00E−06 |
| LILRB2 | −6.70E−05 | −6 | 7.10E−09 | 6.10E−07 |
| LIMCH1 | −3.60E−05 | −3.3 | 0.0012 | 0.01 |
| LIMD2 | −2.10E−05 | −2.7 | 0.0074 | 0.04 |
| LIMS2 | −4.70E−05 | −6.5 | 4.00E−10 | 5.40E−08 |
| LIN7A | −7.30E−05 | −4.1 | 6.10E−05 | 0.001 |
| LMO3 | −0.00014 | −5 | 1.30E−06 | 4.40E−05 |
| LMO7 | −3.90E−05 | −4.3 | 2.60E−05 | 0.00051 |
| LMOD3 | −0.00011 | −3.2 | 0.0018 | 0.014 |
| LMX1A | −0.00016 | −5 | 9.30E−07 | 3.40E−05 |
| LONRF2 | −0.00012 | −4.6 | 7.20E−06 | 0.00018 |
| LONRF3 | −8.90E−05 | −5.9 | 1.10E−08 | 8.80E−07 |
| LOX | −3.80E−05 | −3.5 | 0.00046 | 0.0049 |
| LPAR1 | −5.50E−05 | −6.9 | 3.10E−11 | 6.10E−09 |
| LPPR4 | −4.90E−05 | −5.1 | 8.20E−07 | 3.10E−05 |
| LRRC2 | −0.00013 | −5.6 | 5.90E−08 | 3.50E−06 |
| LRRC4C | −0.00016 | −6.4 | 6.10E−10 | 7.80E−08 |
| LRRK2 | −7.30E−05 | −6.3 | 1.00E−09 | 1.20E−07 |
| LRRN2 | −8.20E−05 | −5.9 | 9.20E−09 | 7.50E−07 |
| LRRTM2 | −6.40E−05 | −4.3 | 2.50E−05 | 0.00049 |
| LSAMP | −1.00E−04 | −7.3 | 2.90E−12 | 8.10E−10 |
| LTA | −5.00E−05 | −3.5 | 0.00056 | 0.0057 |
| LUZP2 | −0.00013 | −4.7 | 3.60E−06 | 1.00E−04 |
| LYZ | −9.00E−05 | −6.3 | 1.40E−09 | 1.60E−07 |
| MAGI2 | −2.80E−05 | −3.3 | 0.0013 | 0.011 |
| MAML3 | −3.80E−05 | −4.6 | 6.40E−06 | 0.00016 |
| MAN1A1 | −4.10E−05 | −4.8 | 3.10E−06 | 9.20E−05 |
| MAP2K6 | −3.40E−05 | −3.4 | 0.00074 | 0.007 |
| MAP6 | −5.20E−05 | −3.9 | 0.00012 | 0.0017 |
| MAP9 | −5.80E−05 | −4.6 | 5.90E−06 | 0.00015 |
| MAPK4 | −9.10E−05 | −3.4 | 0.00088 | 0.008 |
| MAT1A | −5.80E−05 | −2.8 | 0.0052 | 0.031 |
| MCOLN2 | −2.80E−05 | −3 | 0.0033 | 0.022 |
| MDGA1 | −3.00E−05 | −2.6 | 0.0089 | 0.046 |
| MEF2C | −7.40E−05 | −6.5 | 4.00E−10 | 5.40E−08 |
| MERTK | −6.40E−05 | −6.3 | 1.20E−09 | 1.40E−07 |
| MFNG | −3.80E−05 | −4.7 | 3.90E−06 | 0.00011 |
| MGAT4A | −6.40E−05 | −8.1 | 1.70E−14 | 9.40E−12 |
| MMP16 | −9.10E−05 | −5.5 | 9.50E−08 | 5.30E−06 |
| MNDA | −5.70E−05 | −5.5 | 7.20E−08 | 4.20E−06 |
| MPP2 | −4.20E−05 | −3.7 | 0.00026 | 0.0031 |
| MRGPRF | −5.50E−05 | −6.2 | 2.30E−09 | 2.40E−07 |
| MRO | −0.00013 | −8.7 | 3.40E−16 | 3.00E−13 |
| MURC | −7.30E−05 | −4 | 7.50E−05 | 0.0012 |
| MYEF2 | −7.80E−05 | −6 | 5.10E−09 | 4.60E−07 |
| MYO1F | −5.30E−05 | −6.1 | 4.70E−09 | 4.30E−07 |
| MYOCD | −6.80E−05 | −2.9 | 0.0045 | 0.028 |
| MYOZ3 | −7.10E−05 | −3.7 | 0.00025 | 0.003 |
| MYPN | −0.00013 | −3.7 | 0.00029 | 0.0034 |
| MYRIP | −9.00E−05 | −4.8 | 2.80E−06 | 8.50E−05 |
| NAP1L6 | −1.00E−04 | −3.1 | 0.0021 | 0.016 |
| NAT8L | −8.50E−05 | −5 | 9.70E−07 | 3.50E−05 |
| NCAM1 | −9.00E−05 | −5.2 | 4.10E−07 | 1.80E−05 |
| NCAM2 | −0.00013 | −6.1 | 4.10E−09 | 3.80E−07 |
| NEGR1 | −0.00011 | −7.9 | 8.50E−14 | 3.80E−11 |
| NEK10 | −5.70E−05 | −3 | 0.0034 | 0.023 |
| NEXN | −7.30E−05 | −6.2 | 1.70E−09 | 1.90E−07 |
| NHSL2 | −8.60E−05 | −6.5 | 5.40E−10 | 6.90E−08 |
| NID2 | −6.10E−05 | −5.3 | 2.10E−07 | 1.00E−05 |
| NIPSNAP3B | −3.10E−05 | −3.6 | 0.00034 | 0.0038 |
| NKX3-2 | −7.00E−05 | −3.5 | 0.00065 | 0.0064 |
| NLGN4X | −5.20E−05 | −3.1 | 0.002 | 0.015 |
| NLRC3 | −4.10E−05 | −4.4 | 1.90E−05 | 0.00039 |
| NOS1 | −9.60E−05 | −3.6 | 0.00043 | 0.0046 |
| NOTCH4 | −3.70E−05 | −5.1 | 7.10E−07 | 2.80E−05 |
| NPAS3 | −8.10E−05 | −5 | 1.00E−06 | 3.70E−05 |
| NPHP1 | −2.70E−05 | −3.3 | 0.001 | 0.0092 |
| NPTXR | −4.50E−05 | −3.2 | 0.0014 | 0.011 |
| NR3C2 | −5.60E−05 | −3.8 | 0.00015 | 0.0021 |
| NR5A2 | −5.00E−05 | −6.6 | 3.10E−10 | 4.40E−08 |

TABLE 13-continued mRNAs inversely expressed and containing
predicted or validated binding sites to miR-205-5p
(MIMAT0000266)

| Gene | beta | t.stat | p.value | FDR |
|---|---|---|---|---|
| NRG2 | −0.00011 | −5.1 | 5.90E−07 | 2.40E−05 |
| NRIP2 | −2.60E−05 | −3.2 | 0.0015 | 0.012 |
| NRXN3 | −8.30E−05 | −4.3 | 2.70E−05 | 0.00052 |
| NT5C1A | −1.00E−04 | −3.1 | 0.0025 | 0.018 |
| NT5E | −3.60E−05 | −2.7 | 0.0067 | 0.037 |
| NTNG1 | −0.00012 | −4.4 | 1.50E−05 | 0.00033 |
| NXPH3 | −7.80E−05 | −7.9 | 9.50E−14 | 4.20E−11 |
| OGN | −0.00021 | −8.4 | 4.00E−15 | 2.60E−12 |
| ORAI2 | −2.60E−05 | −3.5 | 0.00057 | 0.0057 |
| OTOF | −6.40E−05 | −4.1 | 5.30E−05 | 9.00E−04 |
| OTX2 | −0.00011 | −3 | 0.0028 | 0.019 |
| P2RX7 | −3.50E−05 | −3 | 0.003 | 0.02 |
| P2RY14 | −5.20E−05 | −5.1 | 5.40E−07 | 2.20E−05 |
| PACSIN1 | −8.00E−05 | −5 | 9.60E−07 | 3.50E−05 |
| PAK3 | −0.00017 | −6.2 | 2.40E−09 | 2.50E−07 |
| PALM2 | −6.00E−05 | −6.2 | 2.00E−09 | 2.10E−07 |
| PALM2-AKAP2 | −5.20E−05 | −6.5 | 4.80E−10 | 6.30E−08 |
| PAQR8 | −5.40E−05 | −6.4 | 9.20E−10 | 1.10E−07 |
| PARD3B | −5.10E−05 | −4.6 | 7.50E−06 | 0.00019 |
| PAX7 | −0.00014 | −3.4 | 0.00076 | 0.0072 |
| PBX1 | −3.50E−05 | −2.7 | 0.0064 | 0.036 |
| PCDH10 | −9.10E−05 | −3.1 | 0.0021 | 0.015 |
| PCDH19 | −9.50E−05 | −4.1 | 6.00E−05 | 0.00099 |
| PCDH20 | −0.00011 | −3.5 | 0.00052 | 0.0053 |
| PCDHB16 | −3.60E−05 | −3.4 | 9.00E−04 | 0.0082 |
| PCDHB5 | −6.50E−05 | −4.7 | 3.70E−06 | 0.00011 |
| PCSK1 | −4.30E−05 | −3.2 | 0.0016 | 0.013 |
| PCSK2 | −0.00011 | −3.1 | 0.0024 | 0.018 |
| PCYT1B | −7.30E−05 | −3.2 | 0.0014 | 0.012 |
| PDE11A | −0.00014 | −4.5 | 9.30E−06 | 0.00022 |
| PDE1C | −9.50E−05 | −5.5 | 1.00E−07 | 5.60E−06 |
| PDE3A | −7.20E−05 | −5.9 | 1.10E−08 | 8.70E−07 |
| PDE3B | −4.50E−05 | −3.9 | 0.00012 | 0.0017 |
| PDE5A | −3.10E−05 | −3.7 | 0.00024 | 0.0029 |
| PDE8B | −3.00E−05 | −3.6 | 4.00E−04 | 0.0044 |
| PDK4 | −1.00E−04 | −7.2 | 5.00E−12 | 1.30E−09 |
| PDLIM3 | −8.60E−05 | −5.3 | 2.00E−07 | 9.60E−06 |
| PEG10 | −6.60E−05 | −3.2 | 0.0015 | 0.012 |
| PEG3 | −1.00E−04 | −6.2 | 2.40E−09 | 2.40E−07 |
| PELI2 | −4.80E−05 | −4.4 | 1.90E−05 | 4.00E−04 |
| PGM2L1 | −3.00E−05 | −3.4 | 0.00091 | 0.0083 |
| PGPEP1 | −3.10E−05 | −3.9 | 1.00E−04 | 0.0015 |
| PHACTR1 | −4.80E−05 | −5.2 | 4.40E−07 | 1.90E−05 |
| P115 | −3.40E−05 | −2.7 | 0.0072 | 0.039 |
| P116 | −0.00017 | −7 | 2.30E−11 | 4.70E−09 |
| PIPOX | −5.50E−05 | −4.7 | 4.70E−06 | 0.00013 |
| PKD2L1 | −9.10E−05 | −4.1 | 6.60E−05 | 0.0011 |
| PKHD1 | −0.00011 | −3.6 | 0.00038 | 0.0042 |
| PKIA | −4.50E−05 | −3.3 | 0.0011 | 0.0095 |
| PLA2G16 | −6.70E−05 | −6.8 | 8.90E−11 | 1.50E−08 |
| PLA2G2D | −0.00012 | −4.4 | 1.30E−05 | 0.00029 |
| PLA2G7 | −6.40E−05 | −5.5 | 7.90E−08 | 4.50E−06 |
| PLCB1 | −4.70E−05 | −5.1 | 6.80E−07 | 2.70E−05 |
| PLCL1 | −3.90E−05 | −4.9 | 2.00E−06 | 6.30E−05 |
| PLCXD3 | −0.00011 | −3.6 | 0.00043 | 0.0046 |
| PLEK | −5.10E−05 | −4.6 | 6.10E−06 | 0.00016 |
| PLEKHG1 | −4.80E−05 | −6 | 5.60E−09 | 5.00E−07 |
| PLEKHH2 | −3.00E−05 | −3 | 0.0033 | 0.022 |
| PLN | −0.00012 | −6.9 | 3.50E−11 | 6.70E−09 |
| PLP1 | −7.90E−05 | −2.8 | 0.0052 | 0.031 |
| PLSCR4 | −2.90E−05 | −3.8 | 0.00016 | 0.0021 |
| PLXDC2 | −4.80E−05 | −5.5 | 9.60E−08 | 5.30E−06 |
| PLXNA4 | −6.00E−05 | −5 | 1.00E−06 | 3.80E−05 |
| PLXNC1 | −8.00E−05 | −7.1 | 1.60E−11 | 3.60E−09 |
| PNMA2 | −8.80E−05 | −6.9 | 3.50E−11 | 6.80E−09 |
| PODXL | −3.70E−05 | −5.1 | 7.30E−07 | 2.80E−05 |
| POU6F1 | −3.90E−05 | −5.3 | 2.30E−07 | 1.10E−05 |
| PPAPDC1A | −1.00E−04 | −5 | 1.30E−06 | 4.50E−05 |
| PPM1H | −5.90E−05 | −4.6 | 6.50E−06 | 0.00017 |
| PPM1L | −5.20E−05 | −4.7 | 4.20E−06 | 0.00015 |
| PPP1R3A | −0.00016 | −3.5 | 0.00058 | 0.0059 |
| PRDM16 | −8.60E−05 | −6.8 | 5.80E−11 | 1.00E−08 |
| PREX2 | −0.00011 | −8.8 | 2.20E−16 | 2.10E−13 |
| PRKAG3 | −0.00011 | −2.9 | 0.004 | 0.025 |
| PRLR | −6.50E−05 | −3.6 | 0.00036 | 0.004 |
| PRND | −0.00014 | −6.2 | 2.30E−09 | 2.40E−07 |
| PROX1 | −6.70E−05 | −4.8 | 3.30E−06 | 9.70E−05 |
| PRR15 | −4.70E−05 | −2.6 | 0.0088 | 0.046 |
| PRR16 | −5.70E−05 | −5.4 | 1.20E−07 | 6.40E−06 |
| PRRG3 | −0.00013 | −3.8 | 0.00016 | 0.0021 |
| PRRX1 | −6.40E−05 | −6.1 | 4.00E−09 | 3.80E−07 |
| PRUNE2 | −9.60E−05 | −5.8 | 2.10E−08 | 1.50E−06 |
| PSD | −3.60E−05 | −4.5 | 1.20E−05 | 0.00027 |
| PSD3 | −2.10E−05 | −2.6 | 0.0097 | 0.049 |
| PTCHD1 | −0.00014 | −4.5 | 8.90E−06 | 0.00021 |
| PTGER3 | −7.60E−05 | −5.7 | 3.90E−08 | 2.50E−06 |
| PTGFR | −8.70E−05 | −6.4 | 7.90E−10 | 9.60E−08 |
| PTGIR | −3.70E−05 | −4.4 | 1.90E−05 | 4.00E−04 |
| PTPLAD2 | −2.40E−05 | −2.8 | 0.0064 | 0.036 |
| PTPN7 | −3.50E−05 | −3.2 | 0.0015 | 0.012 |
| PTPRB | −6.30E−05 | −8.7 | 3.60E−16 | 3.30E−13 |
| PTPRC | −6.60E−05 | −5.7 | 4.10E−08 | 2.60E−06 |
| PTPRD | −0.00014 | −8.3 | 7.00E−15 | 4.30E−12 |
| PTPRG | −2.60E−05 | −3.4 | 0.00078 | 0.0074 |
| PTPRJ | −4.20E−05 | −5.3 | 2.70E−07 | 1.20E−05 |
| PTPRM | −4.70E−05 | −6.2 | 2.50E−09 | 2.60E−07 |
| PTPRT | −0.00013 | −4.1 | 6.50E−05 | 0.0011 |
| PTX3 | −1.00E−04 | −5.2 | 3.90E−07 | 1.70E−05 |
| PURG | −0.00011 | −4.4 | 1.60E−05 | 0.00034 |
| PVRL3 | −4.40E−05 | −3.5 | 0.00051 | 0.0053 |
| PYGO1 | −1.00E−04 | −6 | 5.60E−09 | 5.00E−07 |
| RAB15 | −3.70E−05 | −4.9 | 2.00E−06 | 6.30E−05 |
| RAB19 | −0.00013 | −5.6 | 6.40E−08 | 3.80E−06 |
| RAB3B | −8.00E−05 | −3.6 | 4.00E−04 | 0.0044 |
| RAB3C | −0.00012 | −4 | 6.80E−05 | 0.0011 |
| RAB6B | −3.90E−05 | −3 | 0.0034 | 0.023 |
| RAB9B | −0.00012 | −5.5 | 9.80E−08 | 5.40E−06 |
| RARRES3 | −5.10E−05 | −4.6 | 5.90E−06 | 0.00015 |
| RASGRF2 | −7.60E−05 | −7.8 | 2.00E−13 | 8.20E−11 |
| RASGRP1 | −3.50E−05 | −3 | 0.0027 | 0.019 |
| RASL10B | −5.00E−05 | −4.2 | 4.50E−05 | 0.00078 |
| RASSF2 | −5.90E−05 | −6.7 | 1.20E−10 | 2.00E−08 |
| RASSF4 | −5.70E−05 | −6.9 | 4.50E−11 | 8.50E−09 |
| RASSF8 | −3.50E−05 | −4.3 | 2.10E−05 | 0.00043 |
| RBMS3 | −8.30E−05 | −8.6 | 6.30E−16 | 5.30E−13 |
| RBPMS2 | −5.90E−05 | −6.4 | 6.50E−10 | 8.20E−08 |
| RCAN2 | −6.80E−05 | −7.4 | 2.20E−12 | 6.40E−10 |
| REEP2 | −4.30E−05 | −4.2 | 4.20E−05 | 0.00075 |
| RELN | −0.00012 | −5.8 | 1.60E−08 | 1.20E−06 |
| RGAG4 | −5.80E−05 | −5.8 | 1.90E−08 | 1.40E−06 |
| RGS18 | −6.70E−05 | −6.6 | 3.10E−10 | 4.30E−08 |
| RGS5 | −4.80E−05 | −4.5 | 1.00E−05 | 0.00024 |
| RGS8 | −8.10E−05 | −3.4 | 0.00089 | 0.0081 |
| RHOH | −4.30E−05 | −4.1 | 5.90E−05 | 0.00098 |
| RHOU | −3.00E−05 | −3.6 | 0.00033 | 0.0038 |
| RIMKLA | −7.40E−05 | −3.3 | 0.0012 | 0.01 |
| RIMS4 | −0.00018 | −6.9 | 4.70E−11 | 8.80E−09 |
| RLN2 | −7.50E−05 | −2.7 | 0.0073 | 0.04 |
| RNF150 | −0.00011 | −7.1 | 1.10E−11 | 2.60E−09 |
| RNF152 | −2.60E−05 | −2.9 | 0.0035 | 0.023 |
| RNF157 | −6.10E−05 | −6.8 | 5.50E−11 | 1.00E−08 |
| RNF180 | −8.00E−05 | −7.2 | 7.70E−12 | 1.90E−09 |
| ROR2 | −6.00E−05 | −4.7 | 4.10E−06 | 0.00012 |
| RORA | −3.00E−05 | −3.6 | 0.00042 | 0.0045 |
| RPS6KA6 | −0.00016 | −4.7 | 4.90E−06 | 0.00013 |
| RRAGD | −3.50E−05 | −3.4 | 0.00067 | 0.0065 |
| RSPO3 | −0.00015 | −11 | 5.90E−23 | 2.40E−19 |
| RUNX1T1 | −1.00E−04 | −6.9 | 5.00E−11 | 9.20E−09 |
| RUNX2 | −3.10E−05 | −4.4 | 1.90E−05 | 4.00E−04 |
| S1PR1 | −6.10E−05 | −8.6 | 9.60E−16 | 7.70E−13 |
| S1PR3 | −6.80E−05 | −8.3 | 4.90E−15 | 3.20E−12 |
| SALL1 | −7.70E−05 | −3.1 | 0.0019 | 0.015 |
| SALL2 | −6.30E−05 | −5.2 | 3.40E−07 | 1.50E−05 |
| SAMD4A | −3.10E−05 | −3.7 | 0.00023 | 0.0028 |
| SAMD5 | −6.40E−05 | −4.5 | 1.20E−05 | 0.00028 |
| SARDH | −4.20E−05 | −4 | 7.40E−05 | 0.0012 |
| SARM1 | −6.00E−05 | −6.8 | 9.50E−11 | 1.60E−08 |
| SCAMP5 | −2.70E−05 | −3 | 0.0031 | 0.021 |

TABLE 13-continued mRNAs inversely expressed and containing predicted or validated binding sites to miR-205-5p (MIMAT0000266)

| Gene | beta | t.stat | p.value | FDR |
|---|---|---|---|---|
| SCIN | −6.60E−05 | −4.6 | 5.60E−06 | 0.00015 |
| SCML4 | −9.20E−05 | −4.8 | 2.40E−06 | 7.40E−05 |
| SCN3A | −0.00011 | −6.8 | 7.90E−11 | 1.40E−08 |
| SCN7A | −8.80E−05 | −2.9 | 0.0047 | 0.029 |
| SCN9A | −9.20E−05 | −4.8 | 2.60E−06 | 7.80E−05 |
| SCUBE1 | −6.80E−05 | −4.8 | 3.20E−06 | 9.40E−05 |
| SELE | −9.40E−05 | −5.7 | 3.90E−08 | 2.50E−06 |
| SELP | −9.20E−05 | −5.5 | 1.00E−07 | 5.70E−06 |
| SELPLG | −4.40E−05 | −5.3 | 3.00E−07 | 1.40E−05 |
| SEMA3A | −5.90E−05 | −4.4 | 1.60E−05 | 0.00034 |
| SEMA3E | −0.00013 | −3.6 | 0.00034 | 0.0039 |
| SEMA7A | −2.60E−05 | −3.5 | 0.00064 | 0.0063 |
| SERPINA1 | −5.90E−05 | −5.6 | 5.20E−08 | 3.20E−06 |
| SERPINA5 | −0.00012 | −5.7 | 4.20E−08 | 2.70E−06 |
| SERPING1 | −6.20E−05 | −6.8 | 7.10E−11 | 1.20E−08 |
| SFMBT2 | −5.50E−05 | −5.5 | 9.10E−08 | 5.10E−06 |
| SGCD | −0.00011 | −7.7 | 3.30E−13 | 1.20E−10 |
| SGIP1 | −5.00E−05 | −4.5 | 1.10E−05 | 0.00025 |
| SH2D1A | −8.70E−05 | −5.8 | 1.80E−08 | 1.30E−06 |
| SHE | −5.50E−05 | −5.7 | 4.20E−08 | 2.60E−06 |
| SHISA6 | −0.00012 | −3.4 | 0.00082 | 0.0076 |
| SIDT1 | −7.70E−05 | −6 | 7.80E−09 | 6.60E−07 |
| SIGLEC14 | −9.00E−05 | −4.2 | 4.40E−05 | 0.00078 |
| SIGLEC8 | −9.70E−05 | −5.4 | 1.80E−07 | 9.00E−06 |
| SIGLEC9 | −6.50E−05 | −7.5 | 1.10E−12 | 3.60E−10 |
| SIM1 | −0.00011 | −3 | 0.0027 | 0.019 |
| SLA | −5.40E−05 | −5.7 | 2.90E−08 | 2.00E−06 |
| SLAMF1 | −4.70E−05 | −3.9 | 0.00012 | 0.0017 |
| SLC11A1 | −4.60E−05 | −4.5 | 9.00E−06 | 0.00022 |
| SLC12A3 | −8.00E−05 | −3.3 | 0.00095 | 0.0085 |
| SLC16A10 | −5.90E−05 | −6.2 | 1.90E−09 | 2.00E−07 |
| SLC1A2 | −4.10E−05 | −2.8 | 0.0056 | 0.033 |
| SLC22A16 | −6.40E−05 | −2.7 | 0.0069 | 0.038 |
| SLC24A2 | −9.80E−05 | −3.5 | 0.00051 | 0.0053 |
| SLC2A5 | −6.50E−05 | −6.9 | 5.00E−11 | 9.20E−09 |
| SLC39A14 | −2.80E−05 | −3.9 | 0.00013 | 0.0018 |
| SLC46A2 | −7.20E−05 | −4.2 | 3.40E−05 | 0.00063 |
| SLC4A4 | −9.60E−05 | −5 | 1.10E−06 | 3.80E−05 |
| SLC6A1 | −6.80E−05 | −4.2 | 3.40E−05 | 0.00063 |
| SLC6A20 | −9.20E−05 | −3.9 | 0.00011 | 0.0016 |
| SLC6A4 | −7.40E−05 | −2.6 | 0.0094 | 0.048 |
| SLC7A2 | −4.20E−05 | −2.9 | 0.004 | 0.025 |
| SLC7A3 | −0.00011 | −3.8 | 0.00018 | 0.0023 |
| SLC7A7 | −6.70E−05 | −7 | 1.80E−11 | 3.90E−09 |
| SLC8A1 | −5.90E−05 | −6.8 | 5.40E−11 | 9.90E−09 |
| SLC8A3 | −0.00011 | −5.3 | 3.20E−07 | 1.40E−05 |
| SLC9A7 | −3.90E−05 | −4.4 | 1.30E−05 | 0.00029 |
| SLC9A9 | −3.20E−05 | −3.2 | 0.0015 | 0.012 |
| SLCO5A1 | −5.40E−05 | −4.6 | 6.80E−06 | 0.00017 |
| SLFN12L | −3.30E−05 | −3.4 | 0.00085 | 0.0078 |
| SLIT2 | −7.50E−05 | −5.7 | 3.00E−08 | 2.00E−06 |
| SLIT3 | −7.20E−05 | −6.2 | 2.50E−09 | 2.60E−07 |
| SLITRK4 | −0.00016 | −6.5 | 4.30E−10 | 5.70E−08 |
| SMOC1 | −5.30E−05 | −3.3 | 0.00096 | 0.0086 |
| SMTNL1 | −8.00E−05 | −3.6 | 0.00037 | 0.0042 |
| SMTNL2 | −0.00014 | −7.3 | 4.40E−12 | 1.10E−09 |
| SNAP25 | −6.70E−05 | −4.8 | 3.20E−06 | 9.40E−05 |
| SNED1 | −8.70E−05 | −8.6 | 5.70E−16 | 4.90E−13 |
| SNX32 | −7.10E−05 | −3.1 | 0.0022 | 0.016 |
| SORBS1 | −7.20E−05 | −7.3 | 2.80E−12 | 7.90E−10 |
| SOX17 | −6.00E−05 | −7.5 | 1.10E−12 | 3.50E−10 |
| SOX5 | −0.00011 | −7 | 2.10E−11 | 4.40E−09 |
| SP6 | −3.00E−05 | −3.7 | 0.00026 | 0.0032 |
| SPARC | −5.90E−05 | −5.4 | 1.20E−07 | 6.30E−06 |
| SPATA13 | −6.60E−05 | −6.4 | 8.60E−10 | 1.00E−07 |
| SPN | −5.20E−05 | −4.8 | 3.30E−06 | 9.60E−05 |
| SPOCK2 | −4.60E−05 | −4.4 | 1.80E−05 | 0.00038 |
| SRPX2 | −5.50E−05 | −7 | 2.30E−11 | 4.70E−09 |
| SSC5D | −7.10E−05 | −6.2 | 2.70E−09 | 2.70E−07 |
| ST18 | −9.10E−05 | −3.8 | 0.00018 | 0.0023 |
| ST3GAL1 | −2.80E−05 | −3.5 | 0.00062 | 0.0062 |
| ST3GAL6 | −2.20E−05 | −3 | 0.003 | 0.021 |
| ST6GAL1 | −5.60E−05 | −5 | 1.20E−06 | 4.20E−05 |
| ST6GAL2 | −0.00014 | −6.3 | 1.30E−09 | 1.50E−07 |
| ST6GALNAC3 | −6.40E−05 | −8.6 | 1.00E−15 | 8.00E−13 |
| ST6GALNAC5 | −8.00E−05 | −6.1 | 3.30E−09 | 3.20E−07 |
| ST8SIA4 | −5.00E−05 | −6.3 | 1.30E−09 | 1.50E−07 |
| STARD13 | −3.70E−05 | −4.8 | 3.10E−06 | 9.10E−05 |
| STAT1 | −3.20E−05 | −3.6 | 0.00042 | 0.0045 |
| STC1 | −4.40E−05 | −4.3 | 2.10E−05 | 0.00043 |
| STEAP2 | −5.00E−05 | −5.6 | 5.00E−08 | 3.10E−06 |
| SUCNR1 | −5.20E−05 | −3.3 | 0.001 | 0.0091 |
| SULF1 | −8.90E−05 | −7.3 | 4.20E−12 | 1.10E−09 |
| SV2B | −7.10E−05 | −3.6 | 0.00033 | 0.0037 |
| SVIP | −6.00E−05 | −5.1 | 7.20E−07 | 2.80E−05 |
| SYNPO2 | −7.50E−05 | −4.5 | 1.00E−05 | 0.00024 |
| SYP | −4.50E−05 | −4.7 | 3.90E−06 | 0.00011 |
| SYPL2 | −7.40E−05 | −4.2 | 3.30E−05 | 0.00061 |
| SYT13 | −1.00E−04 | −3.1 | 0.002 | 0.015 |
| SYT9 | −9.40E−05 | −2.9 | 0.0039 | 0.025 |
| SYTL4 | −4.90E−05 | −5.9 | 1.30E−08 | 1.00E−06 |
| TBX15 | −6.50E−05 | −4.8 | 2.20E−06 | 6.90E−05 |
| TBX21 | −5.70E−05 | −4.5 | 1.00E−05 | 0.00024 |
| TCN2 | −5.90E−05 | −6.7 | 1.60E−10 | 2.50E−08 |
| TDGF1 | −0.00012 | −3.9 | 0.00013 | 0.0019 |
| TETI | −3.70E−05 | −3.5 | 0.00054 | 0.0055 |
| THBS1 | −4.70E−05 | −4.1 | 5.00E−05 | 0.00085 |
| THSD7A | −0.00011 | −8.6 | 1.10E−15 | 8.50E−13 |
| TIMD4 | −0.00019 | −6.4 | 5.80E−10 | 7.40E−08 |
| TIMP2 | −7.30E−05 | −8.3 | 5.60E−15 | 3.50E−12 |
| TLR4 | −8.60E−05 | −9.5 | 1.80E−18 | 2.90E−15 |
| TLR8 | −8.70E−05 | −6.8 | 9.20E−11 | 1.60E−08 |
| TM4SF18 | −4.50E−05 | −6 | 7.70E−09 | 6.50E−07 |
| TMEM156 | −3.70E−05 | −3.2 | 0.0018 | 0.014 |
| TMEM170B | −7.00E−05 | −8.3 | 5.70E−15 | 3.60E−12 |
| TMEM182 | −2.60E−05 | −3.5 | 0.00064 | 0.0063 |
| TMEM231 | −3.90E−05 | −4.3 | 2.90E−05 | 0.00056 |
| TMEM26 | −6.20E−05 | −5.9 | 1.50E−08 | 1.10E−06 |
| TMEM47 | −6.10E−05 | −6.8 | 8.50E−11 | 1.50E−08 |
| TMEM86A | −2.60E−05 | −2.8 | 0.0055 | 0.032 |
| TMEM98 | −4.10E−05 | −4.9 | 1.70E−06 | 5.50E−05 |
| TMTC1 | −8.40E−05 | −6.6 | 2.60E−10 | 3.70E−08 |
| TNFSF11 | −4.60E−05 | −3.3 | 0.0011 | 0.0098 |
| TNFSF15 | −4.90E−05 | −3.6 | 0.00045 | 0.0048 |
| TNFSF4 | −5.50E−05 | −4.8 | 3.00E−06 | 9.00E−05 |
| TNFSF8 | −8.50E−05 | −5.5 | 9.90E−08 | 5.40E−06 |
| TNIK | −5.80E−05 | −5.2 | 3.20E−07 | 1.40E−05 |
| TNNI1 | −7.10E−05 | −3.5 | 0.00061 | 0.0061 |
| TNR | −0.00012 | −4.1 | 5.50E−05 | 0.00092 |
| TNS3 | −3.80E−05 | −4.9 | 1.40E−06 | 4.90E−05 |
| TOX | −4.70E−05 | −4.2 | 4.00E−05 | 0.00071 |
| TRAT1 | −0.00011 | −4.9 | 2.00E−06 | 6.30E−05 |
| TREM2 | −4.20E−05 | −3.8 | 0.00015 | 0.0021 |
| TREML2 | −4.20E−05 | −2.9 | 0.004 | 0.025 |
| TRHDE | −0.00013 | −3.9 | 0.00011 | 0.0016 |
| TRIM2 | −3.40E−05 | −3.1 | 0.002 | 0.015 |
| TRIM58 | −8.40E−05 | −3.3 | 0.001 | 0.009 |
| TRPC6 | −3.00E−05 | −3.5 | 0.00061 | 0.0061 |
| TRPM8 | −9.60E−05 | −3.6 | 0.00041 | 0.0045 |
| TRPS1 | −2.30E−05 | −2.8 | 0.0052 | 0.031 |
| TSPAN11 | −5.10E−05 | −4.4 | 1.80E−05 | 0.00038 |
| TSPAN18 | −6.80E−05 | −5.6 | 4.80E−08 | 3.00E−06 |
| TSPAN5 | −2.40E−05 | −3 | 0.0031 | 0.021 |
| TSPAN7 | −6.90E−05 | −4.6 | 6.50E−06 | 0.00017 |
| TTC28 | −4.00E−05 | −4.4 | 1.80E−05 | 0.00037 |
| TTLL7 | −3.10E−05 | −2.7 | 0.0077 | 0.041 |
| TTYH2 | −2.50E−05 | −3.1 | 0.0021 | 0.015 |
| TUB | −6.30E−05 | −5.2 | 3.50E−07 | 1.50E−05 |
| TWIST2 | −4.40E−05 | −4.4 | 1.90E−05 | 0.00039 |
| TYRP1 | −9.10E−05 | −3.1 | 0.0024 | 0.017 |
| UBE2QL1 | −3.70E−05 | −2.9 | 0.0041 | 0.026 |
| UBXN10 | −7.60E−05 | −5.2 | 3.30E−07 | 1.50E−05 |
| UGT2B4 | −8.00E−05 | −3 | 0.0032 | 0.021 |
| UNC5C | −9.40E−05 | −4.5 | 1.20E−05 | 0.00027 |
| USP13 | −3.90E−05 | −5 | 1.30E−06 | 4.60E−05 |
| VASH1 | −5.10E−05 | −7 | 2.10E−11 | 4.40E−09 |
| VASH2 | −5.10E−05 | −4.3 | 2.20E−05 | 0.00044 |
| VAT1L | −1.00E−04 | −5.5 | 8.60E−08 | 4.80E−06 |

TABLE 13-continued mRNAs inversely expressed and containing predicted or validated binding sites to miR-205-5p (MIMAT0000266)

| Gene | beta | t.stat | p.value | FDR |
|---|---|---|---|---|
| VENTX | −7.30E−05 | −5.4 | 1.20E−07 | 6.60E−06 |
| VGLL2 | −0.00012 | −2.9 | 0.0039 | 0.025 |
| VGLL3 | −7.00E−05 | −6.2 | 2.00E−09 | 2.10E−07 |
| VSIG10 | −2.30E−05 | −3 | 0.003 | 0.021 |
| VWC2 | −9.00E−05 | −2.6 | 0.0098 | 0.049 |
| WFIKKN2 | −9.70E−05 | −3 | 0.0034 | 0.022 |
| WISP2 | −0.00015 | −8.6 | 1.00E−15 | 8.10E−13 |
| WNT2 | −9.20E−05 | −4.8 | 2.90E−06 | 8.50E−05 |
| WNT5A | −4.30E−05 | −4.4 | 1.60E−05 | 0.00035 |
| WNT5B | −3.50E−05 | −3 | 0.003 | 0.02 |
| XCR1 | −9.00E−05 | −3.8 | 0.00015 | 0.0021 |
| XIRP1 | −8.70E−05 | −3.6 | 0.00043 | 0.0046 |
| ZBTB10 | −5.30E−05 | −5.1 | 8.20E−07 | 3.10E−05 |
| ZBTB16 | −0.00012 | −4.6 | 8.00E−06 | 2.00E−04 |
| ZBTB20 | −3.30E−05 | −3.8 | 0.00016 | 0.0022 |
| ZC4H2 | −4.80E−05 | −4.8 | 3.20E−06 | 9.40E−05 |
| ZDHHC15 | −0.00013 | −6.6 | 2.80E−10 | 4.00E−08 |
| ZEB1 | −6.90E−05 | −8.8 | 1.50E−16 | 1.50E−13 |
| ZEB2 | −6.80E−05 | −8.4 | 3.80E−15 | 2.50E−12 |
| ZFP82 | −4.50E−05 | −4.2 | 3.20E−05 | 6.00E−04 |
| ZIK1 | −3.20E−05 | −3.7 | 0.00025 | 0.003 |
| ZNF154 | −5.00E−05 | −5.7 | 3.00E−08 | 2.00E−06 |
| ZNF208 | −0.00013 | −6.6 | 3.10E−10 | 4.30E−08 |
| ZNF215 | −7.00E−05 | −4.5 | 8.50E−06 | 0.00021 |
| ZNF280B | −7.30E−05 | −3.9 | 0.00012 | 0.0017 |
| ZNF287 | −2.80E−05 | −3 | 0.003 | 0.021 |
| ZNF347 | −4.10E−05 | −3.4 | 0.00066 | 0.0065 |
| ZNF366 | −5.90E−05 | −4.4 | 1.30E−05 | 3.00E−04 |
| ZNF429 | −3.70E−05 | −2.9 | 0.0038 | 0.025 |
| ZNF442 | −2.60E−05 | −3 | 0.0026 | 0.018 |
| ZNF618 | −3.30E−05 | −3.9 | 0.00012 | 0.0017 |
| ZNF701 | −3.60E−05 | −4 | 7.60E−05 | 0.0012 |
| ZNF781 | −5.80E−05 | −3.1 | 0.0024 | 0.017 |
| ZNF788 | −3.60E−05 | −3 | 0.0026 | 0.018 |
| ZNF793 | −4.90E−05 | −2.7 | 0.0068 | 0.038 |
| ZNF843 | −2.40E−05 | −3.3 | 0.0013 | 0.011 |
| ZNF844 | −5.60E−05 | −4.1 | 5.30E−05 | 0.00089 |
| ZSCAN1 | −8.90E−05 | −3.1 | 0.002 | 0.015 |

TABLE 14 mRNAs inversely expressed and containing predicted or validated binding sites to miR-375 (MIMAT0000728)

| Gene | t. stat | p. value | p. adj |
|---|---|---|---|
| ACVR1C | −4.70738 | 3.79E−06 | 8.36E−05 |
| ADAMDEC1 | −2.85571 | 0.004584 | 0.028127 |
| ADAMTS2 | −8.00448 | 2.43E−14 | 5.11E−12 |
| ADAMTS4 | −5.61352 | 4.40E−08 | 1.79E−06 |
| ADAMTS5 | −4.36029 | 1.77E−05 | 0.000308 |
| AFAP1L1 | −5.85642 | 1.21E−08 | 5.81E−07 |
| AFAP1L2 | −3.94692 | 9.80E−05 | 0.001288 |
| AK5 | −3.22616 | 0.001389 | 0.011065 |
| APBA2 | −5.98525 | 5.96E−09 | 3.14E−07 |
| ATP1B4 | −2.80475 | 0.005354 | 0.0317 |
| BAG2 | −6.31936 | 9.12E−10 | 6.02E−08 |
| BCAT1 | −4.44925 | 1.20E−05 | 0.000223 |
| BVES | −2.70341 | 0.007242 | 0.039902 |
| C10orf55 | −7.35354 | 1.73E−12 | 2.33E−10 |
| C15orf54 | −3.29027 | 0.001116 | 0.009302 |
| C1orf180 | −2.80204 | 0.005398 | 0.0319 |
| C1S | −6.47289 | 3.76E−10 | 2.76E−08 |
| C2orf48 | −3.79852 | 0.000175 | 0.002078 |
| C6orf141 | −3.84998 | 0.000143 | 0.001764 |
| C9orf84 | −4.58988 | 6.45E−06 | 0.000131 |
| CALB1 | −3.21159 | 0.001459 | 0.011504 |
| CCDC102B | −5.32761 | 1.92E−07 | 6.44E−06 |
| CD84 | −2.61675 | 0.009312 | 0.048237 |
| CDH6 | −3.95802 | 9.38E−05 | 0.001241 |
| CDK14 | −4.82222 | 2.23E−06 | 5.31E−05 |

TABLE 14-continued mRNAs inversely expressed and containing predicted or validated binding sites to miR-375 (MIMAT0000728)

| Gene | t. stat | p. value | p. adj |
|---|---|---|---|
| CDK5R1 | −2.75412 | 0.006233 | 0.035597 |
| CDK6 | −3.82156 | 0.00016 | 0.001932 |
| CDYL2 | −4.19285 | 3.60E−05 | 0.000559 |
| CENPA | −7.27305 | 2.89E−12 | 3.68E−10 |
| CENPF | −5.77959 | 1.82E−08 | 8.34E−07 |
| CFHR3 | −2.90338 | 0.003957 | 0.025106 |
| CHST11 | −7.11164 | 7.96E−12 | 9.07E−10 |
| CLEC2B | −4.19326 | 3.59E−05 | 0.000559 |
| CLEC5A | −2.80953 | 0.005277 | 0.031352 |
| CNGB1 | −5.47185 | 9.20E−08 | 3.40E−06 |
| COL16A1 | −6.91676 | 2.65E−11 | 2.64E−09 |
| COL27A1 | −7.59153 | 3.74E−13 | 5.94E−11 |
| COL5A1 | −10.2428 | 2.13E−21 | 1.85E−18 |
| COL5A2 | −10.2511 | 2.00E−21 | 1.75E−18 |
| COL5A3 | −7.81021 | 8.90E−14 | 1.64E−11 |
| CRISPLD2 | −4.86085 | 1.86E−06 | 4.55E−05 |
| CSAG1 | −4.01632 | 7.42E−05 | 0.001022 |
| CYSLTR2 | −2.62634 | 0.00906 | 0.047249 |
| DAB2 | −3.593 | 0.00038 | 0.003911 |
| DCLK3 | −4.99615 | 9.79E−07 | 2.62E−05 |
| DDX60L | −4.29871 | 2.30E−05 | 0.000385 |
| DFNA5 | −6.82695 | 4.58E−11 | 4.29E−09 |
| DGKI | −3.21627 | 0.001436 | 0.01136 |
| DKK3 | −3.72321 | 0.000234 | 0.002631 |
| DMBX1 | −3.69276 | 0.000262 | 0.00289 |
| DRP2 | −3.04627 | 0.002516 | 0.017666 |
| DUSP6 | −3.0615 | 0.002395 | 0.016999 |
| E2F7 | −6.80262 | 5.30E−11 | 4.88E−09 |
| ECM2 | −3.70034 | 0.000255 | 0.002824 |
| EIF5A2 | −7.56276 | 4.51E−13 | 7.02E−11 |
| EME1 | −7.30865 | 2.31E−12 | 3.01E−10 |
| ENPEP | −7.33148 | 1.99E−12 | 2.64E−10 |
| ERCC6L | −5.24049 | 2.97E−07 | 9.39E−06 |
| EXO1 | −6.73046 | 8.19E−11 | 7.18E−09 |
| FAM111B | −3.21279 | 0.001453 | 0.011467 |
| FAM198B | −4.22428 | 3.16E−05 | 0.000501 |
| FBLN7 | −5.13553 | 4.98E−07 | 1.47E−05 |
| FBN2 | −5.49402 | 8.20E−08 | 3.08E−06 |
| FCGR2A | −5.69769 | 2.82E−08 | 1.22E−06 |
| FCGR3A | −5.97743 | 6.23E−09 | 3.26E−07 |
| FERMT2 | −2.76737 | 0.005991 | 0.034542 |
| FJX1 | −5.16984 | 4.21E−07 | 1.27E−05 |
| FLRT2 | −5.50011 | 7.95E−08 | 3.00E−06 |
| FN1 | −9.32549 | 2.16E−18 | 1.08E−15 |
| FOXD1 | −6.88267 | 3.26E−11 | 3.18E−09 |
| FOXR2 | −2.61614 | 0.009328 | 0.0483 |
| FPR2 | −3.97456 | 8.78E−05 | 0.001175 |
| FSTL1 | −4.56735 | 7.14E−06 | 0.000143 |
| GAD1 | −2.75515 | 0.006213 | 0.035514 |
| GATA6 | −2.95962 | 0.003318 | 0.021907 |
| GDF6 | −3.57806 | 0.000402 | 0.004089 |
| GINS4 | −4.29356 | 2.35E−05 | 0.000392 |
| GLIPR1 | −5.15516 | 4.52E−07 | 1.35E−05 |
| GLIS3 | −2.88323 | 0.004211 | 0.026349 |
| GNGT2 | −2.98368 | 0.003074 | 0.02065 |
| GOLGA8F | −2.73345 | 0.006628 | 0.037306 |
| GOLGA8G | −3.33689 | 0.00095 | 0.008182 |
| GPR116 | −3.23522 | 0.001347 | 0.010799 |
| GPR137C | −3.77558 | 0.000191 | 0.002234 |
| GPR153 | −2.70662 | 0.007174 | 0.039617 |
| GPR39 | −3.10237 | 0.002096 | 0.015314 |
| GRM5 | −2.83551 | 0.004876 | 0.029502 |
| GRM8 | −3.15477 | 0.001764 | 0.013367 |
| GUCY1A2 | −6.22001 | 1.61E−09 | 9.91E−08 |
| GXYLT2 | −4.60002 | 6.16E−06 | 0.000126 |
| HAPLN1 | −5.46562 | 9.50E−08 | 3.50E−06 |
| HAS2 | −4.90104 | 1.54E−06 | 3.87E−05 |
| HELLS | −3.47233 | 0.000589 | 0.005576 |
| HHIPL1 | −5.11384 | 5.54E−07 | 1.61E−05 |
| HIST1H2AG | −5.61991 | 4.26E−08 | 1.74E−06 |
| HIST1H2BD | −3.40446 | 0.00075 | 0.00677 |
| HIST1H2BO | −5.44492 | 1.06E−07 | 3.84E−06 |
| HIST1H3B | −2.8217 | 0.005085 | 0.030472 |
| HIST1H4E | −3.13256 | 0.001898 | 0.014162 |
| HMX1 | −3.92309 | 0.000108 | 0.001392 |

TABLE 14-continued mRNAs inversely expressed and containing predicted or validated binding sites to miR-375 (MIMAT0000728)

| Gene | t. stat | p. value | p. adj |
|---|---|---|---|
| HOXA10 | −6.33104 | 8.53E−10 | 5.68E−08 |
| HOXB9 | −4.93878 | 1.29E−06 | 3.32E−05 |
| HOXC10 | −6.03467 | 4.54E−09 | 2.47E−07 |
| HOXC11 | −7.25611 | 3.22E−12 | 4.05E−10 |
| HOXC4 | −6.45736 | 4.11E−10 | 2.98E−08 |
| HOXD1 | −4.49567 | 9.81E−06 | 0.000187 |
| HOXD11 | −7.56657 | 4.40E−13 | 6.87E−11 |
| HOXD12 | −3.76912 | 0.000196 | 0.002281 |
| HSPA12A | −3.75646 | 0.000206 | 0.002373 |
| HSPA2 | −2.90069 | 0.00399 | 0.02527 |
| IFI44L | −3.82079 | 0.000161 | 0.001936 |
| IFIT2 | −5.41764 | 1.21E−07 | 4.33E−06 |
| IFNK | −2.63939 | 0.008725 | 0.04593 |
| IGF2BP2 | −4.72804 | 3.45E−06 | 7.71E−05 |
| IGSF6 | −3.83708 | 0.000151 | 0.001838 |
| INHBA | −8.99561 | 2.40E−17 | 9.68E−15 |
| ISL2 | −2.64672 | 0.008543 | 0.045202 |
| ITGA1 | −7.22186 | 3.99E−12 | 4.90E−10 |
| ITGA3 | −4.64266 | 5.09E−06 | 0.000107 |
| ITGB6 | −3.35809 | 0.000883 | 0.007714 |
| KANK4 | −3.77904 | 0.000189 | 0.00221 |
| KCNJ6 | −3.19048 | 0.001566 | 0.012169 |
| KCNMB3 | −2.69746 | 0.007369 | 0.040435 |
| KIAA1644 | −4.81971 | 2.26E−06 | 5.37E−05 |
| KIF4A | −7.37437 | 1.52E−12 | 2.07E−10 |
| KIF4B | −6.56762 | 2.16E−10 | 1.69E−08 |
| KLF7 | −5.6146 | 4.38E−08 | 1.79E−06 |
| KLHL6 | −3.22736 | 0.001383 | 0.011029 |
| KRT82 | −3.0844 | 0.002223 | 0.016034 |
| LAMP3 | −3.2309 | 0.001367 | 0.010926 |
| LHX9 | −3.03305 | 0.002626 | 0.01826 |
| LILRB4 | −4.07083 | 5.95E−05 | 0.000851 |
| LOX | −6.21364 | 1.67E−09 | 1.02E−07 |
| LPAR4 | −2.83169 | 0.004933 | 0.029767 |
| LPPR5 | −4.05481 | 6.35E−05 | 0.000898 |
| LRP8 | −2.72484 | 0.006799 | 0.038033 |
| LTBP2 | −5.09681 | 6.02E−07 | 1.73E−05 |
| MAF | −3.81931 | 0.000162 | 0.001946 |
| MATN3 | −7.12045 | 7.54E−12 | 8.64E−10 |
| MCTP1 | −3.91447 | 0.000111 | 0.001432 |
| MELK | −7.44867 | 9.43E−13 | 1.36E−10 |
| MEST | −3.1584 | 0.001743 | 0.01324 |
| MFRP | −5.76589 | 1.96E−08 | 8.89E−07 |
| MKI67 | −5.92945 | 8.10E−09 | 4.10E−07 |
| MS4A14 | −4.53705 | 8.17E−06 | 0.00016 |
| MS4A7 | −3.29782 | 0.001088 | 0.009112 |
| MYL9 | −3.42878 | 0.000688 | 0.006319 |
| NAV3 | −2.68239 | 0.007702 | 0.041798 |
| NCAM1 | −2.70794 | 0.007146 | 0.0395 |
| NETO1 | −3.66353 | 0.000292 | 0.003161 |
| NEXN | −3.58178 | 0.000396 | 0.004044 |
| NFE2L3 | −3.94766 | 9.77E−05 | 0.001284 |
| NLRP10 | −2.86328 | 0.004479 | 0.027629 |
| NOX5 | −2.86268 | 0.004487 | 0.027669 |
| NT5E | −4.87679 | 1.73E−06 | 4.27E−05 |
| NTM | −5.75521 | 2.08E−08 | 9.34E−07 |
| NTNG2 | −3.39489 | 0.000776 | 0.006955 |
| NXPH4 | −3.73884 | 0.00022 | 0.002507 |
| OLFML2A | −4.36198 | 1.76E−05 | 0.000306 |
| OLR1 | −4.27104 | 2.59E−05 | 0.000425 |
| OPN1SW | −3.45766 | 0.000621 | 0.005817 |
| PAG1 | −3.60653 | 0.000362 | 0.003756 |
| PALM2 | −2.6554 | 0.008331 | 0.044352 |
| PAPLN | −4.68802 | 4.14E−06 | 9.01E−05 |
| PAPSS2 | −3.26239 | 0.001228 | 0.010035 |
| PCDH7 | −3.59138 | 0.000382 | 0.00393 |
| PDE3A | −2.95598 | 0.003356 | 0.022103 |
| PDGFC | −2.97263 | 0.003184 | 0.021221 |
| PDPN | −7.85634 | 6.55E−14 | 1.24E−11 |
| PGM2L1 | −2.79247 | 0.005556 | 0.032613 |
| PIF1 | −6.4856 | 3.49E−10 | 2.58E−08 |
| PIPOX | −2.66955 | 0.007996 | 0.042999 |
| PLEKHG4B | −2.97115 | 0.003199 | 0.021299 |
| PPEF1 | −9.09764 | 1.15E−17 | 4.96E−15 |
| PRKG1 | −2.84047 | 0.004803 | 0.029159 |
| PRNT | −3.87715 | 0.000129 | 0.001617 |
| PSMB9 | −4.71989 | 3.58E−06 | 7.96E−05 |
| PSTPIP1 | −3.69793 | 0.000257 | 0.002845 |
| RASSF4 | −3.99371 | 8.13E−05 | 0.001103 |
| RASSF8 | −3.45857 | 0.000619 | 0.005802 |
| RGS4 | −6.88112 | 3.29E−11 | 3.20E−09 |
| RRM2 | −6.24961 | 1.36E−09 | 8.55E−08 |
| RSAD2 | −5.2935 | 2.28E−07 | 7.47E−06 |
| S1PR5 | −5.42557 | 1.17E−07 | 4.18E−06 |
| SCARB1 | −2.753 | 0.006253 | 0.035687 |
| SCUBE3 | −2.78515 | 0.00568 | 0.033164 |
| SDK2 | −3.22341 | 0.001402 | 0.011147 |
| SEC16B | −3.16386 | 0.001711 | 0.013052 |
| SEMA5B | −4.28609 | 2.43E−05 | 0.000403 |
| SFRP4 | −3.75325 | 0.000208 | 0.002397 |
| SGCD | −2.89289 | 0.004087 | 0.025746 |
| SGIP1 | −6.2358 | 1.47E−09 | 9.16E−08 |
| SH2D7 | −3.07003 | 0.00233 | 0.016635 |
| SHOX2 | −8.26163 | 4.23E−15 | 1.06E−12 |
| SIGLEC15 | −5.56541 | 5.66E−08 | 2.23E−06 |
| SKA3 | −5.776 | 1.86E−08 | 8.48E−07 |
| SLA | −2.83748 | 0.004847 | 0.029366 |
| SLC16A1 | −6.34778 | 7.75E−10 | 5.21E−08 |
| SLC5A12 | −2.75131 | 0.006285 | 0.035824 |
| SLC8A1 | −3.23799 | 0.001334 | 0.010719 |
| SLFN11 | −3.45125 | 0.000635 | 0.005925 |
| SP110 | −3.72725 | 0.00023 | 0.002598 |
| SPOCK1 | −3.93298 | 0.000104 | 0.001348 |
| ST3GAL5 | −4.39456 | 1.53E−05 | 0.000272 |
| ST8SIA2 | −5.50708 | 7.67E−08 | 2.91E−06 |
| STAMBPL1 | −2.89838 | 0.004018 | 0.025409 |
| STARD13 | −4.93888 | 1.29E−06 | 3.32E−05 |
| STON1 | −4.12629 | 4.74E−05 | 0.000704 |
| STON2 | −5.23961 | 2.98E−07 | 9.43E−06 |
| SUCNR1 | −3.03569 | 0.002603 | 0.01814 |
| SULF1 | −6.35395 | 7.48E−10 | 5.05E−08 |
| SULF2 | −6.02724 | 4.73E−09 | 2.56E−07 |
| TBX18 | −2.61611 | 0.009329 | 0.048302 |
| TFRC | −2.73493 | 0.006598 | 0.037182 |
| THBS2 | −5.721 | 2.50E−08 | 1.10E−06 |
| TLL1 | −3.01924 | 0.002745 | 0.018902 |
| TMED7-TICAM2 | −4.38401 | 1.60E−05 | 0.000283 |
| TMEM229B | −3.04848 | 0.002498 | 0.017568 |
| TMEM26 | −7.48025 | 7.70E−13 | 1.13E−10 |
| TNC | −4.77772 | 2.74E−06 | 6.34E−05 |
| TNFRSF9 | −5.19521 | 3.71E−07 | 1.14E−05 |
| TNS3 | −4.86153 | 1.85E−06 | 4.54E−05 |
| TOX2 | −6.5378 | 2.57E−10 | 1.97E−08 |
| TPM1 | −4.57777 | 6.81E−06 | 0.000138 |
| TRPC4 | −5.32987 | 1.90E−07 | 6.38E−06 |
| TSHZ3 | −5.25058 | 2.82E−07 | 8.99E−06 |
| TTC7B | −4.11374 | 4.99E−05 | 0.000735 |
| TYMS | −5.38473 | 1.44E−07 | 5.01E−06 |
| XAF1 | −5.34345 | 1.77E−07 | 6.01E−06 |
| XRCC2 | −5.27422 | 2.51E−07 | 8.12E−06 |
| ZIC1 | −2.82865 | 0.004979 | 0.029979 |
| ZIC5 | −6.58899 | 1.90E−10 | 1.51E−08 |
| ZPLD1 | −5.35131 | 1.70E−07 | 5.80E−06 |

Functional pathway analysis of inversely expressed target genes by IPA identified two of the top cancer disease functions, including cell proliferation (21 mRNAs, p=8.95× $10^{-10}$) and metastasis (23 mRNAs, p=9.54×$10^{-12}$) (Table 15). These networks harbor a diverse repertoire of molecules critically implicated in cancer growth (EGFR, MET, IGF1R, PDGFRB, IRS1, SOCS1, CCNA1), adhesion, migration and invasion (MET, ITGA6, NT5E, SERPINE1), and differentiation (WNT7B/5A, FZD2, CELSR3, CTHRC1). Most of the genes are novel targets of miR-30 and not previously validated by functional characterization.

TABLE 15 mRNAs with inverse relationship to miR-30a-5p expression identified in cancer proliferation and metastasis

| ID | Genes in dataset | Prediction (based on expression direction) | Slope | Findings |
|---|---|---|---|---|
| Proliferation | | | | |
| IRS1 | IRS1 | Affected | −2.612 | Affects (1) |
| NT5E | NT5E | Decreased | −2.675 | Increases (3) |
| EGFR | EGFR | Decreased | −2.693 | Increases (33) |
| GLDC | GLDC | Decreased | −2.718 | Increases (2) |
| SOCS1 | SOCS1 | Increased | −2.843 | Decreases (3) |
| STAT1 | STAT1 | Increased | −2.941 | Increases (5) |
| LOX | LOX | Decreased | −3.093 | Increases (3) |
| PDGFRB | PDGFRB | Decreased | −3.155 | Increases (2) |
| WNT5A | WNT5A | Decreased | −3.212 | Increases (7) |
| CD80 | CD80 | Increased | −3.234 | Decreases (1) |
| CCNA1 | CCNA1 | Decreased | −3.392 | Increases (5) |
| THBS2 | THBS2 | Increased | −3.489 | Decreases (2) |
| IGF1R | IGF1R | Decreased | −3.529 | Increases (6) |
| AFAP1L2 | AFAP1L2 | Affected | −3.575 | Affects (1) |
| CTHRC1 | CTHRC1 | Decreased | −3.813 | Increases (1) |
| MET | MET | Decreased | −4.497 | Increases (17) |
| FAP | FAP | Decreased | −4.575 | Increases (1) |
| SERPINE1 | SERPINE1 | Affected | −6.147 | Affects (5) |
| IL1A | IL1A | Increased | −6.209 | Decreases (10) |
| GJA1 | GJA1 | Increased | −6.454 | Decreases (2) |
| MYBL2 | MYBL2 | Decreased | −7.837 | Increases (1) |
| Metastasis | | | | |
| IRS1 | IRS1 | Affected | −2.612 | Affects (1) |
| TRIM9 | TRIM9 | Affected | −2.634 | Affects (1) |
| NT5E | NT5E | Decreased | −2.675 | Increases (7) |
| EGFR | EGFR | Decreased | −2.693 | Increases (92) |
| SOCS1 | SOCS1 | Increased | −2.843 | Decreases (1) |
| STAT1 | STAT1 | Affected | −2.941 | Affects (1) |
| LOX | LOX | Decreased | −3.093 | Increases (1) |
| EPB41L4B | EPB41L4B | Affected | −3.152 | Affects (2) |
| PDGFRB | PDGFRB | Affected | −3.155 | Affects (37) |
| WNT5A | WNT5A | Increased | −3.212 | Decreases (7) |
| CD80 | CD80 | Increased | −3.234 | Decreases (1) |
| CCNA1 | CCNA1 | Decreased | −3.392 | Increases (5) |
| IGF1R | IGF1R | Decreased | −3.529 | Increases (1) |
| CTHRC1 | CTHRC1 | Decreased | −3.813 | Increases (1) |
| GNRHR | GNRHR | Affected | −4.119 | Affects (15) |
| MET | MET | Decreased | −4.497 | Increases (22) |
| ITGA5 | ITGA5 | Affected | −5.944 | Affects (8) |
| SERPINE1 | SERPINE1 | Increased | −6.147 | Decreases (7) |
| IL1A | IL1A | Decreased | −6.209 | Increases (1) |
| GJA1 | GJA1 | Increased | −6.454 | Decreases (1) |
| ITGA6 | ITGA6 | Affected | −6.763 | Affects (2) |
| SLC7A11 | SLC7A11 | Affected | −7.343 | Affects (1) |
| MYBL2 | MYBL2 | Affected | −7.837 | Affects (1) |

Figure 5:
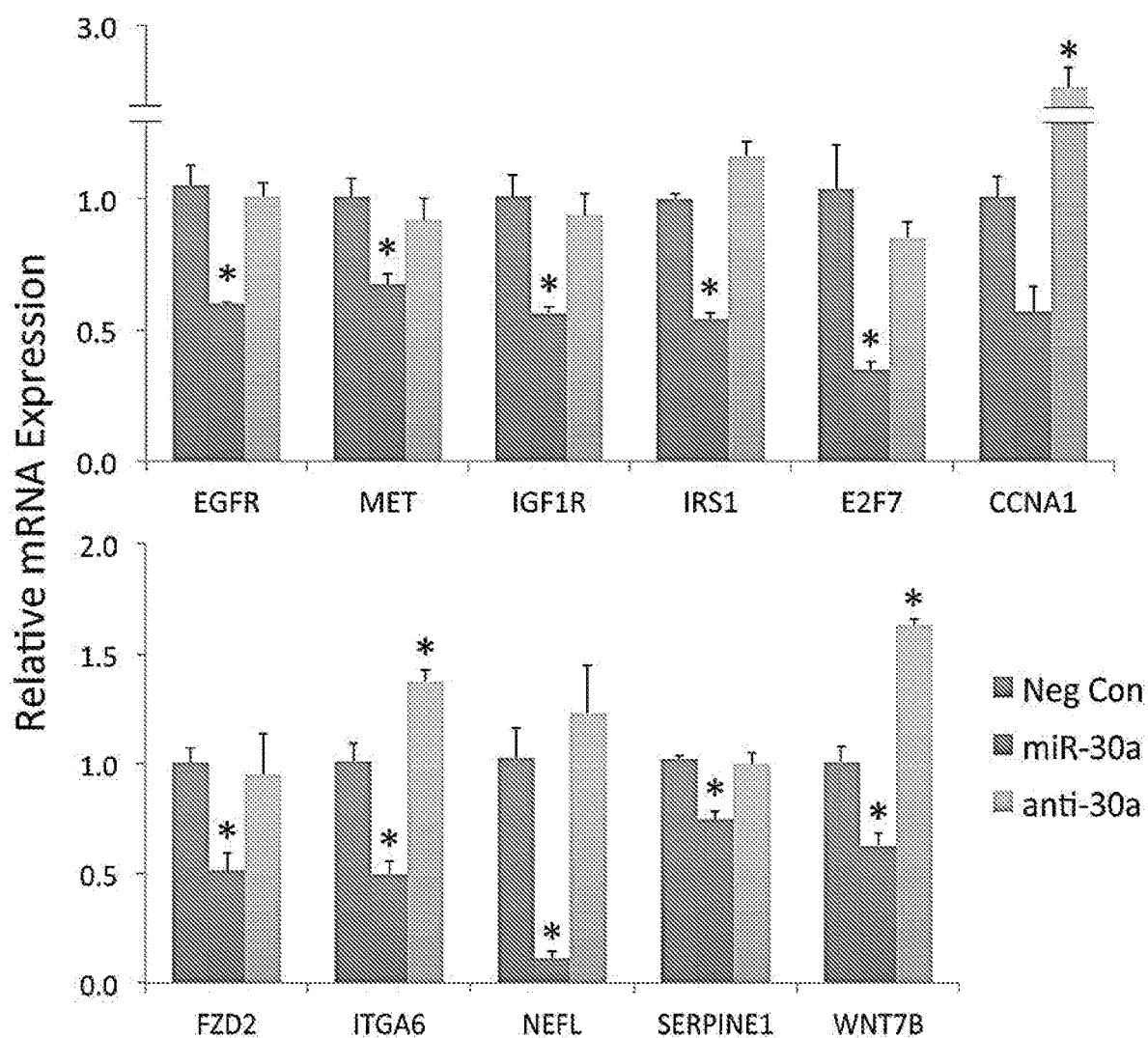
FIG. 5 is a pair of graphs showing qRT-PCR measurement of selected miR-30 target genes in UM-SCC-46 cells transfected with miR negative control (neg Con), miR-30a, or anti-miR-30a control oligonucleotide for 72 hr. All data represent the mean of three independent experiments and error bars represent SEM. * p-value <0.05 by student's T-test.

To validate regulation of inversely expressed mRNAs the effects of ectopic expression of miR-30a-5p (which is more highly expressed in UM-SCC-46 than miR-30e-5p FIG. 7C) or anti-miR30a on potentially targeted mRNAs in the HNSCC line UM-SCC-46, which expresses relatively reduced miR-30a-5p, were examined. After expression of miR-30a-5p, a reduction in mRNA expression was observed for 11 selected mRNAs by qRT-PCR, while expression of anti-miR30a did not suppress or increased these target gene expression (FIG. 5). Both bioinformatics analyses and experimental data support the hypothesis of suppressive function of miR30a on several target genes implicated in pathogenesis of HNSCC.

Example 5

Functional Validation of miR-30a-5p Direct Regulation of Target Gene Expression

Figure 6A:
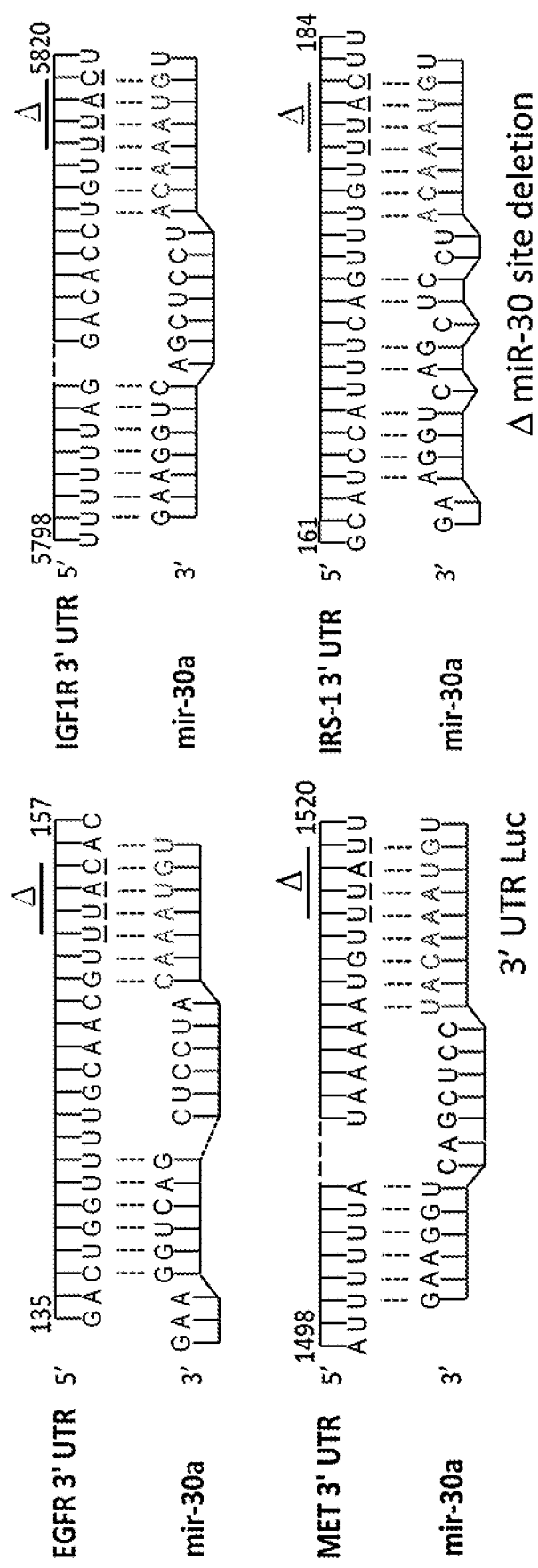
Figure 6B:
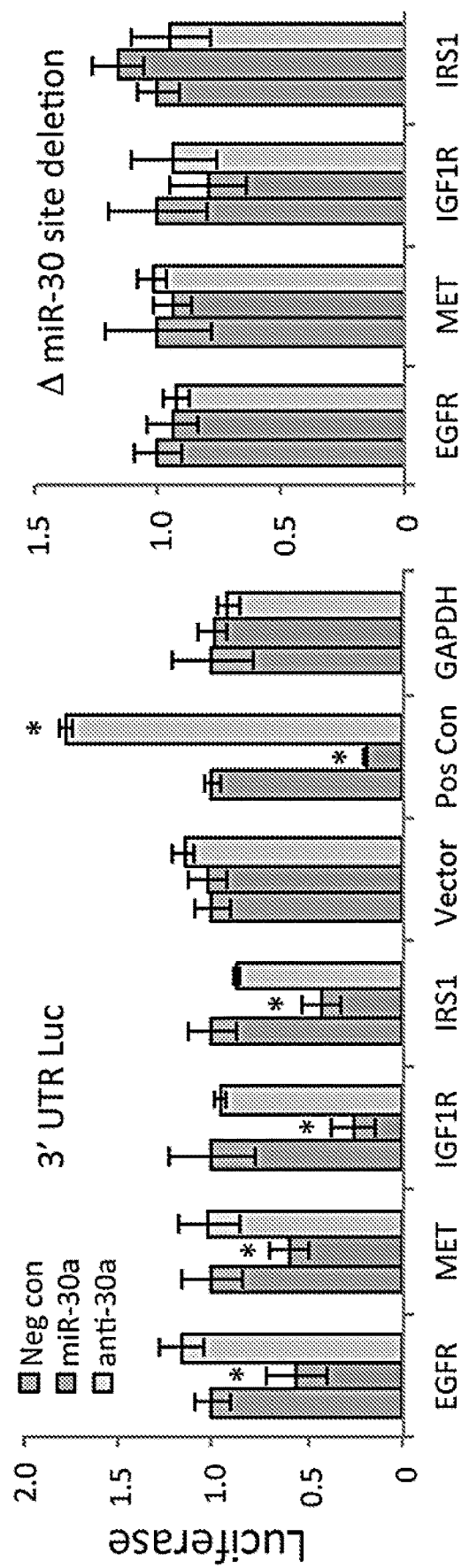

To further validate direct regulation of selected target genes by miR-30-5p family members, luciferase constructs containing the 3' UTR of EGFR, MET, IGF1R and IRS-1, which contains that target binding sites for miR-30a-5p, were utilized (FIG. 6A). Vectors with a deletion in the binding site complementary to the seed sequence of miR-30a-5p were also constructed (FIG. 6A). miR-30a-5p, but not anti-miR30a, suppressed reporter activity, and this was abrogated by AmiR-30 site deletion (FIG. 6B). The effect on expression of several molecules implicated in growth signaling (EGFR, MET, IGF1R, IRS1), adhesion (ITGA6) and differentiation (FZD2) was also confirmed by Western blot (FIGS. 6C and 6E). As these growth factor receptors stimulate several oncogenic signaling pathways, the functional effect of miR30a-5p on signal phosphorylation upon PI3K/mTOR-AKT (Freudlsperger et al., Expert Op in. Ther. Targets 15:63-74, 2011), SRC (Egloff et al., Semin. Oncol. 35:286-297, 2008), and STAT3 signaling (Mali, Oral Oncol. 51:565-569, 2015) was examined. miR-30a-5p decreased downstream phosphorylation of these signaling molecules (FIG. 6D). These data show the direct regulatory effects of miR-30a-5p on the biological targets overexpressed and implicated in malignant phenotype of HNSCC.

Example 6 miR-30a Inhibits Cell Proliferation, Motility, and Invasion by HNSCC Cells

Figure 7A:
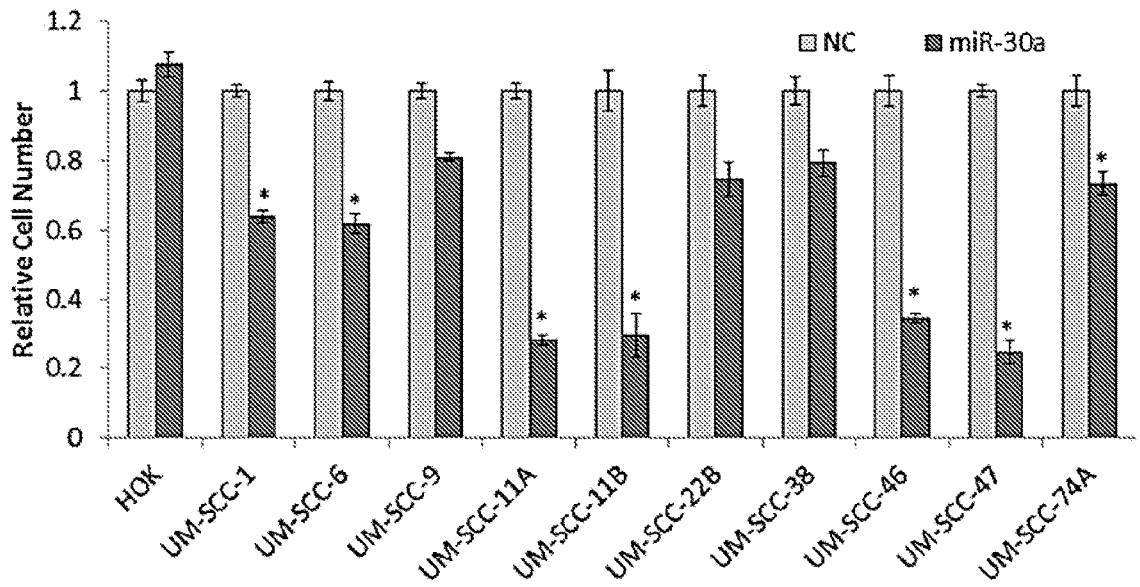
FIGS. 7A-7I are a series of panels showing effect of a miR-30a mimic on HNSCC cell proliferation, colony formation, cisplatin sensitivity, and cell viability.
Figure 7B:
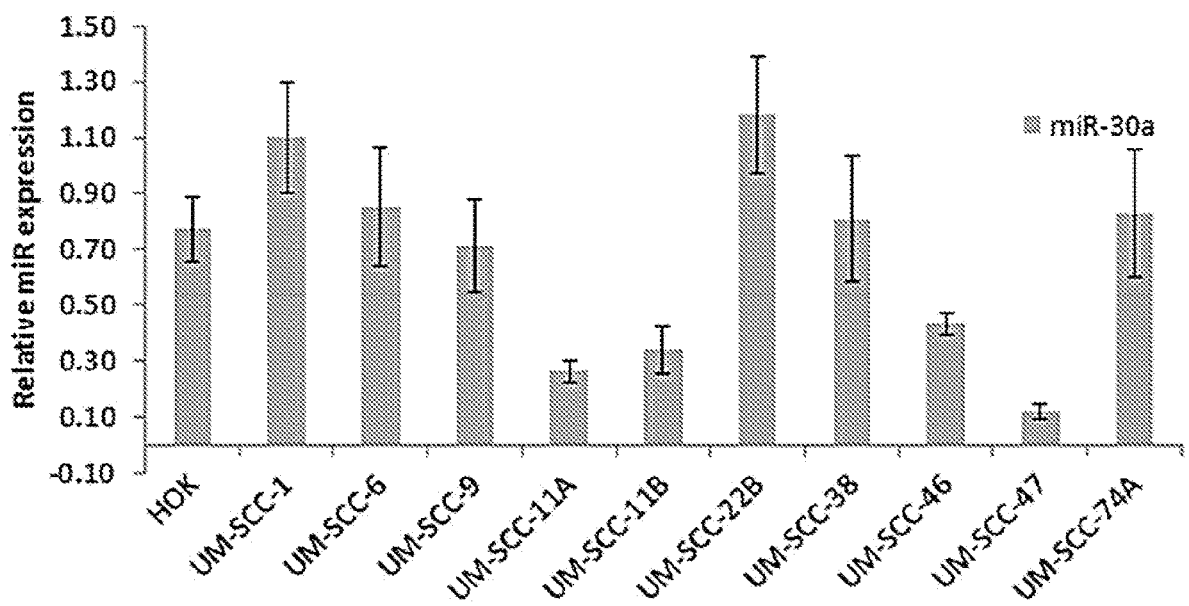
Figure 7C:
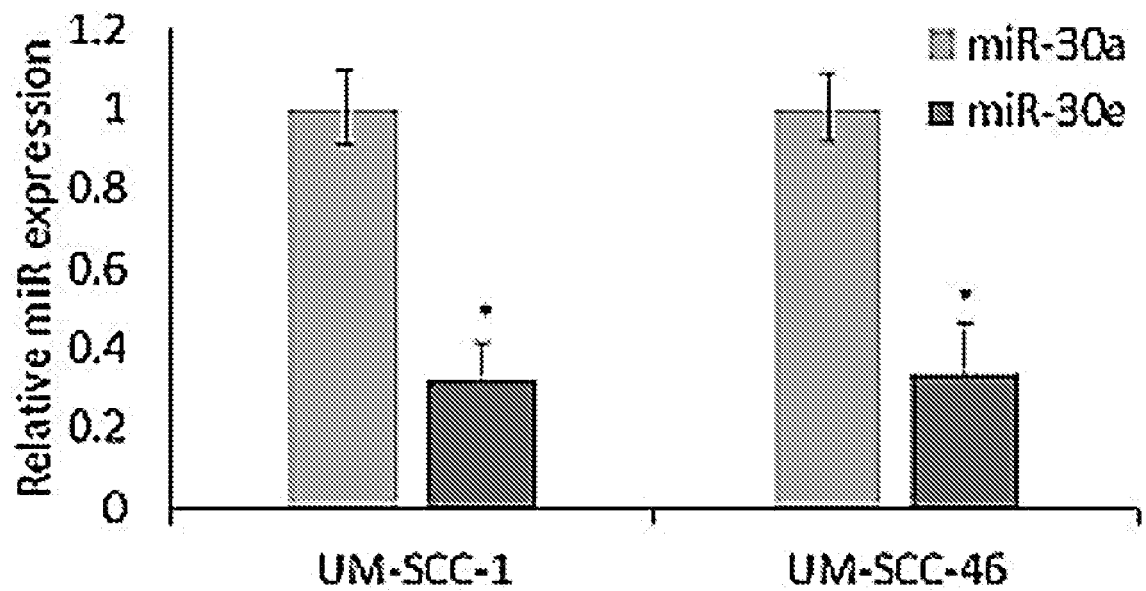
Figure 7D:
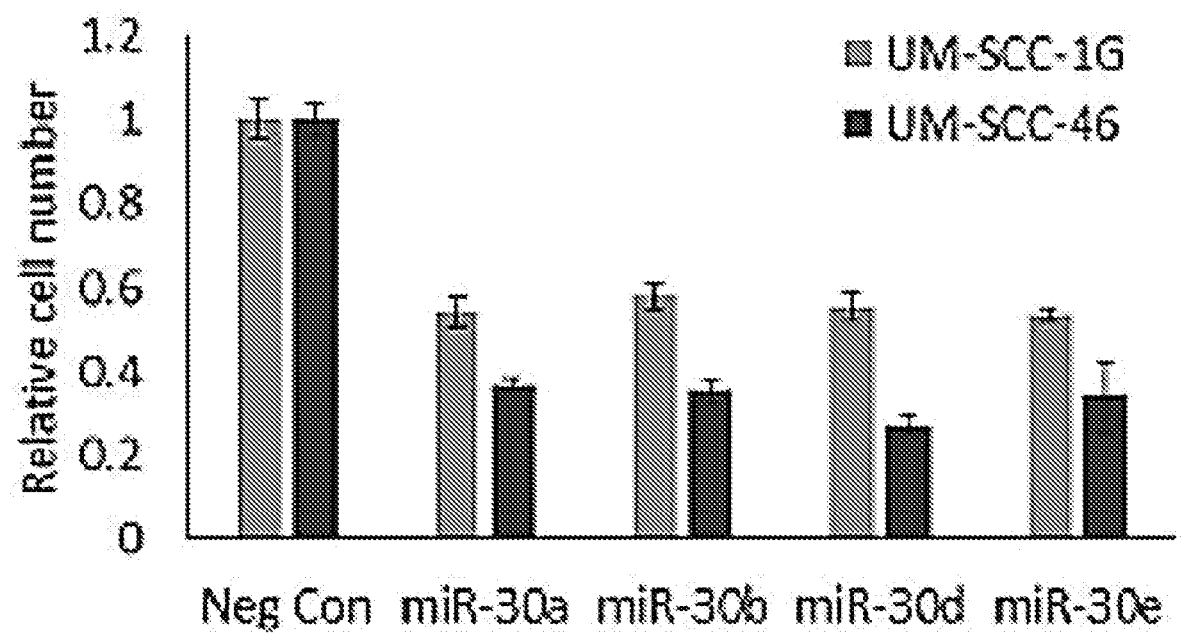
Figure 7E:
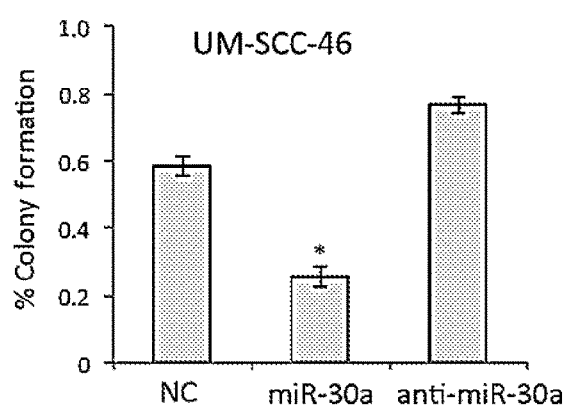
Figure 7F:
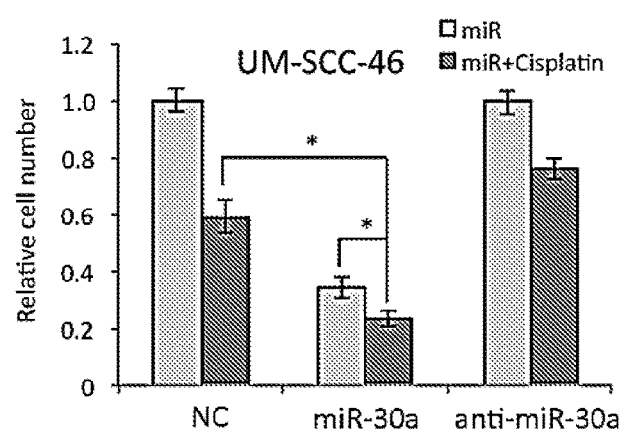
Figure 7G:
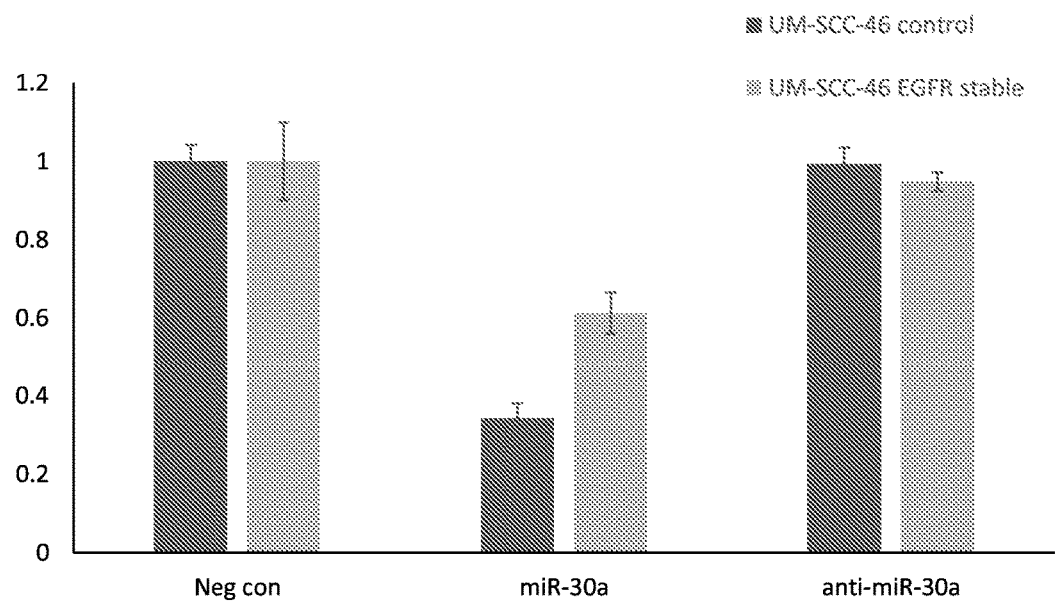
Figure 7H:
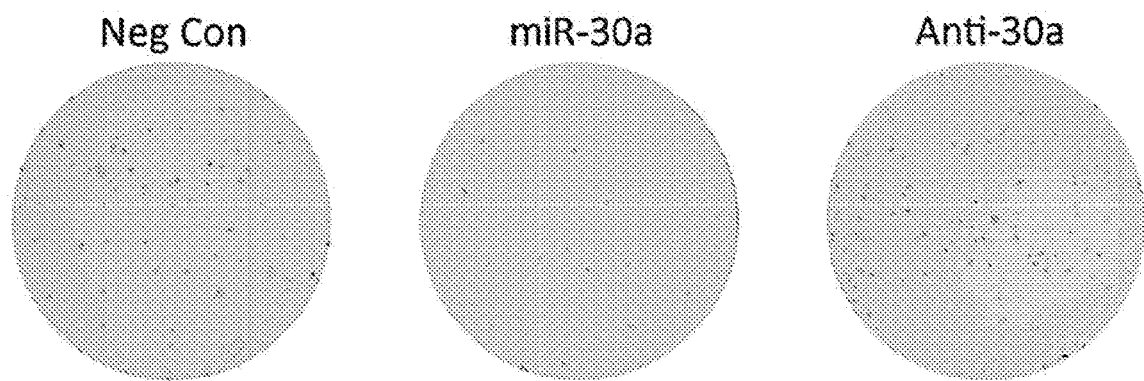
Figure 7I:
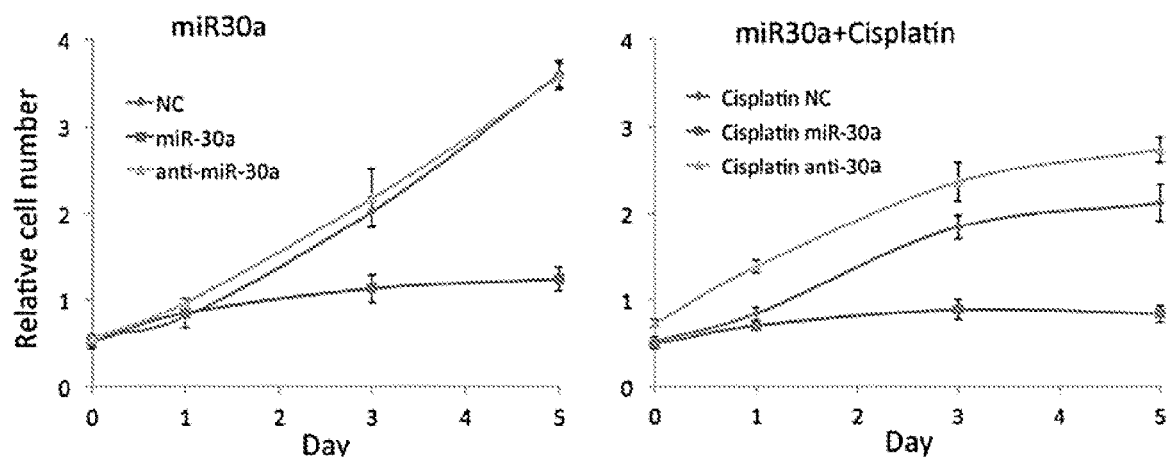

As multiple miR-30a targets can modulate cell growth, anti-proliferative effects of hsa-miR-30a-5p was confirmed in a panel of 11 HNSCC cell lines. Four cells lines (UM-SCC-11A, 11B, 46, 47) displayed significantly decreased cell density of <50% when compared to controls (FIG. 7A), which corresponded with lower expression of miR-30a-5p in these cell lines (FIG. 7B), however, no growth inhibition was observed in HOK cells. Basal level of miR-30a-5p and miR-30e-5p expression in UM-SCC-1 and UM-SCC-46 cells was measured by qRT-PCR (FIG. 7C). Proliferation was also measured in UM-SCC-1 or UM-SCC-46 cells by an XTT assay. Similar inhibition of proliferation was observed between family members (FIG. 7D).

miR-30a-5p also suppressed colony formation by >50% in UM-SCC-46 cells (FIGS. 7E and 7H). As growth signaling can mediate therapeutic resistance, whether miR-30a-5p can augment effects of cisplatin, the most common chemotherapy drug used to treat HNSCC, was examined. Sensitivity to cisplatin was enhanced by ectopic expression of miR-30a-5p (FIG. 7F and FIG. 7I). To test the importance of EGFR in the anti-proliferative effect of miR-30a, a stable cell line of UM-SCC-46 was created over-expressing the EGFR coding sequence without its regulatory 3'UTR in UM-SCC-46. This cell line displayed a significant reduction in the effect of miR-30a-5p on proliferation (FIG. 7G).

Figure 8A:
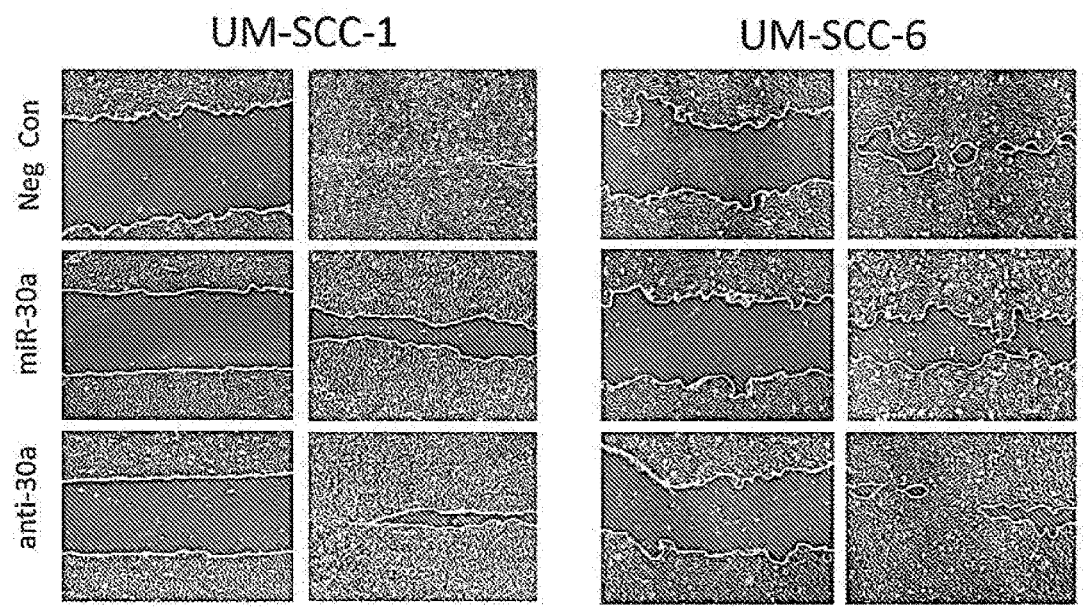
FIGS. 8A-8D are a series of panels showing effect of miR-30a on HNSCC cell motility and invasiveness. UM-SCC-1 (left) and UM-SCC-6 cells (right) were transfected with miR-30a or anti-miR oligonucleotides for 48 hours before wound creation. Cell migration was followed until wound closure in controls. Representative light microscopy images (100×) for wound healing are presented (FIG. 8A). UM-SCC-1, left, time 0; right, time 20 hr. UM-SCC-6, left, time 0; right, time 60 hr. Cell migration over time was quantified (FIG. 8B).
Figure 8B:
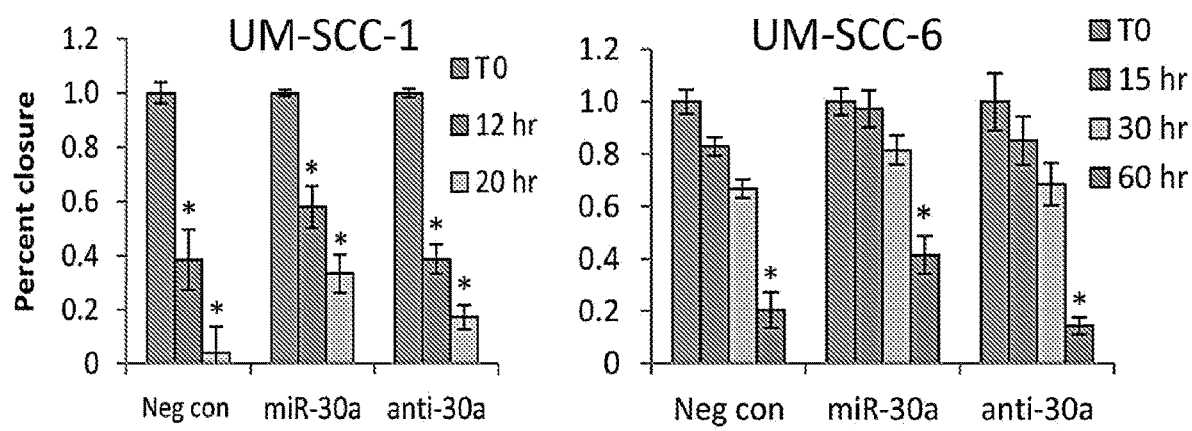
Figure 8C:
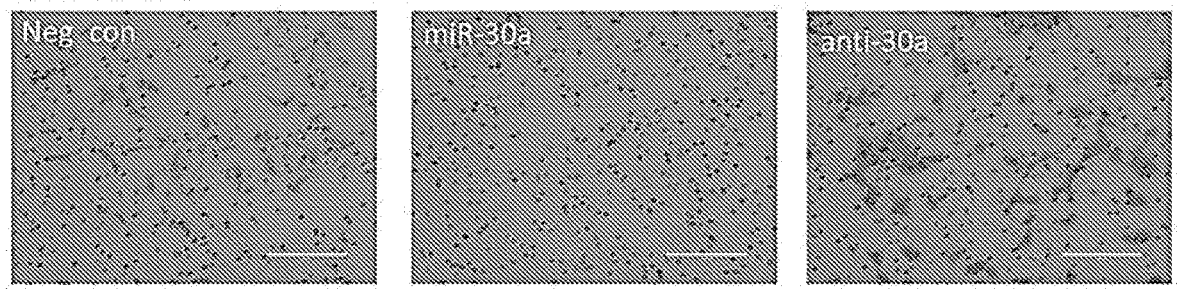
Figure 8D:
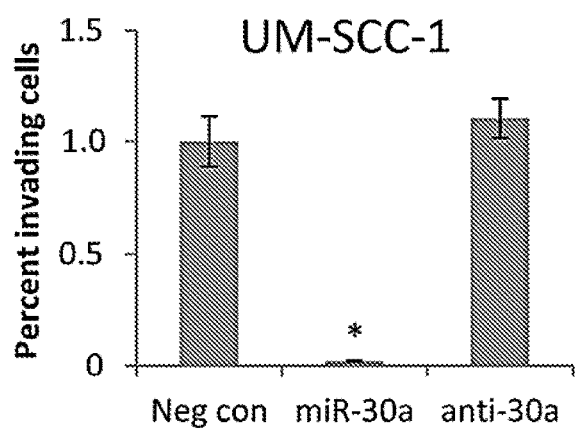
Figure 8D:
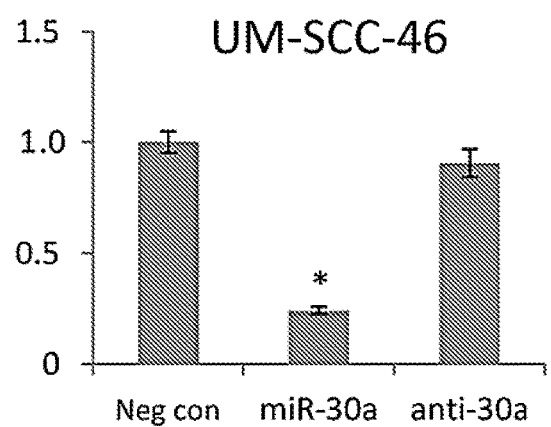

Several of the miR-30-5p family targets in HNSCC are also implicated in cell motility and invasiveness, including EGFR (Freudlsperger et al., Expert Opin. Ther. Targets 15:63-74, 2011), MET (Dong et al., Cancer Res. 61:5911-5918, 2001), ITGA6 (Carey et al., J. Cell Biochem. Suppl. 17F:223-232, 1993), and Serpinel (Karbiener et al., RNA Biol. 8:850-860, 2011). Ectopic expression of hsa-miR-30a-5p significantly slowed cell motility in migration assays in two HNSCC cell lines (FIGS. 8A and 8B), and significantly reduced EGF stimulated invasiveness in MATRIGEL coated transwell migration assays (FIGS. 8C and 8D). In summary, increased expression of miR-30a-5p significantly inhibited cell proliferation, colony formation, migration, and invasion, as well as enhanced chemosensitivity in HNSCC.

Example 7 miR-30a Mimic Suppresses Tumor Growth of Human HNSCC Xenografts

Figure 9A:
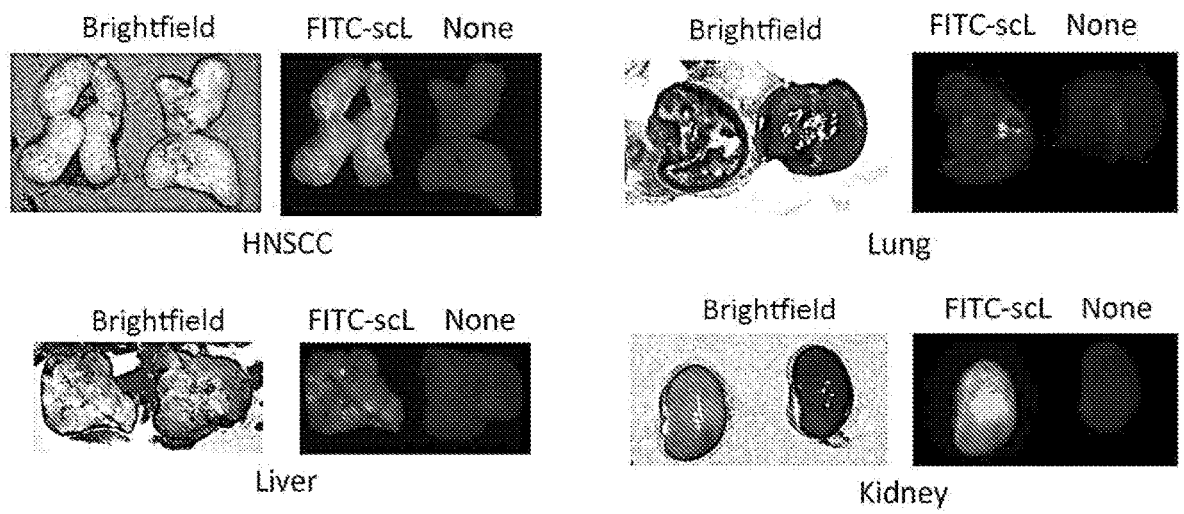
Figure 9B:
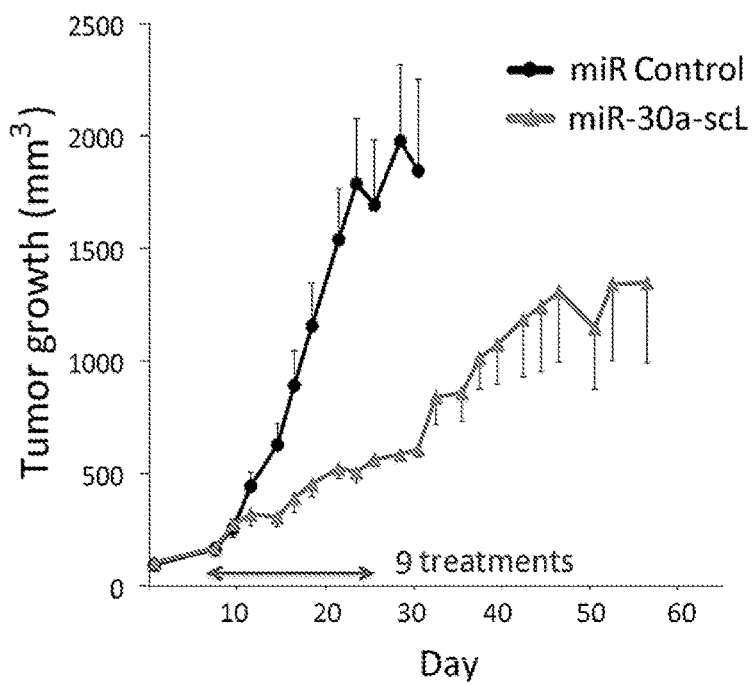

A miR-30a-5p mimic was formulated into a cationic liposomal nanodelivery system (scL) bearing single chain antibody fragment (TfRscFv), which targets overexpressed transferrin receptor on tumor cells for delivery (Pirollo et al., *Cancer Res.* 68:1247-1250, 2008; Pirollo et al., *Hum. Gene Ther.* 17:117-124, 2006). The scL carriers containing FITC-conjugated control oligonucleotide undergo preferential uptake in HNSCC xenografts, when compared to lung or liver, or are excreted via the kidney (FIG. 9A). Nanoliposome particles complexed with a modified miR-30a-5p mimic (miR-30a-scL) or control miR (60 µg or ~3 mg/kg) given in 9 doses intravenously (IV) on Monday, Wednesday, and Friday (MWF) for 3 weeks were tested in mice bearing UM-SCC-46 xenograft tumors. A significant tumor growth delay and prolongation of survival was observed with miR-30a-scL treatment (FIGS. 9B-D). Treatment with miR-30a-scL did not cause a significant reduction in weight suggesting the treatment was well tolerated (FIG. 9C). A similar inhibitory effect on tumor growth in vivo was observed in a second HNSCC xenograft model, UM-SCC47, which is HPV positive (FIG. 9E).

Figure 10A:
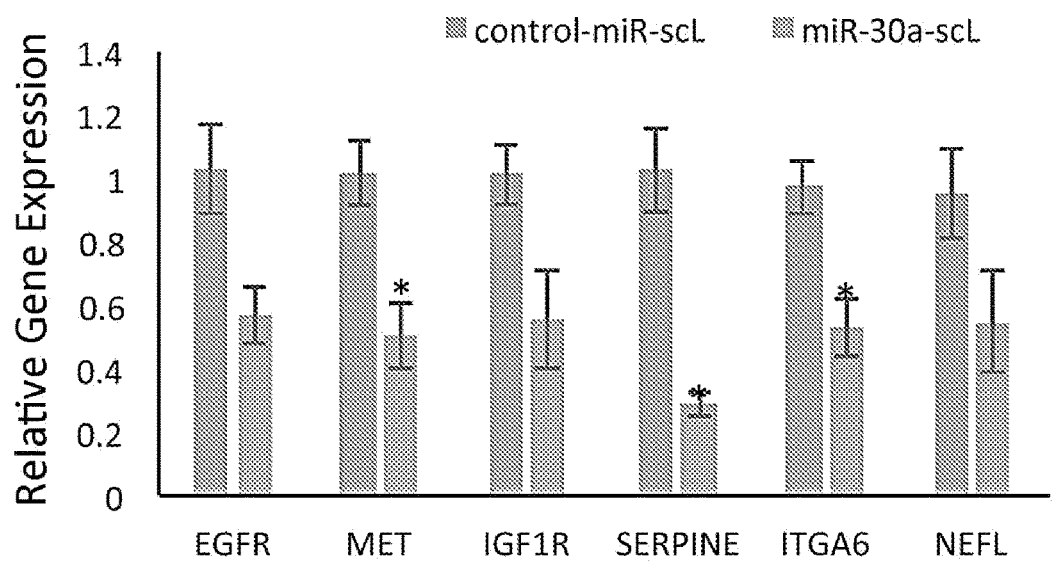
FIG. 10A is a graph showing quantitative real-time PCR of miR-30a-5p target mRNAs in mice implanted with UM-SCC-46 xenograft tumors and injected i.v. with four doses of 60 µg of control miR-ScL or miR-30a-ScL on MWF schedule. Data represent the mean of 3 animals, error bars represent SEM, and (*) denotes p-value <0.05 by student's T-test.
Figure 10B:
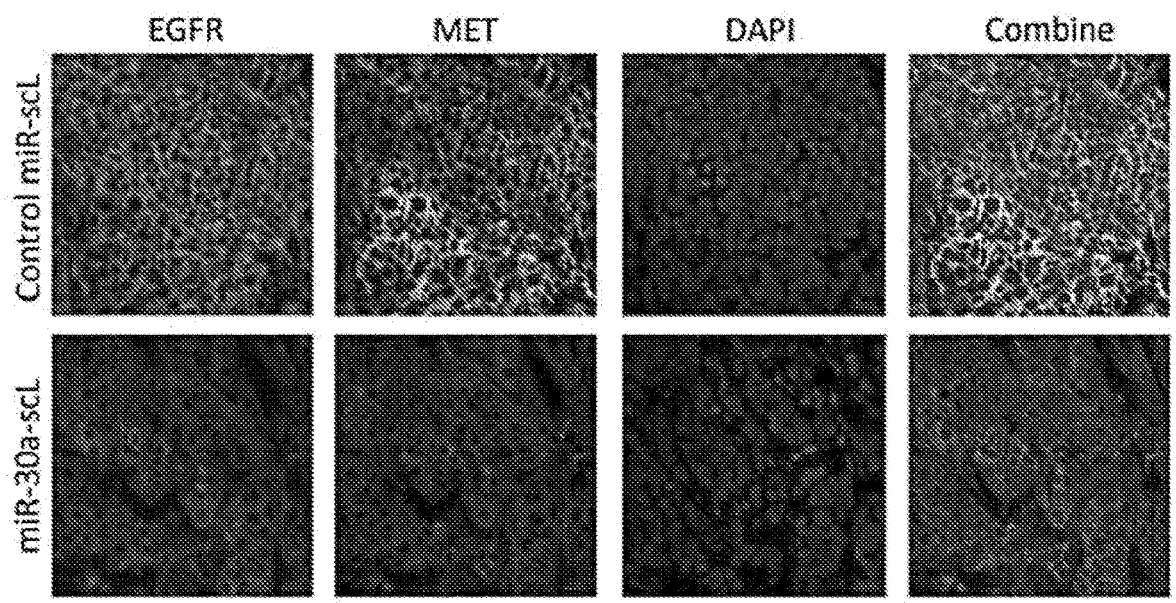
FIG. 10B is a series of digital images showing immunofluorescent staining of EGFR and MET in frozen sections harvested from xenograft tumors after control miR-scL or miR-30a-scL treatment. Scale bars, 20 µm.
Figure 10C:
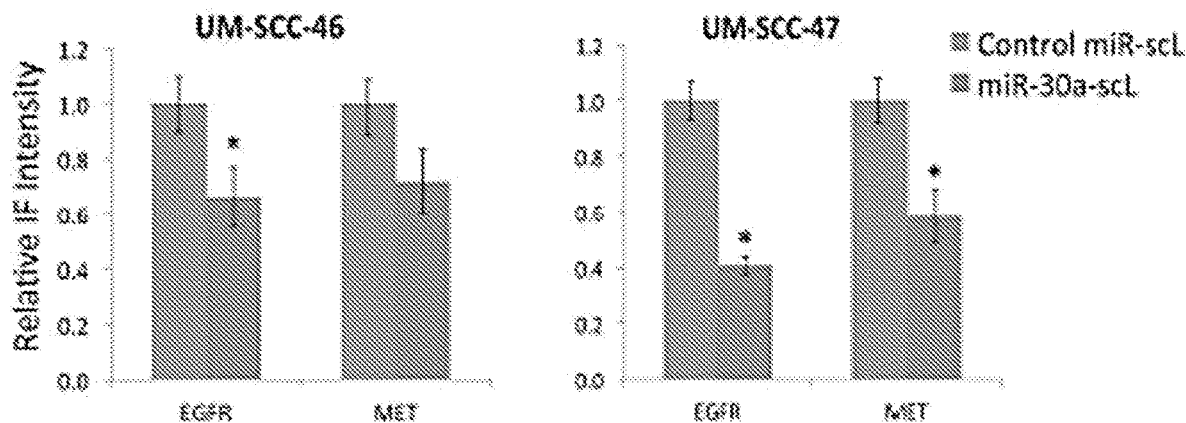
FIG. 10C is a pair of graphs showing mean florescence intensity quantified from six independent 40×fields in UM-SCC-46 (left) and UM-SCC-47 (right) cells. Error bars represent ±SEM, (*) denotes p<0.05 by a student's t-test.
Figure 10D:
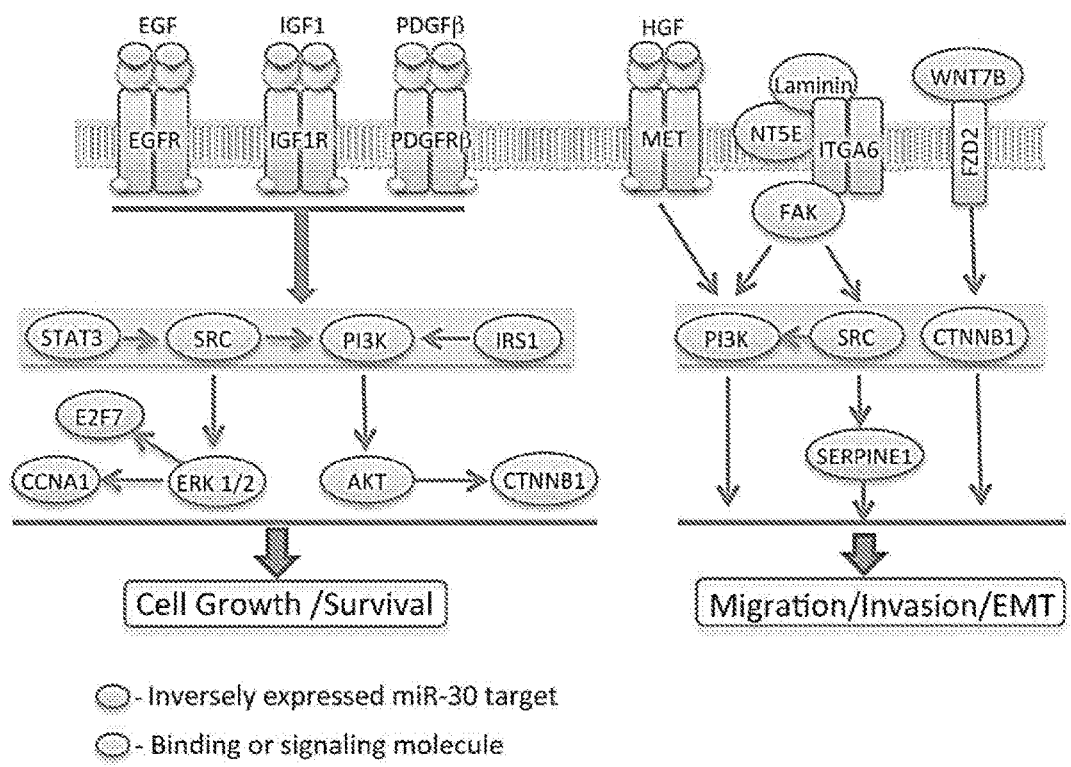
FIG. 10D is a pathway diagram connecting miR30 targeted molecules with reported interactions and function in relation to proliferation and migration by Ingenuity Pathway Analysis. Molecules shown in red are miR-30a-5p target genes with inverse relationship to miR-30a expression. Molecules shown in blue are those exhibiting binding or signaling interactions connecting with the molecules in red.
Figure 10E:
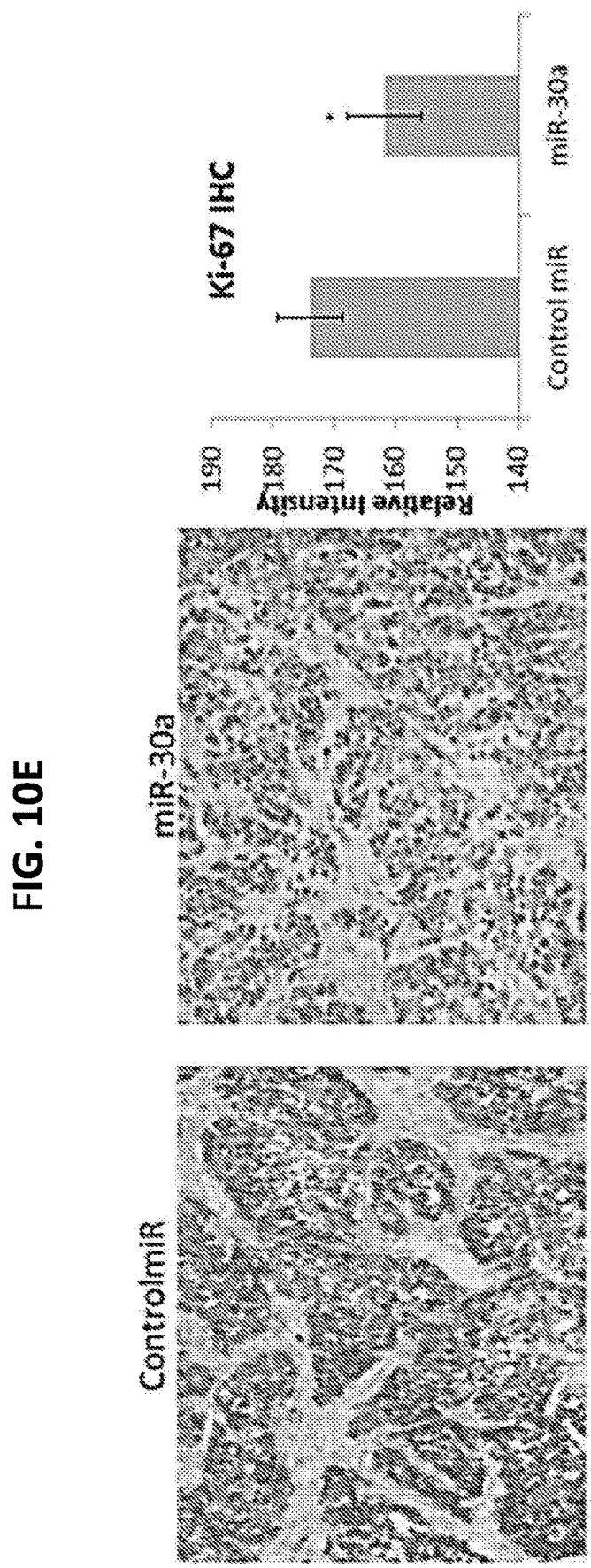
FIG. 10E is representative digital images and quantification of UM-SCC-46 xenograft tumors stained for Ki-67 by immunohistochemistry. Values represent mean intensity quantified from six independent 20× fields and error bars represent ±SEM, (*) denotes p<0.05 by a student's t-test.
Figure 10F:
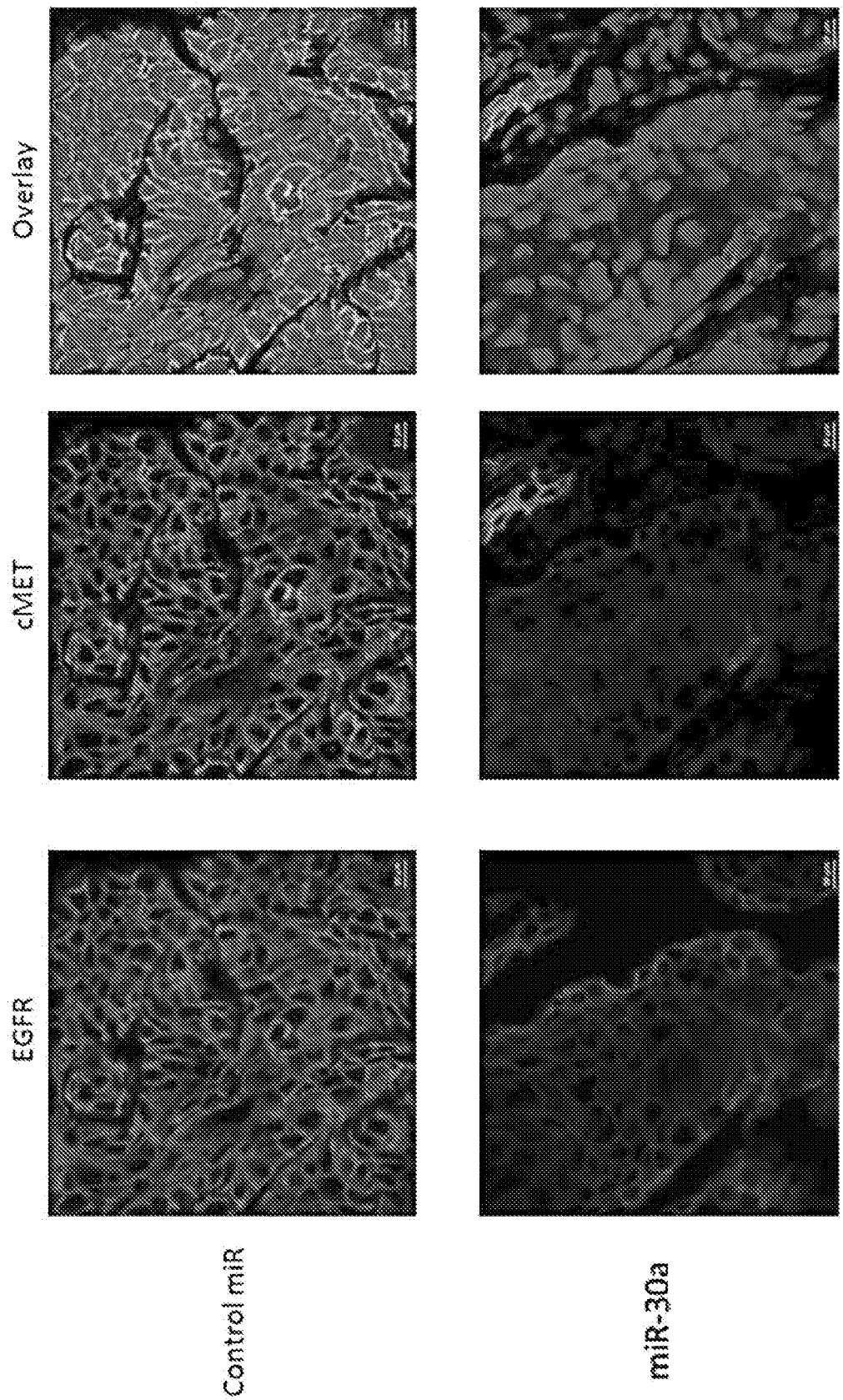
FIG. 10F shows representative images of UM-SCC-47 xenograft tumors stained by immunofluorescence for miR-30 target genes EGFR or MET.

Quantitative RT-PCR of six miR-30a-5p target genes was performed and substantially decreased gene expression was observed after treatment by four doses of miR-30a-scL nanoparticles (FIGS. 10A and 10F). Decreased expression of EGFR and MET by immunofluorescent staining was also observed in frozen sections harvested from xenograft tumors after treatment in vivo (FIGS. 10B and 10C). With confirmation both in vitro and in vivo of several target genes of miR-30a-5p, a pathway diagram connecting reported interactions and function in relation to proliferation and migration as predicted by Ingenuity Pathway Analysis was constructed (FIG. 10D). Confirming miR-30a-5p family's anti-proliferative effect, a decrease in ki-67 staining was also observed (FIG. 10E).

Example 8

Figure 11A:
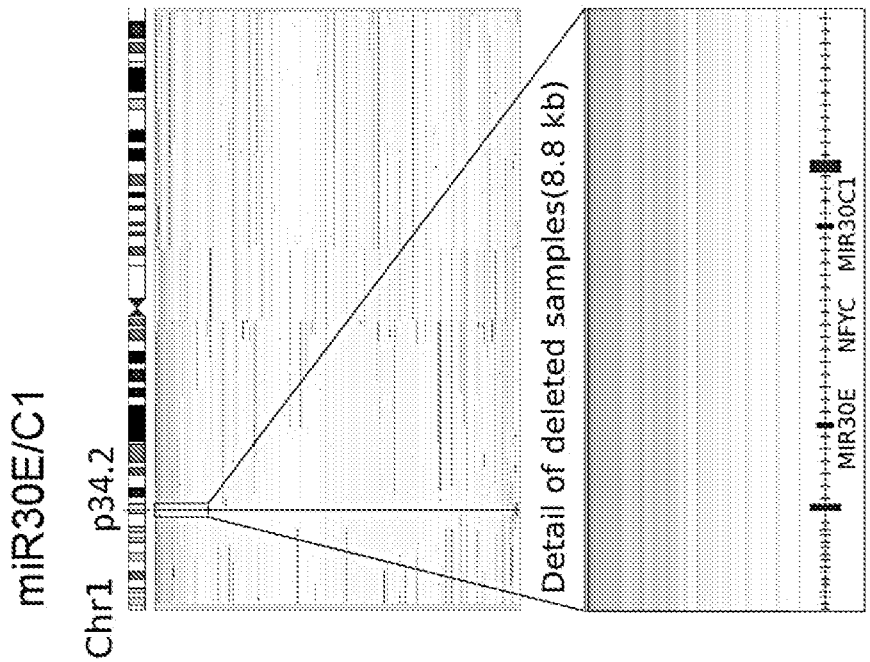
Figure 11B:
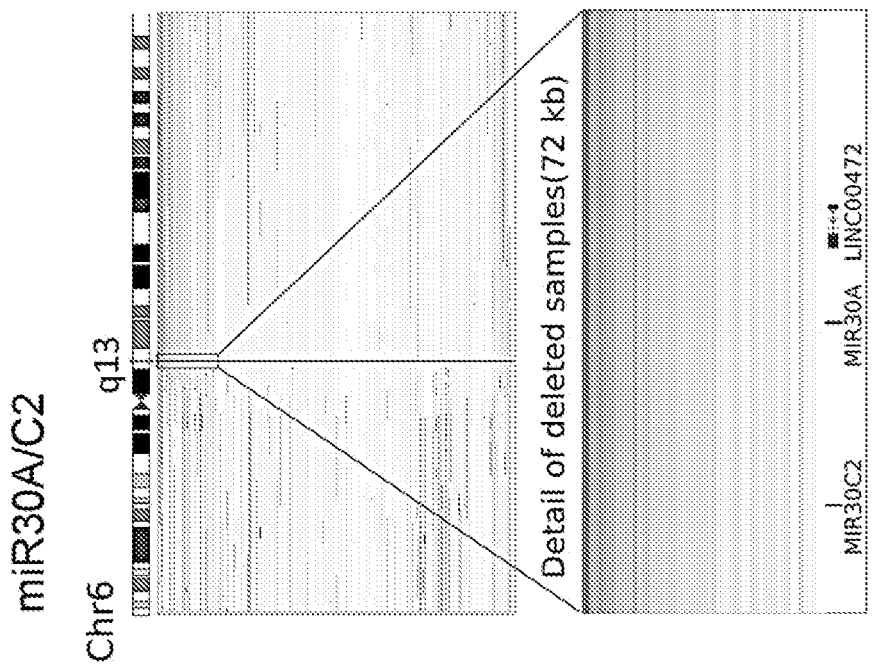

Genetic Alterations of miR-30 Family Members Associated with Clinical Features of HNSCC If loss of expression of miR-30 family members is important in pathogenesis of HNSCC, there may be selective pressure for deletion or epigenetic silencing at the genomic level. To address this question, copy number variation of miR-30 family members from the HNSCC TCGA datasets was analyzed (FIGS. 11A and 11B). The MIR30A and MIR30C2 genes are clustered together on chromosome 6, and the MIR30E and MIR30C1 gene are clustered together on chromosome 1, where 19.7% and 14.7% display at least heterozygous loss at these genetic loci, respectively. Integrative analysis supported a trend or significant correlation of heterozygous copy number loss with decreased expression for miR-30a ($p=0.15$, FIGS. 11A and 11C) and miR-30e ($p=0.0006$, FIGS. 11B and 11D). We further analyzed if the broader decreased expression of miR-30a/e observed was associated with methylation of putative promoters, and compared average DNA methylation along the MIR30A/C2 promoter and coding region (Table 16). A correlation between increasing DNA methylation of MIR30A promoter and lower expression in a subset of tumor specimens was observed ($p=0.00057$, FIGS. 11C and 11F).

Figure 11E:
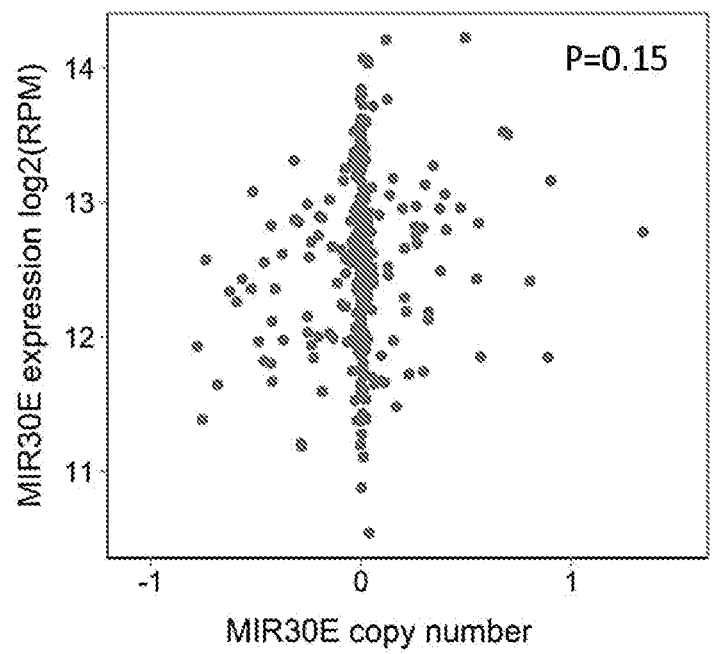
Figure 11F:
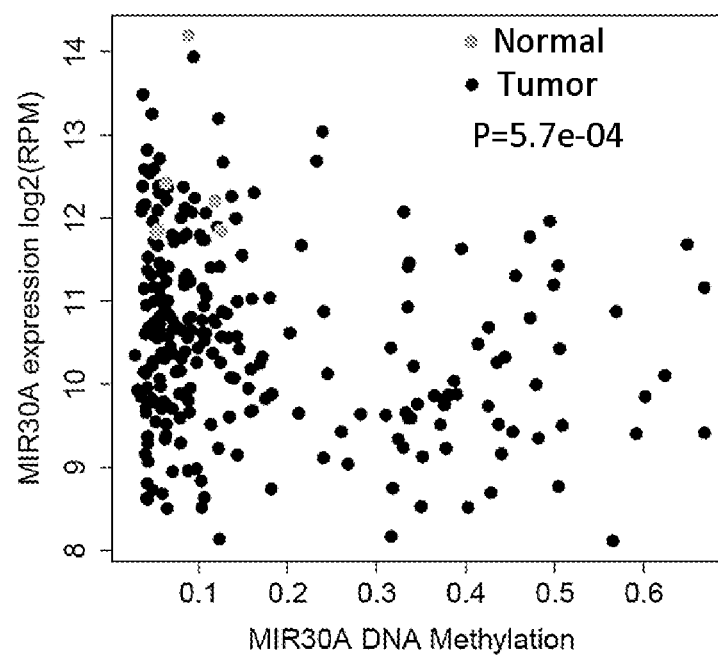

A high percentage of oral cavity tumors (n=87) displayed reduced miR-30a-5p expression and were significantly correlated by Spearman's correlation test with MIR30A hypermethylation of CPZG sites in the MIR30A promoter (p-value 6.15E-07, FIGS. 11C and 11F; Table 17). Reduced expression of miR-30e-5p was correlated with HPV negative status. Additionally, tumors occurring in the laryngeal site were significantly correlated with reduced miR-30e-5p expression and MIR30E copy number deletion (FIG. 11E and Table 17).

TABLE 16

Correlation of expression and methylation of mir-30 family

| probe | gene | mean expr. in unmeth group | mean expr. in meth group | tstat | pval | adj. p. val | mean meth in unmeth group | mean meth in meth group | Spearman corr. |
|---|---|---|---|---|---|---|---|---|---|
| cg20815778 | hsa-mir-30a MIMAT0000087 | 4.634 | 5.119 | −0.227 | 8.34E−01 | 8.52E−01 | 0.086 | 0.441 | −0.064 |
| cg10039188 | hsa-mir-30a | 6.584 | 3.957 | 3.84 | 1.61E−04 | 1.23E−03 | 0.031 | 0.459 | −0.225 |
| cg25210451 | hsa-mir-30a | 6.567 | 3.892 | 3.938 | 1.11E−04 | 1.09E−03 | 0.04 | 0.499 | −0.184 |
| cg15045441 | hsa-mir-30a | 6.814 | 4.003 | 3.79 | 2.01E−04 | 1.23E−03 | 0.052 | 0.435 | −0.225 |
| cg26162616 | hsa-mir-30a | 6.931 | 3.977 | 3.824 | 1.79E−04 | 1.23E−03 | 0.04 | 0.421 | −0.23 |
| cg23281154 | hsa-mir-30a | 6.685 | 4.174 | 3.361 | 1.02E−03 | 3.85E−03 | 0.033 | 0.382 | −0.24 |
| cg22300282 | hsa-mir-30a | 8.386 | 3.984 | 2.256 | 2.87E−02 | 5.86E−02 | 0.077 | 0.518 | −0.199 |
| cg11574469 | hsa-mir-30a | 8.278 | 4.066 | 2.359 | 2.20E−02 | 5.10E−02 | 0.078 | 0.428 | −0.244 |
| cg25141674 | hsa-mir-30a | 7.363 | 4.151 | 2.842 | 5.35E−03 | 1.62E−02 | 0.063 | 0.495 | −0.23 |
| cg24772267 | hsa-mir-30a | 6.694 | 4.29 | 2.359 | 1.98E−02 | 4.84E−02 | 0.077 | 0.472 | −0.122 |
| cg00920327 | hsa-mir-30a | 7.006 | 4.052 | 3.642 | 3.52E−04 | 1.92E−03 | 0.058 | 0.465 | −0.247 |
| cg03318695 | hsa-mir-30a | 7.396 | 4.395 | 1.562 | 1.25E−01 | 1.92E−01 | 0.075 | 0.487 | −0.221 |
| cg20815778 | hsa-mir-30a MIMAT0000088 | 1.936 | 1.845 | 0.081 | 9.40E−01 | 9.40E−01 | 0.086 | 0.441 | −0.073 |
| cg10039188 | hsa-mir-30a | 2.331 | 1.351 | 4.494 | 1.19E−05 | 1.46E−04 | 0.031 | 0.459 | −0.196 |
| cg25210451 | hsa-mir-30a | 2.303 | 1.3 | 4.876 | 2.52E−06 | 8.69E−05 | 0.04 | 0.499 | −0.181 |
| cg15045441 | hsa-mir-30a | 2.44 | 1.361 | 4.62 | 7.85E−06 | 1.28E−04 | 0.052 | 0.435 | −0.216 |
| cg26162616 | hsa-mir-30a | 2.451 | 1.336 | 4.778 | 3.55E−06 | 8.69E−05 | 0.04 | 0.421 | −0.232 |
| cg23281154 | hsa-mir-30a | 2.386 | 1.481 | 3.61 | 5.22E−04 | 2.32E−03 | 0.033 | 0.382 | −0.243 |

TABLE 16-continued

Correlation of expression and methylation of mir-30 family

| probe | gene | mean expr. in unmeth group | mean expr. in meth group | tstat | pval | adj. p. val | mean meth in unmeth group | mean meth in meth group | Spearman corr. |
|---|---|---|---|---|---|---|---|---|---|
| cg22300282 | hsa-mir-30a | 2.752 | 1.385 | 3.396 | 1.24E−03 | 4.35E−03 | 0.077 | 0.518 | −0.222 |
| cg11574469 | hsa-mir-30a | 2.69 | 1.43 | 3.335 | 1.38E−03 | 4.50E−03 | 0.078 | 0.428 | −0.218 |
| cg25141674 | hsa-mir-30a | 2.602 | 1.479 | 3.423 | 8.09E−04 | 3.30E−03 | 0.063 | 0.495 | −0.243 |
| cg24772267 | hsa-mir-30a | 2.37 | 1.637 | 2.132 | 3.70E−02 | 7.26E−02 | 0.077 | 0.472 | −0.138 |
| cg00920327 | hsa-mir-30a | 2.445 | 1.454 | 3.589 | 4.74E−04 | 2.32E−03 | 0.058 | 0.465 | −0.219 |
| cg03318695 | hsa-mir-30a | 2.521 | 1.585 | 2.307 | 2.41E−02 | 5.14E−02 | 0.075 | 0.487 | −0.222 |
| cg22904815 | hsa-mir-30b MIMAT0000420 | 0.266 | 0.174 | 2.449 | 2.29E−02 | 5.10E−02 | 0.078 | 0.326 | −0.151 |
| cg10039188 | hsa-mir-30c-2 | 0.316 | 0.26 | 1.875 | 6.36E−02 | 1.20E−01 | 0.031 | 0.459 | −0.132 |
| cg25210451 | hsa-mir-30c-2 | 0.316 | 0.26 | 1.814 | 7.29E−02 | 1.31E−01 | 0.04 | 0.499 | −0.034 |
| cg15045441 | hsa-mir-30c-2 | 0.321 | 0.271 | 1.451 | 1.51E−01 | 2.18E−01 | 0.052 | 0.435 | −0.095 |
| cg26162616 | hsa-mir-30c-2 | 0.323 | 0.27 | 1.69 | 9.38E−02 | 1.48E−01 | 0.04 | 0.421 | −0.072 |
| cg23281154 | hsa-mir-30c-2 | 0.316 | 0.259 | 1.438 | 1.58E−01 | 2.21E−01 | 0.033 | 0.382 | −0.109 |
| cg22300282 | hsa-mir-30c-2 | 0.272 | 0.256 | 0.438 | 6.62E−01 | 7.05E−01 | 0.077 | 0.518 | −0.025 |
| cg11574469 | hsa-mir-30c-2 | 0.325 | 0.257 | 1.726 | 8.78E−02 | 1.43E−01 | 0.078 | 0.428 | −0.099 |
| cg25141674 | hsa-mir-30c-2 | 0.306 | 0.262 | 1.368 | 1.74E−01 | 2.36E−01 | 0.063 | 0.495 | −0.084 |
| cg24772267 | hsa-mir-30c-2 | 0.286 | 0.255 | 0.801 | 4.27E−01 | 4.98E−01 | 0.077 | 0.472 | −0.016 |
| cg00920327 | hsa-mir-30c-2 | 0.327 | 0.246 | 2.55 | 1.23E−02 | 3.36E−02 | 0.058 | 0.465 | −0.101 |
| cg03318695 | hsa-mir-30c-2 | 0.317 | 0.279 | 0.871 | 3.87E−01 | 4.74E−01 | 0.075 | 0.487 | −0.077 |
| cg22904815 | hsa-mir-30d MIMAT0000245 | 5.321 | 4.432 | 1.504 | 1.48E−01 | 2.18E−01 | 0.078 | 0.326 | −0.137 |
| cg16167741 | hsa-mir-30e MIMAT0000692 | 4.234 | 4.02 | 0.571 | 5.69E−01 | 6.19E−01 | 0.07 | 0.549 | 0.03 |
| cg26783428 | hsa-mir-30e | 5.041 | 4.302 | 0.634 | 5.68E−01 | 6.19E−01 | 0.089 | 0.519 | 0.016 |
| cg27386837 | hsa-mir-30e | 4.655 | 3.407 | 2.447 | 1.69E−02 | 4.36E−02 | 0.086 | 0.46 | −0.151 |
| cg13735974 | hsa-mir-30e | 4.383 | 3.508 | 1.82 | 7.74E−02 | 1.31E−01 | 0.085 | 0.502 | −0.149 |
| cg10336144 | hsa-mir-30e | 4.597 | 3.372 | 2.827 | 5.61E−03 | 1.62E−02 | 0.082 | 0.489 | −0.117 |
| cg14796708 | hsa-mir-30e | 3.92 | 3.828 | 0.213 | 8.32E−01 | 8.52E−01 | 0.082 | 0.429 | 0.018 |
| cg16167741 | hsa-mir-30e MIMAT0000693 | 5.153 | 4.779 | 0.987 | 3.25E−01 | 4.09E−01 | 0.07 | 0.549 | −0.072 |
| cg26783428 | hsa-mir-30e | 6.638 | 5.117 | 0.957 | 4.07E−01 | 4.86E−01 | 0.089 | 0.519 | −0.034 |
| cg27386837 | hsa-mir-30e | 5.98 | 4.76 | 1.794 | 7.75E−02 | 1.31E−01 | 0.086 | 0.46 | −0.184 |
| cg13735974 | hsa-mir-30e | 5.932 | 4.931 | 1.244 | 2.22E−01 | 2.94E−01 | 0.085 | 0.502 | −0.157 |
| cg10336144 | hsa-mir-30e | 5.534 | 4.884 | 1.131 | 2.63E−01 | 3.40E−01 | 0.082 | 0.489 | −0.189 |
| cg14796708 | hsa-mir-30e | 4.657 | 5.054 | −0.77 | 4.43E−01 | 5.05E−01 | 0.082 | 0.429 | 0.027 |

TABLE 17

Association of copy number variation, methylation, and expression of miR30A/E with clinical characteristics in HNSCC from TCGA dataset

| Clinical Features | miR30 Alterations | | P-value |
|---|---|---|---|
| miR30A Methylation | | | |
| Tumor site | Hyper | Hypo | |
| Oral | 58 | 115 | 6.15E−07* |
| Non-oral | 9 | 97 | |
| HPV status | | | |
| HPV(+) | 3 | 26 | 0.0686 |
| HPV(−) | 52 | 163 | |
| miR30A Expression | | | |
| Tumor site | Low | High | |
| Oral | 87 | 68 | 0.00822* |
| Non-oral | 35 | 54 | |
| HPV status | | | |
| HPV(+) | 11 | 18 | 0.117 |
| HPV(−) | 111 | 104 | |
| miR30E Copy Number Variation | | | |
| Tumor site | Deletion | Non-deletion | |
| Larynx | 18 | 46 | 0.00184* |
| Non-larynx | 20 | 160 | |
| HPV status | | | |
| HPV(+) | 0 | 29 | 0.00527* |
| HPV(−) | 38 | 177 | |
| miR30E Expression | | | |
| Tumor site | Low | High | |
| Larynx | 28 | 36 | 0.154 |
| Non-larynx | 94 | 86 | |
| HPV status | | | |
| HPV(+) | 5 | 24 | 0.000121* |
| HPV(−) | 117 | 98 | |

Figure 11G:
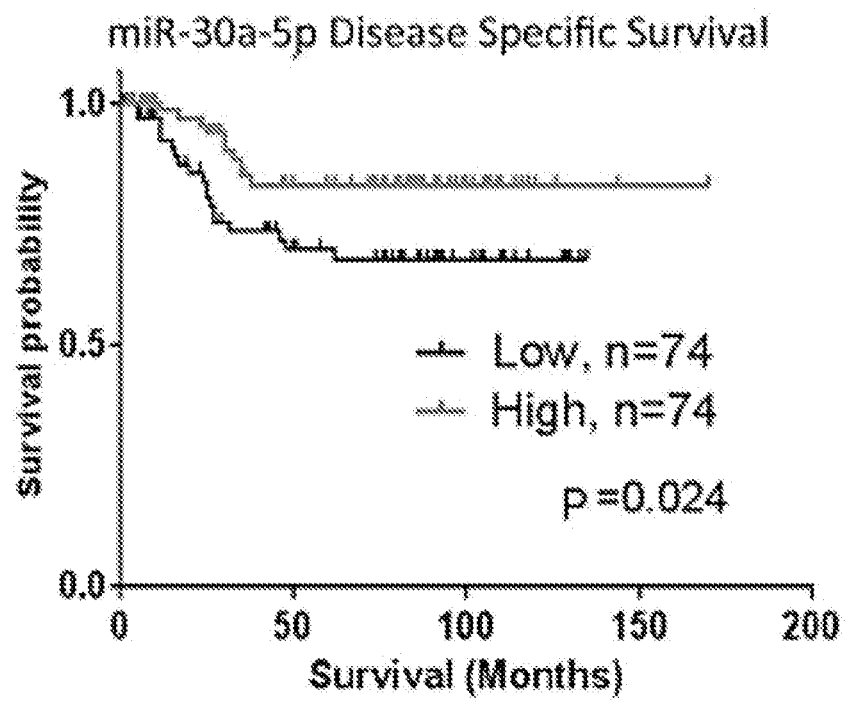
FIGS. 11G and 11H are a pair of graphs showing survival analysis for miR-30a-5p (FIG. 11G) and miR-30e-5p (FIG. 11H) segregated into high and low by median expression. Kaplan-Meier plots and log rank test p-values comparing disease specific survival.
Figure 11H:
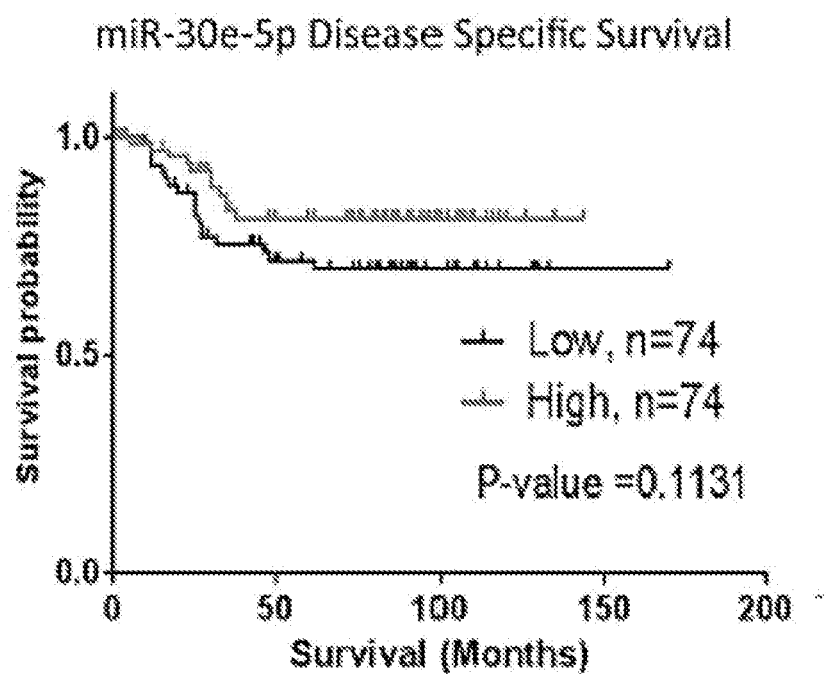
Figure 12A:
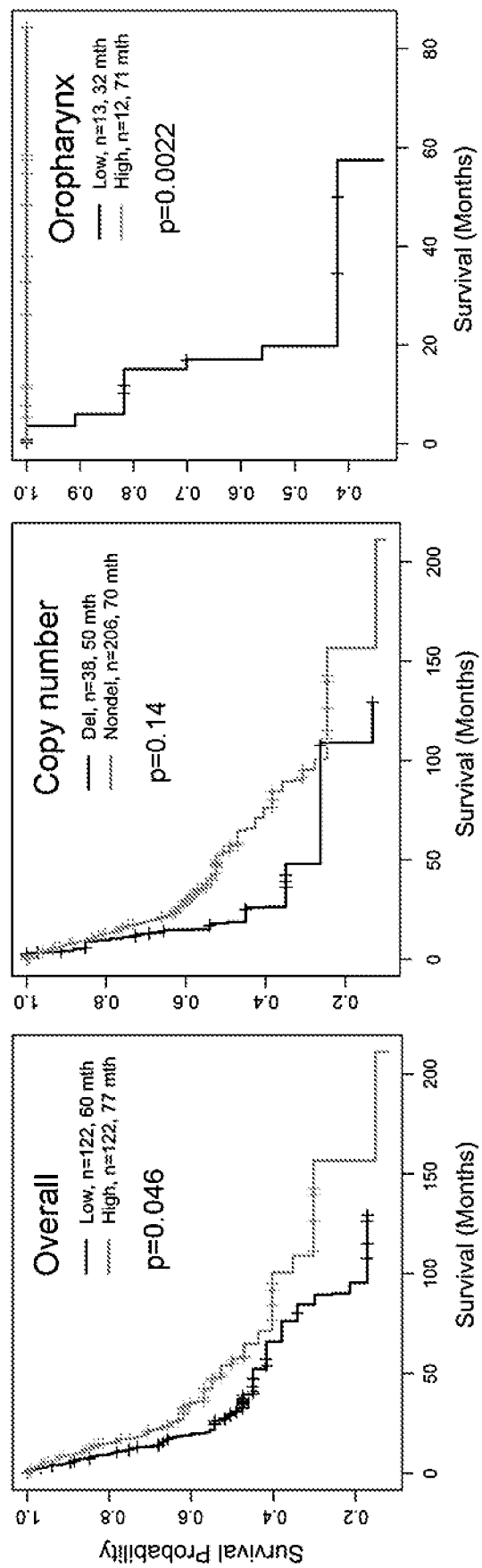

As the prognosis of HPV+ and oropharyngeal cancers is better than HPV− and laryngeal HNSCC, association of miR-30a/e expression with differences in prognosis was examined. Lower expression of miR-30e significantly correlated with lower overall survival (FIG. 12A, left panel), consistent with association with HPV-tumors. A trend towards reduced survival was also observed in the subset of patients that displayed copy number loss of the MIR30E loci, supporting the contribution of genomic copy alteration to decreased miR30e expression in a subset of tumors (FIG. 12A, middle panel). Surprisingly, survival analysis for tumor sub-sites revealed that low expression of miR-30e-5p is associated with worst prognosis in oropharyngeal carcinomas (FIG. 12A, right panel), which are predominantly HPV+ and for which genomic alterations associated with worse prognosis and therapeutic targets have not been well defined. This dataset displayed a strong correlation between low miR-30a-5p expression with poorer disease specific survival (p-value 0.024, FIG. 11G) and a similar trend for miR-30e-5p (p-value 0.113, FIG. 11H). These data suggest that reduced miR-30a/e expression is associated with genetic or epigenetic alterations, HNSCC tumor subsites, HPV status, and prognosis of clinical relevance in HNSCC. In addition, lower expression of miR-26a-5p and miR-26b-5p was correlated with lower overall survival (FIG. 12B).

Example 9

Anti-Proliferation Activity of miR-30a in Cancer Cell Lines

Figure 13:
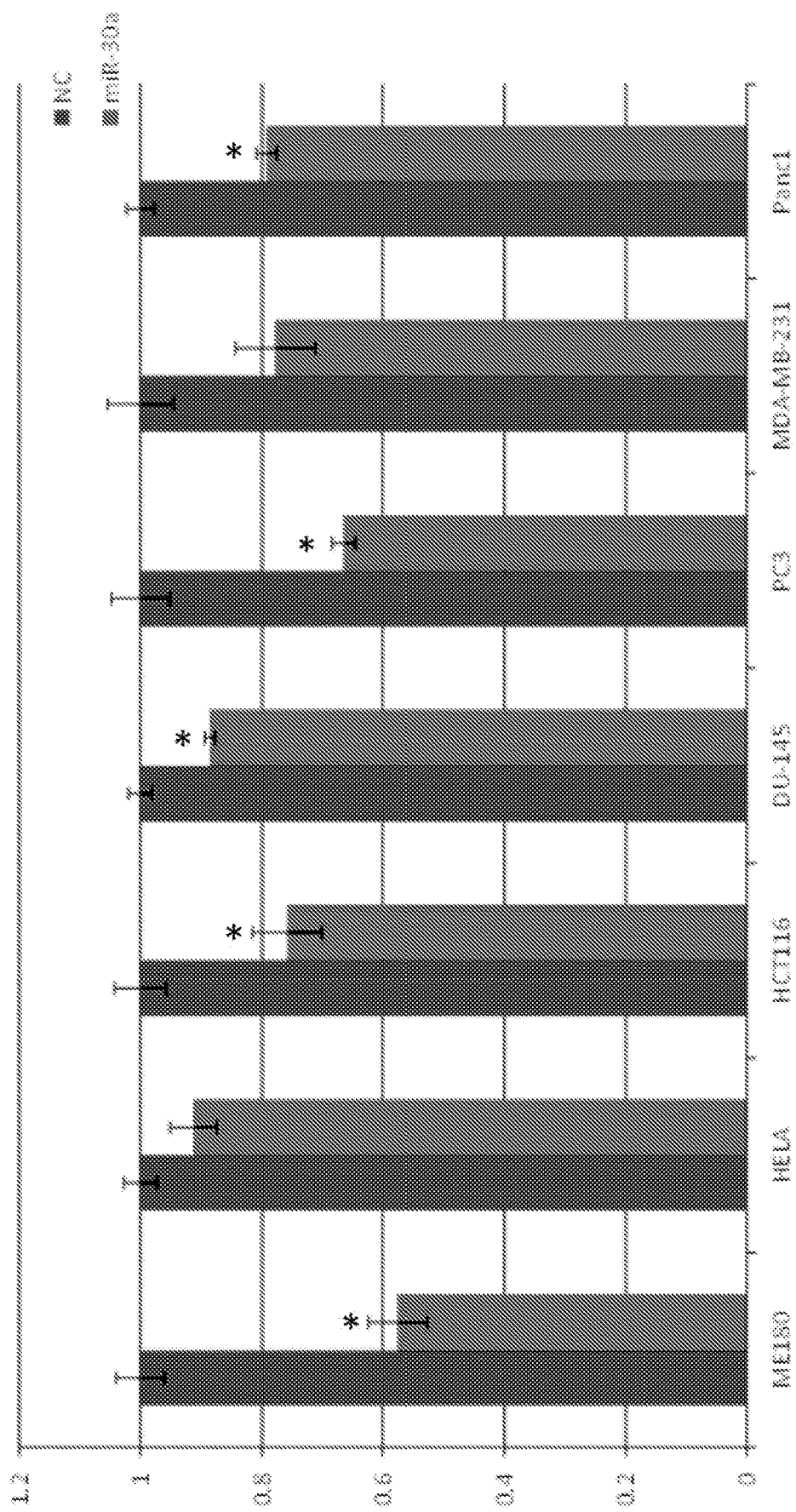
FIG. 13 is a graph showing cell viability of non-HNSCC cancer cell lines transfected with miR-30a, measured by XTT assay. Data represent mean of 6 replicates and error bars represent SEM. *, p<0.05

The effect of miR-30a on proliferation of additional types of cancer was tested on ME180 (cervical squamous cell carcinoma), HeLa (cervical adenocarcinoma), HCT116 (colorectal carcinoma), DU-145 (prostate carcinoma), PC3 (prostate carcinoma), MDA-MB-231 (breast adenocarcinoma), and Pane1 (pancreatic carcinoma) cell lines. Cells were seeded at $2 \times 10^3$ cells/well in 96 well plates and reverse transfected with 15 nM miR-30a duplex for 48 hours with 0.15 μl of RNAiMAX. Following transfection, media was replaced and cells were incubated for 5 days. Following incubation, cell viability was measured by XTT assay. miR-30a decreased cell viability in all cell lines tested (FIG. 13).

Example 10

Modified miR-30a miRNAs

Design and synthesis of several modified precursor hsa-miR-30a mimics and/or mimetics was carried out. Exemplary modified miR-30a nucleic acids are shown in Table 18.

Bases 1, 6, and 20 of the passenger strand were mutated to increase the stability of the resulting duplex. In order to bias strand selection towards the guide strand by RISC a two base overhang was placed on the 3' end of the passenger strand. To further bias strand selection a 5' amino C6 modification at the 5' end of the passenger strand was also tested. It is known that modification of the 2' position of individual nucleic acids in an oligonucleotide can improve affinity to complementary strands and also confer resistance to nucleases. However it is unknown what effect these modification have on microRNA function. To test this, oligonucleotides that contain 2' modification of the three bases at the ends of the passenger strand (Passenger strand 7) were synthesized. Consecutive bases between position 7 and 18 were also modified in separate oligonucleotides (guide strands 1-5). The strands were hybridized to create six different duplex mimics of miR-30a that may bias maturation of the 5p strand.

The effect of strand length on the activity was also tested. Guide strand 11, which is two bases shorter but has a 2' modification of the same bases as guide strand 5, and passenger strand 12, which is also two bases shorter than passenger strand 6 but still contains 2' modification of the 3 bases at the 3' and 5' ends of the oligonucleotide, were synthesized. All strands were combined to create six new mimics (010-015).

TABLE 18

Modified miR-30 constructs

| Oligo | Sequence (5'-3')* | SEQ ID NO: |
|---|---|---|
| Guide strand 1 (G1) | UGUAAACAUCCUCGACUGGAAGCU | 37 |
| Guide strand 2 (G2) | UGUAAACAUCCUCGACUGGAAGCU | 38 |
| Guide strand 3 (G3) | UGUAAACAUCCUCGACUGGAAGCU | 39 |
| Guide stand 4 (G4) | UGUAAACAUCCUCGACUGGAAGCU | 40 |
| Guide strand 5 (G5) | UGUAAACAUCCUCGACUGGAAGCU | 41 |
| Guide strand 11 (G11) | UGUAAACAUCCUCGACUGGAAG | 42 |
| Guide strand 13 (G13) | UGUAAACAUCCUCGACUGGAApsG | 43 |
| Guide strand 15 (G15) | UGUAAACAUCCUCGACUGGApsApsG | 44 |
| Guide strand 16 (G16) | UGUAAACAUCCUCGACUGGAAd-mpG | 45 |
| Guide strand 17 (G17) | UGUAAACAUCCUCGACUGGAd-mpAd-mpG | 46 |
| Guide strand 18 (G18) | UGUAAACAUCCUCGACUGGAAG | 47 |
| Guide strand 19 (G19) | UGUAAACAUCCUCGACUGGApsApsG | 48 |
| Guide strand 20 (G20) | UGUAAACAUCCUACACUCUCAGC | 49 |
| Guide strand 21 (G21) | UGUAAACAUCCUACACUCUCAGC | 50 |
| Guide strand 22 (G22) | UGUAAACAUCCUACACUCUCAGC | 51 |
| Guide strand 23 (G23) | UGUAAACAUCCUACACUCUCApsGpsC | 52 |
| Guide strand 24 (G24) | UfGUAAACAUCCUACACUCUCApsGpsC | 53 |

TABLE 18-continued

Modified miR-30 constructs

| Oligo | Sequence (5'-3')* | SEQ ID NO: |
|---|---|---|
| Passenger strand 6 (P6) | amino C6-AGCUUCCAGUCGGAUGUUUACACG | 54 |
| Passenger strand 7 (P7) | amino C6-<u>AGC</u>UUCCAGUCGGAUGUUUAC<u>ACG</u> | 55 |
| Passenger strand 12 (P12) | amino C6-<u>CUU</u>CCAGUCGGAUGUUUAC<u>ACG</u> | 56 |
| Passenger strand 14 (P14) | Amino C6-<u>UCC</u>AGUCGGAUGUUU<u>ACA</u> | 57 |
| Passenger strand 25 (P25) | Amino C6-<u>UCCAfGUfCGfGAfUGfUUfUAfCA</u> | 58 |
| Passenger strand 26 (P26) | Amino C6-<u>UCCAfGUfCGfGAfUGfUUfUAfpsCpsA</u> | 59 |
| Passenger strand 27 (P27) | Amino C6-<u>UCCAfGUfCGfGAfUGfUUfUAfCd-mpA</u> | 60 |
| Passenger strand 28 (P28) | Amino C6-<u>UGAGAGUAGGAUGUUUACA</u> | 61 |

*underlined residues have 2'OMe modification; ps-phosphorothioate; mp-methyl phosphonate; d-2' deoxy; f-2' Fluor; Mutated bases are shown in bold and italics.

Cell viability was assessed in UM-SCC-46 cells transfected with modified miR-30a mimics UMSCC-46 cells were seeded at 2×10³ cells/well in 96-well plates and reverse transfected with 15 nM duplex for 48 hours with 0.15 µL of RNAiMAX. Following transfection media was replaced and cell were incubated for 5 days. Following incubation cell viability was measured by XTT assay. Data represent the mean of 6 replicates. M-miR30a-006 (G5+P7) M-miR30a-014 (G11+P12), and M-miR-30a-016 (G11+P14) had the greatest effect on cell viability (Table 19).

TABLE 19

Effect of modified miR-30a mimics on UMSCC-46 cell viability

| Mimic name | Strands | % viability control (15 nM) | SEM |
|---|---|---|---|
| Unmodified miR30a | | 0.7545821 | 0.114837 |
| M-miR30a-001 | G3 + P6 | 0.634257 | 0.138051 |
| M-miR30a-002 | G3 + P7 | 0.680829 | 0.164553 |
| M-miR30a-003 | G4 + P6 | 0.773038 | 0.113855 |
| M-miR30a-004 | G4 + P7 | 0.690925 | 0.066221 |
| M-miR30a-005 | G5 + P6 | 0.681762 | 0.152425 |
| M-miR30a-006 | G5 + P7 | 0.331135 | 0.046659 |
| M-miR30a-007 | G3 + P10 | na | na |
| M-miR30a-008 | G4 + P10 | na | na |
| M-miR30a-009 | G5 + P10 | na | na |
| M-miR30a-010 | G3 + P12 | 0.363122 | 0.048457 |
| M-miR30a-011 | G4 + P12 | 0.49771 | 0.035976 |
| M-miR30a-012 | G5 + P12 | 0.385692 | 0.030329 |
| M-miR30a-013 | G11 + P7 | 0.433616 | 0.038817 |
| M-miR30a-014 | G11 + P12 | 0.255287 | 0.043365 |
| M-miR30a-015 | G11 + P6 | 0.424858 | 0.032783 |
| M-miR30a-016 | G11 + P14 | 0.256281 | 0.028257 |

Figure 14A:
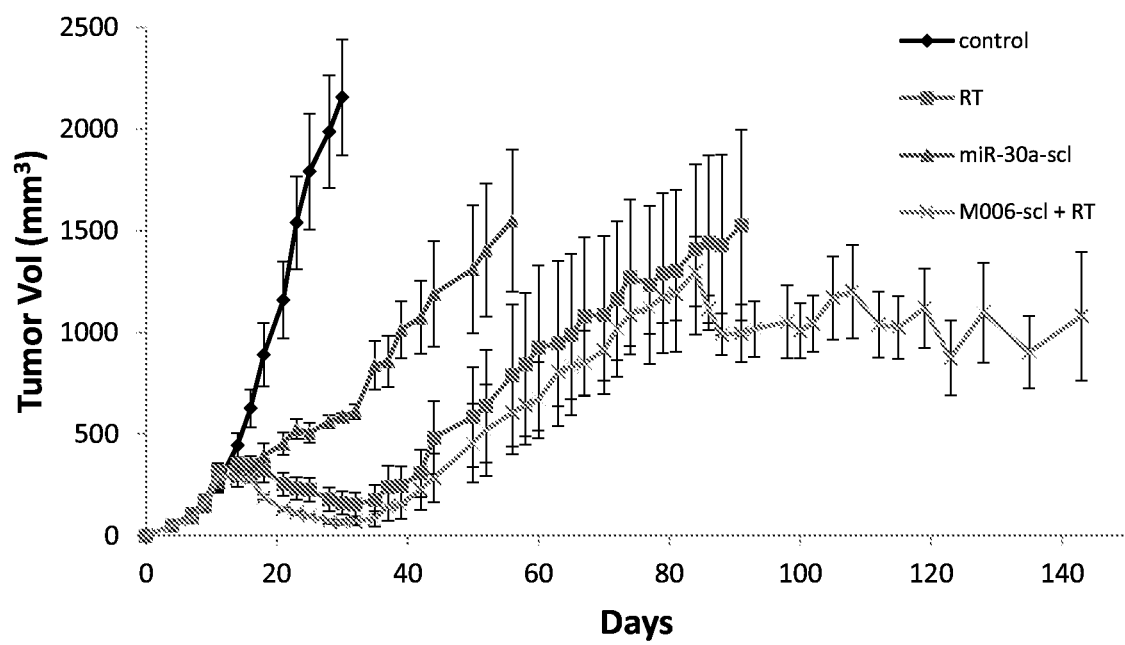
FIGS. 14A-14B are a series of panels showing effect of a modified miR-30a oligonucleotide on a UMSCC-46 xenograft model.
Figure 14B:
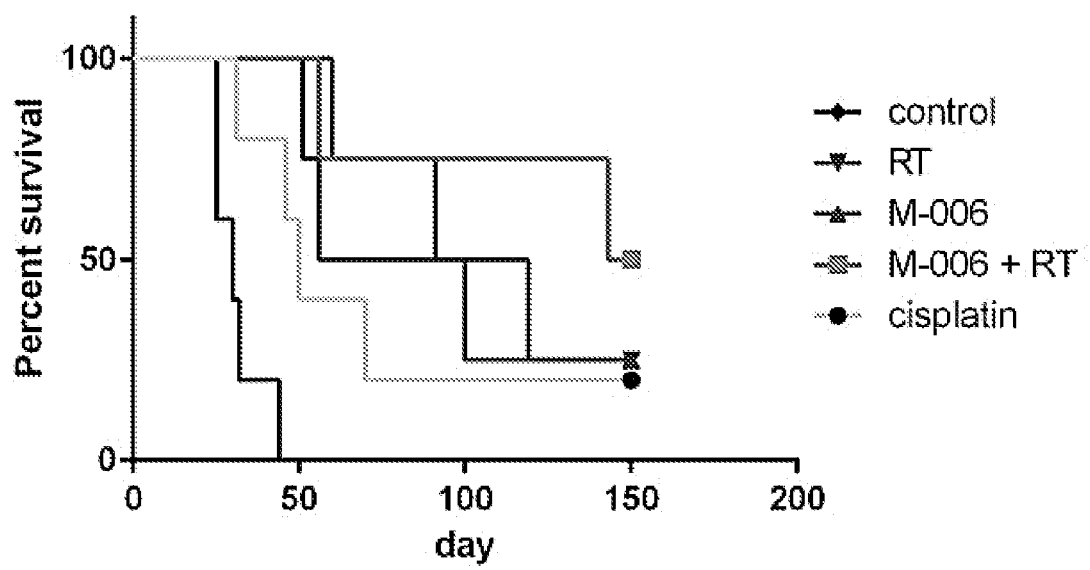

The M-miR30a-006 oligonucleotide was also tested in a mouse model of UMSCC-46 xenograft tumors. Mice with a UMSCC-46 xenograft tumor ~100 mm³ were injected IV with nine doses of 60 µg (~3 mg/kg) of complexed miR-30a mimic or control vehicle on MWF for 3 weeks. Mice were treated with 10×2 Gy fractions of radiation therapy daily (20 Gy total) on day 24 (FIGS. 14A-14B).

Example 11

Effect of Combination miRNA Treatment on Cell Proliferation

Cell viability was assessed in nine HNSCC tumor cell lines transfected with a mixture of four miRNAs—M-miR30a-014, miR-145-5p, miR-26a-5p, and miR-375 at 7.5 nM or 15 nM total duplexes (1.875 nM or 3.75 nM of each duplex respectively). In other experiments, cells were transfected with pairs of miRNAs at 7.5 nM or 15 nM total duplexes. Cells were seeded at 1.5-2×10³ cells/well in 96-well plates and reverse transfected with mixture for 48 hours with 0.15 µL of RNAiMAX. Following overnight transfection, media was replaced and cell were incubated for 4-5 days. Following incubation, cell viability was measured by XTT assay as described in Example 1.

Figure 15:
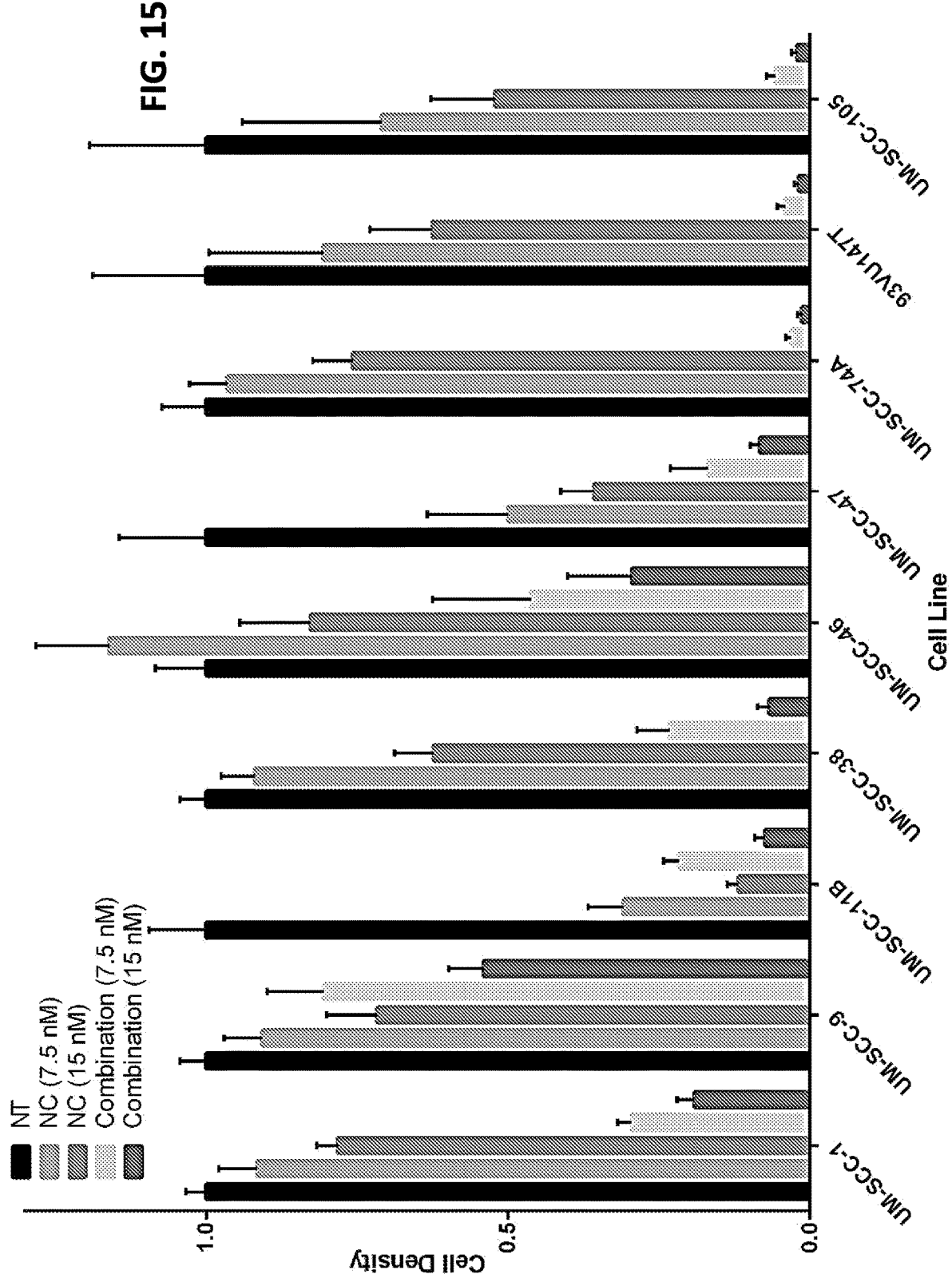
FIG. 15 is a graph showing the effect of an miR combination treatment on cell density of the indicated cell lines. The cells were transfected with a combination of miR-30a-014 (G11+P12 stands), miR-145, miR-26a, and miR-375. Data represent the mean of 6 replicates, and error bars represent SD.
Figure 16A:
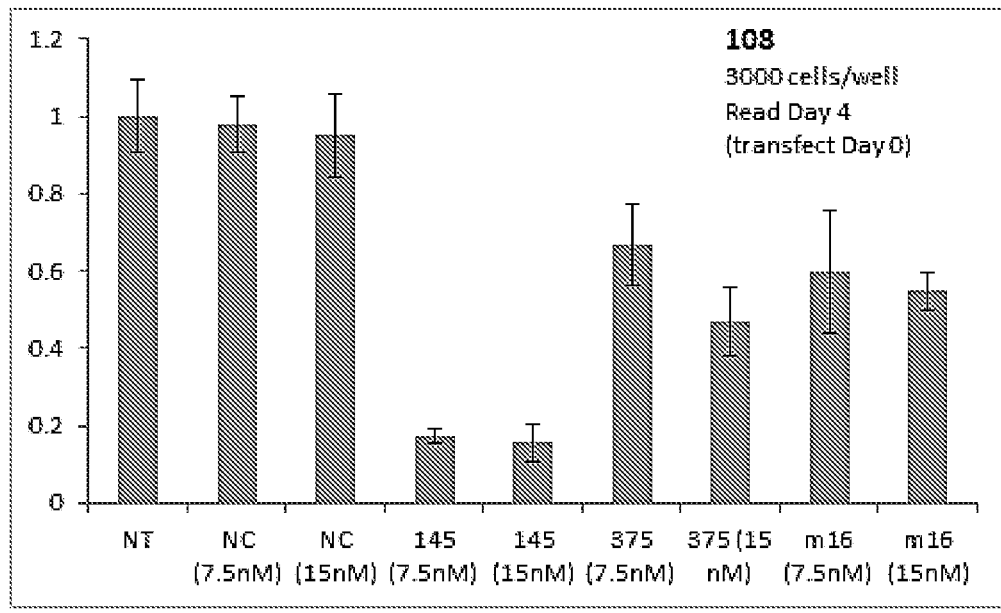
FIGS. 16A-16D are graphs showing the effect of individual miRNAs or pairs of miRNAs on cell density of UM-SCC108 cells (FIG. 16A), UM-SCC-22B cells (FIG. 16B), UM-SCC-47 cells (FIG. 16C), and UM-SCC-1G cells (FIG. 16D). NT, non-transfected; NC, negative control; 145, miR-145-5p; 375, miR-375; m16, M-miR30a-016; 26a, miR-26a-5p; 30a, miR-30a-5p.
Figure 16A:
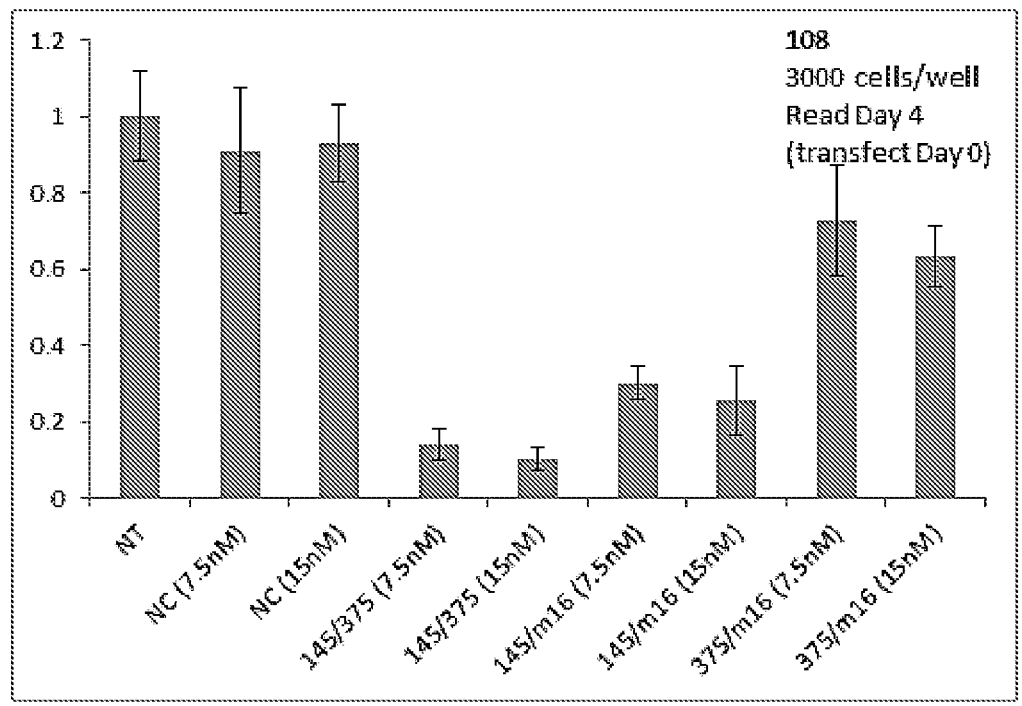
Figure 16B:
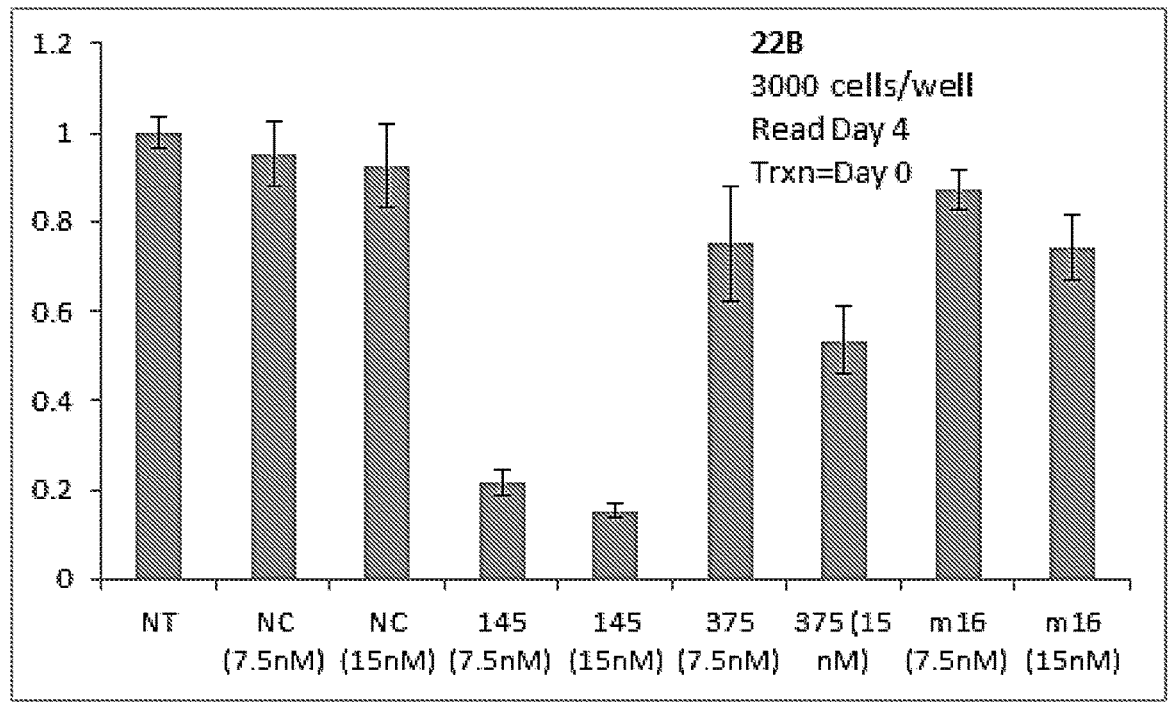
Figure 16B:
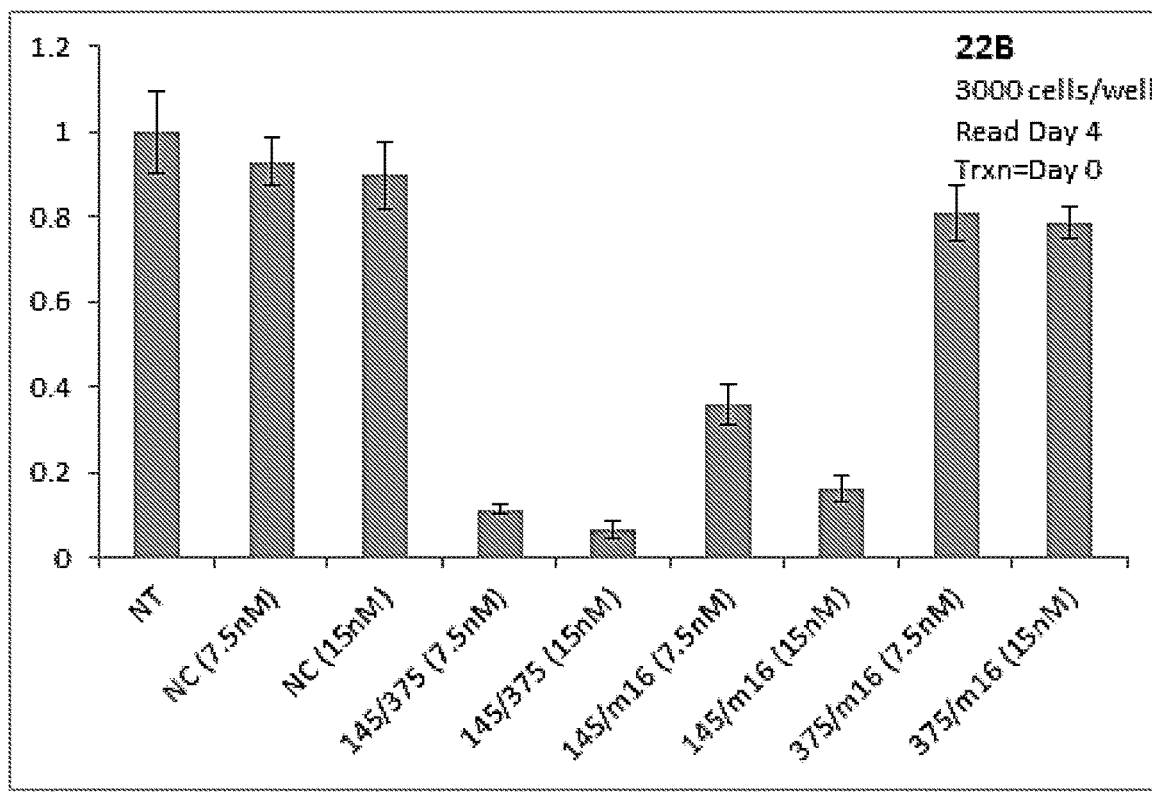
Figure 16C:
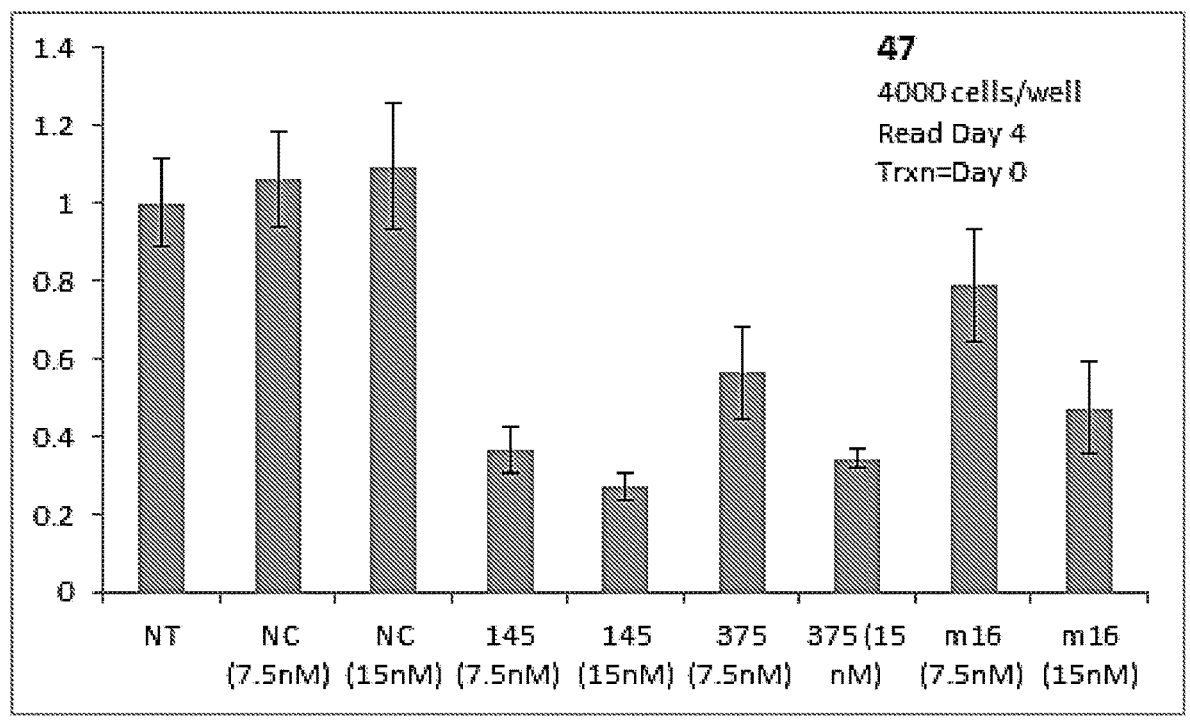
Figure 16C:
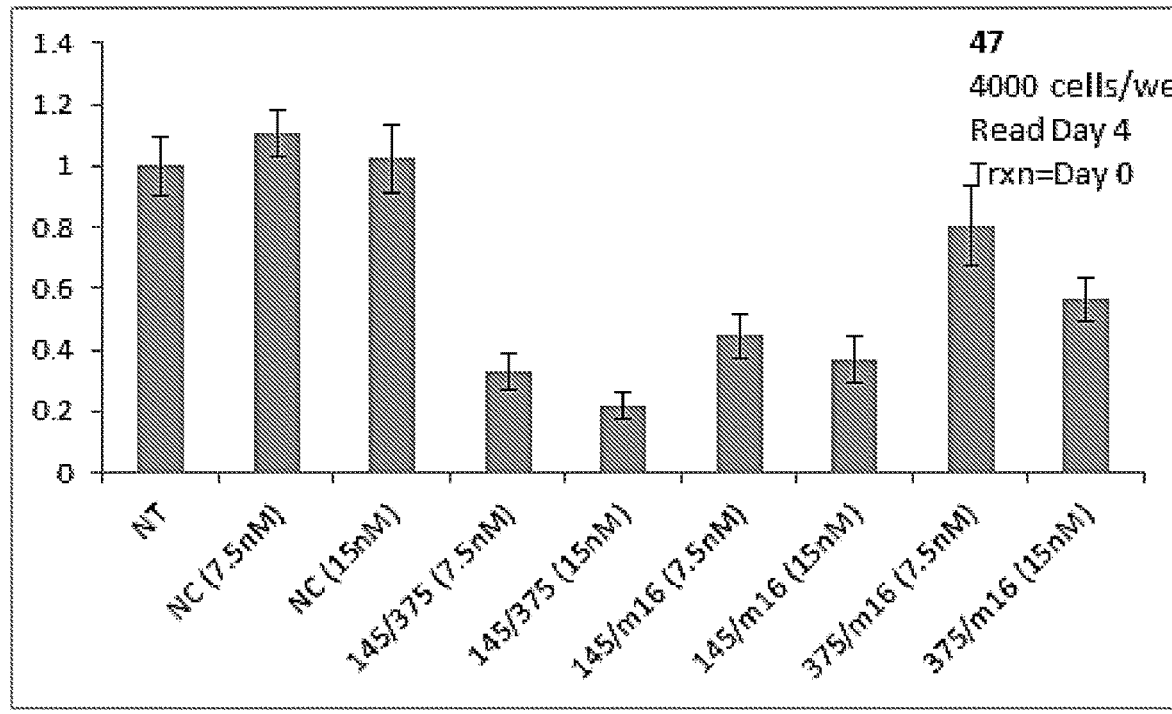
Figure 16D:
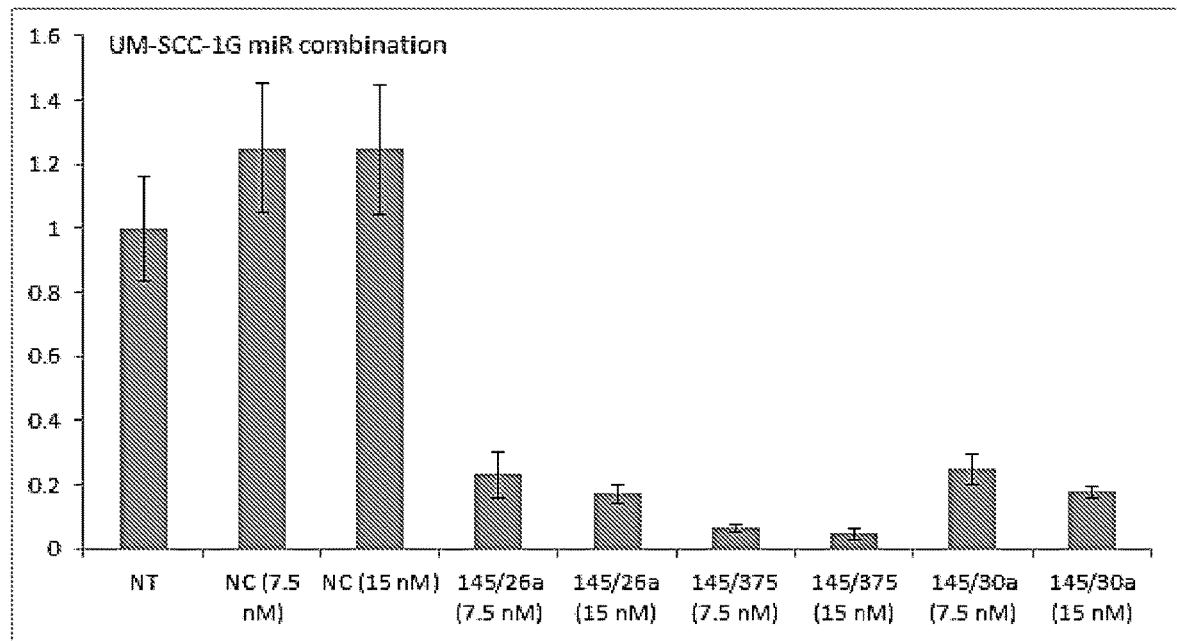
Figure 16D:
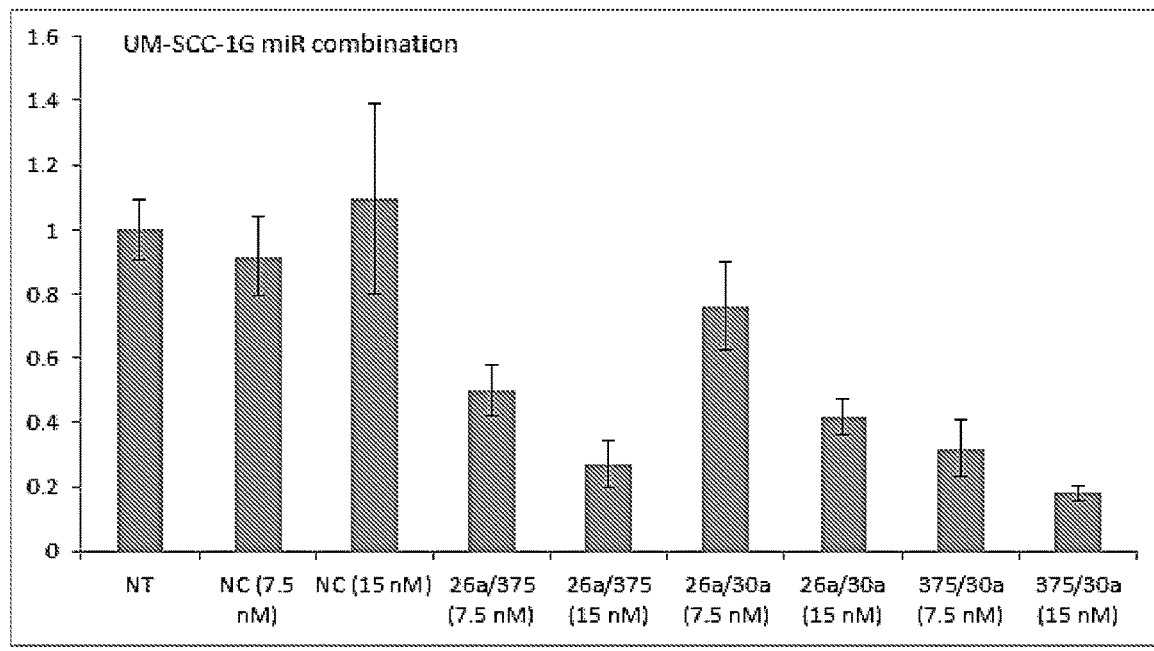

The four miRNA mixture decreased cell density in all cell lines (FIG. 15), particularly at 15 nM concentration. Similarly, the two miRNA combinations also decreased cell density (FIGS. 16A-16D).

Example 12

Effect of Additional miRNAs on Cell Viability

Cell viability was assessed in UM-SCC-1 or UM-SCC-46 cells transfected with miR27-5p or miR-2b-1-5p duplexes. UM-SCC-1 cells were seeded at 1.5×10³ cells/well and UM-SCC-46 cells were seeded at 2×103 cells/well in 96-well plates and reverse transfected with 7.5 nM or 15 nM duplex for 48 hours with 0.15 µL of RNAiMAX. Following transfection, media was replaced and cells were incubated for 5 days. Cell viability was measured by XTT assay.

Figure 17A:
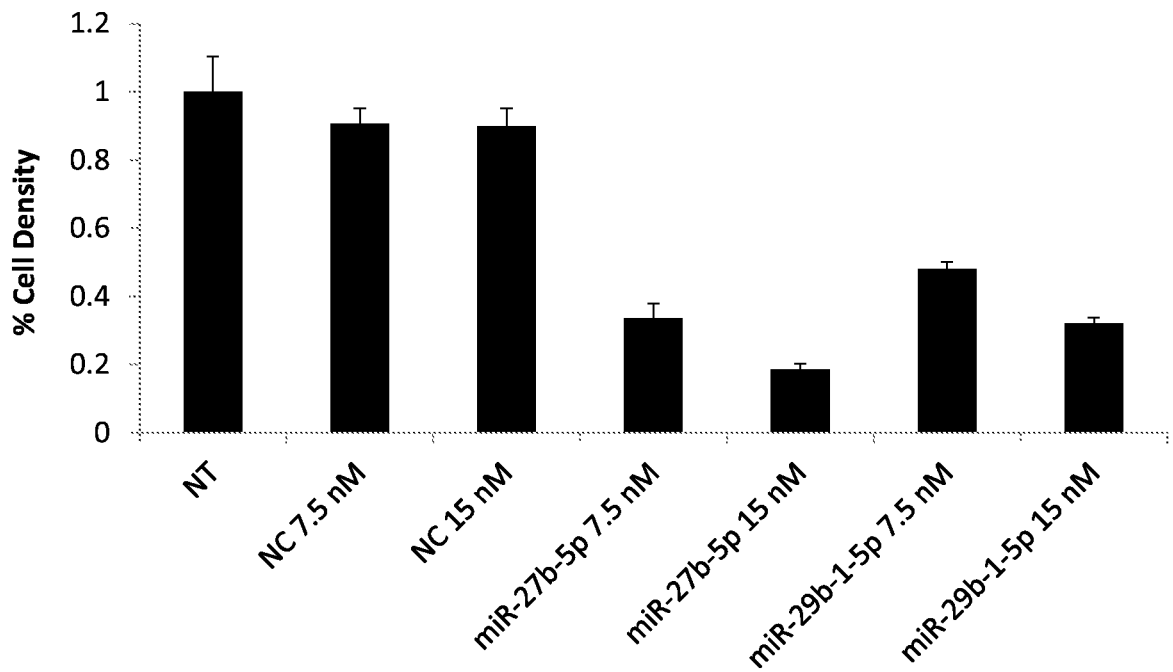
FIGS. 17A and 17B are graphs showing cell viability in UM-SCC-1 (FIG. 17A) or UM-SCC-46 (FIG. 17B) cells transfected with miR-27-5p or miR-26b-1-5p duplexes. Data represent the mean of six replicates. Error bars represent SEM. * p<0.05 by student's T test.
Figure 17B:
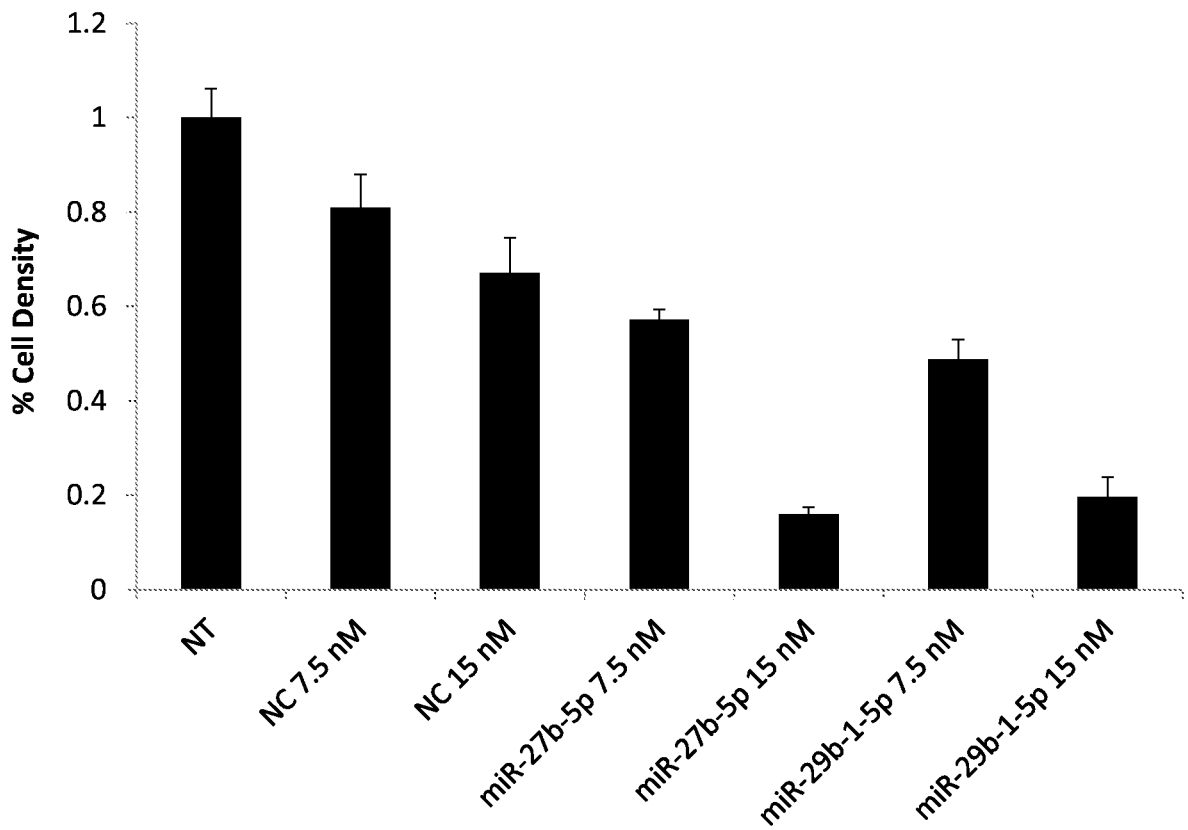

Both miR-27b-5p and miR-29-b-1-5p decreased cell density in both UM-SCC-1 and UM-SCC-46 cells (FIGS. 17A and 17B).

Example 13

Modified miRNAs

Design of several miR mimics and/or mimetics was carried out. Exemplary miR mimics and/or mimetics are shown in Table 20.

TABLE 20

Modified miRs

| Oligo | Sequence (5'-3') | SEQ ID NO: |
|---|---|---|
| hsa-miR-375 mimic/mimetic | | |
| Guide strand (G29) | UUU GUU CGU UCG GCU CGC GUG A | 62 |
| Passenger strand (P30) | Amino C6-AC GCG AGC CGA ACG AAC AAA | 63 |
| miR-26a-5p mimic/mimetic | | |
| Guide strand 31 (G31) | UUC AAG UAA UCC AGG AUA GGC U | 64 |
| Passenger strand (P32) | Amino C6-CCU AUC CCU GA UUA CUU GAA | 65 |
| miR-145-5p mimic/mimetic | | |
| Guide strand (G33) | GUC AG UUU UCC CAG GAA UCC CU | 66 |
| Passenger strand (P34) | Amino C6-GGA UUC CUG GAA AUA CUG GAC | 67 | underlined residues have 2'OMe modification; Mutated bases are shown in bold and italics.

Example 14

Treatment of Head and Neck Squamous Cell Carcinoma

This example describes methods that can be used to treat or inhibit HNSCC in a subject. However, one skilled in the art will appreciate based on the teachings herein that methods that deviate from these specific methods can also be used to successfully treat HNSCC. One of skill in the art will also recognize that these methods can also be used to treat or inhibit other cancers in a subject.

In an example, a subject with HNSCC (or another type of tumor) is selected. In some examples, the subject has an HNSCC tumor. In other examples, the subject has an HNSCC tumor that is determined to have decreased expression of one or more miRNAs (such as one or more of miR-30a family member, miR-26 family member, miR-145-5p, miR-338-3p, and miR-375). In other examples, the subject has a tumor with a deletion in the DNA encoding of one or more miRNAs (such as one or more of MIR30 gene, MIR26 gene, MIR145 gene, MIR338 gene, and MIR375 gene). In other examples, the subject has a tumor with increased methylation of the promoter or in the DNA encoding for one or more miRNAs (such as one or more of MIR30 gene, MIR26 gene, MIR145 gene, MIR338 gene, and MIR375 gene).

Following subject selection, an effective amount of an miRNA nucleic acid (such as miR-30a-5p or a mimic or mimetic thereof) or a mixture of miRNA nucleic acids (such as a mixture of miR-30a, miR-145, miR-26a, and miR-375 or a mimic or mimetic of one or more thereof) is administered to the subject. The amount of the composition administered the subject depends on the subject being treated, the severity (such as TNM stage) of the tumor, and the manner of administration of the composition. Ideally, an effective amount of the miRNA(s) is the amount sufficient to decrease one or more signs and symptoms of the HNSCC in the subject without causing a substantial cytotoxic effect in the subject.

In some examples, a decrease in the number and/or size of tumors, number and/or size of metastases, a decrease (or halt) in disease progression, an increase in survival (such as disease-free survival, progression-free survival, and/or metastasis-free survival), or a combination of two or more thereof, indicates the effectiveness of the treatment.

Example 15

Design and Testing of Additional miR-30 Mimics

Additional modified miR-30-5p guide and passenger strands were designed and are shown in Table 21.

TABLE 21

Modified miR-30-5p miRNAs

| Oligo | Sequence (5'→3') | SEQ ID NO: |
|---|---|---|
| Guide strand 35 (G35) | UGUAAACAUCCUACACUCUCAGC | 50 |
| Guide strand 36 (G36) | UfGUfAAfACfAUfCCfUAfCAfCUfCUfCAfpsGpsCf | 73 |
| Guide strand 37 (G37) | UGfUAAAfCAUfCCfUAfCAfCUfCUfCAfpsGpsCf | 74 |
| Passenger strand 28 (P28) | Amino C6-UGAGAGUAGGAUGUUUACA | 61 | f, 2'-fluoro, underlined, 2'-OME, ps, phosphorothioate, Mutated bases are shown in bold and italics.

Figure 18:
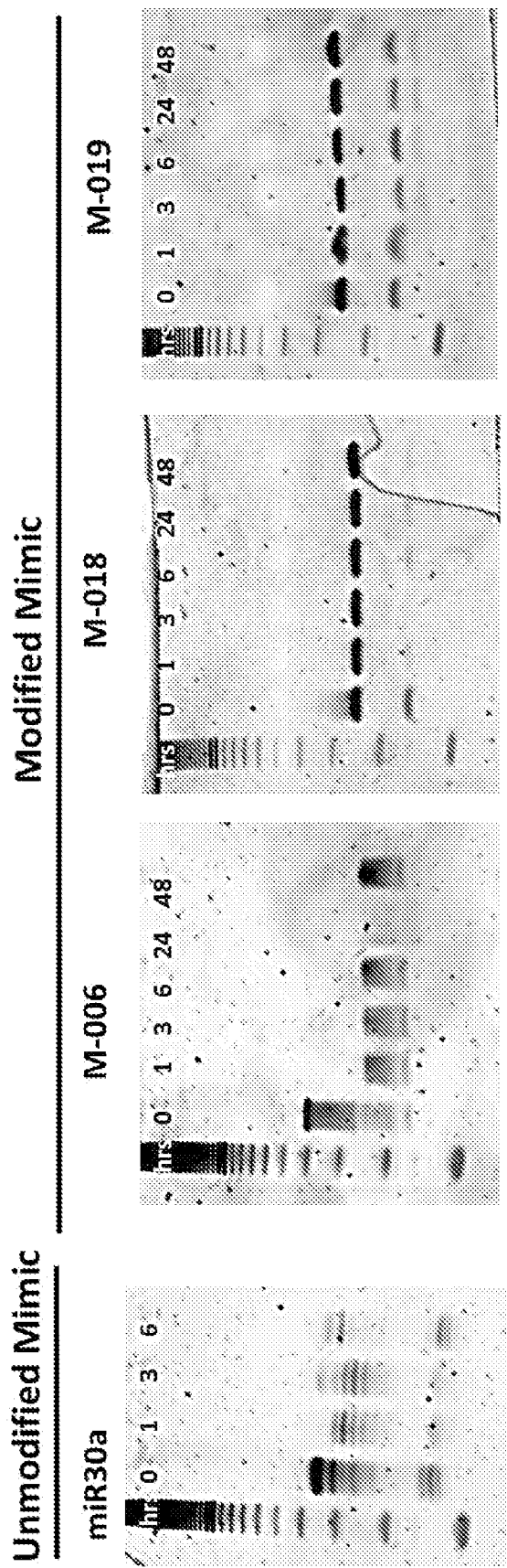
FIG. 18 is a series of digital images showing stability of miR-30a and modified mimics (M-006, M-018, and M-019) in serum over the course of 48 hours.
Figure 19:
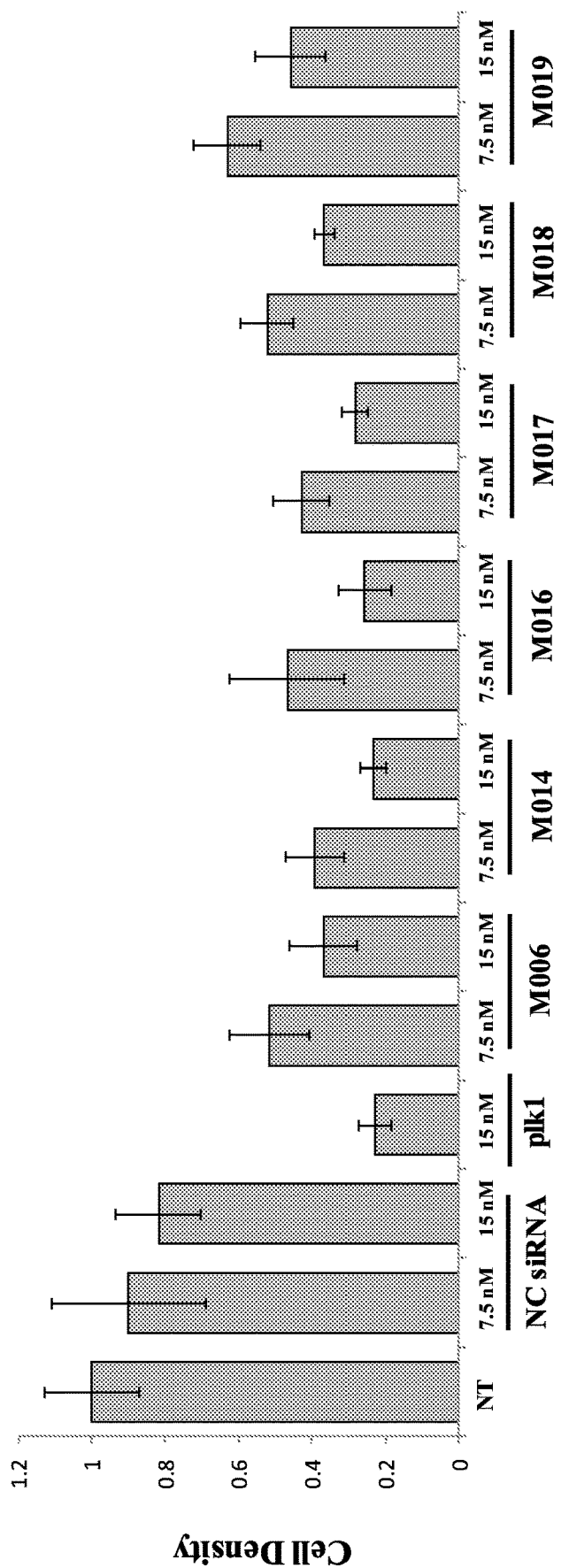
FIG. 19 is a graph showing the effect of miRNA pairs on cell density of UM-SCC-46 cells. NT, non-transfected; NC, negative control; miRNA pairs are as shown in Tables 19 and 22. Error bars represent SD.

Cell viability was assessed in UM-SCC-46 cells transfected with modified miR-30a mimics, as described in Example 11. Data represent the mean of 6 replicates (Table 22). The stability of the mimics in serum was tested (FIG. 18). The chemical modifications incorporated in M-miR30-018 and M-miR30-019 imparted long term resistant to nuclease with >50× increased stability in human serum (FIG. 18). Cell viability was assessed UM-SCC-46 cells transfected with the indicated miRNA duplexes (7.5 nM or 15 nM total duplexes) as described in Example 11 (FIG. 19). M-miR30-018 and M-miR30-019 still maintained potency inhibiting proliferation of cancer cells equal to M-006 which is vastly improved over the biological microRNA (FIG. 19 and Table 22).

TABLE 22

Effect of modified miR-30a mimics on UMSCC-46 cell viability

| Mimic name | Strands | % viability control (15 nM) | SEM |
|---|---|---|---|
| M-miR30-017 | G35 + P28 | 0.281711 | 0.038428 |
| M-miR30-018 | G36 + P28 | 0.363828 | 0.024757 |
| M-miR30-019 | G37 + P28 | 0.457675 | 0.100329 |

Example 16

Additional miR Mimics

Design of additional miR mimics and/or mimetics was carried out. Exemplary miR mimics and/or mimetics are shown in Table 23.

TABLE 23

Modified miRs

| Oligo | Sequence (5'-3') | SEQ ID NO: |
|---|---|---|
| miR-30 mimics | | |
| Guide strand 39 (G39) | UfGUf AAA CAUf CCfU CfGAf CUfG GfApsAfpsG | 75 |
| Guide strand 40 (G40) | UfGUf AAA CAUf CCfU CGA CUG GApsApsG | 76 |
| Guide strand 41 (G41) | UfGUf AAAf CAUf CCfU CfGAf CUfG GfApsAfpsG | 77 |
| Guide strand 42 (G42) | UfGUf AAfA CfAUf CCfU CfGAf CUfG GfApsAfpsG | 78 |
| Guide strand 43 (G43) | UfGUf AAfAf CAUf CCfU CfGAf CUfG GfApsAfpsG | 79 |
| Guide strand 44 (G44) | UfGUf AAfA CfAUf CCfU CGA CUG GfApsAfpsG | 80 |
| Guide strand 45 (G45) | UfGUf AAA CAUf CCfU CGA CUG GfApsAfpsG | 81 |
| Guide strand 46 (G46) | UfGUf AAfA CfAUf CCfU CGA CUG GApsApsG | 82 |
| Guide strand 47 (G47) | UfGUf AAA CAU CCU CGA CUG GApsApsG | 83 |
| Guide strand 48 (G48) | UfGUf AAA CAU CCU CGA CUG GApsAfpsG | 84 |
| Guide strand 49 (G49) | UfGUf AAA CAU CCU CGA CUG GApsApsGf | 85 |
| Guide strand 50 (G50) | UfGU AAA CAU CCU CGA CUG GApsApsGf | 86 |
| Guide strand 51 (G51) | UfGU AAA CAU CCU CGA CUG GApsAfpsG | 87 |
| Guide strand 52 (G52) | UfGU AAA CAU CCU CGA CUG GApsApsGf | 88 |
| Guide strand 53 (G53) | UfGU AAA CAU CfCU CGA CUG GApsApsGf | 89 |
| Guide strand 54 (G54) | UfGU AAA CAUf CCU CGA CUG GApsApsGf | 90 |

TABLE 23-continued

Modified miRs

| Oligo | Sequence (5'-3') | SEQ ID NO: |
|---|---|---|
| Guide strand 55 (G55) | UfGUf AAA CAU CCfU CfGAf CUfG GfApsAfpsG | 91 |
| Passenger strand 56 (P56) | Amino C6-UCCAfGUfCGfGAUGUfUUfACA | 92 |
| miR-375 mimics | | |
| Guide strand 57 (G57) | UfUUf GUU CGU UCG GCU CGC GUpsGfps A | 93 |
| Guide strand 58 (G58) | UfUU GUU CGU UCG GCU CGC GUpsGfps A | 94 |
| Guide strand 59 (G59) | UfUUf GUU CGU UCG GCU CGC GfUpsGfps A | 95 |
| Guide strand 60 (G60) | UfUUf GUfU CGU UCG GCU CGC GfUpsGfps A | 96 |
| Guide strand 61 (G61) | UfUUf GUfU CGU UCG GCU CGfC GfUpsGfps A | 97 |
| Guide strand 62 (G62) | UfUUf GUfU CfGU UCG GCU CGfC GfUpsGfps A | 98 |
| Guide strand 63 (G63) | UfUUf GUU CGU UCG GCU CGfC GfUpsGfps A | 99 |
| Guide strand 64 (G64) | UUU GUU CGU UCG GCU CGfC GfUpsGfps A | 100 |
| Guide strand 65 (G65) | UUU GUU CGU UCG GCU CGfC GfUpsGfps A | 101 |
| Guide strand 66 (G66) | UfUUf GUfU CfGUf UCfG GfCUf CGfC GfUpsGfps A | 102 |
| Guide strand 67 (G67) | UfUUf GUU CGU UCfG GfCUf CGfC GfUpsGfps A | 103 |
| Passenger strand 68 (P68) | Amino C6-AC GCfG AfGCf CGA ACfG AfACf AAA | 104 |
| miR-26 mimics | | |
| Guide strand 69 (G69) | UfUCf AAG UAA UCC AGG AUA GGpsCfps U | 105 |
| Guide strand 70 (G70) | UfUC AAG UAA UCC AGG AUA GGpsCfps U | 106 |
| Guide strand 71 (G71) | UfUCf AAG UAA UCC AGG AUA GfGpsCfps U | 107 |
| Guide strand 72 (G72) | UfUCf AAG UAA UCC AGG AUA GfGpsCfps U | 108 |
| Guide strand 73 (G73) | UfUCf AAfG UAA UCC AGG AUA GfGpsCfps U | 109 |
| Guide strand 74 (G74) | UfUCf AAfG UAA UCC AGG AUAf GfGpsCfps U | 110 |
| Guide strand 75 (G75) | UfUCf AAfG UfAA UCC AGG AUAf GfGpsCfps U | 111 |
| Guide strand 76 (G76) | UfUCf AAfG UfAA UCC AGG AUAf GfGpsCfps U | 112 |
| Guide strand 77 (G77) | UfUCf AAfG UfAA UCC AGG AfUAf GfGpsCfps U | 113 |
| Guide strand 78 (G78) | UfUCf AAfG UfAAf UCfC AfGGf AUfA GfGpsCfps U | 114 |
| Passenger strand 79 (P79) | Amino C6-CCU AfUCf CCfU GGA UUfA CfUUf GAA | 115 |
| miR-145-5p mimics | | |
| Guide strand 80 (G80) | GfUC CAG UUU UCC CAG GAA UCCps CfpsU | 116 |
| Guide strand 81 (G81) | GfUCf CAG UUU UCC CAG GAA UCCps CfpsU | 117 |
| Guide strand 82 (G82) | GfUCf CAG UUU UCC CAG GAA UCfCps CfpsU | 118 |
| Guide strand 83 (G83) | GfUCf CAfG UUU UCC CAG GAA UCfCps CfpsU | 119 |
| Guide strand 84 (G84) | GfUCf CAfG UUU UCC CAG GAAf UCfCps CfpsU | 120 |
| Guide strand 85 (G85) | GfUCf CAfG UfUU UCC CAG GAAf UCfCps CfpsU | 121 |
| Guide strand 86 (G86) | GfUCf CAfG UfUU UCC CAG GfAAf UCfCps CfpsU | 122 |

TABLE 23-continued

Modified miRs

| Oligo | Sequence (5'-3') | SEQ ID NO: |
|---|---|---|
| Guide strand 87 (G87) | GfUCf CAfG UfUUf UCfC CfAGf GfAAf UCfCps CfpsU | 123 |
| Guide strand 88 (G88) | GfUCf CAfG UfUUf UCfC CfAGf GAfA UfCCfps CpsUf | 124 |
| Passenger strand 89 (P89) | Amino C6-GGA UfUCf CUfG GAA AUfA CfUGf GAC | 125 |
| miR-101 mimics | | |
| Guide strand 89 (G89) | UAC AGU ACU GUG AUA ACU GAA | 126 |
| Guide strand 90 (G90) | UfAC AGU ACU GUG AUA ACU GpsAfpsA | 127 |
| Guide strand 91 (G91) | UfACf AGU ACU GUG AUA ACU GpsAfpsA | 128 |
| Guide strand 92 (G92) | UfACf AGU ACU GUG AUA ACUf GpsAfpsA | 129 |
| Guide strand 93 (G93) | UfACf AGfU ACU GUG AUA ACUf GpsAfpsA | 130 |
| Guide strand 94 (G94) | UfACf AGfU ACU GUG AUA AfCUf GpsAfpsA | 131 |
| Guide strand 95 (G95) | UfACf AGfU AfCU GUG AUA AfCUf GpsAfpsA | 132 |
| Guide strand 96 (G96) | UfACf AGfU AfCUf GUfG AfUAf ACfU GfpsApsAf | 133 |
| Passenger strand 97 (P97) | Amino C6-CAG UUA UCA CAG UAC UGU A | 134 |
| Passenger strand 98 (P98) | Amino C6-CAG UfUAf UCfA CAG UAfC UfGU A | 135 |
| miR-29 mimics | | |
| Guide strand 99 (G99) | GCU GGU UUC AUA UGG UGG UUU AGA | 136 |
| Guide strand 100 (G100) | GfCU GGU UUC AUA UGG UGG UUU ApsGfpsA | 137 |
| Guide strand 101 (G101) | GfCUf GGU UUC AUA UGG UGG UUU ApsGfpsA | 138 |
| Guide strand 102 (G102) | GfCUf GGU UUC AUA UGG UGG UUUf ApsGfpsA | 139 |
| Guide strand 103 (G103) | GfCUf GGfU UUC AUA UGG UGG UUUf ApsGfpsA | 140 |
| Guide strand 104 (G104) | GfCUf GGfU UUC AUA UGG UGG UfUUf ApsGfpsA | 141 |
| Guide strand 105 (G105) | GfCUf GGfU UfUC AUA UGG UGG UfUUf ApsGfpsA | 142 |
| Guide strand 106 (G106) | GfCUf GGfU UfUC AUA UGG UGfG UfUUf ApsGfpsA | 143 |
| Guide strand 107 (G107) | GfCUf GGfU UfUC AUA UGG UGfG UfUUf ApsGfpsA | 144 |
| Guide strand 107 (G107) | GfCUf GGfU UfUCf AfUA UfGGf UGfG UfUUf ApsGfpsA | 145 |
| Passenger strand108 (P108) | Amino C6-UAA ACC ACC AUA UGA AAC CAG C | 146 |
| miR-27 mimics | | |
| Guide strand 109 (G109) | AGA GCU UAG CUG AUU GGU GAA C | 147 |
| Guide strand 110 (G110) | AfGA GCU UAG CUG AUU GGU GApsAfps C | 148 |
| Guide strand 111 (G111) | AfGAf GCU UAG CUG AUU GGU GApsAfps C | 149 |
| Guide strand 112 (G112) | AfGAf GCU UAG CUG AUU GGU GfApsAfps C | 150 |
| Guide strand 112 (G112) | AfGAf GCfU UAG CUG AUU GGU GfApsAfps C | 151 |
| Guide strand 113 (G113) | AfGAf GCfU UAG CUG AUU GGUf GfApsAfps C | 152 |
| Guide strand 114 (G114) | AfGAf GCfU UfAG CUG AUU GGUf GfApsAfps C | 153 |
| Guide strand 115 (G115) | AfGAf GCfU UfAG CUG AUU GfGUf GfApsAfps C | 154 |
| Guide strand 116 (G116) | AfGAf GCfU UfAGf CUfG AfUUf GGfU GfApsAfps Cf | 155 |
| Passenger strand 117 (P117) | Amino C6-GUU CAC CAA UCA GCU AAG CUC U | 156 |

TABLE 23-continued

Modified miRs

| Oligo | Sequence (5'-3') | SEQ ID NO: |
|---|---|---|
| Passenger strand 118 (P118) | Amino C6-<u>GUU</u> Cf<u>A</u>Cf CAfA UCA GfCUf AAfG Cf<u>UC U</u> | 157 |
| Passenger strand 119 (P119) | Amino C6-<u>UAA</u> AfCCf <u>AC</u>f<u>C</u> AUA Uf<u>G</u>Af AAfC Cf<u>AG</u> C | 158 | f, 2'-fluoro, underlined, 2'-OME, ps, phosphorothioate. Mutated bases are shown in bold and italics.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A composition comprising:
   at least one miR-30-5p mimic or mimetic nucleic acid, wherein the miR-30-5p mimic or mimetic nucleic acid comprises:
   (a) a guide strand and a passenger strand, wherein the guide strand is of about 16 to about 27 nucleotides in length and comprises one or more of 2'-O-methyl- and 2'-fluoro-modified nucleotides in any position from the ninth 5' residue to the nineteenth 5' residue, when that residue is present in the guide strand; or
   (b) a guide strand and a passenger strand, wherein the passenger strand is of about 16 to about 27 nucleotides in length and comprises one or more of 2'-O-methyl- and 2'-fluoro-modified nucleotides in any position within the three residues at the 5' end and the three residues at the 3' end and a 5'-amino C6 modification; or
   (c) guide strand and a passenger strand, wherein the guide strand is of about 16 to about 27 nucleotides in length and comprises one or more of 2'-O-methyl- and 2'-fluoro-modified nucleotides in any position from the ninth 5' residue to the nineteenth 5' residue, when that residue is present in the guide strand, and wherein the passenger strand is of about 16 to about 27 nucleotides in length and comprises one or more of 2'-O-methyl- and 2'-fluoro-modified nucleotides in any position within the three residues at the 5' end and the three residues at the 3' end and a 5'-amino C6 modification.

2. The composition of claim 1, wherein the miR-30-5p mimic or mimetic nucleic acid comprises a passenger strand that does not have a 3' overhang.

3. The composition of claim 1, wherein the miR-30-5p mimic or mimetic nucleic acid comprises a guide strand with bases deleted to generate a 3' overhang.

4. The composition of claim 1, wherein the miR-30-5p mimic or mimetic nucleic acid comprises a passenger strand with one or more of 2'-O-methyl- and 2'-fluoro-modified nucleotides in any position within the three residues at the 5' end and the three residues at the 3' end.

5. The composition of claim 1, wherein the miR-30-5p mimic or mimetic nucleic acid comprises:
   any one of SEQ ID NOs: 37-61, a duplex of SEQ ID NOs: 42 and 56, or a duplex of SEQ ID NOs: 42 and 57; any one of SEO ID NOs: 73-92, a duplex of SEQ ID NOs: 50 and 61, a duplex of SEQ ID NOs: 73 and 61, or a duplex of SEQ ID NOs: 74 and 61.

6. The composition of claim 1, wherein the miR-30-5p mimic or mimetic nucleic acid is incorporated in a nanoparticle or liposome.

7. The composition of claim 6, wherein the liposome further comprises one or more molecules targeting the nanoparticle or liposome to a tumor.

8. The composition of claim 7, wherein the targeting molecule comprises an anti-transferrin receptor antibody or fragment thereof.

9. The composition of claim 1, further comprising a pharmaceutically acceptable carrier.

10. A composition comprising:

at least one miR-30-5p mimic or mimetic nucleic acid, wherein the miR-30-5p mimic or mimetic nucleic acid comprises:

(a) a guide strand and a passenger strand, wherein the guide strand is of about 16 to about 27 nucleotides in length and comprises 2'-O-methyl-modified nucleotides at every even position residue, 2' fluoro-modified nucleotides at every odd position residue, or 2' O-methyl-modified nucleotides at every odd position residue and 2' fluoro-modified nucleotides at every even position residue; or (b) a guide strand and a passenger strand, wherein the passenger strand is of about 16 to about 27 nucleotides in length and comprises one or more of 2'-O-methyl- and 2'-fluoro-modified nucleotides in any position within the three residues at the 5' end and the three residues at the 3' end and a 5'-amino C6 modification; or (c) a guide strand and a passenger strand, wherein the guide strand is of about 16 to about 27 nucleotides in length and comprises 2'-O-methyl-modified nucleotides at every even position residue, 2'-fluoro-modified nucleotides at every odd position residue, or 2'-O-methyl-modified nucleotides at every odd position residue and 2'-fluoro-modified nucleotides at every even position residue, and wherein the passenger strand is of about 16 to about 27 nucleotides in length and comprises one or more of 2'-O-methyl- and 2'-fluoro-modified nucleotides in any position within the three residues at the 5' end and the three residues at the 3' end and a 5'-amino C6 modification.

* * * * *